United States Patent
Panicker et al.

(10) Patent No.: US 12,421,320 B2
(45) Date of Patent: Sep. 23, 2025

(54) PROTEIN S ANTIBODIES, METHODS OF MAKING AND USES THEREOF

(71) Applicant: Vega Therapeutics, Inc., South San Francisco, CA (US)

(72) Inventors: Sandip Panicker, South San Francisco, CA (US); Adam David Rosenthal, South San Francisco, CA (US); Tony Sang Young Byun, South San Francisco, CA (US); Quehuong Thi Dong, South San Francisco, CA (US)

(73) Assignee: Vega Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 18/817,152

(22) Filed: Aug. 27, 2024

(65) Prior Publication Data

US 2024/0425613 A1 Dec. 26, 2024

Related U.S. Application Data

(60) Division of application No. 18/506,872, filed on Nov. 10, 2023, now Pat. No. 12,145,999, which is a continuation of application No. 17/923,503, filed as application No. PCT/US2021/030900 on May 5, 2021.

(60) Provisional application No. 63/169,755, filed on Apr. 1, 2021, provisional application No. 63/020,505, filed on May 5, 2020.

(51) Int. Cl.
| | |
|---|---|
| C07K 16/36 | (2006.01) |
| A61K 47/68 | (2017.01) |
| A61P 7/04 | (2006.01) |
| A61K 39/00 | (2006.01) |

(52) U.S. Cl.
CPC .......... *C07K 16/36* (2013.01); *A61K 47/6843* (2017.08); *A61P 7/04* (2018.01); *A61K 2039/505* (2013.01); *A61K 2039/54* (2013.01); *A61K 2039/545* (2013.01); *C07K 2317/21* (2013.01); *C07K 2317/24* (2013.01); *C07K 2317/32* (2013.01); *C07K 2317/34* (2013.01); *C07K 2317/52* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 5,147,638 A | 9/1992 | Esmon et al. |
| 5,187,067 A | 2/1993 | Koike et al. |
| 5,366,861 A | 11/1994 | Hosoda et al. |
| 6,180,370 B1 * | 1/2001 | Queen .............. A61P 19/02 435/69.6 |
| 6,423,313 B1 | 7/2002 | Esmon et al. |
| RE38,202 E | 7/2003 | Mertens et al. |
| 7,041,458 B2 | 5/2006 | Dahlbäck |
| 8,669,263 B2 | 3/2014 | Lemke et al. |
| 9,233,144 B2 | 1/2016 | Bernard-Pierrot et al. |
| 9,447,147 B2 | 9/2016 | Dockal et al. |
| 12,145,999 B2 | 11/2024 | Panicker et al. |
| 2003/0124118 A1 | 7/2003 | Rojkjaer |
| 2003/0143759 A1 | 7/2003 | Dahlback |
| 2003/0165485 A1 | 9/2003 | Bertilsson et al. |
| 2004/0033561 A1 | 2/2004 | O'Keefe et al. |
| 2007/0077603 A1 | 4/2007 | Heeb et al. |
| 2008/0057059 A1 | 3/2008 | Rojkjaer |
| 2015/0246947 A1 | 9/2015 | Dockal et al. |
| 2016/0297892 A1 | 10/2016 | Heibroch Petersen et al. |
| 2023/0083243 A1 | 3/2023 | Panicker et al. |
| 2023/0174672 A1 | 6/2023 | Panicker et al. |
| 2024/0084038 A1 | 3/2024 | Panicker et al. |

FOREIGN PATENT DOCUMENTS

| | | | |
|---|---|---|---|
| EP | 0944837 A1 | 9/1999 | |
| EP | 0944837 B1 | 12/2004 | |
| EP | 0972781 B1 | 1/2007 | |
| EP | 1780219 A2 | 5/2007 | |
| WO | WO-9301209 A1 * | 1/1993 | .......... C07K 14/745 |
| WO | WO-9823963 A1 | 6/1998 | |
| WO | WO-2007014749 A2 | 2/2007 | |
| WO | WO-2007018511 A1 | 2/2007 | |
| WO | WO-2021226243 A1 | 11/2021 | |
| WO | WO-2021226245 A1 | 11/2021 | |
| WO | WO-2022002880 A1 | 1/2022 | |
| WO | WO-2024124136 A1 | 6/2024 | |

OTHER PUBLICATIONS

Chowdary, Pratima. "Nonfactor therapies: new approaches to prophylactic treatment of haemophilia." Hämostaseologie 41.04 (2021): 247-256 (Year: 2021).*
Arruda, Valder R., Bhavya S. Doshi, and Benjamin J. Samelson-Jones. "Emerging therapies for hemophilia: controversies and unanswered questions." F1000Research 7 (2018) (Year: 2018).*
Bolton-Maggs, Paula HB, D. J. Perry, and E. A. Chalmers. "The rare coagulation disorders." Treatment of hemophilia. World Federation of Hemophilia, Montreal 39 (2006): 1-2 (Year: 2006).*

(Continued)

*Primary Examiner* — Zachariah Lucas
*Assistant Examiner* — Lia E Taylor
(74) *Attorney, Agent, or Firm* — Cooley LLP

(57) ABSTRACT

Provided here are antibodies that bind Protein S, and methods of making and using such antibodies. In some embodiments, the Protein S antibodies provided herein are useful for treating a bleeding disorder or platelet disorder, or a condition characterized by reduced or impaired blood coagulation and/or clotting.

21 Claims, 53 Drawing Sheets

Specification includes a Sequence Listing.

(56) References Cited

OTHER PUBLICATIONS

Leong, Lilley, et al. "Pre-clinical characterization of VGA039, an anti-protein S monoclonal antibody being developed as a universal hemostatic agent for various bleeding disorders." Blood 140. Supplement 1 (2022): 1666-1667 (Year: 2022).*
Kipriyanov, Sergey M., and Fabrice Le Gall. "Generation and production of engineered antibodies." Molecular biotechnology 26.1 (2004): 39-60. (Year: 2004).*
Janeway, Charles A. "Immunobiology: The Immune System in Health and Disease." 2001 (Year: 2001).*
Baroni, M., et al.; "Membrane binding and anticoagulant properties of protein S natural variants," Thromb Res. (2010); 125(2):e33-e39.
Bologna, L., et al.; "Blocking Protein S Improves Hemostasis in Hemophilia a and B," Blood (2016); 128(22):79, 3 pages.
Borgel, D., et al.; "Implication of protein S thrombin-sensitive region with membrane binding via conformational changes in the gamma-carboxyglutamic acid-rich domain," Biochem J. (2001); 360(Pt 2):499-506.
Bos, M.H.A., et al.; "Does activated protein C-resistant factor V contribute to thrombin generation in hemophilic plasma?" J Thromb Haemost. (2005); 3(3):522-530.
Castoldi et al. (2009). "Hereditary and acquired protein S deficiencies are associated with low TFPI levels in plasma." Journal of Thrombosis and Haemostasis, 8:294-300.
ClinicalTrials.gov, ID NCT05776069. Study of VGA039 in Healthy Volunteers and Patients With Von Willebrand Disease [online]. Version 1, dated Mar. 8, 2023 [retrieved on Nov. 30, 2023]. Retrieved from the Internet: https://clinicaltrials.gov/study/NCT05776069?term=NCT05776069&rank=1&tab=history&a=1; 7 printed pages.
ClinicalTrials.gov, ID NCT05776069. Study of VGA039 in Healthy Volunteers and Patients With Von Willebrand Disease [online]. Version 3, dated Apr. 4, 2023 [retrieved on Nov. 30, 2023]. Retrieved from the Internet: https://clinicaltrials.gov/study/NCT05776069?term=NCT05776069&rank=1&tab=history&a=3; 7 printed pages.
Colman, P.M. (1994) "Effects of amino acid sequence changes on antibody-antigen interactions" Research in Immunology, 145(1):33-36.
Dahlbäck, B. (2022) "Calcium-dependent monoclonal antibody against Gla-domain of protein S efficiently inhibiting both protein C and TFPI anticoagulant pathways," International Society on Thrombosis and Haemostasis (ISTH) 2022 Congress, July 9-13, London. 2022 Congress Abstracts [online], 2 pages. Retrieved from: https://abstracts.isth.org/abstract/calcium-dependent-monoclonal-antibody-against-gla-domain-of-protein-s-efficiently-inhibiting-both-protein-c-and-tfpi-anticoagulant-pathways/.
Dahlbäck, B. et al. (1990) "Characterization of Functionality Important Domains in Human Vitamin K-dependent Protein S Using Monoclonal Antibodies," J Biol Chem, 265(14):8127-8135.
Hackeng T. M., et al., "Protein S Stimulates Inhibition of the Tissue Factor Pathway by Tissue Factor Pathway Inhibitor," Proceedings of the National Academy of Sciences of the United States of America, Feb. 2006, vol. 103 (9), pp. 3106-3111.
Hackeng, T.M., et al.; "Human protein S inhibits prothrombinase complex activity on endothelial cells and platelets via direct interactions with factors Va and Xa," J Biol Chem., (1994); 269(33):21051-21058.
International Preliminary Report on Patentability for International Application No. PCT/US2021/030900 dated Nov. 17, 2022, 8 pages.
International Preliminary Report on Patentability for International Application No. PCT/US2021/030902 dated Nov. 17, 2022, 8 pages.
International Search Report and Written Opinion for International Application No. PCT/US2021/030900, mailed Sep. 16, 2021, 12 pages.
International Search Report and Written Opinion for International Application No. PCT/US2021/030902, mailed Aug. 20, 2021, 16 pages.
Janeway et al., "The interaction of the antibody molecule with specific antigen," Immunobiology: The Immune System in Health and Disease, 5th Edition, Garland Science, 2001, 5 pages.
Kaufman, R.J., et al.; "Molecular approaches for improved clotting factors for hemophilia," Blood (2013); 122(22):3568-3574.
Kipriyanov, S.M., et al.; "Generation and production of engineered antibodies," Mol Biotechnol.; 6(1):39-60 (2004).
Prince, R., et al.; "Targeting anticoagulant protein S to improve hemostasis in hemophilia," Blood (2018), 131(12):1360-1371.
Sakurai et al. (2018). "A microengineered vascularized bleeding model that integrates the principal components of hemostasis" Nature Communications. 9:509, pp. 1-9.
Saller, F., et al.; "The protein S thrombin-sensitive region modulates phospholipid binding and the gamma-carboxyglutamic acid-rich (Gla) domain conformation in a non-specific manner," J Thromb Haemost (2006); 4(3):704-706.
Santa Cruz Biotechnology: Protein S Antibody (PS7): sc-52720, Product Sheet; [retrieved online May 30, 2024] URL: https://www.scbt.com/p/protein-s-antibody-ps7#citations, 3 pages.
Stryer, L., et al.; "Protein structure and function," Part 1, Chapter 2, Biochemistry (4th ed.) New York: W. H. Freeman and Company (1995), pp. 19-23.
Von Drygalski, A., et al.; "Superior in Vivo Hemostatic Properties of an Engineered Factor Va Variant for Hemophilia Mice," Blood (2012); 120(21):17, 2 pages.
Nath, N., et al.; "Antibody Labeling with Fluorescent Dyes Using Magnetic Protein A and Protein G Beads," J Vis Exp., 115:54545: pp. 1-6 (2016).
Kirchmaier, C.M., et al.; "Diagnosis and Management of Inherited Platelet Disorders," Transfus Med Hemother.; 37(5):237-246 (2010).
Panteli, M., et al.; "Pharmacological adjuncts to stop bleeding: options and effectiveness," Eur J Trauma Emerg Surg.; 42(3):303-310 (2016).
Szanto, T., et al.; "Platelets compensate for poor thrombin generation in type 3 von Willebrand disease," Platelets; 31(1):103-111 (2020).
Hackeng, T.M., et al.; "Protein S binding to human endothelial cells is required for expression of cofactor activity for activated protein C," J Biol Chem.; 268(6):3993-4000 (Feb. 1993).

* cited by examiner

TFPI Cofactor Assay

APC Cofactor Assay

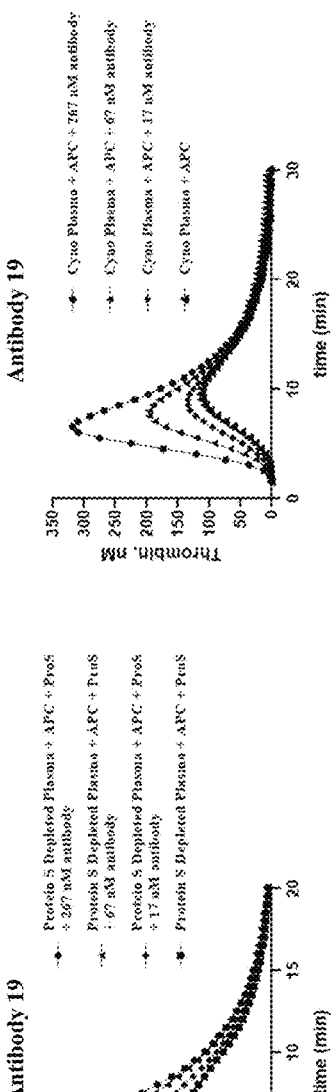
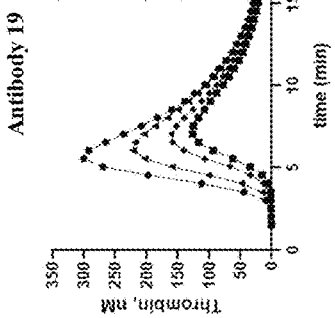
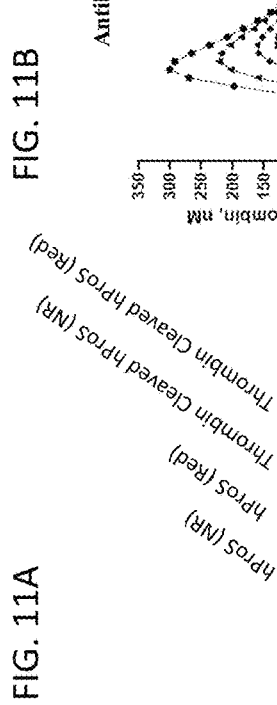
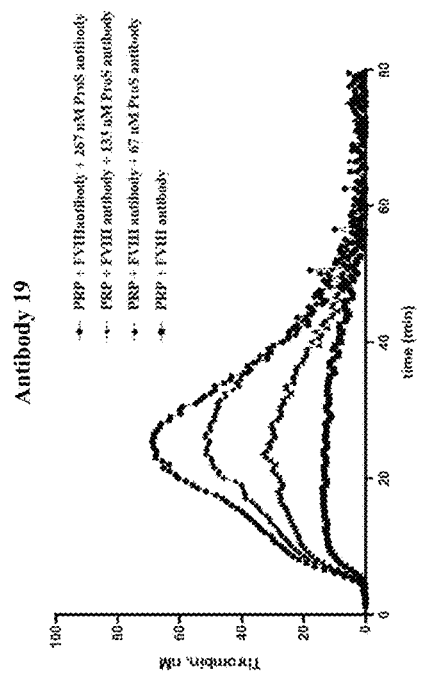
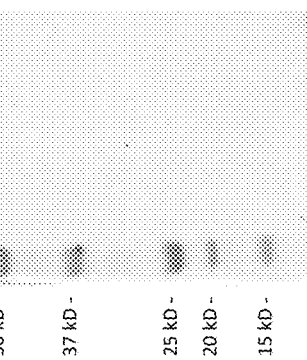
FIG. 11A
FIG. 11B
FIG. 11C
FIG. 11D

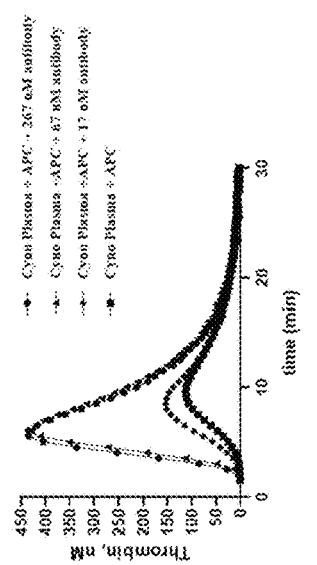
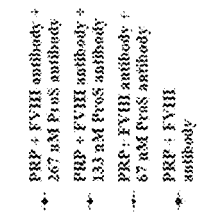
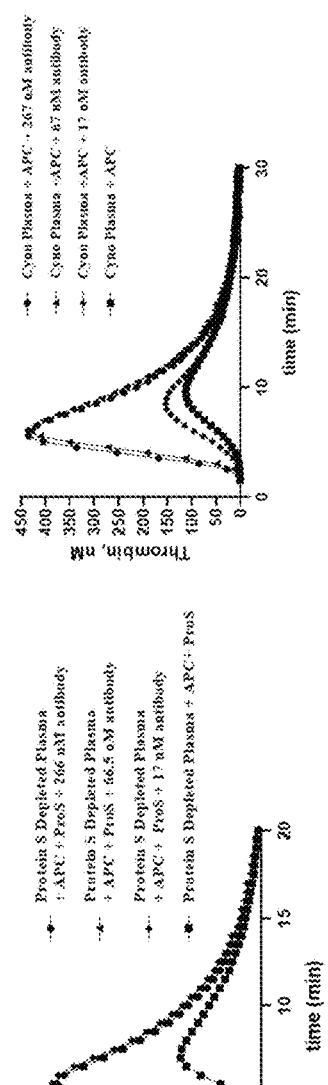
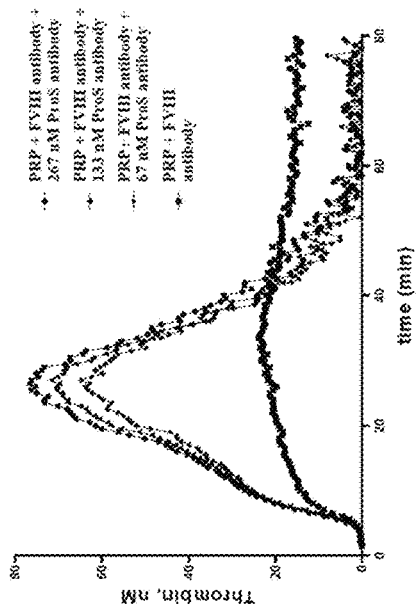
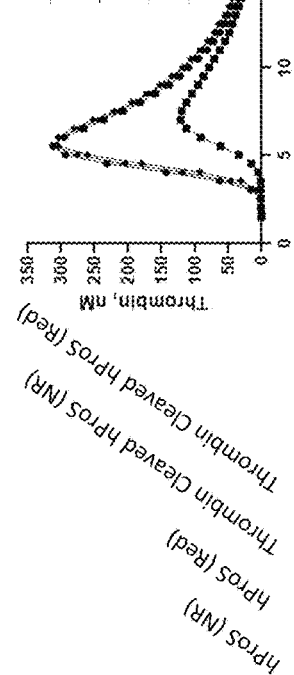
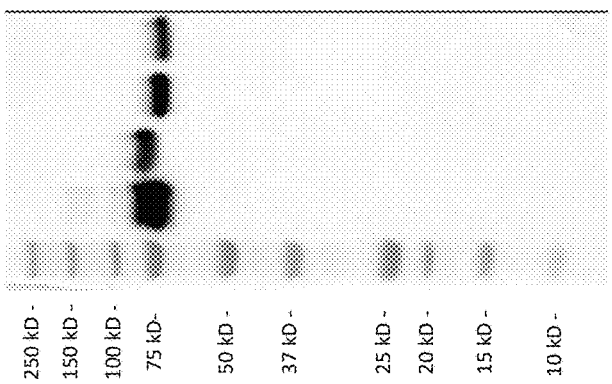
FIG. 12A
FIG. 12B
FIG. 12C
FIG. 12D

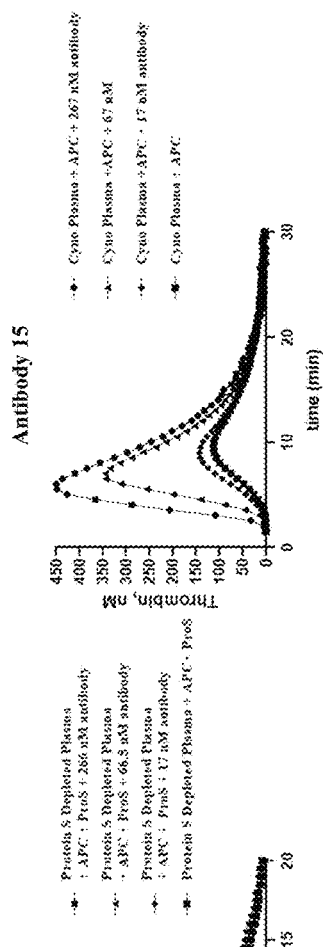
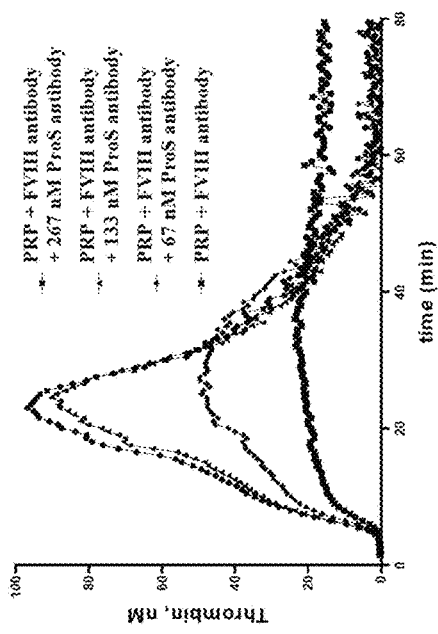
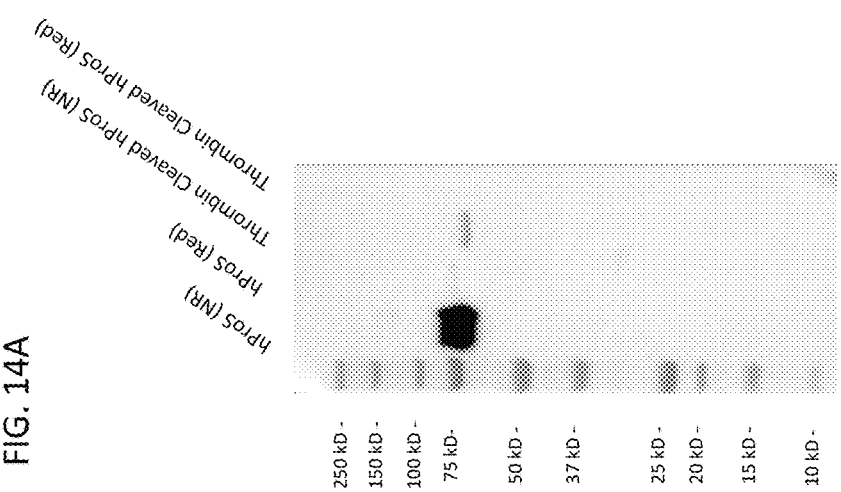
FIG. 14A
FIG. 14B
FIG. 14C
FIG. 14D

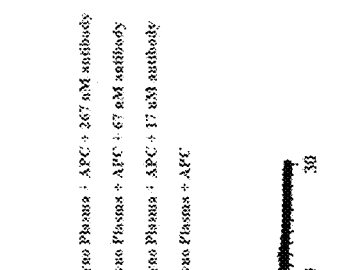
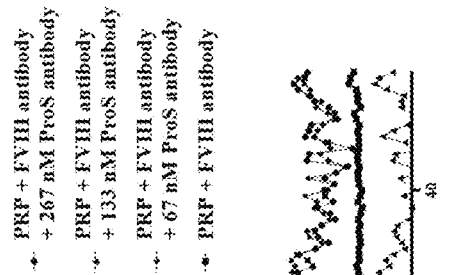
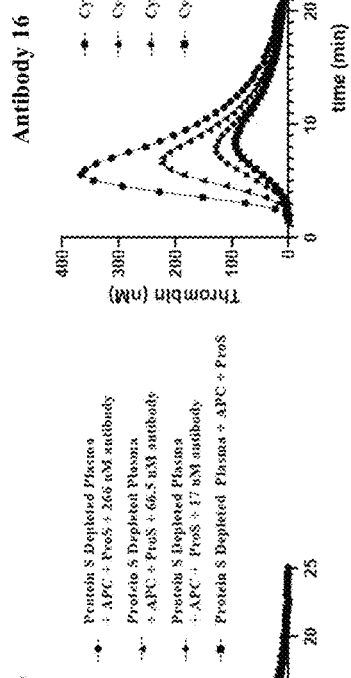
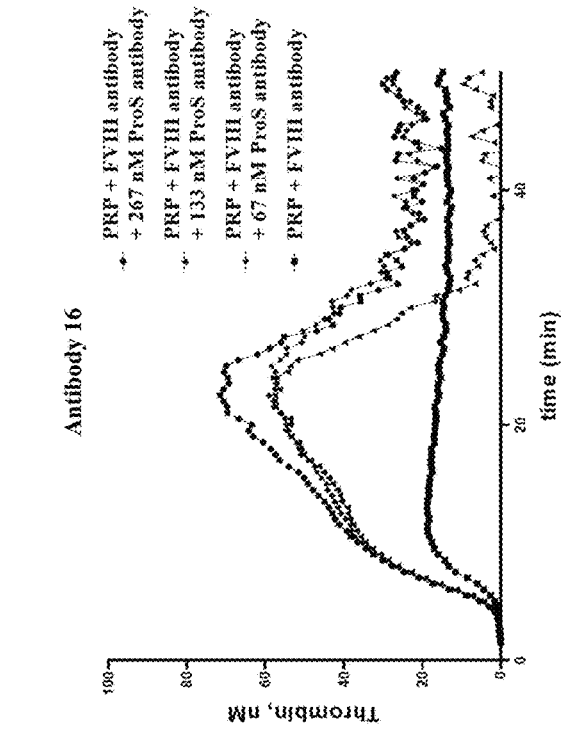
FIG. 15A
FIG. 15B
FIG. 15C
FIG. 15D

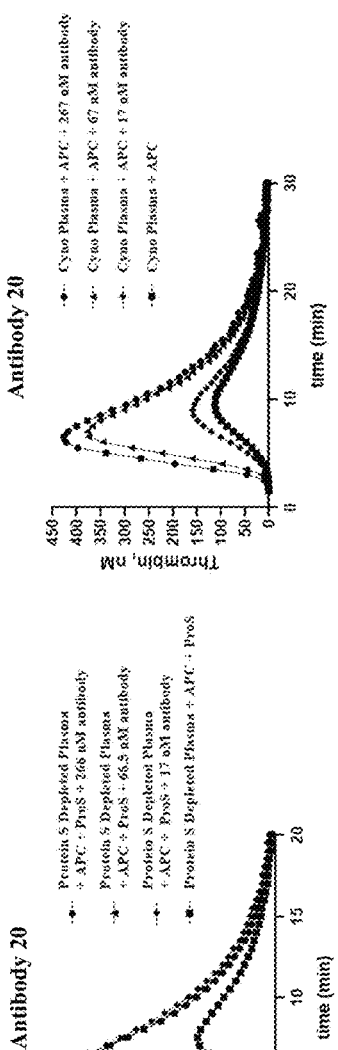
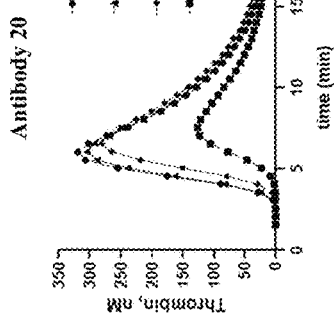
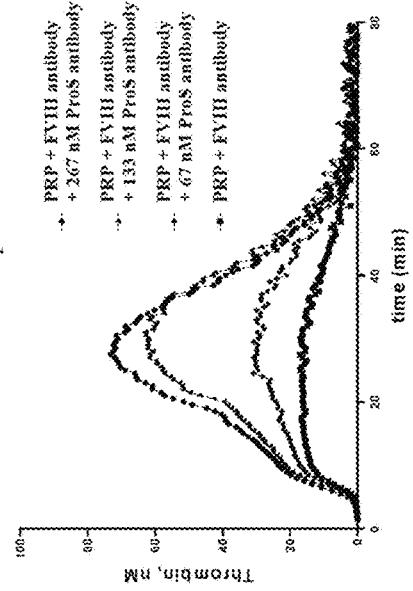
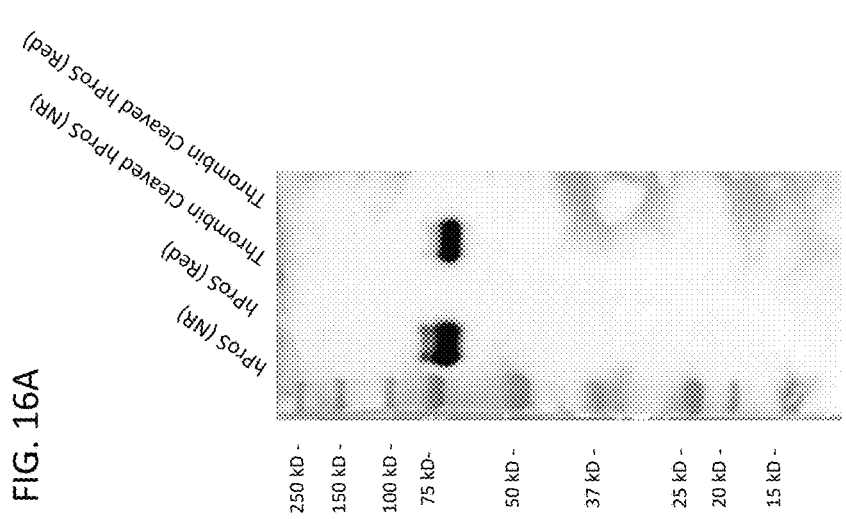
FIG. 16A
FIG. 16B
FIG. 16C
FIG. 16D

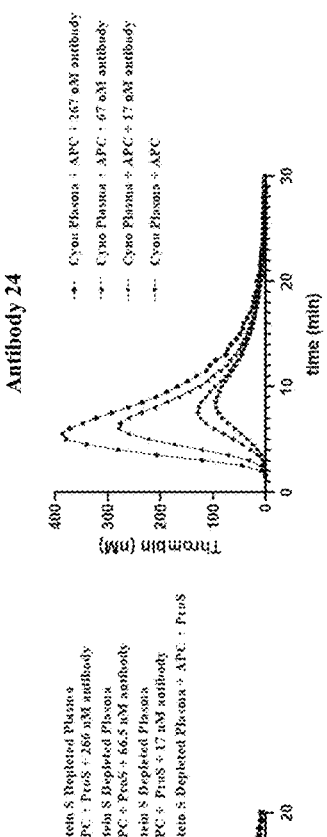
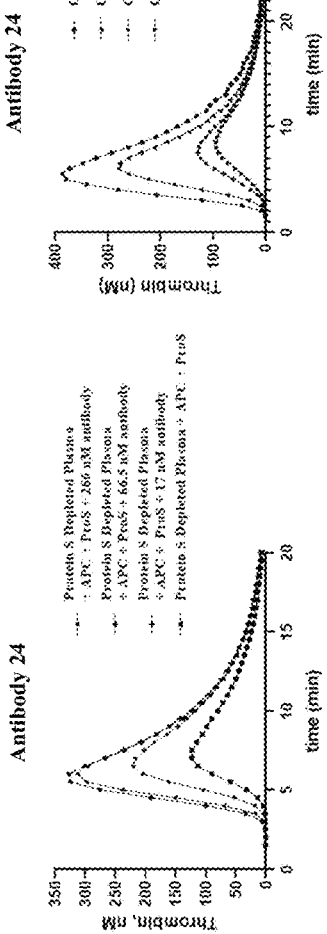
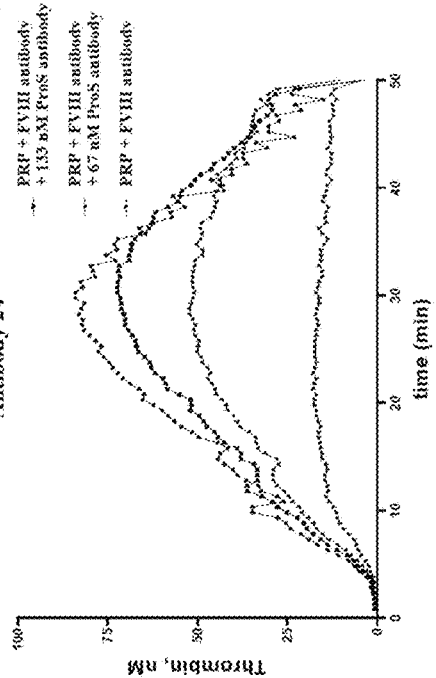
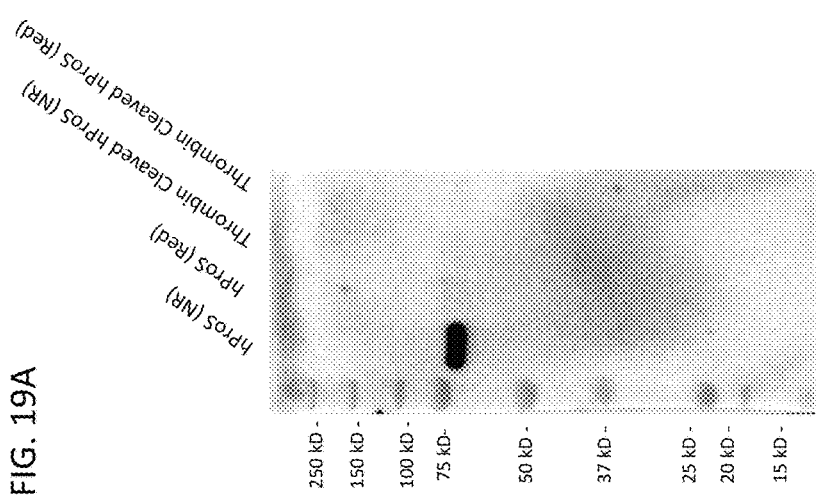
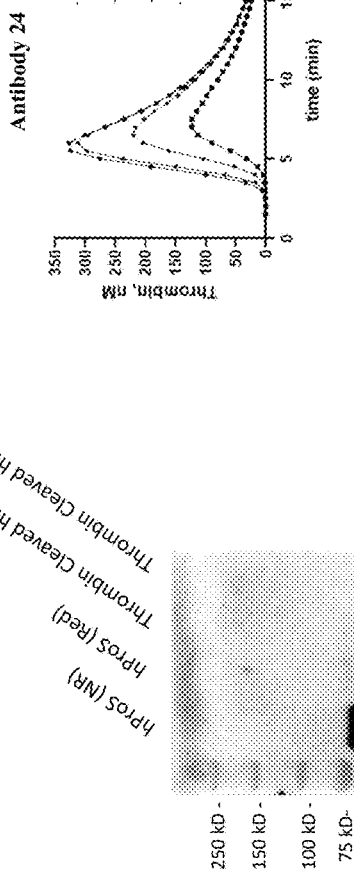
FIG. 19A
FIG. 19B
FIG. 19C
FIG. 19D

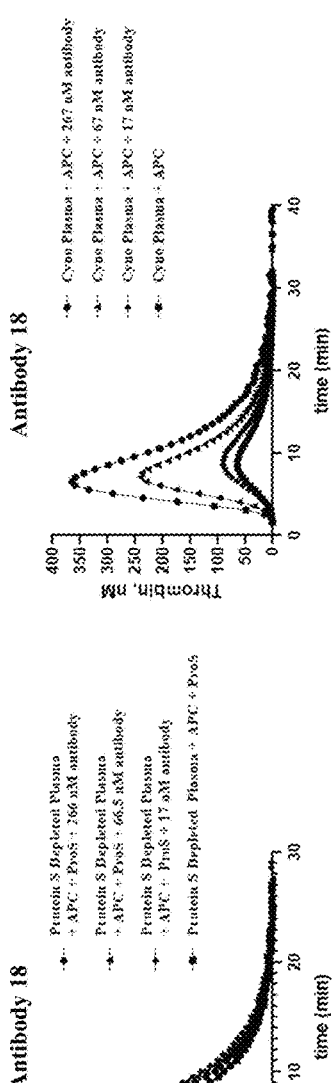
FIG. 20A
FIG. 20B
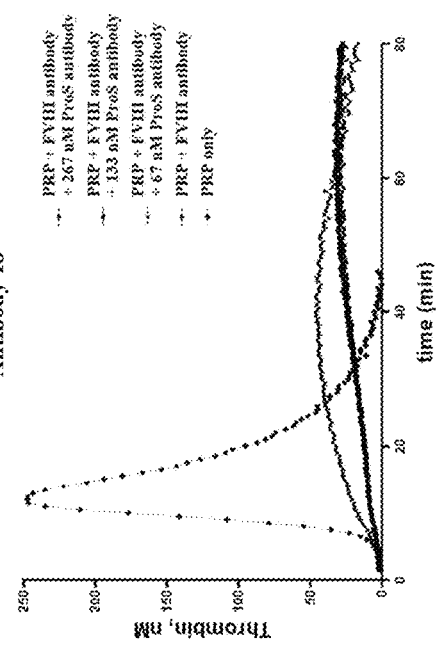
FIG. 20C
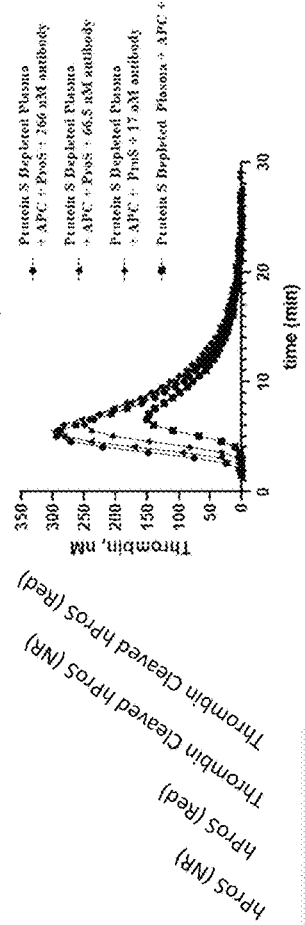
FIG. 20D

PROTEIN S ANTIBODIES, METHODS OF MAKING AND USES THEREOF

CROSS REFERENCE TO RELATED APPLICATIONS

This application is a divisional of U.S. patent application Ser. No. 18/506,872, filed on Nov. 10, 2023, which is continuation of U.S. patent application Ser. No. 17/923,503, filed on Nov. 4, 2022, which is a U.S. National Stage Application under 35 U.S.C. § 371 of International Application No. PCT/US2021/030900, filed on May 5, 2021, which claims priority to U.S. Provisional Patent Application No. 63/020,505, filed on May 5, 2020, and to U.S. Provisional Patent Application No. 63/169,755, filed on Apr. 1, 2021. The contents of each of the preceding applications are incorporated by reference herein in their entirety.

INCORPORATION OF SEQUENCE LISTING

The Sequence Listing associated with this application is provided electronically in XML file format and is hereby incorporated by reference into the specification. The name of the XML file containing the Sequence Listing is VEGA_001_04US_SeqList_ST26.xml. The XML file is 246,134 bytes and was created on Aug. 12, 2024.

BACKGROUND

Protein S (also known as ProS, ProS1) is a vitamin K-dependent plasma protein involved in the anti-coagulation cascade. The protein is multi-modular, comprising a γ-carboxy-glutamic acid domain (Gla domain), an epidermal growth factor-like domain (EGF domain), a thrombin-sensitive region (TSR), and a sex hormone binding globulin-like domain (SHBG-like domain). The protein is found in both a free form and as part of a complex with proteins such C4 binding protein (C4BP) and tissue factor pathway inhibitor (TFPI). Among other functions, in its free form, Protein S is a cofactor in at least two pathways of the anti-coagulation cascade: (1) Protein S is a cofactor for plasma activated Protein C (APC), involved in the inactivation and degradation of coagulation factors Factor Va and Factor VIIIa; and (2) Protein S is also a cofactor for TFPI, also present in plasma, involved in the inactivation of coagulation factors Factor Xa and Factor VIIa.

Protein S is a potential therapeutic target for bleeding disorders, thus there is a need for agents that bind and modulate its activities within the coagulation pathway.

SUMMARY

Provided here are antibodies that bind Protein S, and methods of making and using such antibodies. In some embodiments, the Protein S antibodies provided herein are useful for treating a bleeding disorder, or a condition characterized by reduced or impaired blood coagulation and/or clotting.

Accordingly, in one aspect, provided herein are antibodies that bind Protein S, wherein the antibodies are inhibitors of the cofactor activity of Protein S for activated Protein C (APC), inhibitors of the cofactor activity of Protein S for tissue factor pathway inhibitor (TFPI), or inhibitors of the cofactor activity of Protein S for both APC and TFPI (dual inhibitor of cofactor activity), and wherein the antibody is human, humanized, or chimeric. In some preferred embodiments, the antibodies provided herein specifically bind Protein S.

In another aspect, provided herein are antibodies that bind Protein S, wherein the antibodies are capable of promoting coagulation and/or modulating a component in the coagulation cascade.

In another aspect, provided herein are exemplary Protein S antibodies comprising any one or more of the amino acid sequences of the complementarity determining region (CDR) sequences provided in Tables 1A, 1B, 1C, 2A, 2B, and 2C. In another aspect, the exemplary Protein S antibodies comprise any one of the CDR-L1 amino acid sequences of Table 1A; any one of the CDR-L2 amino acid sequences of Table 1B; any one of the CDR-L3 amino acid sequences of Table 1C; any one of the CDR-H1 amino acid sequences of Table 2A; any one of the CDR-H2 amino acid sequences of Table 2B; any one of the CDR-H3 amino acid sequences of Table 2B. In another aspect, provided herein are exemplary Protein S antibodies comprising the combinations of variable light chains and variable heavy chains presented in Table 4C. In another aspect, provided herein are the sequences of different antibodies as presented in Table 6. In another aspect, provided herein are nucleic acids encoding for any of the Protein S antibodies provided herein.

In another aspect, provided herein are pharmaceutical compositions comprising any one of the Protein S antibodies provided herein, and optionally a pharmaceutically acceptable excipient.

Provided herein are methods of using the exemplary Protein S antibodies described herein. Accordingly, in one aspect, provided herein is an in vitro method of promoting the coagulation of blood, comprising contacting any one of the Protein S antibodies provided herein with a blood sample.

In another aspect, provided herein is a method of promoting the coagulation of blood in a subject in need thereof, comprising administering to the subject any of the exemplary Protein S antibodies provided herein, or pharmaceutical compositions provided herein. In exemplary embodiments, the route of administration is subcutaneous.

In another aspect, provided herein is a method of promoting the generation of thrombin in a subject in need thereof, comprising administering to the subject any of the Protein S antibodies provided herein, or pharmaceutical compositions provided herein.

In another aspect, provided herein is a method of treating a condition in a subject in need thereof, comprising administering to the subject any of the Protein S antibodies provided herein, or pharmaceutical compositions provided herein, wherein the condition is selected from the group consisting of: bleeding disorders, platelet disorders, trauma, bleeding resulting from a surgery or a medical procedure, and combinations thereof.

In another aspect, provided herein is the use of any one of the Protein S antibodies or pharmaceutical compositions provided herein, for the treatment of a condition in a subject in need thereof. The condition may be selected from the group consisting of: bleeding disorders, platelet disorders, trauma, bleeding resulting from a surgery or a medical procedure, and combinations thereof.

In another aspect, any one of the Protein S antibodies or pharmaceutical compositions provided herein, may be used for the manufacture of a medicament for the treatment of a condition in a subject in need thereof. The condition may be selected from the group consisting of bleeding disorders, platelet disorders, trauma, bleeding resulting from a surgery or a medical procedure, and combinations thereof.

BRIEF DESCRIPTION OF THE DRAWINGS

FIGS. 5, 6), an APC cofactor inhibitor (Antibody 21; FIGS. 7, 8), and a TFPI cofactor inhibitor (Antibody 23; FIGS. 9, 10) when using a TFPI cofactor assay and an APC cofactor assay.

FIGS. 11A-11H depict the characterization of Antibody 19 and Antibody 7, antibodies sharing the same human variable region, and are characterized as dual inhibitors.

FIGS. 12A-12H depict the characterization of Antibody 13 and Antibody 1, antibodies sharing the same human variable region, and are characterized as dual inhibitors.

FIGS. 14A-14H depict the characterization of Antibody 15 and Antibody 3, antibodies sharing the same human variable region, and are characterized as dual inhibitors.

FIGS. 15A-15H depict the characterization of Antibody 16 and Antibody 4, antibodies sharing the same human variable region, and are characterized as dual inhibitors.

FIGS. 16A-16H depict the characterization of Antibody 20 and Antibody 8, antibodies sharing the same human variable region, and are characterized as dual inhibitors.

FIGS. 19A-19H depict the characterization of Antibody 24 and Antibody 12, antibodies sharing the same human variable region, and are characterized as dual inhibitors.

FIGS. 20A-20H depict the characterization of Antibody 18 and Antibody 6, antibodies sharing the same human variable region, and are characterized as APC cofactor inhibitors.

DETAILED DESCRIPTION

Figure 1:
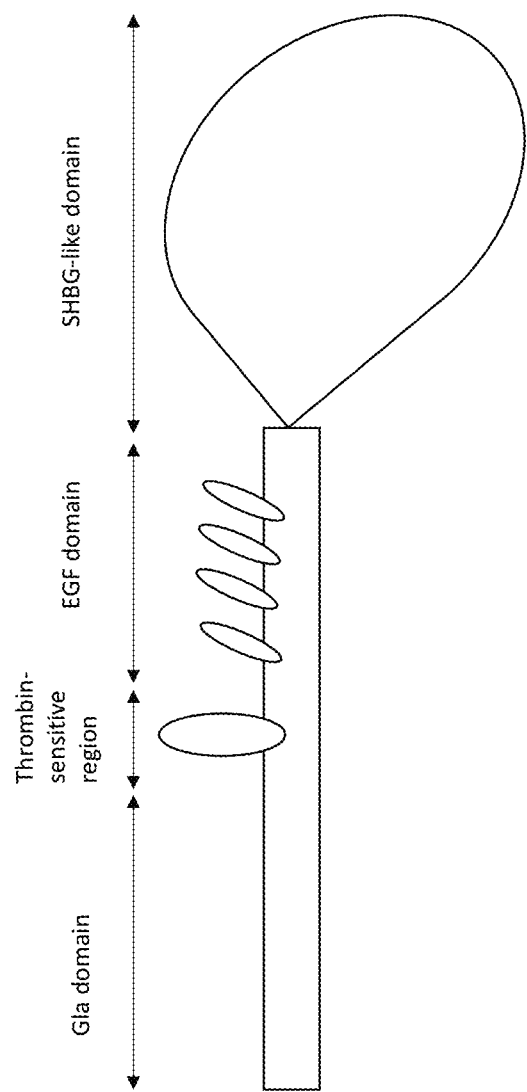
FIG. 1 depicts a schematic diagram of Protein S showing the modular domains of Protein S.

Provided herein are antibodies that bind Protein S, and methods of making and using such antibodies. In some embodiments, the Protein S antibodies provided herein specifically bind Protein S. For example, antibodies that bind to Protein S and inhibit its cofactor activity for TFPI and/or APC, may be useful in the treatment of bleeding disorders and other related diseases by promoting clot formation Where elements are presented in a list format (e.g., in a Markush group), it should be understood that each possible subgroup of the elements is also disclosed, and that any one or more elements can be removed from the list or group.

It should be understood that, unless clearly indicated, in any method described or disclosed herein that includes more than one act, the order of the acts is not necessarily limited to the order in which the acts of the method are recited, but the disclosure encompasses exemplary embodiments in which the order of the acts is so limited.

The terms used throughout the specification are defined as follows unless otherwise limited in specific instances. As used in the specification and the claims, the singular forms "a," "an," and "the" include plural referents unless the context clearly dictates otherwise. All technical and scientific terms, acronyms, and abbreviates used in the specification and claims have the same meaning as commonly understood by one of ordinary skill in the art to which the disclosure pertains, unless defined or stated otherwise. All numerical ranges are inclusive of the values defining the range as well as all integer values in between, unless indicated or defined otherwise.

The term "antibody" as used herein throughout is used in the broadest sense and may include a monoclonal antibody, polyclonal antibody, human antibody, humanized antibody, non-human antibody, chimeric antibody, a monovalent antibody, an antigen-binding fragment (e.g., a Fab fragment, a Fab'2 fragment, an scFv), and other antibody fragments that retain specificity for and binding of Protein S. In some embodiments, the antibodies are monoclonal antibodies. In some embodiments, the antibodies are monoclonal antibodies. In some embodiments, the antibodies are monoclonal human antibodies. In some embodiments, the antibodies are monoclonal humanized antibodies. In some embodiments, the antibodies are monoclonal chimeric antibodies.

Also provided herein are antibody-drug conjugates, bispecific antibodies, and multispecific antibodies that exhibit specificity for and binding of Protein S.

The terms "polynucleotide" and "nucleic acid" are used interchangeably herein, and refer to a polymeric form of nucleotides of any length, which may be ribonucleotides or deoxyribonucleotides. The terms include, but are not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. The terms encompass nucleic acids containing known analogues of natural nucleotides and having similar binding properties, and are metabolized in a manner similar to naturally-occurring nucleotides, unless specifically limited or stated otherwise.

When a nucleic acid or amino acid sequence is said to have a certain percent "sequence identity" or "identity" or is a certain percent "identical" to another nucleic acid or amino acid sequence, that percentage of bases or amino acids are the same, and in the same relative position, when the sequences are aligned, when comparing the two sequences.

The term "subject," as used herein refers to any subject for whom treatment or therapy is provided. The subject may be a mammalian subject. Mammalian subjects include, e. g., humans, non-human primates (e.g., cynomolgus monkey), rodents, (e.g., rats, mice), lagomorphs (e.g., rabbits), ungulates (e.g., cows, sheep, pigs, horses, goats, and the like), etc. In some embodiments, the subject is a human. In some embodiments, the subject is a non-human primate, e.g. a cynomolgus monkey. In some embodiments, the subject is a companion animal (e.g. cats, dogs).

All publications, patents, and patent applications mentioned in this specification are herein incorporated by reference to the same extent as if each individual publication, patent, or patent application was specifically and individually indicated to be incorporated by reference.

I. Antibodies that Bind and Modulate Protein S Activity

A. Protein S Antibodies

Provided here are antibodies that bind to Protein S, and in some embodiments are specific for Protein S. The Protein S can be of any species, e.g. any mammalian species. In some embodiments, the Protein S antibody binds to human Protein S. In some embodiments, the Protein S antibody binds to the Protein S of non-human primates. In some embodiments, the non-human primate is cynomolgus monkey.

The amino acid sequence of human Protein S, targeted by antibodies of the disclosure, is shown below as SEQ ID. NO: 216.

```
                              (SEQ ID. NO: 216)
         10         20         30         40
  MRVLGGRCGA LLACLLLVLP VSEANFLSKQ QASQVLVRKR 50         60         70         80
  RANSLLEETK QGNLERECIE ELCNKEEARE VFENDPETDY
```

-continued
```
         90        100        110        120
  FYPKYLVCLR SFQTGLFTAA RQSTNAYPDL RSCVNAIPDQ 130        140        150        160
  CSPLPCNEDG YMSCKDGKAS FTCTCKPGWQ GEKCEFDINE 170        180        190        200
  CKDPSNINGG CSQICDNTPG SYHCSCKNGF VMLSNKKDCK 210        220        230        240
  DVDECSLKPS ICGTAVCKNI PGDFECECPE GYRYNLKSKS 250        260        270        280
  CEDIDECSEN MCAQLCVNYP GGYTCYCDGK KGFKLAQDQK 290        300        310        320
  SCEVVSVCLP LNLDTKYELL YLAEQFAGVV LYLKFRLPEI 330        340        350        360
  SRFSAEFDFR TYDSEGVILY AESIDHSAWL LIALRGGKIE 370        380        390        400
  VQLKNEHTSK ITTGGDVINN GLWNMVSVEE LEHSISIKIA 410        420        430        440
  KEAVMDINKP GPLFKPENGL LETKVYFAGF PRKVESELIK 450        460        470        480
  PINPRLDGCI RSWNLMKQGA SGIKEIIQEK QNKHCLVTVE 490        500        510        520
  KGSYYPGSGI AQFHIDYNNV SSAEGWHVNV TLNIRPSTGT 530        540        550        560
  GVMLALVSGN NTVPFAVSLV DSTSEKSQDI LLSVENTVIY 570        580        590        600
  RIQALSLCSD QQSHLEFRVN RNNLELSTPL KIETISHEDL 610        620        630        640
  QRQLAVLDKA MKAKVATYLG GLPDVPFSAT PVNAFYNGCM 650        660        670
  EVNINGVQLD LDEAISKHND IRAHSCPSVW KKTKNS
```

In some embodiments, provided herein are Protein S antibodies comprising a binding affinity (KD) to Protein S of about 0.0005 nM or lower, 0.001 nM or lower, 0.005 nM or lower, 0.01 nM or lower, 0.05 nM or lower, about 0.1 nM or lower, about 0.5 nM or lower, about 1 nM or lower, about 5 nM or lower, about 10 nM or lower, about 50 nM or lower, about 100 nM or lower, about 500 nM or lower, or about 1 µM or lower.

The Protein S antibodies provided herein are capable of modulating one or more activities of Protein S, including, for example, modulating Protein S cofactor activity, as well as promoting coagulation and altering levels of markers associated with coagulation, and modulating a component in the coagulation cascade.

In some embodiments, the Protein S antibodies provided herein are capable of modulating the Protein S ability to act as a cofactor within pathways of the coagulation cascade.

Accordingly, in some embodiments, the Protein S antibodies provided herein are useful for reducing or inhibiting the cofactor activity of Protein S for activated Protein C ("APC").

In some embodiments, the Protein S antibodies provided herein are useful for reducing or inhibiting the cofactor activity of Protein S for tissue factor pathway inhibitor ("TFPI"). TFPI is an inhibitor of procoagulant activity and is produced as at least two alternatively spliced isoforms in humans, TFPIα, and TFPIβ, which differ in domain structure and mechanism for cell surface association. TFPIα, but not TFPIβ contains Kunitz domain 3, the domain which is believed to be involved in binding to Protein S. Without being held to any theory or mechanism, it is believed that the Protein S antibodies of the disclosure inhibit the cofactor activity of Protein S for at least TFPIα, as it contains Kunitz domain 3.

In some embodiments, the Protein S antibodies provided herein are useful for reducing or inhibiting the cofactor activity of Protein S for APC, but show negligible or no effect on cofactor activity of Protein S for TFPI (such antibodies are referred to interchangeably herein as "APC cofactor inhibitors", "APC cofactor specific inhibitors", or "APC pathway inhibitors").

In some embodiments, the Protein S antibodies provided herein are useful for reducing or inhibiting the cofactor activity of Protein S for TFPI, but show negligible or no effect on cofactor activity of Protein S for APC (such antibodies are referred to interchangeably herein as "TFPI cofactor inhibitors", "TFPI cofactor specific inhibitors", or "TFPI pathway inhibitors").

In some embodiments, the Protein S antibodies provided herein are useful for reducing or inhibiting the cofactor activity of Protein S for both APC and TFPI (such antibodies are referred to herein as "dual inhibitors"). The dual inhibitors of the disclosure may reduce the activities of APC and TFPI to different degrees.

In some embodiments, the Protein S antibodies provided herein are capable of causing a reduction in the activity of APC. For example, APC activity may be reduced by about 10%, about 20%, about 30%, about 40%, about 50%, about 60%, about 70%, about 80%, about 90%, or about 100% as compared to in the absence of the Protein S antibodies.

In some embodiments, the Protein S antibodies provided herein are capable of causing a reduction in the activity of TFPI. For example, TFPI activity may be reduced by about 10%, about 20%, about 30%, about 40%, about 50%, about 60%, about 70%, about 80%, about 90%, or about 100% as compared to in the absence of the Protein S antibodies.

In some embodiments, the Protein S antibodies provided herein are capable of causing a reduction in the activity of both APC and TFPI. For example, APC activity may be reduced by about 10%, about 20%, about 30%, about 40%, about 50%, about 60%, about 70%, about 80%, about 90%, or about 100%, and TFPI activity may also be reduced by about 10%, about 20%, about 30%, about 40%, about 50%, about 60%, about 70%, about 80%, about 90%, or about 100% as compared to in the absence of the Protein S antibodies. The reduction in APC activity and TFPI activity may be affected to different degrees by the same Protein S antibody.

In some embodiments, the Protein S antibodies provided herein are APC cofactor inhibitors, and the capability of the antibody for affecting the cofactor activity of Protein S for TFPI is negligible. In other embodiments, the Protein S antibodies provided herein are TFPI cofactor inhibitors, and the capability of the antibody for affecting the cofactor activity of Protein S for APC is negligible.

In some embodiments, the Protein S antibodies provided herein are capable of promoting coagulation and/or modulating a component in the coagulation cascade, e.g., in a subject in need thereof, or in a sample. In some embodiments, the Protein S antibodies provided herein are capable of promoting the clotting of blood. In some embodiments, the antibodies are capable of promoting clotting of blood by reducing the ability of Protein S to act as a cofactor for APC. For example, clotting of blood may be promoted by reducing APC activity by about 10%, about 20%, about 30%, about 40%, about 50%, about 60%, about 70%, about 80%, about 90%, or about 100%, as compared to in the absence of the Protein S antibodies.

In some embodiments, the antibodies are capable of promoting clotting of blood by reducing an ability of Protein S to act as a cofactor for TFPI. For example, clotting of blood may be promoted by reducing TFPI activity by about 10%, about 20%, about 30%, about 40%, about 50%, about 60%, about 70%, about 80%, about 90%, or about 100%, as compared to in the absence of the Protein S antibodies.

In some embodiments, the antibodies are capable of promoting clotting of blood by reducing an ability of Protein S to act as a cofactor for both APC and TFPI. For example, clotting of blood may be promoted by reducing both APC activity and TFPI activity by about 10%, about 20%, about 30%, about 40%, about 50%, about 60%, about 70%, about 80%, about 90%, or about 100%, as compared to in the absence of the Protein S antibodies.

In some embodiments, the Protein S antibodies provided herein are capable of promoting the generation of a marker associated with coagulation activity, and this can be exhibited in vitro (e.g. in a sample) and/or in vivo (e.g. upon administration to a subject). Such markers include, but are not limited to, thrombin, fibrin, D-dimer, clot formation, thrombin-antithrombin complex, fibrin degradation products, and prothrombin fragment F1.2.

In some embodiments, the Protein S antibodies provided herein are capable of promoting thrombin generation (e.g. includes restoring thrombin generation or restoring the levels of thrombin, e.g., in a subject in need thereof, or in a sample). In some embodiments, the antibodies are capable of promoting generation of thrombin in a subject in need thereof. In some embodiments, the generation of thrombin does not exceed a predetermined threshold level. In some embodiments, the generation of thrombin is partially restored. In some embodiments, the generation of thrombin does not exceed a predetermined percentage of a maximum thrombin generation. In some embodiments, the generation of thrombin does not exceed a predetermined percentage of an area under the curve of the maximum thrombin generation. In some embodiments, thrombin generation may be increased by about 5-fold to 50-fold, e.g. by about 5-fold, by about 10-fold, by about 15-fold, by about 20-fold, by about 25-fold, by about 30-fold, by about 35-fold, by about 40-fold, by about 45-fold, or even by about 50-fold, as compared to in the absence of the Protein S antibodies. Exemplary antibodies that promote thrombin generation are described in greater detail below, and include, but are not limited to antibodies that (a) comprise the light chain variable domain comprising the amino acid sequence of SEQ ID NO: 71 and the heavy chain variable domain comprising the amino acid sequence of SEQ ID NO: 72, (b) comprise the light and heavy CDR amino acid sequences of SEQ ID NO: 2, SEQ ID NO: 13, SEQ ID NO: 22, SEQ ID NO: 34, SEQ ID NO: 46, and SEQ ID NO: 58, (c) comprise the amino acid sequence of SEQ ID NO: 75 and the heavy chain variable domain comprising the amino acid sequence of SEQ ID NO: 76, (d) comprise the light and heavy CDR amino acid sequences of SEQ ID NO: 1, SEQ ID NO: 15, SEQ ID NO: 24, SEQ ID NO: 36, SEQ ID NO: 48, and SEQ ID NO: 60, (e) comprise the amino acid sequence of SEQ ID NO: 69 and the heavy chain variable domain comprising the amino acid sequence of SEQ ID NO: 70, (f) comprise the light and heavy CDR amino acid sequences of SEQ ID NO: 1, SEQ ID NO: 12, SEQ ID NO: 21, SEQ ID NO: 33, SEQ ID NO: 45, and SEQ ID NO: 57, (g) comprise the amino acid sequence of SEQ ID NO: 89 and the heavy chain variable domain comprising the amino acid sequence of SEQ ID NO: 90, and (h) comprise the light and heavy CDR amino acid sequences of SEQ ID NO: 10, SEQ ID NO: 16, SEQ ID NO: 31, SEQ ID NO: 43, SEQ ID NO: 55, and SEQ ID NO: 67.

In some embodiments, the Protein S antibodies provided herein can restore or promote thrombin generation in a subject who is deficient in coagulation factors. In some exemplary embodiments, the coagulation factor deficiency is congenital. In some exemplary embodiments, the coagulation factor deficiency is acquired. In some embodiments, the Protein S antibodies provided herein can promote thrombin generation in a subject who is deficient in Factor VII, Factor VIII, Factor IX, Factor XI. For example, thrombin generation can be increased by about 5-fold to 50-fold, e.g. by about 5-fold, by about 10-fold, by about 15-fold, by about 20-fold, by about 25-fold, by about 30-fold, by about 35-fold, by about 40-fold, by about 45-fold, or even by about 50-fold, as compared to in the absence of the Protein S antibodies, when used to promote thrombin generation in a sample from a subject with a factor deficiency.

In some embodiments, the Protein S antibodies provided herein can promote thrombin generation in a subject who suffers from von Willebrand Disease (vWD) disease. In some embodiments, the vWD is a subtype selected from: vWD Type 1, vWD Type 2A, vWD Type 2B, vWD Type 2N, vWD Type 2M, vWD Type 3, and acquired vWD. In some exemplary embodiments, the vWD is a subtype selected from Type 1, Type 2, or Type 3. For example, thrombin generation can be increased by about 5-fold to 50-fold, e.g. by about 5-fold, by about 10-fold, by about 15-fold, by about 20-fold, by about 25-fold, by about 30-fold, by about 35-fold, by about 40-fold, by about 45-fold, or even by about 50-fold, as compared to in the absence of the Protein S antibodies, when used to promote thrombin generation in a sample from a subject with vWD disease.

Exemplary antibodies that may promote thrombin generation in a subject who is deficient in a coagulation factor (such as Factor VII, Factor VIII, Factor IX, Factor XI) or who has von Willebrand disease (such as Type 1, Type 2A, Type 2B, Type 2M, Type 2N or Type 3) include, but are not limited to antibodies that (a) comprise the light chain variable domain comprising the amino acid sequence of SEQ ID NO: 71 and the heavy chain variable domain comprising the amino acid sequence of SEQ ID NO: 72, (b) comprise the light and heavy CDR amino acid sequences of SEQ ID NO: 2, SEQ ID NO: 13, SEQ ID NO: 22, SEQ ID NO: 34, SEQ ID NO: 46, and SEQ ID NO: 58, (c) comprise the amino acid sequence of SEQ ID NO: 75 and the heavy chain variable domain comprising the amino acid sequence of SEQ ID NO: 76, (d) comprise the light and heavy CDR amino acid sequences of SEQ ID NO: 1, SEQ ID NO: 15, SEQ ID NO: 24, SEQ ID NO: 36, SEQ ID NO: 48, and SEQ ID NO: 60, (e) comprise the amino acid sequence of SEQ ID NO: 69 and the heavy chain variable domain comprising the amino acid sequence of SEQ ID NO: 70, (f) comprise the light and heavy CDR amino acid sequences of SEQ ID NO: 1, SEQ ID NO: 12, SEQ ID NO: 21, SEQ ID NO: 33, SEQ ID NO: 45, and SEQ ID NO: 57, (g) comprise the amino acid sequence of SEQ ID NO: 89 and the heavy chain variable domain comprising the amino acid sequence of SEQ ID NO: 90, and (h) comprise the light and heavy CDR amino acid sequences of SEQ ID NO: 10, SEQ ID NO: 16, SEQ ID NO: 31, SEQ ID NO: 43, SEQ ID NO: 55, and SEQ ID NO: 67.

In some embodiments, the Protein S antibodies provided herein are capable of promoting fibrin generation, e.g., in a subject in need thereof, or in a sample. In some embodiments, the Protein S antibodies provided herein are capable of promoting fibrin deposition e.g., in a sample. In some embodiments, the Protein S antibodies provided herein are capable of promoting coagulation activity, wherein the coagulation activity is marked by a promotion of fibrin generation. For example, fibrin generation may be increased by about 5-fold to 50-fold, e.g. by about 5-fold, by about 10-fold, by about 15-fold, by about 20-fold, by about 25-fold, by about 30-fold, by about 35-fold, by about 40-fold, by about 45-fold, or even by about 50-fold, as compared to in the absence of the Protein S antibodies. as compared to in the absence of the Protein S antibodies. Exemplary antibodies that may promote fibrin generation include, but are not limited to antibodies that (a) comprise the light chain variable domain comprising the amino acid sequence of SEQ ID NO: 71 and the heavy chain variable domain comprising the amino acid sequence of SEQ ID NO: 72, (b) comprise the light and heavy CDR amino acid sequences of SEQ ID NO: 2, SEQ ID NO: 13, SEQ ID NO: 22, SEQ ID NO: 34, SEQ ID NO: 46, and SEQ ID NO: 58, (c) comprise the amino acid sequence of SEQ ID NO: 75 and the heavy chain variable domain comprising the amino acid sequence of SEQ ID NO: 76, (d) comprise the light and heavy CDR amino acid sequences of SEQ ID NO: 1, SEQ ID NO: 15, SEQ ID NO: 24, SEQ ID NO: 36, SEQ ID NO: 48, and SEQ ID NO: 60, (e) comprise the amino acid sequence of SEQ ID NO: 69 and the heavy chain variable domain comprising the amino acid sequence of SEQ ID NO: 70, (f) comprise the light and heavy CDR amino acid sequences of SEQ ID NO: 1, SEQ ID NO: 12, SEQ ID NO: 21, SEQ ID NO: 33, SEQ ID NO: 45, and SEQ ID NO: 57, (g) comprise the amino acid sequence of SEQ ID NO: 89 and the heavy chain variable domain comprising the amino acid sequence of SEQ ID NO: 90, and (h) comprise the light and heavy CDR amino acid sequences of SEQ ID NO: 10, SEQ ID NO: 16, SEQ ID NO: 31, SEQ ID NO: 43, SEQ ID NO: 55, and SEQ ID NO: 67.

In some embodiments, the Protein S antibodies provided herein are capable of promoting increasing D-dimer levels, e.g., in a subject in need thereof, or in a sample. In some embodiments, the Protein S antibodies provided herein are capable of promoting coagulation activity, wherein the coagulation activity is marked by an increase in D-dimer levels. For example, D-dimer levels may be increased by about two-fold to about 10,000-fold. Exemplary antibodies that may promote an increase in D-dimer levels include, but are not limited to antibodies that (a) comprise the light chain variable domain comprising the amino acid sequence of SEQ ID NO: 71 and the heavy chain variable domain comprising the amino acid sequence of SEQ ID NO: 72, (b) comprise the light and heavy CDR amino acid sequences of SEQ ID NO: 2, SEQ ID NO: 13, SEQ ID NO: 22, SEQ ID NO: 34, SEQ ID NO: 46, and SEQ ID NO: 58, (c) comprise the amino acid sequence of SEQ ID NO: 75 and the heavy chain variable domain comprising the amino acid sequence of SEQ ID NO: 76, (d) comprise the light and heavy CDR amino acid sequences of SEQ ID NO: 1, SEQ ID NO: 15, SEQ ID NO: 24, SEQ ID NO: 36, SEQ ID NO: 48, and SEQ ID NO: 60, (e) comprise the amino acid sequence of SEQ ID NO: 69 and the heavy chain variable domain comprising the amino acid sequence of SEQ ID NO: 70, (f) comprise the light and heavy CDR amino acid sequences of SEQ ID NO: 1, SEQ ID NO: 12, SEQ ID NO: 21, SEQ ID NO: 33, SEQ ID NO: 45, and SEQ ID NO: 57, (g) comprise the amino acid sequence of SEQ ID NO: 89 and the heavy chain variable domain comprising the amino acid sequence of SEQ ID NO: 90, and (h) comprise the light and heavy CDR amino acid sequences of SEQ ID NO: 10, SEQ ID NO: 16, SEQ ID NO: 31, SEQ ID NO: 43, SEQ ID NO: 55, and SEQ ID NO: 67.

In some embodiments, the Protein S antibodies provided herein are capable of promoting coagulation in a sample or in a subject. In some embodiments, the Protein S antibodies provided herein alter the levels of markers associated with coagulation activity in a sample or in a subject. For example, in some embodiments, the antibodies are capable of restoring or promoting thrombin generation in a sample, or in a subject. In some embodiments, the antibodies are capable of restoring fibrin deposition in a sample, or in a subject. In some embodiments, the antibodies provided herein are capable of promoting a restoration of fibrin deposition. In some embodiments, the antibodies provided herein are capable of increasing the levels of D-dimer in a sample, or in a subject. In some embodiments, the antibodies provided herein are capable of promoting an increase of D-dimer. In some embodiments, activity of the antibodies provided herein is dose-dependent. In some embodiments, activity of the antibodies provided herein is measured in vitro. In some embodiments, activity of the antibodies provided herein is measured in vivo.

In some embodiments, the Protein S antibodies provided herein are administered to a subject, wherein the antibody remains active in the subject for a period of time.

Figure 24B:
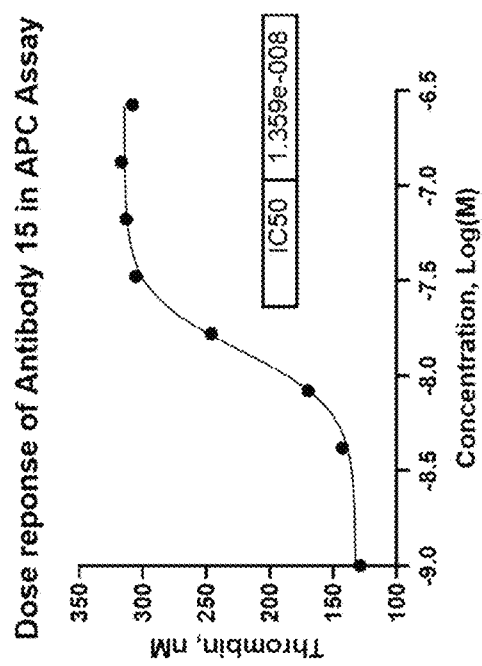
FIGS. 24A-24B depict exemplary dose response curves exhibited by antibodies 19 and 15 in an APC cofactor screening assay. The antibodies exhibit graded inhibition and switch-like inhibition, respectively, in the assay.
Figure 24A:
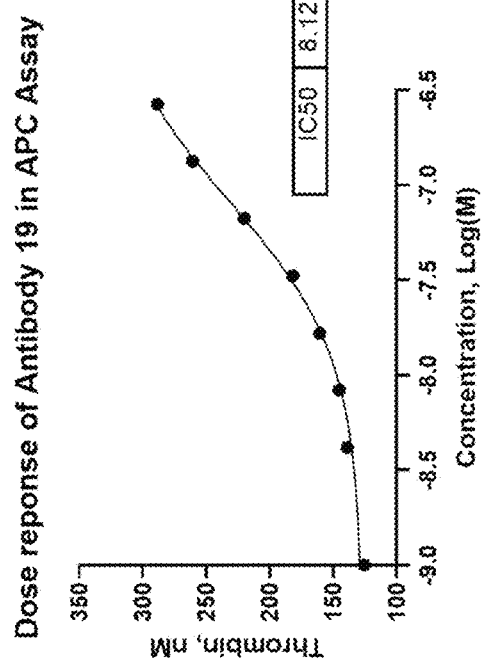

In some embodiments, the Protein S antibodies provided herein are administered to a subject, wherein the effect of the antibody is dose-dependent, such antibodies exhibit graded inhibition. FIG. 24A (Antibody 19) depicts an exemplary dose response curve of thrombin generation resulting from an antibody exhibiting graded inhibition. Antibodies exhibiting graded inhibition show concentration-dependent inhibition in vitro, where increasing concentrations of antibody result in incremental increases in thrombin generation over a wide concentration range. Exemplary antibodies that exhibit such graded inhibition include, but are not limited to, antibodies that comprise (a) the CDR amino acid sequences of SEQ ID NO: 1, SEQ ID NO: 12, SEQ ID NO: 21, SEQ ID NO: 33, SEQ ID NO: 45, and SEQ ID NO: 57; or (b) the CDR amino acid sequences of SEQ ID NO: 10, SEQ ID NO: 16, SEQ ID NO: 31, SEQ ID NO: 43, SEQ ID NO: 55, SEQ ID NO: 67.

In such embodiments, the graded inhibition can allow for increasing the dose of administration of the Protein S antibodies to a subject for added efficacy, or decreasing the dose to prevent excess thrombin generation, and/or potential thromboembolic complications, for example. Effectively, the dose can be adjusted to achieve the desired level of inhibition.

In some embodiments, the Protein S antibodies provided herein exhibit switch-like inhibition, wherein inhibition can be switched on or off. FIG. 24B (Antibody 15) depicts an exemplary dose response curve resulting from an antibody exhibiting switch-like inhibition. Antibodies exhibiting switch-like inhibition show abrupt concentration-dependent increases in thrombin generation in vitro, where upon reaching a concentration capable of promoting thrombin generation, achieves maximal thrombin generated within a narrow concentration range. Exemplary antibodies that exhibit such graded inhibition include, but are not limited to, antibodies that comprise (a) the CDR amino acid sequences of SEQ ID NO: 2, SEQ ID NO: 13, SEQ ID NO: 22, SEQ ID NO: 34, SEQ ID NO: 46, and SEQ ID NO: 58; or (b) the CDR amino acid sequences of SEQ ID NO: 1, SEQ ID NO: 15, SEQ ID NO: 24, SEQ ID NO: 36, SEQ ID NO: 48, and SEQ ID NO: 60.

In some embodiments, the Protein S antibodies provided herein are antibody fragments. In some embodiments, the antibody fragments are antigen-binding fragments (Fab), variable fragments (Fv) containing VH and VL, single chain variable fragments (scFv) containing VH and VL linked together in one chain, or other antibody variable region fragments, such as Fab', F(ab)2, F(ab')2, dsFv diabody, Fc, and Fd polypeptide fragments. The antibody fragments contain a Fc domain.

In some embodiments, the Protein S antibodies provided herein are monoclonal antibodies (mAbs). In some embodiments, the Protein S antibodies provided herein are human antibodies. In some embodiments, the Protein S antibodies provided herein are monoclonal human antibodies. In some embodiments, the Protein S antibodies provided herein are humanized antibodies. In some embodiments, the Protein S antibodies provided herein are monoclonal humanized antibodies. In some embodiments, the Protein S antibodies provided herein are chimeric antibodies. In some embodiments, the Protein S antibodies provided herein are monoclonal chimeric antibodies.

In some embodiments, the Protein S antibodies provided herein are full-length antibodies.

In some embodiments, the Protein S antibodies provided herein contain an Fc domain (either are full-length or for example, a single chain antibody linked to a Fc domain).

In some embodiments, the constant region (herein referred to also as a Fc domain, a Fc sequence or simply as a Fc) of a Protein S antibody is a human Fc domain. In some embodiments, the Fc domain of a full-length Protein S antibody is human IgG1, human IgG2, human IgG3, or human IgG4. In some embodiments, the Fc domain of a full-length Protein S antibody is that of a rat. In some embodiments, the Fc domain of a full-length Protein S antibody is rat IgG1 or rat IgG2b. In some embodiments, the Fc domain of a full-length Protein S antibody is that of a non-human primate, e.g. it is a cynomolgus monkey Fc domain.

In some embodiments, the Protein S antibodies provided herein are chimeric and comprise a variable region from one species, and a constant region from another species, e.g. comprise a human variable region and a rat constant region. In some embodiments, the rat constant region is rat IgG1 or IgG2b. In some embodiments, the antibodies comprise a human variable region and a human constant region. In exemplary embodiments, the human constant region is human IgG1, or human IgG4.

In some embodiments, the Protein S antibody contains an Fc domain, and the Fc domain of the antibody is a human IgG1 Fc. Exemplary, but non-limiting, human IgG1 Fc domain sequences are provided as SEQ ID NOS: 217.

```
                                        (SEQ ID NO: 217)
  1 ASTKGPSVFP LAPSSKSTSG GTAALGCLVK

DYFPEPVTVS WNSGALTSGV HTFPAVLQSS

61 GLYSLSSVVT VPSSSLGTQT YICNVNHKPS

NTKVDKKVEP KSCDKTHTCP PCPAPELLGG

121 PSVFLFPPKP KDTLMISRTP EVTCVVVDVS

HEDPEVKFNW YVDGVEVHNA KTKPREEQYN

181 STYRVVSVLT VLHQDWLNGK EYKCKVSNKA

LPAPIEKTIS KAKGQPREPQ VYTLPPSRDE
```

```
241 LTKNQVSLTC LVKGFYPSDI AVEWESNGQP

ENNYKTTPPV LDSDGSFFLY SKLTVDKSRW

301 QQGNVFSCSV MHEALHNHYT QKSLSLSPGK
```

In some embodiments, the Protein S antibody contains an Fc domain, and the Fc domain of the antibody is a human IgG4 Fc. An exemplary human IgG4 heavy chain Fc domain sequence is provided as SEQ ID NO: 218.

```
                                    (SEQ ID NO: 218)
ASTKGPSVFPLAPCSRSTSESTAALGCLVKDYFPEPVT

VSWNSGALTSGVHTFPAVLQSSGLYSLSSVVTVPSSSL

GTKTYTCNVDHKPSNTKVDKRVESKYGPPCPSCPAPEF

LGGPSVFLFPPKPKDTLMISRTPEVTCVVVDVSQEDPE

VQFNWYVDGVEVHNAKTKPREEQFNSTYRVVSVLTVLH

QDWLNGKEYKCKVSNKGLPSSIEKTISKAKGQPREPQV

YTLPPSQEEMTKNQVSLTCLVKGFYPSDIAVEWESNGQ

PENNYKTTPPVLDSDGSFFLYSRLTVDKSRWQEGNVFS

CSVMHEALHNHYTQKSLSLSLGK
```

The EU numbering scheme is one of many available antibody numbering schemes based on the residue numbers assigned to a canonical antibody sequence. Accordingly, a skilled artisan would understand that reference to a particular residue using the EU numbering scheme may or may not be exactly the residue in one of the antibodies of the disclosure. For example, if a Protein S antibody of the disclosure comprises a V215A substitution in the Fc, wherein the position number of the amino acid residue is of the EU numbering scheme, the residue may not be the actual residue 215 in that particular Protein S antibody. It may be actual residue number 213, or 214, or 215, or 216. Accordingly a skilled artisan will understand how to correspond the recited residue using the EU numbering scheme, to the actual residue in a Protein S antibody of the disclosure. The EU numbering system for antibodies is known in the art and is described, for example, at imgt.org/IMGTScientificChart/Numbering/Hu_IGHGnber.html.

In some embodiments, the Fc domain of a Protein S antibody is an IgG1 or IgG4 human Fc domain, and Fc variants comprise at least one amino acid substitution at a position selected from the group consisting of: 215, 221, 222, 228, 234, 235, 236, 239, 240, 241, 243, 244, 245, 247, 250, 252, 254, 256, 262, 263, 264, 265, 266, 267, 268, 269, 270, 292, 296, 297, 298, 299, 300, 305, 313, 324, 325, 326, 327, 328, 329, 330, 332, 333, 334, 345, 396, 428, 430, 433, 434, and 440, wherein the position numbers of the amino acid residues are of the EU numbering scheme.

In some embodiments, the Fc domain of a Protein S antibody is a human IgG1, and substitutions are introduced to reduce effector function, including N297A, N297Q, N297G, L235E, L234A, and L235A, wherein the position numbers of the amino acid residues are of the EU numbering scheme. In some embodiments, the Fc domain of a full-length Protein S antibody is human IgG4, and substitutions are introduced to reduce effector function, including L235E, and F234A/L235A, wherein the position numbers of the amino acid residues are of the EU numbering scheme. In some embodiments, the Fc domain of a full-length Protein S antibody is human IgG2, and substitutions are introduced to reduce effector function, including H268Q/V309L/A330S/P331S and V234A/G237A/P238S/H268A/V309L/A330S/P33IS, wherein the position numbers of the amino acid residues are of the EU numbering scheme.

In some embodiments, the Fc domain of a Protein S antibody is a human IgG1, and substitutions are introduced to increase effector function, including G236A/S239D,/I332E, K326W/E333S, S267E/H268F/S324T, and E345R/E430G/S440Y, wherein the position numbers of the amino acid residues are of the EU numbering scheme.

In some embodiments, the Fc domain of a Protein S antibody is an IgG4 human Fc domain, and the antibody is prone to the dynamic process of Fab-arm exchange. Accordingly, in some embodiments the IgG4 Fc domain comprises a S228P substitution, resulting in the reduction of this process, wherein the position number of the amino acid residues are of the EU numbering scheme.

In other embodiments, the Fc domain of a Protein S antibody is altered to increase its serum half-life. Such alterations include substitutions of a human IgG1 (e.g. SEQ ID NO: 217) such as T250Q/M428L, M252Y/S254T/T256E, M428L/N434S, S267E/L328F, N325S/L328F, and H433K/N434F, wherein the position number of the amino acid residues are of the EU numbering scheme.

In other embodiments, the Fc domain of a Protein S antibody is altered to increase its serum half-life. Such alterations include substitutions of a human IgG4 (e.g. SEQ ID NO: 218) such as T250Q/M428L, M252Y/S254T/T256E, M428L/N434S, S267E/L328F, N325S/L328F, and H433K/N434F, wherein the position number of the amino acid residues are of the EU numbering scheme.

In some embodiments, the Fc domain of a Protein S antibody is an IgG1 human Fc domain, and substitutions are introduced enhance effector function, including F243L/R292P/Y300L/V305I/P396L, S239D/I332E, S298A/E333A/K334A, L234Y/L235Q/G236W/S239M/H268D/D270E/S298A, D270E/K326D/A330M/K334E, wherein the position number of the amino acid residues are of the EU numbering scheme.

Exemplary Protein S Antibodies—CDR Sequences

Provided herein are exemplary CDR sequences of the Protein S antibodies disclosed herein.

Exemplary CDR sequences presented in Tables 1A-1C and 2A-2C below. As referred below, a light chain variable (VL) domain CDR1 region is referred to as CDR-L1; a VL CDR2 region is referred to as CDR-L2; a VL CDR3 region is referred to as CDR-L3; a heavy chain variable (VH) domain CDR1 region is referred to as CDR-H1; a VH CDR2 region is referred to as CDR-1H2; and a VH CDR3 region is referred to as CDR-H3.

TABLE 1A

| Exemplary Protein S Antibody CDR-L1 Sequences |
|---|
| KLGDKY (SEQ ID NO: 1) |
| SLRNYY (SEQ ID NO: 2) |
| SSDVGGYEF (SEQ ID NO: 3) |
| QSVSIY (SEQ ID NO: 4) |
| QRINSN (SEQ ID NO: 5) |
| QSLLHSNGYNY (SEQ ID NO: 6) |
| TGAVTASNY (SEQ ID NO: 9) |

TABLE 1A-continued

Exemplary Protein S Antibody CDR-L1 Sequences

QSVTSN (SEQ ID NO: 10)

QSLVHSDGNTY (SEQ ID NO: 11)

QGINNY (SEQ ID NO: 117)

QSISTF (SEQ ID NO: 127)

QSVGSSY (SEQ ID NO: 136)

QNIHMW (SEQ ID NO: 141)

QSISSY (SEQ ID NO: 174)

NIGGKS (SEQ ID NO: 184)

KLGDKY (SEQ ID NO: 194)

KLGDKY (SEQ ID NO: 204)

TABLE 1B

Exemplary Protein S Antibody CDR-L2 Sequences

QDT (SEQ ID NO: 12)

GKN (SEQ ID NO: 13)

DVS (SEQ ID NO: 14)

QNS (SEQ ID NO: 15)

DAS (SEQ ID NO: 16)

GAS (SEQ ID NO: 17)

LGS (SEQ ID NO: 18)

STN (SEQ ID NO: 19)

KIS (SEQ ID NO: 20)

AAS (SEQ ID NO: 118)

ATS (SEQ ID NO: 128)

KTS (SEQ ID NO: 142)

AAS (SEQ ID NO: 175)

DDS (SEQ ID NO: 185)

QDS (SEQ ID NO: 195)

QDN (SEQ ID NO: 205)

TABLE 1C

Exemplary Protein S Antibody CDR-L3 Sequences

QAWDSNTVV (SEQ ID NO: 21)

NSRDSSGNHVV (SEQ ID NO: 22)

SSYTRSSTVV (SEQ ID NO: 23)

QAWDSSTWV (SEQ ID NO: 24)

QQRSNWPLT (SEQ ID NO: 25)

QQYDNWPLT (SEQ ID NO: 26)

TABLE 1C-continued

Exemplary Protein S Antibody CDR-L3 Sequences

MQALQTFT (SEQ ID NO: 27)

ALWYSDHFV (SEQ ID NO: 30)

QQYNNWPT (SEQ ID NO: 31)

MQATQFPHLT (SEQ ID NO: 32)

QQYNSYPRT (SEQ ID NO: 119)

QQYNSYPIT (SEQ ID NO: 123)

QQSYSTPRT (SEQ ID NO: 129)

QQYGSSPYT (SEQ ID NO: 137)

LQGQSYPFT (SEQ ID NO: 143)

QQSYSSLT (SEQ ID NO: 176)

QVWEITSDHPA (SEQ ID NO: 186)

QAWDSSTVG (SEQ ID NO: 196)

QAWDSSTAV (SEQ ID NO: 206)

TABLE 2A

Exemplary Protein S Antibody CDR-H1 Sequences

GGSISSSSYY (SEQ ID NO: 33)

GGTFSSYS (SEQ ID NO: 34)

GGSITSDGYH (SEQ ID NO: 35)

GFTFDDYA (SEQ ID NO: 36)

GFTFSTYG (SEQ ID NO: 37)

GYSISSGYY (SEQ ID NO: 38)

GDTFSNHA (SEQ ID NO: 39)

GHTFTGYY (SEQ ID NO: 42)

GGSISSTNW (SEQ ID NO: 43)

GGSISNYY (SEQ ID NO: 44)

GGSITNSNYY (SEQ ID NO: 120)

GFTFSSYN (SEQ ID NO: 124)

GGSISGNY (SEQ ID NO: 130)

GDSVSNNNAA (SEQ ID NO: 138)

GYTFTNHW (SEQ ID NO: 144)

GISFSNAW (SEQ ID NO: 179)

GFTFSSYS (SEQ ID NO: 189)

GYTFTNYY (SEQ ID NO: 199)

GYTFTSYY (SEQ ID NO: 209)

TABLE 2B

Exemplary Protein S Antibody CDR-H2 Sequences

IYYSGNT (SEQ ID NO: 45)

IIPIFGTT (SEQ ID NO: 46)

IYYTGNT (SEQ ID NO: 47)

ITWNSGNI (SEQ ID NO: 48)

IYYDGINK (SEQ ID NO: 49)

IYYSGST (SEQ ID NO: 50)

YIPIFGTT (SEQ ID NO: 51)

INPNSGDT (SEQ ID NO: 54)

IYQTGST (SEQ ID NO: 55)

IYYIGIT (SEQ ID NO: 56)

VYYSGTT (SEQ ID NO: 121)

ISSSSSYI (SEQ ID NO: 125)

TYYRSKWYN (SEQ ID NO: 139)

IYPGGGYT (SEQ ID NO: 145)

IKANPDGGTT (SEQ ID NO: 180)

ISSSTRTI (SEQ ID NO: 190)

ITPSGGTT (SEQ ID NO: 200)

TSPSGRST (SEQ ID NO: 210

TABLE 2C

Exemplary Protein S Antibody CDR-H3 Sequences

ARCSGYGYSSGRSYFDY (SEQ ID NO: 57)

EGGRVGADFDY (SEQ ID NO: 58)

ARRLSTGPYFDY (SEQ ID NO: 59)

AKGRAVSDTFDI (SEQ ID NO: 60)

AESDLDY (SEQ ID NO: 61)

ATTYSDIVTGYYNDAFDI (SEQ ID NO: 62)

ARGGLAGSHYKNYYYDGMDV (SEQ ID NO: 63)

ARDSQILWFGELGY (SEQ ID NO: 66)

ARRFGELDY (SEQ ID NO: 67)

AALSGDHAFDI (SEQ ID NO: 68)

VRESESYYYYGSDV (SEQ ID NO: 122)

ARDEEWELLTGFDY (SEQ ID NO: 126)

ARDLDYFTWGAYSDWYFDL (SEQ ID NO: 131)

ARGSSWYRFFDY (SEQ ID NO: 140)

SRFGDQNWAWFAY (SEQ ID NO: 146)

TTELDILLWFTSFDY (SEQ ID NO: 181)

ARERSAFDY (SEQ ID NO: 191)

TABLE 2C-continued

Exemplary Protein S Antibody CDR-H3 Sequences

ARAGVQLDRRGWFDP (SEQ ID NO: 201)

ARGGVTIHLERRGYFDY (SEQ ID NO: 211)

In some embodiments, the Protein S antibodies provided herein include any one or more of the amino acid sequences of the CDR sequences provided in Tables 1A, 1B, 1C, 2A, 2B, and 2C.

In some embodiments, provided herein are Protein S antibodies, wherein the antibodies comprise:
  (a) any one of the CDR-L1 amino acid sequences of Table 1A;
  (b) any one of the CDR-L2 amino acid sequences of Table 1B;
  (c) any one of the CDR-L3 amino acid sequences of Table 1C;
  (d) any one of the CDR-H1 amino acid sequences of Table 2A;
  (e) any one of the CDR-H2 amino acid sequences of Table 2B; and
  (f) any one of the CDR-H3 amino acid sequences of Table 2C.

In some embodiments, provided herein are Protein S antibodies, wherein the light chain variable domain of the antibodies comprises:
  (a) a CDR-L1 comprising the amino acid sequence of any one of SEQ ID NOs: 1-6, 9-11, 117, 127, 136, 141, 174, 184, 194, and 204;
  (b) a CDR-L2 comprising the amino acid sequence of any one of SEQ ID NOs: 12-20, 118, 128, 142, 175, 185, 195, and 205; and
  (c) a CDR-L3 comprising the amino acid sequence of any one of SEQ ID NOs: 21-27, 30-32, 119, 123, 129, 137, 143, 176, 186, 196, and 206.

In some embodiments, provided herein are Protein S antibodies, wherein the heavy chain variable domain of the antibodies comprises:
  (a) a CDR-H1 comprising the amino acid sequence of any one of SEQ ID NOs: 33-39, 42-44, 120, 124, 130, 138, 144, 179, 189, 199, and 209;
  (b) a CDR-H2 comprising the amino acid sequence of any one of SEQ ID NOs: 45-51, 54-56, 121, 125, 139, 145, 180, 190, 200, and 210;
  (c) a CDR-H3 comprising the amino acid sequence of any one of SEQ ID NOs: 57-63, 66-68, 122, 126, 131, 140, 146, 181, 191, 201, and 211.

In some embodiments, provided herein are Protein S antibodies, wherein the light chain variable domain of the antibody comprises:
  (a) a CDR-L1 comprising the amino acid sequence of SEQ ID NO: 1;
  (b) a CDR-L2 comprising the amino acid sequence of SEQ ID NO: 12; and
  (c) a CDR-L3 comprising the amino acid sequence of SEQ ID NO: 21.

In some embodiments, provided herein are Protein S antibodies, wherein the light chain variable domain of the antibody comprises:
  (a) a CDR-L1 comprising the amino acid sequence of SEQ ID NO: 2;
  (b) a CDR-L2 comprising the amino acid sequence of SEQ ID NO: 13; and (c) a CDR-L3 comprising the amino acid sequence of SEQ ID NO: 22.

In some embodiments, provided herein are Protein S antibodies, wherein the light chain variable domain of the antibody comprises:
(a) a CDR-L1 comprising the amino acid sequence of SEQ ID NO: 3;
(b) a CDR-L2 comprising the amino acid sequence of SEQ ID NO: 14; and
(c) a CDR-L3 comprising the amino acid sequence of SEQ ID NO: 23.

In some embodiments, provided herein are Protein S antibodies, wherein the light chain variable domain of the antibody comprises:
(a) a CDR-L1 comprising the amino acid sequence of SEQ ID NO: 1;
(b) a CDR-L2 comprising the amino acid sequence of SEQ ID NO: 15; and
(c) a CDR-L3 comprising the amino acid sequence of SEQ ID NO: 24.

In some embodiments, provided herein are Protein S antibodies, wherein the light chain variable domain of the antibody comprises:
(a) a CDR-L1 comprising the amino acid sequence of SEQ ID NO: 4;
(b) a CDR-L2 comprising the amino acid sequence of SEQ ID NO: 16; and
(c) a CDR-L3 comprising the amino acid sequence of SEQ ID NO: 25.

In some embodiments, provided herein are Protein S antibodies, wherein the light chain variable domain of the antibody comprises:
(a) a CDR-L1 comprising the amino acid sequence of SEQ ID NO: 5;
(b) a CDR-L2 comprising the amino acid sequence of SEQ ID NO: 17; and
(c) a CDR-L3 comprising the amino acid sequence of SEQ ID NO: 26.

In some embodiments, provided herein are Protein S antibodies, wherein the light chain variable domain of the antibody comprises:
(a) a CDR-L1 comprising the amino acid sequence of SEQ ID NO: 6;
(b) a CDR-L2 comprising the amino acid sequence of SEQ ID NO: 18; and
(c) a CDR-L3 comprising the amino acid sequence of SEQ ID NO: 27.

In some embodiments, provided herein are Protein S antibodies, wherein the light chain variable domain of the antibody comprises:
(a) a CDR-L1 comprising the amino acid sequence of SEQ ID NO: 9;
(b) a CDR-L2 comprising the amino acid sequence of SEQ ID NO: 19; and
(c) a CDR-L3 comprising the amino acid sequence of SEQ ID NO: 30.

In some embodiments, provided herein are Protein S antibodies, wherein the light chain variable domain of the antibody comprises:
(a) a CDR-L1 comprising the amino acid sequence of SEQ ID NO: 10;
(b) a CDR-L2 comprising the amino acid sequence of SEQ ID NO: 16; and
(c) a CDR-L3 comprising the amino acid sequence of SEQ ID NO: 31.

In some embodiments, provided herein are Protein S antibodies, wherein the light chain variable domain of the antibody comprises:
(a) a CDR-L1 comprising the amino acid sequence of SEQ ID NO: 11;
(b) a CDR-L2 comprising the amino acid sequence of SEQ ID NO: 20; and
(c) a CDR-L3 comprising the amino acid sequence of SEQ ID NO: 32.

In some embodiments, provided herein are Protein S antibodies, wherein the light chain variable domain of the antibody comprises:
(a) a CDR-L1 comprising the amino acid sequence of SEQ ID NO: 117;
(b) a CDR-L2 comprising the amino acid sequence of SEQ ID NO: 118; and
(c) a CDR-L3 comprising the amino acid sequence of SEQ ID NO: 119.

In some embodiments, provided herein are Protein S antibodies, wherein the light chain variable domain of the antibody comprises:
(a) a CDR-L1 comprising the amino acid sequence of SEQ ID NO: 117;
(b) a CDR-L2 comprising the amino acid sequence of SEQ ID NO: 118; and
(c) a CDR-L3 comprising the amino acid sequence of SEQ ID NO: 123.
(d)

In some embodiments, provided herein are Protein S antibodies, wherein the light chain variable domain of the antibody comprises:
(a) a CDR-L1 comprising the amino acid sequence of SEQ ID NO: 127;
(b) a CDR-L2 comprising the amino acid sequence of SEQ ID NO: 128; and
(c) a CDR-L3 comprising the amino acid sequence of SEQ ID NO: 129.

In some embodiments, provided herein are Protein S antibodies, wherein the light chain variable domain of the antibody comprises:
(a) a CDR-L1 comprising the amino acid sequence of SEQ ID NO: 136;
(b) a CDR-L2 comprising the amino acid sequence of SEQ ID NO: 17; and
(c) a CDR-L3 comprising the amino acid sequence of SEQ ID NO: 137.

In some embodiments, provided herein are Protein S antibodies, wherein the light chain variable domain of the antibody comprises:
(a) a CDR-L1 comprising the amino acid sequence of SEQ ID NO: 141;
(b) a CDR-L2 comprising the amino acid sequence of SEQ ID NO: 142; and
(c) a CDR-L3 comprising the amino acid sequence of SEQ ID NO: 143.

In some embodiments, provided herein are Protein S antibodies, wherein the light chain variable domain of the antibody comprises:
(a) a CDR-L1 comprising the amino acid sequence of SEQ ID NO: 174;
(b) a CDR-L2 comprising the amino acid sequence of SEQ ID NO: 175; and
(c) a CDR-L3 comprising the amino acid sequence of SEQ ID NO: 176.

In some embodiments, provided herein are Protein S antibodies, wherein the light chain variable domain of the antibody comprises:

(a) a CDR-L1 comprising the amino acid sequence of SEQ ID NO: 184;
(b) a CDR-L2 comprising the amino acid sequence of SEQ ID NO: 185; and
(c) a CDR-L3 comprising the amino acid sequence of SEQ ID NO: 186.

In some embodiments, provided herein are Protein S antibodies, wherein the light chain variable domain of the antibody comprises:
(a) a CDR-L1 comprising the amino acid sequence of SEQ ID NO: 194;
(b) a CDR-L2 comprising the amino acid sequence of SEQ ID NO: 195; and
(c) a CDR-L3 comprising the amino acid sequence of SEQ ID NO: 196.

In some embodiments, provided herein are Protein S antibodies, wherein the light chain variable domain of the antibody comprises:
(a) a CDR-L1 comprising the amino acid sequence of SEQ ID NO: 204;
(b) a CDR-L2 comprising the amino acid sequence of SEQ ID NO: 205; and
(c) a CDR-L3 comprising the amino acid sequence of SEQ ID NO: 206.

In some embodiments, provided herein are Protein S antibodies, wherein the heavy chain variable domain of the antibodies comprises:
(a) a CDR-H1 comprising the amino acid sequence of SEQ ID NO: 33;
(b) a CDR-H2 comprising the amino acid sequence of SEQ ID NO: 45; and
(c) a CDR-H3 comprising the amino acid sequence of SEQ ID NO: 57.

In some embodiments, provided herein are Protein S antibodies, wherein the heavy chain variable domain of the antibodies comprises:
(a) a CDR-H1 comprising the amino acid sequence of SEQ ID NO: 34;
(b) a CDR-H2 comprising the amino acid sequence of SEQ ID NO: 46; and
(c) a CDR-H3 comprising the amino acid sequence of SEQ ID NO: 58.

In some embodiments, provided herein are Protein S antibodies, wherein the heavy chain variable domain of the antibodies comprises:
(a) a CDR-H1 comprising the amino acid sequence of SEQ ID NO: 35;
(b) a CDR-H2 comprising the amino acid sequence of SEQ ID NO: 47; and
(c) a CDR-H3 comprising the amino acid sequence of SEQ ID NO: 59.

In some embodiments, provided herein are Protein S antibodies, wherein the heavy chain variable domain of the antibodies comprises:
(a) a CDR-H1 comprising the amino acid sequence of SEQ ID NO: 36;
(b) a CDR-H2 comprising the amino acid sequence of SEQ ID NO: 48; and
(c) a CDR-H3 comprising the amino acid sequence of SEQ ID NO: 60.

In some embodiments, provided herein are Protein S antibodies, wherein the heavy chain variable domain of the antibodies comprises:
(a) a CDR-H1 comprising the amino acid sequence of SEQ ID NO: 37;
(b) a CDR-H2 comprising the amino acid sequence of SEQ ID NO: 49; and
(c) a CDR-H3 comprising the amino acid sequence of SEQ ID NO: 61.

In some embodiments, provided herein are Protein S antibodies, wherein the heavy chain variable domain of the antibodies comprises:
(a) a CDR-H1 comprising the amino acid sequence of SEQ ID NO: 38;
(b) a CDR-H2 comprising the amino acid sequence of SEQ ID NO: 50; and
(c) a CDR-H3 comprising the amino acid sequence of SEQ ID NO: 62.

In some embodiments, provided herein are Protein S antibodies, wherein the heavy chain variable domain of the antibodies comprises:
(a) a CDR-H1 comprising the amino acid sequence of SEQ ID NO: 39;
(b) a CDR-H2 comprising the amino acid sequence of SEQ ID NO: 51; and
(c) a CDR-H3 comprising the amino acid sequence of SEQ ID NO: 63.

In some embodiments, provided herein are Protein S antibodies, wherein the heavy chain variable domain of the antibodies comprises:
(a) a CDR-H1 comprising the amino acid sequence of SEQ ID NO: 42;
(b) a CDR-H2 comprising the amino acid sequence of SEQ ID NO: 54; and
(c) a CDR-H3 comprising the amino acid sequence of SEQ ID NO: 66.

In some embodiments, provided herein are Protein S antibodies, wherein the heavy chain variable domain of the antibodies comprises:
(a) a CDR-H1 comprising the amino acid sequence of SEQ ID NO: 43;
(b) a CDR-H2 comprising the amino acid sequence of SEQ ID NO: 55; and
(c) a CDR-H3 comprising the amino acid sequence of SEQ ID NO: 67.

In some embodiments, provided herein are Protein S antibodies, wherein the heavy chain variable domain of the antibodies comprises:
(a) a CDR-H1 comprising the amino acid sequence of SEQ ID NO: 44;
(b) a CDR-H2 comprising the amino acid sequence of SEQ ID NO: 56; and
(c) a CDR-H3 comprising the amino acid sequence of SEQ ID NO: 68.

In some embodiments, provided herein are Protein S antibodies, wherein the heavy chain variable domain of the antibodies comprises:
(a) a CDR-H1 comprising the amino acid sequence of SEQ ID NO: 120;
(b) a CDR-H2 comprising the amino acid sequence of SEQ ID NO: 121; and
(c) a CDR-H3 comprising the amino acid sequence of SEQ ID NO: 122.

In some embodiments, provided herein are Protein S antibodies, wherein the heavy chain variable domain of the antibodies comprises:
(a) a CDR-H1 comprising the amino acid sequence of SEQ ID NO: 124;
(b) a CDR-H2 comprising the amino acid sequence of SEQ ID NO: 125; and
(c) a CDR-H3 comprising the amino acid sequence of SEQ ID NO: 126.

In some embodiments, provided herein are Protein S antibodies, wherein the heavy chain variable domain of the antibodies comprises:
(a) a CDR-H1 comprising the amino acid sequence of SEQ ID NO: 130;
(b) a CDR-H2 comprising the amino acid sequence of SEQ ID NO: 50; and
(c) a CDR-H3 comprising the amino acid sequence of SEQ ID NO: 131.

In some embodiments, provided herein are Protein S antibodies, wherein the heavy chain variable domain of the antibodies comprises:
(a) a CDR-H1 comprising the amino acid sequence of SEQ ID NO: 138;
(b) a CDR-H2 comprising the amino acid sequence of SEQ ID NO: 139; and
(c) a CDR-H3 comprising the amino acid sequence of SEQ ID NO: 140.

In some embodiments, provided herein are Protein S antibodies, wherein the heavy chain variable domain of the antibodies comprises:
(a) a CDR-H1 comprising the amino acid sequence of SEQ ID NO: 144;
(b) a CDR-H2 comprising the amino acid sequence of SEQ ID NO: 145; and
(c) a CDR-H3 comprising the amino acid sequence of SEQ ID NO: 146.

In some embodiments, provided herein are Protein S antibodies, wherein the heavy chain variable domain of the antibodies comprises:
(a) a CDR-H1 comprising the amino acid sequence of SEQ ID NO: 179;
(b) a CDR-H2 comprising the amino acid sequence of SEQ ID NO: 180; and
(c) a CDR-H3 comprising the amino acid sequence of SEQ ID NO: 181.

In some embodiments, provided herein are Protein S antibodies, wherein the heavy chain variable domain of the antibodies comprises:
(a) a CDR-H1 comprising the amino acid sequence of SEQ ID NO: 189;
(b) a CDR-H2 comprising the amino acid sequence of SEQ ID NO: 190; and
(c) a CDR-H3 comprising the amino acid sequence of SEQ ID NO: 191.

In some embodiments, provided herein are Protein S antibodies, wherein the heavy chain variable domain of the antibodies comprises:
(a) a CDR-H1 comprising the amino acid sequence of SEQ ID NO: 199;
(b) a CDR-H2 comprising the amino acid sequence of SEQ ID NO: 200; and
(c) a CDR-H3 comprising the amino acid sequence of SEQ ID NO: 201.

In some embodiments, provided herein are Protein S antibodies, wherein the heavy chain variable domain of the antibodies comprises:
(a) a CDR-H1 comprising the amino acid sequence of SEQ ID NO: 209;
(b) a CDR-H2 comprising the amino acid sequence of SEQ ID NO: 210; and
(c) a CDR-H3 comprising the amino acid sequence of SEQ ID NO: 211.

In some embodiments, provided herein are Protein S antibodies, wherein the light chain variable domain of the antibodies comprises a CDR-L1 from Table 1A, a CDR-L2 from Table 1B, and a CDR-L3 from Table 1C, and wherein the heavy chain variable domain of the antibodies comprises:
(a) a CDR-H1 comprising the amino acid sequence of SEQ ID NO: 33;
(b) a CDR-H2 comprising the amino acid sequence of SEQ ID NO: 45; and
(c) a CDR-H3 comprising the amino acid sequence of SEQ ID NO: 57.

In some embodiments, provided herein are Protein S antibodies, wherein the light chain variable domain of the antibodies comprises a CDR-L1 from Table 1A, a CDR-L2 from Table 1B, and a CDR-L3 from Table 1C, and wherein the heavy chain variable domain of the antibodies comprises:
(a) a CDR-H1 comprising the amino acid sequence of SEQ ID NO: 34;
(b) a CDR-H2 comprising the amino acid sequence of SEQ ID NO: 46; and
(c) a CDR-H3 comprising the amino acid sequence of SEQ ID NO: 58.

In some embodiments, provided herein are Protein S antibodies, wherein the light chain variable domain of the antibodies comprises a CDR-L1 from Table 1A, a CDR-L2 from Table 1B, and a CDR-L3 from Table 1C, and wherein the heavy chain variable domain of the antibodies comprises:
(a) a CDR-H1 comprising the amino acid sequence of SEQ ID NO: 35;
(b) a CDR-H2 comprising the amino acid sequence of SEQ ID NO: 47; and
(c) a CDR-H3 comprising the amino acid sequence of SEQ ID NO: 59.

In some embodiments, provided herein are Protein S antibodies, wherein the light chain variable domain of the antibodies comprises a CDR-L1 from Table 1A, a CDR-L2 from Table 1B, and a CDR-L3 from Table 1C, and wherein the heavy chain variable domain of the antibodies comprises:
(a) a CDR-H1 comprising the amino acid sequence of SEQ ID NO: 36;
(b) a CDR-H2 comprising the amino acid sequence of SEQ ID NO: 48; and
(c) a CDR-H3 comprising the amino acid sequence of SEQ ID NO: 60.

In some embodiments, provided herein are Protein S antibodies, wherein the light chain variable domain of the antibodies comprises a CDR-L1 from Table 1A, a CDR-L2 from Table 1B, and a CDR-L3 from Table 1C, and wherein the heavy chain variable domain of the antibodies comprises:
(a) a CDR-H1 comprising the amino acid sequence of SEQ ID NO: 37;
(b) a CDR-H2 comprising the amino acid sequence of SEQ ID NO: 49; and
(c) a CDR-H3 comprising the amino acid sequence of SEQ ID NO: 61.

In some embodiments, provided herein are Protein S antibodies, wherein the light chain variable domain of the antibodies comprises a CDR-L1 from Table 1A, a CDR-L2 from Table 1B, and a CDR-L3 from Table 1C, and wherein the heavy chain variable domain of the antibodies comprises:
(a) a CDR-H1 comprising the amino acid sequence of SEQ ID NO: 38;
(b) a CDR-H2 comprising the amino acid sequence of SEQ ID NO: 50; and (c) a CDR-H3 comprising the amino acid sequence of SEQ ID NO: 62.

In some embodiments, provided herein are Protein S antibodies, wherein the light chain variable domain of the antibodies comprises a CDR-L1 from Table 1A, a CDR-L2 from Table 1B, and a CDR-L3 from Table 1C, and wherein the heavy chain variable domain of the antibodies comprises:
- (a) a CDR-H1 comprising the amino acid sequence of SEQ ID NO: 39;
- (b) a CDR-H2 comprising the amino acid sequence of SEQ ID NO: 51; and
- (c) a CDR-H3 comprising the amino acid sequence of SEQ ID NO: 63.

In some embodiments, provided herein are Protein S antibodies, wherein the light chain variable domain of the antibodies comprises a CDR-L1 from Table 1A, a CDR-L2 from Table 1B, and a CDR-L3 from Table 1C, and wherein the heavy chain variable domain of the antibodies comprises:
- (a) a CDR-H1 comprising the amino acid sequence of SEQ ID NO: 42;
- (b) a CDR-H2 comprising the amino acid sequence of SEQ ID NO: 54; and
- (c) a CDR-H3 comprising the amino acid sequence of SEQ ID NO: 66.

In some embodiments, provided herein are Protein S antibodies, wherein the light chain variable domain of the antibodies comprises any one or more of the sequences provided in Tables 1A, 1B, and 1C, and wherein the heavy chain variable domain of the antibodies comprises:
- (a) a CDR-H1 comprising the amino acid sequence of SEQ ID NO: 43;
- (b) a CDR-H2 comprising the amino acid sequence of SEQ ID NO: 55; and
- (c) a CDR-H3 comprising the amino acid sequence of SEQ ID NO: 67.

In some embodiments, provided herein are Protein S antibodies, wherein the light chain variable domain of the antibodies comprises a CDR-L1 from Table 1A, a CDR-L2 from Table 1B, and a CDR-L3 from Table 1C, and wherein the heavy chain variable domain of the antibodies comprises:
- (a) a CDR-H1 comprising the amino acid sequence of SEQ ID NO: 44;
- (b) a CDR-H2 comprising the amino acid sequence of SEQ ID NO: 56; and
- (c) a CDR-H3 comprising the amino acid sequence of SEQ ID NO: 68.

In some embodiments, provided herein are Protein S antibodies, wherein the light chain variable domain of the antibodies comprises a CDR-L1 from Table 1A, a CDR-L2 from Table 1B, and a CDR-L3 from Table 1C, and wherein the heavy chain variable domain of the antibodies comprises:
- (a) a CDR-H1 comprising the amino acid sequence of SEQ ID NO: 120;
- (b) a CDR-H2 comprising the amino acid sequence of SEQ ID NO: 121; and
- (c) a CDR-H3 comprising the amino acid sequence of SEQ ID NO: 122.

In some embodiments, provided herein are Protein S antibodies, wherein the light chain variable domain of the antibodies comprises a CDR-L1 from Table 1A, a CDR-L2 from Table 1B, and a CDR-L3 from Table 1C, and wherein the heavy chain variable domain of the antibodies comprises:
- (a) a CDR-H1 comprising the amino acid sequence of SEQ ID NO: 124;
- (b) a CDR-H2 comprising the amino acid sequence of SEQ ID NO: 125; and
- (c) a CDR-H3 comprising the amino acid sequence of SEQ ID NO: 126.

In some embodiments, provided herein are Protein S antibodies, wherein the light chain variable domain of the antibodies comprises a CDR-L1 from Table 1A, a CDR-L2 from Table 1B, and a CDR-L3 from Table 1C, and wherein the heavy chain variable domain of the antibodies comprises:
- (a) a CDR-H1 comprising the amino acid sequence of SEQ ID NO: 130;
- (b) a CDR-H2 comprising the amino acid sequence of SEQ ID NO: 50; and
- (c) a CDR-H3 comprising the amino acid sequence of SEQ ID NO: 131.

In some embodiments, provided herein are Protein S antibodies, wherein the light chain variable domain of the antibodies comprises a CDR-L1 from Table 1A, a CDR-L2 from Table 1B, and a CDR-L3 from Table 1C, and wherein the heavy chain variable domain of the antibodies comprises:
- (a) a CDR-H1 comprising the amino acid sequence of SEQ ID NO: 138;
- (b) a CDR-H2 comprising the amino acid sequence of SEQ ID NO: 139; and
- (c) a CDR-H3 comprising the amino acid sequence of SEQ ID NO: 140.

In some embodiments, provided herein are Protein S antibodies, wherein the light chain variable domain of the antibodies comprises a CDR-L1 from Table 1A, a CDR-L2 from Table 1B, and a CDR-L3 from Table 1C, and wherein the heavy chain variable domain of the antibodies comprises:
- (a) a CDR-H1 comprising the amino acid sequence of SEQ ID NO: 144;
- (b) a CDR-H2 comprising the amino acid sequence of SEQ ID NO: 145; and
- (c) a CDR-H3 comprising the amino acid sequence of SEQ ID NO: 146.

In some embodiments, provided herein are Protein S antibodies, wherein the light chain variable domain of the antibodies comprises a CDR-L1 from Table 1A, a CDR-L2 from Table 1B, and a CDR-L3 from Table 1C, and wherein the heavy chain variable domain of the antibodies comprises:
- (d) a CDR-H1 comprising the amino acid sequence of SEQ ID NO: 179;
- (e) a CDR-H2 comprising the amino acid sequence of SEQ ID NO: 180; and
- (f) a CDR-H3 comprising the amino acid sequence of SEQ ID NO: 181.

In some embodiments, provided herein are Protein S antibodies, wherein the light chain variable domain of the antibodies comprises a CDR-L1 from Table 1A, a CDR-L2 from Table 1B, and a CDR-L3 from Table 1C, and wherein the heavy chain variable domain of the antibodies comprises:
- (a) a CDR-H1 comprising the amino acid sequence of SEQ ID NO: 189;
- (b) a CDR-H2 comprising the amino acid sequence of SEQ ID NO: 190; and
- (c) a CDR-H3 comprising the amino acid sequence of SEQ ID NO: 191.

In some embodiments, provided herein are Protein S antibodies, wherein the light chain variable domain of the antibodies comprises a CDR-L1 from Table 1A, a CDR-L2 from Table 1B, and a CDR-L3 from Table 1C, and wherein the heavy chain variable domain of the antibodies comprises:
(a) a CDR-H1 comprising the amino acid sequence of SEQ ID NO: 199;
(b) a CDR-H2 comprising the amino acid sequence of SEQ ID NO: 200; and
(c) a CDR-H3 comprising the amino acid sequence of SEQ ID NO: 201.

In some embodiments, provided herein are Protein S antibodies, wherein the light chain variable domain of the antibodies comprises a CDR-L1 from Table 1A, a CDR-L2 from Table 1B, and a CDR-L3 from Table 1C, and wherein the heavy chain variable domain of the antibodies comprises:
(a) a CDR-H1 comprising the amino acid sequence of SEQ ID NO: 209;
(b) a CDR-H2 comprising the amino acid sequence of SEQ ID NO: 210; and
(c) a CDR-H3 comprising the amino acid sequence of SEQ ID NO: 211.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the antibodies comprises:
(a) a CDR-L1 comprising the amino acid sequence of SEQ ID NO: 1;
(b) a CDR-L2 comprising the amino acid sequence of SEQ ID NO: 12; and
(c) a CDR-L3 comprising the amino acid sequence of SEQ ID NO: 21.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the antibodies comprises:
(a) a CDR-L1 comprising the amino acid sequence of SEQ ID NO: 2;
(b) a CDR-L2 comprising the amino acid sequence of SEQ ID NO: 13; and
(c) a CDR-L3 comprising the amino acid sequence of SEQ ID NO: 22.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the antibodies comprises:
(a) a CDR-L1 comprising the amino acid sequence of SEQ ID NO: 3;
(b) a CDR-L2 comprising the amino acid sequence of SEQ ID NO: 14; and
(c) a CDR-L3 comprising the amino acid sequence of SEQ ID NO: 23.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the antibodies comprises:
(a) a CDR-L1 comprising the amino acid sequence of SEQ ID NO: 1;
(b) a CDR-L2 comprising the amino acid sequence of SEQ ID NO: 15; and
(c) a CDR-L3 comprising the amino acid sequence of SEQ ID NO: 24.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the antibodies comprises:
(a) a CDR-L1 comprising the amino acid sequence of SEQ ID NO: 4;
(b) a CDR-L2 comprising the amino acid sequence of SEQ ID NO: 16; and
(c) a CDR-L3 comprising the amino acid sequence of SEQ ID NO: 25.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the antibodies comprises:
(a) a CDR-L1 comprising the amino acid sequence of SEQ ID NO: 5;
(b) a CDR-L2 comprising the amino acid sequence of SEQ ID NO: 17; and
(c) a CDR-L3 comprising the amino acid sequence of SEQ ID NO: 26.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the antibodies comprises:
(a) a CDR-L1 comprising the amino acid sequence of SEQ ID NO: 6;
(b) a CDR-L2 comprising the amino acid sequence of SEQ ID NO: 18; and
(c) a CDR-L3 comprising the amino acid sequence of SEQ ID NO: 27.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the antibodies comp comprises rise:
(a) a CDR-L1 comprising the amino acid sequence of SEQ ID NO: 9;
(b) a CDR-L2 comprising the amino acid sequence of SEQ ID NO: 19; and
(c) a CDR-L3 comprising the amino acid sequence of SEQ ID NO: 30.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the antibodies comprises:
(a) a CDR-L1 comprising the amino acid sequence of SEQ ID NO: 10;
(b) a CDR-L2 comprising the amino acid sequence of SEQ ID NO: 16; and
(c) a CDR-L3 comprising the amino acid sequence of SEQ ID NO: 31.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the antibodies comprises:
(a) a CDR-L1 comprising the amino acid sequence of SEQ ID NO: 11;
(b) a CDR-L2 comprising the amino acid sequence of SEQ ID NO: 20; and (c) a CDR-L3 comprising the amino acid sequence of SEQ ID NO: 32.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the antibodies comprises:
(a) a CDR-L1 comprising the amino acid sequence of SEQ ID NO: 117;
(b) a CDR-L2 comprising the amino acid sequence of SEQ ID NO: 118; and
(c) a CDR-L3 comprising the amino acid sequence of SEQ ID NO: 119.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the antibodies comprises:
(a) a CDR-L1 comprising the amino acid sequence of SEQ ID NO: 117;
(b) a CDR-L2 comprising the amino acid sequence of SEQ ID NO: 118; and
(c) a CDR-L3 comprising the amino acid sequence of SEQ ID NO: 123.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the antibodies comprises:
(a) a CDR-L1 comprising the amino acid sequence of SEQ ID NO: 127;
(b) a CDR-L2 comprising the amino acid sequence of SEQ ID NO: 128; and
(c) a CDR-L3 comprising the amino acid sequence of SEQ ID NO: 129.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the antibodies comprises:
(a) a CDR-L1 comprising the amino acid sequence of SEQ ID NO: 136;
(b) a CDR-L2 comprising the amino acid sequence of SEQ ID NO: 17; and
(c) a CDR-L3 comprising the amino acid sequence of SEQ ID NO: 137.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the antibodies comprises:
(a) a CDR-L1 comprising the amino acid sequence of SEQ ID NO: 141;
(b) a CDR-L2 comprising the amino acid sequence of SEQ ID NO: 142; and
(c) a CDR-L3 comprising the amino acid sequence of SEQ ID NO: 143.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the antibodies comprises:
(a) a CDR-L1 comprising the amino acid sequence of SEQ ID NO: 174;
(b) a CDR-L2 comprising the amino acid sequence of SEQ ID NO: 175; and
(c) a CDR-L3 comprising the amino acid sequence of SEQ ID NO: 176.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the antibodies comprises:
(a) a CDR-L1 comprising the amino acid sequence of SEQ ID NO: 184;
(b) a CDR-L2 comprising the amino acid sequence of SEQ ID NO: 185; and
(c) a CDR-L3 comprising the amino acid sequence of SEQ ID NO: 186.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the antibodies comprises:
(a) a CDR-L1 comprising the amino acid sequence of SEQ ID NO: 194;
(b) a CDR-L2 comprising the amino acid sequence of SEQ ID NO: 195; and
(c) a CDR-L3 comprising the amino acid sequence of SEQ ID NO: 196.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the antibodies comprises:
(a) a CDR-L1 comprising the amino acid sequence of SEQ ID NO: 204;
(b) a CDR-L2 comprising the amino acid sequence of SEQ ID NO: 205; and
(c) a CDR-L3 comprising the amino acid sequence of SEQ ID NO: 206.

In some embodiments, provided herein are Protein S antibodies, wherein the antibodies comprise the CDR amino acid sequences of SEQ ID NO: 1, SEQ ID NO: 12, SEQ ID NO: 21, SEQ ID NO: 33, SEQ ID NO: 45, and SEQ ID NO: 57.

In some embodiments, provided herein are Protein S antibodies, wherein the antibodies comprise the CDR amino acid sequences of SEQ ID NO: 2, SEQ ID NO: 13, SEQ ID NO: 22, SEQ ID NO: 34, SEQ ID NO: 46, and SEQ ID NO: 58.

In some embodiments, provided herein are Protein S antibodies, wherein the antibodies comprise the CDR amino acid sequences of SEQ ID NO: 3, SEQ ID NO: 14, SEQ ID NO: 23, SEQ ID NO: 35, SEQ ID NO: 47, and SEQ ID NO: 59.

In some embodiments, provided herein are Protein S antibodies, wherein the antibodies comprise the CDR amino acid sequences of SEQ ID NO: 1, SEQ ID NO: 15, SEQ ID NO: 24, SEQ ID NO: 36, SEQ ID NO: 48, and SEQ ID NO: 60.

In some embodiments, provided herein are Protein S antibodies, wherein the antibodies comprise the CDR amino acid sequences of SEQ ID NO: 4, SEQ ID NO: 16, SEQ ID NO: 25, SEQ ID NO: 37, SEQ ID NO: 49, and SEQ ID NO: 61.

In some embodiments, provided herein are Protein S antibodies, wherein the antibodies comprise the CDR amino acid sequences of SEQ ID NO: 5, SEQ ID NO: 17, SEQ ID NO: 26, SEQ ID NO: 38, SEQ ID NO: 50, and SEQ ID NO: 62.

In some embodiments, provided herein are Protein S antibodies, wherein the antibodies comprise the CDR amino acid sequences of SEQ ID NO: 6, SEQ ID NO: 18, SEQ ID NO: 27, SEQ ID NO: 39, SEQ ID NO: 51, and SEQ ID NO: 63.

In some embodiments, provided herein are Protein S antibodies, wherein the antibodies comprise the CDR amino acid sequences of SEQ ID NO: 9, SEQ ID NO: 19, SEQ ID NO: 30, SEQ ID NO: 42, SEQ ID NO: 54, and SEQ ID NO: 66.

In some embodiments, provided herein are Protein S antibodies, wherein the antibodies comprise the CDR amino acid sequences of SEQ ID NO: 10, SEQ ID NO: 16, SEQ ID NO: 31, SEQ ID NO: 43, SEQ ID NO: 55, and SEQ ID NO: 67.

In some embodiments, provided herein are Protein S antibodies, wherein the antibodies comprise the CDR amino acid sequences of SEQ ID NO: 11, SEQ ID NO: 20, SEQ ID NO: 32, SEQ ID NO: 44, SEQ ID NO: 56, and SEQ ID NO: 68.

In some embodiments, provided herein are Protein S antibodies, wherein the antibodies comprise the CDR amino acid sequences of SEQ ID NO: 117, SEQ ID NO: 118, SEQ ID NO: 119, SEQ ID NO: 120, SEQ ID NO: 121, and SEQ ID NO: 122.

In some embodiments, provided herein are Protein S antibodies, wherein the antibodies comprise the CDR amino acid sequences of SEQ ID NO: 117, SEQ ID NO: 118, SEQ ID NO: 123, SEQ ID NO: 124, SEQ ID NO: 125, and SEQ ID NO: 126.

In some embodiments, provided herein are Protein S antibodies, wherein the antibodies comprise the CDR amino acid sequences of SEQ ID NO: 127, SEQ ID NO: 128, SEQ ID NO: 129, SEQ ID NO: 130, SEQ ID NO: 50, and SEQ ID NO: 131.

In some embodiments, provided herein are Protein S antibodies, wherein the antibodies comprise the CDR amino acid sequences of SEQ ID NO: 136, SEQ ID NO: 17, SEQ ID NO: 137, SEQ ID NO: 138, SEQ ID NO: 139, and SEQ ID NO: 140.

In some embodiments, provided herein are Protein S antibodies, wherein the antibodies comprise the CDR amino acid sequences of SEQ ID NO: 141, SEQ ID NO: 142, SEQ ID NO: 143, SEQ ID NO: 144, SEQ ID NO: 145, and SEQ ID NO: 146.

In some embodiments, provided herein are Protein S antibodies, wherein the antibodies comprise the CDR amino acid sequences of SEQ ID NO: 174, SEQ ID NO: 175, SEQ ID NO: 176, SEQ ID NO: 179, SEQ ID NO: 180, and SEQ ID NO: 181.

In some embodiments, provided herein are Protein S antibodies, wherein the antibodies comprise the CDR amino acid sequences of SEQ ID NO: 184, SEQ ID NO: 185, SEQ ID NO: 186, SEQ ID NO: 189, SEQ ID NO: 190, and SEQ ID NO: 191.

In some embodiments, provided herein are Protein S antibodies, wherein the antibodies comprise the CDR amino acid sequences of SEQ ID NO: 194, SEQ ID NO: 195, SEQ ID NO: 196, SEQ ID NO: 199, SEQ ID NO: 200, and SEQ ID NO: 201.

In some embodiments, provided herein are Protein S antibodies, wherein the antibodies comprise the CDR amino acid sequences of SEQ ID NO: 204, SEQ ID NO: 205, SEQ ID NO: 206, SEQ ID NO: 209, SEQ ID NO: 210, and SEQ ID NO: 211.

Exemplary Protein S Antibodies—Kappa and Lambda Light Chains

Provided herein are amino acid sequences for the kappa and lambda light chain constant regions of exemplary Protein S antibodies of the disclosure. Any of the Protein S antibodies provided herein (provided in the preceding section) may have a kappa light chain constant region or a lambda light chain constant region. The sequences of the kappa and lambda light chain constant regions are provided in Table 3.

TABLE 3

| Kappa light chain sequence | RTVAAPSVFIFPPSDEQLKSGTASV VCLLNNFYPREAKVQWKVDNALQS GNSQESVTEQDSKDSTYSLSSTLT LSKADYEKHKVYACEVTHQGLSSP VTKSFNRGEC (SEQ ID NO: 214) |
|---|---|
| Lambda light chain sequence | GQPKAAPSVTLFPPSSEELQANKAT LVCLISDFYPGAVTVAWKADSSPVK AGVETTTPSKQSNNKYAASSYLSLT PEQWKSHRSYSCQVTHEGSTVEKTV APTECS (SEQ ID NO: 215) |

In exemplary embodiments, the Protein S antibody having the light chain sequence of SEQ ID NO: 214 comprises CDRs having the amino acid sequences as set forth in SEQ ID NO: 2, SEQ ID NO: 13, SEQ ID NO: 22, SEQ ID NO: 34, SEQ ID NO: 46, and SEQ ID NO: 58.

In exemplary embodiments, the Protein S antibody having the light chain sequence of SEQ ID NO: 215 comprises CDRs having the amino acid sequences as set forth in SEQ ID NO: 2, SEQ ID NO: 13, SEQ ID NO: 22, SEQ ID NO: 34, SEQ ID NO: 46, and SEQ ID NO: 58.

In exemplary embodiments, the Protein S antibody having the light chain sequence of SEQ ID NO: 214 comprises CDRs having the amino acid sequences as set forth in SEQ ID NO: 10, SEQ ID NO: 16, SEQ ID NO: 31, SEQ ID NO: 43, SEQ ID NO: 55, and SEQ ID NO: 67.

In exemplary embodiments, the Protein S antibody having the light chain sequence of SEQ ID NO: 215 comprises CDRs having the amino acid sequences as set forth in SEQ ID NO: 10, SEQ ID NO: 16, SEQ ID NO: 31, SEQ ID NO: 43, SEQ ID NO: 55, and SEQ ID NO: 67.

In exemplary embodiments, the Protein S antibody having the light chain sequence of SEQ ID NO: 214 comprises CDRs having the amino acid sequences as set forth in SEQ ID NO: 174, SEQ ID NO: 175, SEQ ID NO: 176, SEQ ID NO: 179, SEQ ID NO: 180, and SEQ ID NO: 181.

In exemplary embodiments, the Protein S antibody having the light chain sequence of SEQ ID NO: 215 comprises CDRs having the amino acid sequences as set forth in SEQ ID NO: 174, SEQ ID NO: 175, SEQ ID NO: 176, SEQ ID NO: 179, SEQ ID NO: 180, and SEQ ID NO: 181.

In exemplary embodiments, the Protein S antibody having the light chain sequence of SEQ ID NO: 214 comprises the variable heavy and variable light chains having the amino acid sequences as set forth in SEQ ID NO: 71 and SEQ ID NO: 72.

In exemplary embodiments, the Protein S antibody having the light chain sequence of SEQ ID NO: 215 comprises the variable heavy and variable light chains having the amino acid sequences as set forth in SEQ ID NO: 71 and SEQ ID NO: 72.

In exemplary embodiments, the Protein S antibody having the light chain sequence of SEQ ID NO: 214 comprises the variable heavy and variable light chains having the amino acid sequences as set forth in SEQ ID NO: 89 and SEQ ID NO: 90.

In exemplary embodiments, the Protein S antibody having the light chain sequence of SEQ ID NO: 215 comprises the variable heavy and variable light chains having the amino acid sequences as set forth in SEQ ID NO: 89 and SEQ ID NO: 90.

In exemplary embodiments, the Protein S antibody having the light chain sequence of SEQ ID NO: 214 comprises the variable heavy and variable light chains having the amino acid sequences as set forth in SEQ ID NO: 177 and SEQ ID NO: 182.

In exemplary embodiments, the Protein S antibody having the light chain sequence of SEQ ID NO: 215 comprises the variable heavy and variable light chains having the amino acid sequences as set forth in SEQ ID NO: 177 and SEQ ID NO: 182.

Exemplary Protein S Antibodies—Variable Region Sequences

Provided herein are amino acid sequences for the variable domains of exemplary Protein S antibodies of the disclosure. The exemplary variable light chain amino acid sequences and exemplary variable heavy chain amino acid sequences are presented in Tables 4A and 4B below. Table 4C presents exemplary combinations of variable heavy and variable light chains.

Accordingly, in some embodiments, the Protein S antibodies of the disclosure comprise the variable chain amino acid sequence of any one of the combinations provided in Table 4C. In some embodiments, provided herein are Protein S antibodies, wherein the antibodies comprise a variable light chain comprising the amino acid sequence selected from SEQ ID NO: 69, 71, 73, 75, 77, 79, 81, 87, 89, 91, 148, 150, 152, 156 158, 177, 187, 197, and 207. In some embodiments, provided herein are Protein S antibodies, wherein the antibodies comprise a variable heavy chain comprising the amino acid sequence selected from SEQ ID NO: 70, 72, 74, 76, 78, 80, 82, 88, 90, 92, 149, 151, 153, 157 159, 182, 192, 202, and 212.

TABLE 4A

Exemplary Variable Light Chain Amino Acid Sequences of Protein S Monoclonal Antibodies SYELTQPPSVSVSPGQTASITCSGDKLGDKYACWY
QQKPGQSPVLVIYQDTKRPSGIPERFSGSNSGNTA
TLTISGTQAMDEADYYCQAWDSNTVVFGGGTKLTV
L
(SEQ ID NO: 69)

SSDLTQGPAVSVALGQTVRITCQGDSLRNYYASWY
QQKPGQAPVPVIYGKNDRPSGIPDRFSGSISGNTA
SLTITGAQAEDEAHYYCNSRDSSGNHVVFGGGTKL
TVL
(SEQ ID NO: 71)

QSALTQPASVSGSPGQSITISCTGTSSDVGGYEFV
SWYQHHPGKAPKLMIYDVSSRPSGVSNRFSGSKSG
NTASLTISGLQAEDEADYYCSSYTRSSTVVFGGGA
RLTVL
(SEQ ID NO: 73)

SYELNQPPSVSVSPGQTASITCSGDKLGDKYASWY
QQKPGQSPVVAIYQNSKRPSGIPERFSASNSGNTA
TLTISGTQALDEADYYCQAWDSSTWVFGGGTKLTV
L
(SEQ ID NO: 75)

EIVLTQSPATLSLSPGERATLSCRASQSVSIYLAW
YQQKPGQAPRLLIYDASNRATGIPARFSGSGSGTD
FTLTISSLEPEDFAVYYCQQRSNWPLTFGPGTKVD
IK
(SEQ ID NO: 77)

TABLE 4A-continued

Exemplary Variable Light Chain Amino Acid Sequences of Protein S Monoclonal Antibodies EIVMTQSPATLSVSPGERATLSCRASQRINSNLAW
YQQKPGQAPRLLIYGASTRATGIPARFSGSGSGTE
FTLTISSLQSEDFAAYYCQQYDNWPLTFGGGTKVE
IK
(SEQ ID NO: 79)

DIVMTQSPLSLPVTPGEPASISCRSSQSLLHSNGY
NYLDWYLQKPGQSPQLLIYLGSNRASGVPDRFSGS
GSGTDFTLKISRVEAEDVGVYYCMQALQTFTFGPG
TKVDIK
(SEQ ID NO: 81)

QAVVTQESALTTSPGETVTLTCRSSTGAVTASNYA
NWVQEKPDHLFTGLIGSTNNRAPGVPARFSGSLIG
DKAALTITGAQTEDEAIYFCALWYSDHFVFGGGTK
LTVL
(SEQ ID NO: 87)

EIVMTQSPATLSVSPGERATLSCRASQSVTSNLAW
YQQKPGQAPRLLIYDASTRATGIPARFSGSGSGTE
FTLTISSLQSEDFAIYYCQQYNNWPTFGQGTRLEI
K
(SEQ ID NO: 89)

DIVMTQTPLSSPVTLGQPASISCRSSQSLVHSDGN
TYLSWLQQRPGQPPRLLIYKISNRFSGVPDRFSGS
GAGTDFTLKISRVEAEDVGVYYCMQATQFPHLTFG
GGTKVEIK
(SEQ ID NO: 91)

DIQMTQSPSSLSASVGDRVTITCRASQGINNYLAW
FQQKPGKAPKSLIYAASSLQSGVPSKFSGSGSGTD
FTLTISSLQPEDFATYYCQQYNSYPRTFGQGTKVE
IK
(SEQ ID NO: 148)

DIQMTQSPSSLSASVGDRVTITCRASQGINNYLAW
FQQKPGKAPKSLIYAASNLQSGVPLKFSGSGSGTD
FTLTISSLQPEDFATYYCQQYNSYPITFGQGTRLE
IK
(SEQ ID NO: 150)

DIQMTQSPSSLSASVGDRVTITCRASQSISTFLNW
YQQKPGKAPKLLIYATSSLRSGVPSRFSGSGSGTD
FTLTISSLQPEDFAIYYCQQSYSTPRTFGQGTQVE
IK
(SEQ ID NO: 152)

EIVLTQSPGTLSLSPGERATLSCRASQSVGSSYLA
WYQQKPGQAPRLLISGASGRATGIPDRFSGSGSGT
DFTLTISRLEPEDFTVYYCQQYGSSPYTFGQGTKL
EIK
(SEQ ID NO: 156)

DIQMNQSPSSLSASLGDTITITCRASQNIHMWLSW
YQQKPGNIPKLLIFKTSNLHTGVPSRFSGSGSGTD
FTLTISSLQPEDIATYYCLQGQSYPFTFGGGTKLE
IK
(SEQ ID NO: 158)

DIQMTQSPSSLSASVGDRVTITCRASQSISSYLNW
YQQKPGKAPKLLIYAASSLQSGVPSRFSGSGSGTD
FTLTISSLQPEDFATYYCQQSYSSLTFGQGTRLEI
K
(SEQ ID NO: 177)

SYVLTQPPSVSVAPGQTARITCGGDNIGGKSVHWY
QQKPGQAPVMVVYDDSDRPSGIPERFAGSNSGNTA
TLAISRVEAGDEADYYCQVWEITSDHPAFGGGTR
LTVL
(SEQ ID NO: 187)

TABLE 4A-continued

Exemplary Variable Light Chain Amino
Acid Sequences of Protein S
Monoclonal Antibodies SYELTQPPSVSVSPGQTASITCSGDKLGDKYVFWY
QQKPGQSPVLVIYQDSKRPSGIPERFSGSNSGNTA
TLTISGTQTMDEADYYCQAWDSSTVGFGGGTKLAV
L
(SEQ ID NO: 197)

SYELTQPPSVSVSPGQTASITCSGDKLGDKYAFWY
QQKPGQSPVLVIYQDNKRPSGIPERFSGSNSGNTA
TLTISGTQAVDEADYYCQAWDSSTAVFGGGTKLTV
L
(SEQ ID NO: 207)

TABLE 4B

Exemplary Variable Heavy Chain Amino
Acid Sequences of Protein S
Monoclonal Antibodies QLQLQESGPGLVKPSETLSLTCTVSGGSISSSSYY
WGWIRQPPGKGLEWIGNIYYSGNTYYNPSLKSRVT
ISVDTSKNQFSLKLSSMTAADTAVYYCARCSGYGY
SSGRSYFDYWGQETLVTVSS
(SEQ ID NO: 70)

QVQLVQSGAEVKKPGSSVKVSCKVSGGTFSSYSIS
WVRQAPGQGLEWMGGIIPIFGTTNYAQKFQGRVTI
TADESTSTAYMDLSSLKSEDTAMYYCEGGRVGADF
DYWGQGTLVTVSS
(SEQ ID NO: 72)

QVQLQESGPGLVKPSQTLSLTCTVSGGSITSDGYH
WSWIRQYPGKGLDWIGYIYYTGNTYYNPSLKSRVT
ISVGTSQNQFSLKLISVTAADTAVYYCARRLSTGP
YFDYWGQGTLVTVSS
(SEQ ID NO: 74)

EVQLVESGGGLVQPGRSLRLSCAASGFTFDDYAMH
WVRQAPGKGLEWVSGITWNSGNIGYADSVI<GRFT
ISRDNAI<NSLYLHMNSLRIEDTAFYYCAI<GRAV
SDTFDIWGQGTMVTVSS
(SEQ ID NO: 76)

QVQLVESGGGVVQPGRSLRLSCAASGFTFSTYGFH
WVRQPPGKGLEWVAVIYYDGINKYYADSVKGRFTI
SRDNSKNTLFLQMNSLRAEDTAVYYCAESDLDYWG
QGTLVTVSS
(SEQ ID NO: 78)

QVQLQESGPGLVKPSETLSLTCAVSGYSISSGYYW
GWIRQPPGKGLDWIGSIYYSGSTYYNPSLKSRVTI
SVDTSKNQISLKLSSVTAADTAVYYCATTYSDIVT
GYYNDAFDIWGQGTMVTVSS
(SEQ ID NO: 80)

QVQLVQSGAEVKKPGSSVKVSCKASGDTFSNHAIN
WVRQAPGQGLEWMGGYIPIFGTTNSAQKFRGRVTI
TADKSTNTAYMALSSLRSEDTAVYYCARGGLAGSH
YKNYYYDGMDVWGQGTTVTVSS
(SEQ ID NO: 82)

QVQLVQSGAEVKKPGASVKVSCKSSGHTFTGYYMH
WVRQAPGQGLEWMGWINPNSGDTNYAQKFQGRVTM
TRDTSISTAYMEMSRLRSDDTAVYYCARDSQILWF
GELGYWGQGTLVTVSS
(SEQ ID NO: 88)

QVQLQESGPGLVKPSETLSLTCGVSGGSISSTNWW
SWVRQPPGKGLEWIGEIYQTGSTDYDPSLKSRVTI
SIDKSKNQFSLKLYSVTAADTAVYYCARRFGELDY
WGQGTLVTVSS
(SEQ ID NO: 90)

TABLE 4B-continued

Exemplary Variable Heavy Chain Amino
Acid Sequences of Protein S
Monoclonal Antibodies QVQLQESGPGLVKPSETLSLTCTVSGGSISNYYWN
WIRQPPGKGLEWIGYIYYIGITDYNPSLKSRVTIS
VDTSKNQFSLKVTSVTAADTAVYYCAALSGDHAFD
IWGQGTLVTVSS
(SEQ ID NO: 92)

QLQLQESGPGLVKPSETLSLTCTVSGGSITNSNYY
WGWIRQPPGKGLEWIGSVYYSGTTYYNPSLKSRVT
ISVDPSKNQFSLKLSSVTAADTAVYYCVRESESYY
YYGSDVWGQGTTVTVSS
(SEQ ID NO: 149)

EVQLVESGGGLVKPGGSLRLSCAASGFTFSSYNMN
WVRQAPGRGLDWVSSISSSSSYIYYADSVKGRFTI
SRDNAKNSLYLQMNTLRAEDTAVYYCARDEEWELL
TGFDYWGQGTLVTVSS
(SEQ ID NO: 151)

QVQLQESGPGLVKPSETLSLTCTVSGGSISGNYWS
WIRQPPGKGLEWIGYIYYSGSTNYNPSLKSRVTIS
VDTSKNQFSLKLSSVTAADTAVYYCARDLDYFTWG
AYSDWYFDLWGRGTLVTVSS
(SEQ ID NO: 153)

QVQLQQSGPGLVKPSQTLSLTCAISGDSVSNNNAA
WNWIRQSPSRGLEWLGGTYYRSKWYNDYAVSVKSR
IIINPVTSKNQFSLQLNSVTPEDTAVYYCARGSSW
YRFFDYWGQGTLVTVSS
(SEQ ID NO: 157)

QVQLQQSGTELVRPGTSVKMSCKAAGYTFTNHWIG
WVKQRPGHGLEWIGDIYPGGGYTNYNEKFKGKASL
TADTSSTTAYMQLSSLTSEDSAIYYCSRFGDQNWA
WFAYWGQGTLVTVSA
(SEQ ID NO: 159)

EVQLVESGGGLVKPGGSLRLSCAASGISFSNAWMS
WVRQAPGKGLEWVGRIKANPDGGTTDYAAPVKGRF
TISRDDSKNTLYLQMNSLKTEDTAVYYCTTELDIL
LWFTSFDYWGQGTLVTVSS
(SEQ ID NO: 182)

EVQLVESGGGLVQPGGSLRLSCAASGFTFSSYSMN
WVRQAPGKGLEWVAYISSSTRTIFYADSVKGRFTI
SRDNAKNSLYLQMNSLRDEDTAFYYCARERSAFDY
WGQGTLVTVSS
(SEQ ID NO: 192)

QVQLVQSGSEVKKPGASVKVSCKASGYTFTNYYIH
WVRQAPGQGLEWMGIITPSGGTTSYAQKFQGRVTM
TRDTSTNTVYMGLSSLRSEDTAMYYCARAGVQLDR
RGWFDPWGQGTLVTVSS
(SEQ ID NO: 202)

QVQLVQSGAEVKKPGASVKVSCKASGYTFTSYYIH
WVRQAPGQGLEWMGVTSPSGRSTSFAQKFQGRVTM
TRDTSTSAVYMDLSLRSEDTAVYYCARGGVTIHL
ERRGYFDYWGQGTLVIVSS
(SEQ ID NO: 212)

TABLE 4C

Exemplary Variable Light Chain and Variable Heavy Chain Amino
Acid Sequence Combinations of Protein S Monoclonal Antibodies

| Combination Number | Variable Light Chain Amino Acid Sequence | Variable Heavy Chain Amino Acid Sequence |
|---|---|---|
| Combination 1 | SEQ ID NO: 69 | SEQ ID NO: 70 |
| Combination 2 | SEQ ID NO: 71 | SEQ ID NO: 72 |
| Combination 3 | SEQ ID NO: 73 | SEQ ID NO: 74 |
| Combination 4 | SEQ ID NO: 75 | SEQ ID NO: 76 |

TABLE 4C-continued

Exemplary Variable Light Chain and Variable Heavy Chain Amino Acid Sequence Combinations of Protein S Monoclonal Antibodies

| Combination Number | Variable Light Chain Amino Acid Sequence | Variable Heavy Chain Amino Acid Sequence |
|---|---|---|
| Combination 5 | SEQ ID NO: 77 | SEQ ID NO: 78 |
| Combination 6 | SEQ ID NO: 79 | SEQ ID NO: 80 |
| Combination 7 | SEQ ID NO: 81 | SEQ ID NO: 82 |
| Combination 10 | SEQ ID NO: 87 | SEQ ID NO: 88 |
| Combination 11 | SEQ ID NO: 89 | SEQ ID NO: 90 |
| Combination 12 | SEQ ID NO: 91 | SEQ ID NO: 92 |
| Combination 13 | SEQ ID NO: 148 | SEQ ID NO: 149 |
| Combination 14 | SEQ ID NO: 150 | SEQ ID NO: 151 |
| Combination 15 | SEQ ID NO: 152 | SEQ ID NO: 153 |
| Combination 17 | SEQ ID NO: 156 | SEQ ID NO: 157 |
| Combination 18 | SEQ ID NO: 158 | SEQ ID NO: 159 |
| Combination 19 | SEQ ID NO: 177 | SEQ ID NO: 182 |
| Combination 20 | SEQ ID NO: 187 | SEQ ID NO: 192 |
| Combination 21 | SEQ ID NO: 197 | SEQ ID NO: 202 |
| Combination 22 | SEQ ID NO: 207 | SEQ ID NO: 212 |

In some embodiments, the heavy and light chain variable domains of the Protein S antibodies provided herein include the amino acid sequence of any one of the numbered combinations presented in Table 4C.

In some embodiments, provided herein are Protein S antibodies, wherein the light chain variable domain of the antibodies comprise the amino acid sequence of SEQ ID NO: 69 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibodies comprise the amino acid sequence of SEQ ID NO: 70, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 69 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and wherein the heavy chain variable domain of the antibody comprises the amino acid sequence of SEQ ID NO: 70, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 1, SEQ ID NO: 12, SEQ ID NO: 21, SEQ ID NO: 33, SEQ ID NO: 45, and SEQ ID NO: 57.

In some embodiments, provided herein are Protein S antibodies, wherein the light chain variable domain of the antibodies comprise the amino acid sequence of SEQ ID NO: 71 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibody comprises the amino acid sequence of SEQ ID NO: 72, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 71 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 72, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 2, SEQ ID NO: 13, SEQ ID NO: 22, SEQ ID NO: 34, SEQ ID NO: 46, and SEQ ID NO: 58.

In some embodiments, provided herein are Protein S antibodies, wherein the light chain variable domain of the antibodies comprise the amino acid sequence of SEQ ID NO: 73 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibody comprises the amino acid sequence of SEQ ID NO: 74, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 73 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 74, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 3, SEQ ID NO: 14, SEQ ID NO: 23, SEQ ID NO: 35, SEQ ID NO: 47, and SEQ ID NO: 59.

In some embodiments, provided herein are Protein S antibodies, wherein the light chain variable domain of the antibodies comprise the amino acid sequence of SEQ ID NO: 75 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibody comprises the amino acid sequence of SEQ ID NO: 76, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 75 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 76, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 1, SEQ ID NO: 15, SEQ ID NO: 24, SEQ ID NO: 36, SEQ ID NO: 48, and SEQ ID NO: 60.

In some embodiments, provided herein are Protein S antibodies, wherein the light chain variable domain of the antibodies comprise the amino acid sequence of SEQ ID NO: 77 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibody comprises the amino acid sequence of SEQ ID NO: 78, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 77 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 78, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 4, SEQ ID NO: 16, SEQ ID NO: 25, SEQ ID NO: 37, SEQ ID NO: 49, and SEQ ID NO: 61.

In some embodiments, provided herein are Protein S antibodies, wherein the light chain variable domain of the antibodies comprise the amino acid sequence of SEQ ID NO: 79 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibody comprises the amino acid sequence of SEQ ID NO: 80, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 79 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 80, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 5, SEQ ID NO: 17, SEQ ID NO: 26, SEQ ID NO: 38, SEQ ID NO: 50, and SEQ ID NO: 62.

In some embodiments, provided herein are Protein S antibodies, wherein the light chain variable domain of the antibodies comprise the amino acid sequence of SEQ ID NO: 81 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibody comprises the amino acid sequence of SEQ ID NO: 82, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 81 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 82, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 6, SEQ ID NO: 18, SEQ ID NO: 27, SEQ ID NO: 39, SEQ ID NO: 51, and SEQ ID NO: 63.

In some embodiments, provided herein are Protein S antibodies, wherein the light chain variable domain of the antibodies comprise the amino acid sequence of SEQ ID NO: 87 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibody comprises the amino acid sequence of SEQ ID NO: 88, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 87 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 88, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 9, SEQ ID NO: 19, SEQ ID NO: 30, SEQ ID NO: 42, SEQ ID NO: 54, and SEQ ID NO: 66.

In some embodiments, provided herein are Protein S antibodies, wherein the light chain variable domain of the antibodies comprise the amino acid sequence of SEQ ID NO: 89 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibody comprises the amino acid sequence of SEQ ID NO: 90, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 89 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 90, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 10, SEQ ID NO: 16, SEQ ID NO: 31, SEQ ID NO: 43, SEQ ID NO: 55, and SEQ ID NO: 67.

In some embodiments, provided herein are Protein S antibodies, wherein the light chain variable domain of the antibodies comprise the amino acid sequence of SEQ ID NO: 91 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibody comprises the amino acid sequence of SEQ ID NO: 92, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 91 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 92, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 11, SEQ ID NO: 20, SEQ ID NO: 32, SEQ ID NO: 44, SEQ ID NO: 56, and SEQ ID NO: 68.

In some embodiments, provided herein are Protein S antibodies, wherein the light chain variable domain of the antibodies comprise the amino acid sequence of SEQ ID NO: 148 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibody comprises the amino acid sequence of SEQ ID NO: 149, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 148 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 149, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 117, SEQ ID NO: 118, SEQ ID NO: 119, SEQ ID NO: 120, SEQ ID NO: 121, and SEQ ID NO: 122.

In some embodiments, provided herein are Protein S antibodies, wherein the light chain variable domain of the antibodies comprise the amino acid sequence of SEQ ID NO: 150 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibody comprises the amino acid sequence of SEQ ID NO: 151, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 150 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 151, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 117, SEQ ID NO: 118, SEQ ID NO: 123, SEQ ID NO: 124, SEQ ID NO: 125, and SEQ ID NO: 126.

In some embodiments, provided herein are Protein S antibodies, wherein the light chain variable domain of the antibodies comprise the amino acid sequence of SEQ ID NO: 152 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibody comprises the amino acid sequence of SEQ ID NO: 153, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 152 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 153, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 127, SEQ ID NO: 128, SEQ ID NO: 129, SEQ ID NO: 130, SEQ ID NO: 50, and SEQ ID NO: 131.

In some embodiments, provided herein are Protein S antibodies, wherein the light chain variable domain of the antibodies comprise the amino acid sequence of SEQ ID NO: 156 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibody comprises the amino acid sequence of SEQ ID NO: 157, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 156 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 157, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 136, SEQ ID NO: 17, SEQ ID NO: 137, SEQ ID NO: 138, SEQ ID NO: 139, and SEQ ID NO: 140.

In some embodiments, provided herein are Protein S antibodies, wherein the light chain variable domain of the antibodies comprise the amino acid sequence of SEQ ID NO: 158 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibody comprises the amino acid sequence of SEQ ID NO: 159, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 158 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 159, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 141, SEQ ID NO: 142, SEQ ID NO: 143, SEQ ID NO: 144, SEQ ID NO: 145, and SEQ ID NO: 146.

In some embodiments, provided herein are Protein S antibodies, wherein the light chain variable domain of the antibodies comprise the amino acid sequence of SEQ ID NO: 177 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibody comprises the amino acid sequence of SEQ ID NO: 182, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 177 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 182, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 174, SEQ ID NO: 175, SEQ ID NO: 176, SEQ ID NO: 179, SEQ ID NO: 180, and SEQ ID NO: 181.

In some embodiments, provided herein are Protein S antibodies, wherein the light chain variable domain of the antibodies comprise the amino acid sequence of SEQ ID NO: 187 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibody comprises the amino acid sequence of SEQ ID NO: 192, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 187 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 192, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 184, SEQ ID NO: 185, SEQ ID NO: 186, SEQ ID NO: 189, SEQ ID NO: 190, and SEQ ID NO: 191.

In some embodiments, provided herein are Protein S antibodies, wherein the light chain variable domain of the antibodies comprise the amino acid sequence of SEQ ID NO: 197, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibody comprises the amino acid sequence of SEQ ID NO: 202, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 197 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 202, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 194, SEQ ID NO: 195, SEQ ID NO: 196, SEQ ID NO: 199, SEQ ID NO: 200, and SEQ ID NO: 201.

In some embodiments, provided herein are Protein S antibodies, wherein the light chain variable domain of the antibodies comprise the amino acid sequence of SEQ ID NO: 207, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibody comprises the amino acid sequence of SEQ ID NO: 212, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 207, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 212, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 204, SEQ ID NO: 205, SEQ ID NO: 206, SEQ ID NO: 209, SEQ ID NO: 210, and SEQ ID NO: 211.

As noted above, Protein S comprises four domains: the γ-carboxy-glutamic acid domain (Gla-domain), the thrombin-sensitive region (TSR), the epidermal growth factor-like domain (EGF domain), and the sex hormone binding globulin-like domain (SHBG domain). FIG. 1 depicts the schematic diagram of Protein S showing these modular domains of Protein S. The TSR is within the heavy chain of Protein S. The heavy chain of Protein S represents amino acids 42-296 of Protein S, the TSR represents amino acids 88-116, the signal peptide represents amino acids 1-24 and the propeptide represents amino acids 25-41.

In some embodiments, the Protein S antibodies provided herein bind to the Gla domain of Protein S. In some embodiments, the Protein S antibodies provided herein bind to the Gla domain and inhibit the cofactor activity of Protein S for both APC and TFPI. Exemplary antibodies that bind to the Gla domain and inhibit the cofactor activity of Protein S for both APC and TFPI may comprise the light chain variable domain comprising the amino acid sequence of SEQ ID NO: 77 and the heavy chain variable domain comprising the amino acid sequence of SEQ ID NO: 78; or such antibodies may comprise the light and heavy CDR amino acid sequences of SEQ ID NO: 4, SEQ ID NO: 16, SEQ ID NO: 25, SEQ ID NO: 37, SEQ ID NO: 49, and SEQ ID NO: 61.

In some embodiments, the Protein S antibodies provided herein bind to EGF domain of Protein S. In some embodiments, the Protein S antibodies provided herein bind to the SHBG-like domain of Protein S. In some embodiments, the Protein S antibodies provided herein bind to the C-terminal region of Protein S. In some embodiments, the Protein S antibodies provided herein bind the C-terminal region of Protein S, and inhibit the cofactor activity of Protein S for TFPI.

In some embodiments, the Protein S antibodies provided herein bind to Protein S fragments. The Protein S fragments are referred to herein as the Protein S heavy chain when they are expressed recombinantly in a cell line, such as HEK293 cells, for example. The Protein S heavy chain comprises amino acids 42-296. In some embodiments, the Protein S antibodies provided herein bind the Protein S heavy chain. Exemplary antibodies that bind to the Protein S heavy chain may comprise the light chain variable domain comprising the amino acid sequence of SEQ ID NO: 69 and the heavy chain variable domain comprising the amino acid sequence of SEQ ID NO: 70, or may comprise the light and heavy CDR amino acid sequences of SEQ ID NO: 1, SEQ ID NO: 12, SEQ ID NO: 21, SEQ ID NO: 33, SEQ ID NO: 45, and SEQ ID NO: 57. As another example, antibodies that bind to the Protein S heavy chain may comprise the light chain variable domain comprising the amino acid sequence of SEQ ID NO: 79 and the heavy chain variable domain comprising the amino acid sequence of SEQ ID NO: 80, or may comprise the light and heavy CDR amino acid sequences of SEQ ID NO: 5, SEQ ID NO: 17, SEQ ID NO: 26, SEQ ID NO: 38, SEQ ID NO: 50, and SEQ ID NO: 62.

In some embodiments, the Protein S antibodies provided herein bind to the Protein S heavy chain comprising the TSR. In some embodiments, the Protein S antibodies provided herein bind to the Protein S heavy chain not comprising the TSR.

In some embodiments, the Protein S antibodies provided herein bind to the TSR of Protein S. In some embodiments, the Protein S antibodies provided herein do not bind to the TSR. In some embodiments, the Protein S antibodies provided herein bind to the heavy chain of Protein S, but do not bind the TSR region of the heavy chain. In some embodiments, the Protein S antibodies provided are dual inhibitors of APC and TFPI, and bind to the TSR of Protein S. In some embodiments, the Protein S antibodies provided are dual inhibitors of APC and TFPI, and do not bind to the TSR of Protein S. In some embodiments, the Protein S antibodies provided are inhibitors of APC, and do not bind to the TSR of Protein S. In some embodiments, the Protein S antibodies provided are inhibitors of TFPI, and do not bind to the TSR of Protein S.

Exemplary antibodies that bind to the TSR and are dual inhibitors of APC and TFPI may comprise the light chain variable domain comprising the amino acid sequence of SEQ ID NO: 89 and the heavy chain variable domain comprising the amino acid sequence of SEQ ID NO: 90, or may comprise the light and heavy CDR amino acid sequences of SEQ ID NO: 10, SEQ ID NO: 16, SEQ ID NO: 31, SEQ ID NO: 43, SEQ ID NO: 55, and SEQ ID NO: 67. As another example, antibodies that bind to the TSR and are dual inhibitors of APC and TFPI may comprise the light chain variable domain comprising the amino acid sequence of SEQ ID NO: 75 and the heavy chain variable domain comprising the amino acid sequence of SEQ ID NO: 76, or may comprise the light and heavy CDR amino acid sequences of SEQ ID NO: 1, SEQ ID NO: 15, SEQ ID NO: 24, SEQ ID NO: 36, SEQ ID NO: 48, and SEQ ID NO: 60.

In some embodiments, the Protein S antibodies provided herein do not bind to the TSR of Protein S, and cause a dual inhibition of the activity of APC and TFPI. In some embodiments, the Protein S antibodies provided herein do not bind to the TSR of Protein S, and cause an inhibition of the activity of APC. In some embodiments, the Protein S antibodies provided herein do not bind to the TSR of Protein S, and cause an inhibition of the activity of TFPI.

Exemplary antibodies that do not bind to the TSR and are dual inhibitors of APC and TFPI may comprise the light chain variable domain comprising the amino acid sequence of SEQ ID NO: 73 and the heavy chain variable domain comprising the amino acid sequence of SEQ ID NO: 74, or may comprise the light and heavy CDR amino acid sequences of SEQ ID NO: 3, SEQ ID NO: 14, SEQ ID NO: 23, SEQ ID NO: 35, SEQ ID NO: 47, and SEQ ID NO: 59.

In some embodiments, the Protein S antibodies provided herein bind to a linear epitope of Protein S. Exemplary antibodies that bind to a linear epitope of Protein S may comprise the light chain variable domain comprising the amino acid sequence of SEQ ID NO: 77 and the heavy chain variable domain comprising the amino acid sequence of SEQ ID NO: 78, or may comprise the light and heavy CDR amino acid sequences of SEQ ID NO: 4, SEQ ID NO: 16, SEQ ID NO: 25, SEQ ID NO: 37, SEQ ID NO: 49, and SEQ ID NO: 61.

In some embodiments, the Protein S antibodies provided herein bind to a conformational epitope, i.e., an epitope that is non-linear. Exemplary antibodies that bind to a non-linear epitope and inhibit the cofactor activity of Protein S for APC may comprise the light chain variable domain comprising the amino acid sequence of SEQ ID NO: 91 and the heavy chain variable domain comprising the amino acid sequence of SEQ ID NO: 92, or may comprise the light and heavy CDR amino acid sequences of SEQ ID NO: 11, SEQ ID NO: 20, SEQ ID NO: 32, SEQ ID NO: 44, SEQ ID NO: 56, and SEQ ID NO: 68. Exemplary antibodies that bind to a non-linear epitope and inhibit the cofactor activity of Protein S for APC and TFPI may comprise the light chain variable domain comprising the amino acid sequence of SEQ ID NO: 89 and the heavy chain variable domain comprising the amino acid sequence of 90, or may comprise the light and heavy CDR amino acid sequences of SEQ ID NO: 10, SEQ ID NO: 16, SEQ ID NO: 31, SEQ ID NO: 43, SEQ ID NO: 55, and SEQ ID NO: 67.

As discussed above, Protein S can be found in a free form, or in a complexed form. Protein S can form a complex with at least TFPI, or with C4b-binding protein (C4BP). In some embodiments, the Protein S antibodies provided herein are capable of binding to Protein S in a free form, but not when in complexed form. In some embodiments, the Protein S antibodies provided herein are capable of binding to Protein S when Protein S is complexed, but not in free form. In some embodiments, the Protein S antibodies provided herein are capable of binding to Protein S that is either in free or complexed form. In some embodiments, the Protein S antibodies provided herein bind to a complexed Protein S, wherein the Protein S is bound to TFPI. In some embodiments, the Protein S antibodies provided herein bind to a complexed Protein S, wherein the Protein S is bound to C4BP.

In some embodiments, the Protein S antibodies provided herein bind Protein S, and the binding affinity of the antibodies to Protein S is calcium-dependent. In some embodiments, the Protein S antibodies provided herein bind Protein S, and the binding affinity of the antibodies to Protein S is not calcium-dependent. In some embodiments, the Protein S antibodies provided herein are dual inhibitors of APC and TFPI, and the binding affinity of the antibodies to Protein S is calcium-dependent. In some embodiments, the Protein S antibodies provided herein are dual inhibitors of APC and TFPI, and the binding affinity of the antibodies to Protein S is calcium-independent. In some embodiments, the Protein S antibodies provided herein are inhibitors of APC, and the binding affinity of the antibodies to Protein S is calcium-dependent. In some embodiments, the Protein S antibodies provided herein are inhibitors of APC, and the binding affinity of the antibodies to Protein S is calcium-independent. In some embodiments, the Protein S antibodies provided herein are inhibitors of TFPI, and the binding affinity of the antibodies to Protein S is calcium-independent. In some embodiments, the Protein S antibodies provided herein are inhibitors of TFPI, and the binding affinity of the antibodies to Protein S is calcium-dependent.

Exemplary antibodies that are dual inhibitors of the Protein S cofactor activity of APC and TFPI, wherein the binding affinity of the antibodies to Protein S is calcium-independent, may comprise the light chain variable domain comprising the amino acid sequence of SEQ ID NO: 71 and the heavy chain variable domain comprising the amino acid sequence of 72, or may comprise the light and heavy CDR amino acid sequences of SEQ ID NO: 2, SEQ ID NO: 13, SEQ ID NO: 22, SEQ ID NO: 34, SEQ ID NO: 46, and SEQ ID NO: 58.

Exemplary antibodies that are inhibitors of the Protein S cofactor activity of TFPI, wherein the wherein the binding affinity of the antibodies to Protein S is calcium-independent, may comprise the light chain variable domain comprising the amino acid sequence of SEQ ID NO: 87 and the heavy chain variable domain comprising the amino acid sequence of 88, or may comprise the light and heavy CDR amino acid sequences of SEQ ID NO: 9, SEQ ID NO: 19, SEQ ID NO: 30, SEQ ID NO: 42, SEQ ID NO: 54, and SEQ ID NO: 66.

Exemplary antibodies that are inhibitors of the Protein S cofactor activity of APC, wherein the wherein the binding affinity of the antibodies to Protein S is calcium-dependent, may comprise the light chain variable domain comprising the amino acid sequence of SEQ ID NO: 91 and the heavy chain variable domain comprising the amino acid sequence of 92, or may comprise the light and heavy CDR amino acid sequences of SEQ ID NO: 11, SEQ ID NO: 20, SEQ ID NO: 32, SEQ ID NO: 44, SEQ ID NO: 56, and SEQ ID NO: 68.

Exemplary antibodies that are dual inhibitors of the Protein S cofactor activity of APC and TFPI, wherein the wherein the binding affinity of the antibodies to Protein S is calcium-dependent, may comprise the light chain variable domain comprising the amino acid sequence of SEQ ID NO: 89 and the heavy chain variable domain comprising the amino acid sequence of 90, or may comprise the light and heavy CDR amino acid sequences of SEQ ID NO: 10, SEQ ID NO: 16, SEQ ID NO: 31, SEQ ID NO: 43, SEQ ID NO: 55, and SEQ ID NO: 67.

B. Generation of Protein S Antibodies

Production of the Protein S antibodies provided herein may be by use of any method known to those of ordinary skill in the art. In some embodiments, the antibodies are produced by hybridomas. In some embodiments, the antibodies are encoded by a nucleic acid and are expressed, purified, and isolated.

Accordingly, provided herein are nucleic acids encoding any of the antibodies disclosed herein, vectors comprising any of the nucleic acids encoding such antibodies, and host cells comprising such vectors. Also provided herein are exemplary nucleic acid sequences encoding for the variable heavy chains and variable light chains of the Protein S antibodies disclosed herein.

Tables 5A and 5B provide exemplary variable light chain nucleic acid sequences and exemplary variable heavy chain nucleic acid sequences. Exemplary combinations of nucleic acid sequences encoding for the variable heavy and light chain domains of the Protein S antibodies disclosed herein are presented in Table 5C. The exemplary amino acid sequences of Tables 4A-4C correspond to the nucleic acid sequences of Tables 5A-5C. The exemplary combinations of Table 5C correspond to the numbered combinations presented in Table 4C.

The person of ordinary skill in the art will appreciate that, because of redundancy in the triplet code, multiple nucleic acids may encode the same amino acid sequence. Thus, nucleic acid sequences that are not identical to those set forth in the tables below may still encode the Protein S antibodies of the disclosure.

TABLE 5A

Exemplary Variable Light Chain Nucleic
Acid Sequences of Anti-
Protein S Monoclonal Antibodies TCCTATGAGCTGACTCAGCCACCCTCAGTGTCCGT
GTCCCCAGGACAGACAGCCAGCATCACCTGCTCTG
GAGATAAATTGGGGGATAAATATGCTTGCTGGTAT
CAGCAGAAGCCAGGCCAGTCCCCTGTACTGGTCAT
CTATCAAGATACTAAGCGGCCCTCAGGGATCCCTG
AGCGATTCTCTGGCTCCAACTCTGGGAACACAGCC
ACTCTGACCATCAGCGGGACCCAGGCTATGGATGA
GGCTGACTATTACTGTCAGGCGTGGGACAGCAACA
CTGTGGTCTTCGGCGGAGGGACCAAGCTGACCGTC
CTA
(SEQ ID NO: 93)

TCCTCTGACCTGACTCAGGGCCCTGCTGTGTCTGT
GGCCCTGGGACAGACAGTCAGGATCACATGCCAAG
GAGACAGCCTCAGAAACTATTATGCAAGCTGGTAC
CAGCAGAAGCCAGGACAGGCCCCTGTACCTGTCAT
CTATGGTAAAAACGACCGGCCCTCAGGGATCCCAG
ACCGATTCTCTGGCTCCATCTCAGGAAACACAGCT
TCCTTGACCATCACTGGGGCTCAGGCGGAAGATGA
GGCTCACTATTACTGTAACTCCCGGGACAGCAGTG
GTAACCATGTGGTATTCGGCGGAGGGACCAAGCTG
ACCGTCCTG
(SEQ ID NO: 95)

CAGTCTGCCCTGACTCAGCCTGCCTCCGTGTCTGG
GTCTCCTGGACAGTCGATCACCATCTCCTGCACTG
GAACCAGCAGTGACGTTGGTGGTTATGAATTTGTC
TCCTGGTACCAACATCACCCAGGCAAAGCCCCCAA
ACTCATGATTTATGATGTCAGTAGTCGGCCCTCAG
GGGTTTCTAATCGCTTCTCTGGCTCCAAGTCTGGC
AACACGGCCTCCCTGACCATCTCTGGGCTCCAGGC
TGAGGACGAGGCTGATTATTACTGCAGCTCATATA
CGCGCAGCAGCACTGTGGTGTTCGGCGGCGGGGCC
AGGCTGACCGTCCTA
(SEQ ID NO: 97)

TCCTATGAGCTGAATCAGCCACCCTCAGTGTCCGT
GTCCCCAGGACAGACAGCCAGCATCACCTGCTCTG
GAGATAAATTGGGGGATAAATATGCTTCCTGGTAT
CAGCAGAAGCCAGGCCAGTCCCCTGTGGTGGCCAT
CTATCAAAATAGCAAGCGGCCCTCAGGGATCCCTG
AGCGATTCTCTGCCTCCAACTCTGGGAACACAGCC
ACTCTGACCATCAGCGGGACCCAGGCTTTGGATGA
GGCTGACTATTACTGTCAGGCGTGGGACAGCAGCA
CTTGGGTGTTCGGCGGAGGGACCAAGCTGACCGTC
CTA
(SEQ ID NO: 99)

GAAATTGTGTTGACACAGTCTCCAGCCACCCTGTC
TTTGTCTCCAGGGGAAAGAGCCACCCTCTCCTGCA
GGGCCAGTCAGAGTGTTAGTATCTACTTAGCCTGG

TABLE 5A-continued

Exemplary Variable Light Chain Nucleic
Acid Sequences of Anti-
Protein S Monoclonal Antibodies TACCAACAGAAACCTGGCCAGGCTCCCAGGCTCCT
CATCTATGATGCATCCAACAGGGCCACTGGCATCC
CAGCCAGGTTCAGTGGCAGTGGGTCTGGGACAGAC
TTCACTCTCACCATCAGCAGCCTAGAGCCTGAAGA
TTTTGCAGTTTATTACTGTCAGCAGCGTAGCAACT
GGCCCCTCACTTTCGGCCCTGGGACCAAAGTGGAT
ATCAAA
(SEQ ID NO: 101)

GAAATAGTGATGACGCAGTCTCCAGCCACCCTGTC
TGTGTCTCCAGGGGAAAGAGCCACCCTCTCCTGCA
GGGCCAGTCAGAGGATTAACAGCAACTTAGCCTGG
TACCAGCAGAAACCTGGCCAGGCTCCCAGGCTCCT
CATCTATGGTGCATCCACCAGGGCCACTGGTATCC
CCGCCAGGTTCAGTGGCAGTGGGTCTGGGACAGAG
TTCACTCTCACCATCAGCAGCCTGCAGTCTGAAGA
TTTTGCAGCTTATTACTGTCAGCAGTATGATAACT
GGCCGCTCACTTTCGGCGGAGGGACCAAGGTGGAG
ATCAAA
(SEQ ID NO: 103)

GATATTGTGATGACTCAGTCTCCACTCTCCCTGCC
CGTCACCCCTGGAGAGCCGGCCTCCATCTCCTGCA
GGTCTAGTCAGAGCCTCCTGCATAGTAATGGATAC
AACTATTTGGATTGGTACCTGCAGAAGCCAGGGCA
GTCTCCACAGCTCCTGATCTATTTGGGTTCTAATC
GGGCCTCCGGGGTCCCTGACAGGTTCAGTGGCAGT
GGATCAGGCACAGATTTTACACTGAAAATCAGCAG
AGTGGAGGCTGAGGATGTTGGGGTTTATTATTGTA
TGCAAGCTCTACAAACTTTCACTTTCGGCCCTGGG
ACCAAAGTGGATATCAAA
(SEQ ID NO: 105)

CAGGCTGTTGTGACTCAGGAATCTGCACTCACCAC
ATCACCTGGTGAAACAGTCACACTCACTTGTCGCT
CAAGTACTGGGGCTGTTACAGCTAGTAACTATGCC
AACTGGGTCCAAGAAAAACCAGATCATTTGTTCAC
TGGTCTAATAGGTAGTACCAATAACCGAGCTCCAG
GTGTTCCTGCCAGATTCTCAGGCTCCCTGATTGGA
GACAAGGCTGCCCTCACCATCACAGGGGCACAGAC
TGAGGATGAGGCAATATATTTCTGTGCTCTATGGT
ACAGCGACCATTTCGTGTTCGGTGGAGGAACCAAA
CTGACTGTCCTA
(SEQ ID NO: 111)

GAAATAGTGATGACGCAGTCTCCAGCCACCCTGTC
TGTGTCTCCAGGGGAAAGAGCCACCCTCTCCTGCA
GGGCCAGTCAGAGTGTTACCAGCAACTTAGCCTGG
TACCAGCAGAAACCTGGCCAGGCTCCCAGGCTCCT
CATCTATGATGCATCCACCAGGGCCACTGGTATCC
CAGCCAGGTTCAGTGGCAGTGGGTCTGGGACAGAG
TTCACTCTCACCATCAGCAGCCTGCAGTCTGAAGA
TTTTGCAATTTATTACTGTCAGCAGTATAATAACT
GGCCCACCTTCGGCCAAGGGACACGACTGGAGATT
AAA
(SEQ ID NO: 113)

GATATTGTGATGACCCAGACTCCACTCTCCTCACC
TGTCACCCTTGGACAGCCGGCCTCCATCTCCTGCA
GGTCTAGTCAAAGCCTCGTACACAGTGATGGAAAC
ACCTACTTGAGTTGGCTTCAGCAGAGGCCAGGCCA
GCCTCCAAGACTCCTAATTTATAAGATTTCTAACC
GGTTCTCTGGGGTCCCAGACAGATTCAGTGGCAGT
GGGGCAGGGACAGATTTCACACTGAAAATCAGCAG
GGTGGAAGCTGAGGATGTCGGGGTTTATTACTGCA
TGCAAGCTACACAATTTCCCCATCTCACTTTCGGC
GGAGGGACCAAGGTGGAGATCAAA
(SEQ ID NO: 115)

GACATCCAGATGACCCAGTCTCCATCCTCACTGTC
TGCATCTGTAGGAGACAGAGTCACCATCACTTGTC
GGGCGAGTCAGGGCATTAACAATTATTTAGCCTGG
TTTCAGCAGAAACCAGGGAAAGCCCCTAAGTCCCT
GATCTATGCTGCATCCAGTTTGCAAAGTGGGGTCC
CATCAAAGTTCAGCGGCAGTGGATCTGGGACAGAT
TTCACTCTCACCATCAGCAGCCTGCAGCCTGAAGA

TABLE 5A-continued

Exemplary Variable Light Chain Nucleic
Acid Sequences of Anti-
Protein S Monoclonal Antibodies TTTTGCAACTTATTACTGCCAACAGTATAATAGTT
ACCCTCGGACGTTCGGCCAAGGGACCAAGGTGGAA
ATCAAA
(SEQ ID NO: 162)

GACATCCAGATGACCCAGTCTCCATCCTCACTGTC
TGCATCTGTAGGAGACAGAGTCACCATCACTTGTC
GGGCGAGTCAGGGCATTAACAATTATTTAGCCTGG
TTTCAGCAGAAACCAGGGAAAGCCCCTAAGTCCCT
GATCTATGCTGCATCCAATTTGCAAAGTGGGGTCC
CATTAAAGTTCAGCGGCAGTGGATCTGGGACAGAT
TTCACTCTCACCATCAGCAGCCTGCAGCCTGAAGA
TTTTGCAACTTATTACTGCCAACAGTATAATAGTT
ACCCGATCACCTTCGGCCAAGGGACACGACTGGAG
ATTAAA
(SEQ ID NO: 164)

GACATCCAGATGACCCAGTCTCCATCCTCCCTGTC
TGCATCTGTAGGAGACAGAGTCACCATCACTTGCC
GGGCAAGTCAGAGCATTAGCACCTTTTTAAATTGG
TATCAGCAGAAACCAGGGAAAGCCCCTAAACTCCT
GATCTATGCTACATCCAGTTTGCAAGTGGGGTCC
CATCAAGGTTCAGTGGCAGTGGATCTGGGACAGAT
TTCACTCTCACCATCAGCAGTCTGCAACCTGAAGA
TTTTGCAATTTATTATTGTCAACAGAGTTACAGTA
CCCCTCGGACGTTCGGCCAAGGGACCCAGGTGGAA
ATCAAA
(SEQ ID NO: 166)

GAAATTGTGTTGACGCAGTCTCCAGGCACCCTGTC
TTTGTCTCCAGGGGAAAGAGCCACCCTCTCCTGCA
GGGCCAGTCAGAGTGTTGGCAGCAGCTACTTAGCC
TGGTACCAGCAGAAACCTGGCCAGGCTCCCAGGCT
CCTCATCTCTGGTGCATCCGGCAGGGCCACTGGCA
TCCCAGACAGGTTCAGTGGCAGTGGGTCTGGGACA
GACTTCACTCTCACCATCAGCAGACTGGAGCCTGA
AGATTTTACAGTGTATTACTGTCAGCAGTATGGTA
GCTCACCGTACACTTTTGGCCAGGGGACCAAGCTG
GAGATCAAA
(SEQ ID NO: 170)

GACATCCAGATGAACCAGTCTCCATCCAGTCTGTC
TGCATCCCTCGGAGACACAATTACCATCACTTGCC
GTGCCAGTCAGAACATTCATATGTGGTTAAGCTGG
TACCAGCAGAAACCAGGAAAATATTCCTAAACTATT
GATCTTTAAGACTTCCAATTTGCACACAGGCGTCC
CATCAAGGTTTAGTGGCAGTGGATCTGGAACAGAT
TTCACATTAACCATCAGCAGTCTGCAGCCTGAAGA
CATTGCCACTTACTACTGTCTACAGGGTCAAAGTT
ATCCGTTCACGTTCGGAGGGGGGACCAAGCTGGAA
ATAAAG
(SEQ ID NO: 172)

GACATCCAGATGACCCAGTCTCCATCCTCCCTGTC
TGCATCTGTAGGAGACAGAGTCACCATCACTTGCC
GGGCAAGTCAGAGCATTAGCAGCTATTTAAATTGG
TATCAGCAGAAACCAGGGAAAGCCCCTAAGCTCCT
GATCTATGCTGCATCCAGTTTGCAAAGTGGGGTCC
CATCAAGGTTCAGTGGCAGTGGATCTGGGACAGAT
TTCACTCTCACCATCAGCAGTCTGCAACCTGAAGA
TTTTGCAACTTACTACTGTCAACAGAGTTACAGTT
CCCTCACCTTCGGCCAAGGGACACGACTGGAGATT
AAA
(SEQ ID NO: 178)

TCCTATGTGCTGACTCAGCCACCCTCGGTGTCAGT
GGCCCCAGGACAGACGGCCAGGATTACCTGTGGG
GAGACAACATTGGAGGTAAAAGTGTGCACTGGTAC
CAGCAGAAGCCAGGCCAGGCCCCTGTGATGGTCGT
CTATGATGATAGCGACCGGCCCTCAGGGATCCCTG
AGCGATTCGCTGGCTCCAATTCTGGGAACACGGCC
ACCCTGGCCATCAGCAGGGTCGAAGCCGGGGATGA
GGCCGACTATTACTGTCAGGTGTGGGAGATAACTA
GTGATCATCCGGCATTCGGCGGAGGGACCAGGCTG
ACCGTCCTA
(SEQ ID NO: 188)

TABLE 5A-continued

Exemplary Variable Light Chain Nucleic
Acid Sequences of Anti-
Protein S Monoclonal Antibodies TCCTATGAGCTGACTCAGCCACCCTCAGTGTCCGT
GTCCCCAGGACAGACAGCCAGCATCACCTGCTCTG
GAGATAAATTGGGGGATAAATATGTTTTCTGGTAT
CAGCAGAAGCCAGGCCAGTCCCCTGTGTTGGTCAT
CTATCAAGATAGCAAGCGGCCCTCAGGGATCCCTG
AGCGATTCTCTGGCTCCAACTCTGGGAACACAGCC
ACTCTGACCATCAGCGGGACCCAGACTATGGATGA
GGCTGACTATTACTGTCAGGCGTGGGACAGCAGCA
CTGTGGGATTCGGCGGAGGGACCAAGCTGGCCGTC
CTG
(SEQ ID NO: 198)

TCCTATGAGCTGACTCAGCCACCCTCAGTGTCCGT
GTCCCCGGGACAGACAGCCAGCATCACCTGCTCTG
GAGATAAATTGGGGGATAAATATGCTTTCTGGTAT
CAGCAGAAGCCAGGCCAGTCCCCTGTGCTGGTCAT
CTATCAAGATAACAAGCGGCCCTCAGGGATCCCTG
AGCGATTCTCTGGCTCCAACTCTGGGAACACAGCC
ACTCTAACCATCAGCGGGACCCAGGCTGTGGATGA
GGCTGACTATTACTGTCAGGCGTGGGACAGCAGCA
CTGCGGTATTCGGCGGAGGGACCAAGCTGACCGTC
CTA
(SEQ ID NO: 208)

TABLE 5B

Exemplary Variable Heavy Chain Nucleic
Acid Sequences of Anti-
Protein S Monoclonal Antibodies CAGCTGCAGCTGCAGGAGTCGGGCCCAGGACTGGT
GAAGCCTTCGGAGACCCTGTCCCTCACCTGCACTG
TCTCTGGTGGCTCCATCAGCAGTAGTAGTTACTAC
TGGGGCTGGATCCGCCAGCCCCCGGGAAGGGACT
GGAGTGGATTGGGAATATCTATTATAGTGGGAACA
CCTACTACAACCCGTCCCTCAAGAGTCGAGTCACC
ATATCCGTAGACACGTCCAAGAACCAGTTCTCCCT
GAAGCTGAGCTCTATGACCGCCGCAGACACGGCTG
TGTATTACTGTGCGAGATGTAGTGGCTACGGGTAT
AGCAGTGGCCGGTCCTACTTTGACTACTGGGGCCA
GGGAAACCCTGGTCACCGTCTCCTCA
(SEQ ID NO: 94)

CAGGTGCAGCTGGTGCAGTCTGGGGCTGAGGTGAA
GAAGCCTGGGTCCTCGGTGAAGGTCTCCTGCAAGG
TTTCTGGAGGCACCTTCAGCAGCTATTCTATCAGC
TGGGTGCGACAGGCCCCTGGACAAGGGCTTGAGTG
GATGGGAGGGATCATCCCTATATTTGGTACAACAA
ACTACGCACAGAAGTTCCAGGGCAGAGTCACGATC
ACCGCGGACGAATCCACGAGCACAGCCTACATGGA
TCTGAGCAGCCTGAAATCTGAGGACACGGCCATGT
ATTACTGTGAGGGGGTAGAGTGGGAGCGGACTTT
GACTACTGGGGCCAGGGAACCCTGGTCACCGTCTC
CTCA
(SEQ ID NO: 96)

CAGGTGCAGCTGCAGGAGTCGGGCCCAGGACTGGT
GAAGCCTTCACAGACCCTGTCCCTCACCTGCACTG
TCTCTGGTGGCTCCATCACCAGTGATGGTTACCAC
TGGAGCTGGATCCGCCAGTACCCAGGGAAGGGCCT
GGACTGGATTGGATACATCTATTACACTGGGAACA
CCTACTACAACCCGTCCCTCAAGAGTCGAGTGACC
ATATCAGTAGGCAGCGGGACACGGCCG
TTTATTACTGTGCGAGAAGGCTGTCGACTGGGCCC
TACTTTGACTACTGGGGCCAGGGAACCCTGGTCAC
CGTCTCCTCC
(SEQ ID NO: 98)

GAAGTGCAGCTGGTGGAGTCTGGGGGAGGCTTGGT
ACAGCCTGGCAGGTCCCTGAGACTCTCCTGTGCAG
CCTCTGGATTCACCTTTGATGATTATGCCATGCAC

TABLE 5B-continued

Exemplary Variable Heavy Chain Nucleic Acid Sequences of Anti-Protein S Monoclonal Antibodies TGGGTCCGGCAAGCTCCAGGGAAGGGCCTGGAATG
GGTCTCAGGTATTACTTGGAATAGTGGTAACATAG
GCTATGCGGACTCTGTGAAGGGCCGATTCACCATC
TCCAGAGACAACGCCAAGAACTCCCTGTATCTGCA
CATGAACAGTCTGAGAATTGAGGACACGGCCTTCT
ATTACTGTGCAAAAGGCCGAGCAGTGTCTGATACT
TTTGATATCTGGGGCCAAGGGACAATGGTCACCGT
CTCTTCA
(SEQ ID NO: 100)

CAGGTGCAGTTGGTGGAATCTGGGGGAGGCGTGGT
CCAGCCTGGGAGGTCCCTGAGACTCTCCTGTGCAG
CGTCTGGATTCACCTTCAGTACCTATGGCTTTCAC
TGGGTCCGCCAGCCTCCAGGCAAGGGACTGGAGTG
GGTGGCAGTTATATATTATGATGGAATTAATAAAT
ATTATGCAGACTCCGTGAAGGGCCGATTCACCATC
TCCAGAGACAATTCCAAGAACACGCTGTTTCTTCA
AATGAACAGCCTGAGAGCCGAGGACACGGCTGTGT
ATTACTGTGCGGAGTCCGACTTGGACTACTGGGGC
CAGGGAACCCTGGTCACCGTCTCCTCA
(SEQ ID NO: 102)

CAGGTGCAGCTGCAGGAGTCGGGCCCAGGACTGGT
GAAGCCTTCGGAGACCCTGTCCCTCACCTGCGCTG
TCTCTGGTTATTCCATCAGCAGTGGTTACTACTGG
GGCTGGATCCGGCAGCCCCCAGGGAAGGGGCTGGA
CTGGATTGGGAGTATCTATTATAGTGGGAGTACCT
ACTACAACCCGTCCCTCAAGAGTCGAGTCACCATA
TCAGTTGACACGTCCAAGAACCAGATCTCCCTGAA
GCTGAGCTCTGTGACCGCCGCAGACACGGCCGTGT
ATTACTGTGCGACCACGTATTCCGATATTGTGACT
GGTTATTATAATGATGCTTTTGATATCTGGGGCCA
AGGGACAATGGTCACCGTGTCTTCA
(SEQ ID NO: 104)

CAGGTGCAGCTGGTGCAGTCTGGGGCTGAGGTGAA
GAAGCCTGGGTCCTCGGTGAAGGTCTCCTGTAAGG
CTTCTGGAGACACCTTCAGCAACCATGCTATCAAC
TGGGTGCGACAGGCCCCTGGACAAGGGCTTGAGTG
GATGGGAGGGTACATCCCTATCTTTGGTACAACAA
ACTCCGCACAGAAGTTCCGGGGCAGAGTCACGATT
ACCGCGGACAAATCCACGAACACAGTACTACATGG
GCTGAGCAGCCTGAGATCTGAGGACACGGCCGTTT
ATTACTGTGCGAGAGGGGGGCTCGCGGGGAGTCAT
TATAAGAACTACTACTATGACGGTATGGACGTCTG
GGGCCAGGGGACCACGGTCACCGTCTCCTCA
(SEQ ID NO: 106)

CAGGTGCAACTGGTGCAGTCTGGGGCTGAGGTGAA
GAAGCCTGGGGCCTCAGTGAAGGTCTCCTGCAAGT
CTTCTGGCCACACCTTCACCGGCTACTATATGCAC
TGGGTGCGACAGGCCCCTGGACAAGGGCTTGAGTG
GATGGGATGGATCAACCCTAACAGTGGTGACACAA
ACTACGCACAGAAGTTCAGGGCAGGGTCACCATG
ACCAGGGACACGTCCATCAGCACAGCCTACATGGA
GATGAGCAGGCTGAGATCTGACGACACGGCCGTGT
ATTACTGTGCGAGAGACTCCCAAATACTATGGTTC
GGGGAGTTAGGCTACTGGGGCCAGGGAACCCTGGT
CACCGTCTCCTCC
(SEQ ID NO: 112)

CAGGTGCAGCTGCAGGAGTCGGGCCCAGGACTGGT
GAAGCCTTCGGAGACCCTGTCCCTCACCTGCGGTG
TCTCTGGTGGCTCCATCAGCAGTACTAACTGGTGG
AGTTGGGTCCGCCAGCCCCCAGGGAAGGGGCTGGA
GTGGATTGGGAAATCTATCAAACTGGGAGTACCG
ACTACAACCCGTCCCTCAAGAGTCGAGTCACCATA
TCAATAGACAAGTCCAAGAACCAGTTCTCCCTGAA
GCTGTACTCTGTGACCGCCGCGGACACGGCCGTGT
ATTACTGTGCGAGAAGGTTCGGGGAGTTAGACTAC
TGGGGCCAGGGAACCCTGGTCACCGTCTCCTCA
(SEQ
ID NO: 114)

CAGGTGCAGCTGCAGGAGTCGGGCCCAGGACTGGT
GAAGCCTTCGGAGACCCTGTCCCTCACCTGCACTG
TCTCTGGTGGCTCCATCAGTAATTACTACTGGAAC
TGGATCCGGCAGCCCCCAGGGAAGGGACTGGAGTG
GATTGGGTATATCTATTACATTGGGATCACCGACT
ACAACCCCTCCCTCAAGAGTCGAGTCACCATATCA
GTAGACACGTCCAAGAACCAGTTCTCCCTGAAGGT
GACCTCTGTGACCGCTGCGGACACGGCCGTGTATT
ACTGTGCGGCTCTAAGTGGGGATCATGCTTTTGAC
ATCTGGGGCCAAGGGACACTGGTCACCGTCTCTTC
A
(SEQ ID NO: 116)

CAGCTGCAGCTGCAGGAGTCGGGCCCAGGACTGGT
GAAGCCTTCGGAGACCCTGTCCCTCACCTGCACTG
TCTCTGGTGGCTCCATCACCAATAGTAATTACTAC
TGGGGCTGGATCCGCCAGCCCCAGGGAAGGGACT
GGAGTGGATTGGGAGTGTCTATTATAGTGGGACCA
CCTACTACAACCCGTCCCTCAAGAGTCGAGTCACC
ATATCCGTAGACCCGTCCAAGAACCAGTTCTCCCT
GAAGCTGAGCTCTGTGACCGCCGCAGACACGGCTG
TGTATTACTGTGTGAGAGAGAGTGAGAGCTACTAC
TACTACGGTTCGGACGTCTGGGGCCAAGGGACCAC
GGTCACCGTCTCCTCA
(SEQ ID NO: 163)

GAGGTGCAGCTGGTTGAGTCTGGGGGAGGCCTGGT
CAAGCCTGGGGGGTCCCTGAGACTCTCCTGTGCAG
CCTCTGGATTCACCTTCAGTAGCTATAACATGAAC
TGGGTCCGCCAGGCTCCAGGGAGGGGCTGGACTG
GGTCTCATCCATTAGTAGTAGTAGTGGTACATAT
ACTACGCAGACTCAGTGAAGGGCCGATTCACCATC
TCCAGAGACAACGCCAAGAACTCACTGTATCTGCA
AATGAATACCCTGAGAGCCGAGGACACGGCTGTTT
ATTACTGTGCGAGAGATGAGGAGTGGGAGCTACTG
ACGGGCTTTGACTACTGGGGCCAGGGAACCCTGGT
CACCGTCTCCTCA
(SEQ ID NO: 165)

CAGGTGCAGCTGCAGGAGTCGGGCCCAGGACTGGT
GAAGCCTTCGGAGACCCTGTCCCTCACCTGCACTG
TCTCTGGTGGCTCCATCAGTGGTAACTACTGGAGC
TGGATCCGGCAGCCCCCAGGGAAGGGACTGGAGTG
GATTGGGTATATCTATTACAGTGGGAGCACCAACT
ACAATCCCTCCCTCAAGAGTCGAGTCACCATATCA
GTTGACACGTCCAAGAACCAGTTCTCCCTGAAGCT
GAGCTCTGTGACCGCTGCGGATACGGCCGTGTATT
ACTGTGCGAGACTTGATTACTTTACTTGGGGG
GCTTATTCTGACTGGTACTTCGATCTCTGGGGCCG
TGGCACCCTGGTCACTGTCTCCTCA
(SEQ ID NO: 167)

CAGGTACAGCTGCAGCAGTCAGGTCCAGGACTGGT
GAAGCCCTCGCAGACCCTCTCACTCACCTGTGCCA
TCTCCGGGGACAGTGTCTCTAACAACAATGCTGCT
TGGAACTGGATCAGGCAGTCCCCATCGAGAGGCCT
TGAGTGGCTGGGAGGGACATACTACAGGTCCAAGT
GGTATAATGATTATGCAGTATCTGTGAAAAGTCGA
ATAATCATCAACCCAGTCACATCCAAGAACCAGTT
CTCCCTACAGCTGAACTCTGTGACTCCCGAGGACA
CGGCTGTGTATTACTGTGCAAGAGGCAGCAGCTGG
TACAGGTTTTTGACTACTGGGGCCAGGGAACCCT
GGTCACCGTCTCCTCA
(SEQ ID NO: 171)

CAGGTCCAGCTGCAGCAGTCTGGAACTGAGCTGGT
AAGGCCTGGGACTTCAGTGAAGATGTCCTGTAAGG
CTGCTGGATACACCTTCACTAACCACTGGATAGGT
TGGGTAAAGCAGAGGCCTGGACATGGCCTTGAGTG
GATTGGAGATATTTACCCTGGAGGTGGTTATACTA
ACTACAATGAGAAGTTCAAGGGCAAGGCCTCACTG
ACTGCAGACACATCCTCCACCACAGCCTACATGCA
GCTCAGCAGCCTGACATCTGAGGACTCTGCCATCT
ATTACTGTTCAAGATTCGGGGATCAAAACTGGGCC
TGGTTTGCTTACTGGGCCAAGGGACTCTGGTCAC
TGTCTCTGCA
(SEQ ID NO: 173)

TABLE 5B-continued

Exemplary Variable Heavy Chain Nucleic
Acid Sequences of Anti-
Protein S Monoclonal Antibodies GAGGTGCAGCTGGTGGAGTCTGGGGGAGGCTTGGT
AAAGCCTGGGGGGTCCCTTAGACTCTCCTGTGCAG
CCTCTGGAATCAGTTTCAGTAACGCCTGGATGAGC
TGGGTCCGCCAGGCTCCAGGGAAGGGGCTGGAATG
GGTTGGCCGTATTAAAGCCAATCCTGATGGTGGGA
CAACAGACTACGCTGCACCCGTGAAAGGCAGATTC
ACCATCTCAAGAGATGATTCAAAAAACACGCTATA
TCTGCAAATGAACAGCCTGAAAACCGAGGACACAG
CCGTGTATTACTGTACCACAGAGTTGGACATTTTA
CTATGGTTCACCTCCTTTGACTACTGGGGCCAGGG
AACCCTGGTCACCGTCTCCTCA
(SEQ ID NO: 183)

GAGGTGCAGCTGGTGGAGTCTGGGGGAGGCTTGGT
ACAGCCTGGGGGGTCCCTGAGACTCTCCTGTGCAG
CCTCTGGATTCACCTTCAGTAGCTATAGCATGAAC
TGGGTCCGCCAGGCTCCAGGGAAGGGGCTGGAGTG
GGTTGCATACATTAGTAGTAGTACTCGTACCATAT
TCTACGCAGACTCTGTGAAGGGCCGATTCACCATC
TCCAGAGACAATGCCAAGAACTCACTGTATCTGCA
AATGAACAGCCTGAGAGACGAGGACACGGCTTTTT
ATTATTGTGCGAGAGAACGTTCGGCCTTTGACTAC
TGGGGCCAGGGAACCCTGGTCACCGTCTCCTCA
(SEQ ID NO: 193)

CAGGTGCAGCTGGTGCAGTCTGGGTCTGAGGTGAA
GAAGCCTGGGGCCTCAGTGAAGGTTTCCTGCAAGG
CATCTGGATACACCTTCACCAACTACTATATACAC
TGGGTGCGGCAGGCCCCTGGACAAGGGCTTGAGTG
GATGGGAATAATCACCCCTAGTGGTGGTACCACAA
GCTACGCACAGAAGTTCCAGGGCAGAGTCACTATG
ACCAGGGACACGTCCACGAACACAGTCTACATGGG
GCTGAGCAGCCTGAGATCTGAGGACACGGCCATGT
ATTACTGTGCGAGAGCCGGGGTACAACTGGATCGA
CGAGGGTGGTTCGACCCCTGGGGCCAGGGAACCCT
GGTCACCGTCTCCTCA
(SEQ ID NO: 203)

CAGGTGCAGCTGGTGCAGTCTGGGGCTGAGGTGAA
GAAGCCTGGGGCCTCAGTGAAGGTTTCCTGCAAGG
CATCTGGATACACCTTCACCAGCTACTATATACAC
TGGGTACGACAGGCCCCTGGACAAGGGCTTGAGTG
GATGGGAGTAACCAGCCCTAGTGGTCGTAGCACAA
GCTTCGCACAGAAGTTCCAGGGCAGAGTCACCATG
ACCAGGGACACGTCCACGAGCGCAGTCTATATGGA
CCTGGACAGCCTGAGATCTGAGGACACGGCCGTGT
ATTACTGTGCGAGAGGGGAGTGACGATACACCTG
GAACGACGGGCTACTTTGACTACTGGGGCCAGGG
AACCCTGGTCATTGTCTCCTCA
(SEQ ID NO: 213)

TABLE 5C

Exemplary Variable Light Chain and Variable Heavy Chain Nucleic
Acid Sequences of Anti-Protein S Monoclonal Antibodies

| Combination Number | Variable Light Chain Nucleic Acid Sequence | Variable Heavy Chain Nucleic Acid Sequence |
|---|---|---|
| Combination 1 | SEQ ID NO: 93 | SEQ ID NO: 94 |
| Combination 2 | SEQ ID NO: 95 | SEQ ID NO: 96 |
| Combination 3 | SEQ ID NO: 97 | SEQ ID NO: 98 |
| Combination 4 | SEQ ID NO: 99 | SEQ ID NO: 100 |
| Combination 5 | SEQ ID NO: 101 | SEQ ID NO: 102 |
| Combination 6 | SEQ ID NO: 103 | SEQ ID NO: 104 |
| Combination 7 | SEQ ID NO: 105 | SEQ ID NO: 106 |
| Combination 10 | SEQ ID NO: 111 | SEQ ID NO: 112 |
| Combination 11 | SEQ ID NO: 113 | SEQ ID NO: 114 |
| Combination 12 | SEQ ID NO: 115 | SEQ ID NO: 116 |
| Combination 13 | SEQ ID NO: 162 | SEQ ID NO: 163 |
| Combination 14 | SEQ ID NO: 164 | SEQ ID NO: 165 |
| Combination 15 | SEQ ID NO: 166 | SEQ ID NO: 167 |

TABLE 5C-continued

Exemplary Variable Light Chain and Variable Heavy Chain Nucleic
Acid Sequences of Anti-Protein S Monoclonal Antibodies

| Combination Number | Variable Light Chain Nucleic Acid Sequence | Variable Heavy Chain Nucleic Acid Sequence |
|---|---|---|
| Combination 17 | SEQ ID NO: 170 | SEQ ID NO: 171 |
| Combination 18 | SEQ ID NO: 172 | SEQ ID NO: 173 |
| Combination 19 | SEQ ID NO: 178 | SEQ ID NO: 183 |
| Combination 20 | SEQ ID NO: 188 | SEQ ID NO: 193 |
| Combination 21 | SEQ ID NO: 198 | SEQ ID NO: 203 |
| Combination 22 | SEQ ID NO: 208 | SEQ ID NO: 213 |

In some embodiments, provided herein are nucleic acids encoding any of the Protein S antibodies disclosed herein. In some embodiments, provided herein are nucleic acids comprising any one or more of the nucleic acid sequences of Tables 5A-5B3. In some embodiments, the heavy chain and light chain variable domains of the Protein S antibodies disclosed herein are encoded by a nucleic acid comprising any one or more of the nucleic acid sequences of Tables 5A-5B.

In some embodiments, the variable domain of the Protein S antibodies of the disclosure are encoded by a nucleic acid, wherein the light chain variable domain of the antibody is encoded by the nucleic acid sequence of SEQ ID NO: 93 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 94, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 93 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 94, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 95 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 96, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 95 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 96, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 97 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 98, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 97 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 98, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 99 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 100, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 99 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 100, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 101 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 102, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 101 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 102, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 103 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 104, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 103 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 104, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 105 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 106, or a nucleic acid sequence with at least 80%, 81%, 82%, 83%, 84%, 85%, 86%, 87%, 88%, 89%, 90%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 105 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 106, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 111 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 112, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 111 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 112, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 113 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 114, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 113 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 114, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 115 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 116, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 115 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 116, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 162 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 163, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 162 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 163, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 164 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 165, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 164 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 165, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 166 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 167, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 166 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 167, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 170 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 171, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 170 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 171, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 172 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 173, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 172 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 173, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 178 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 183, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 178 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 183, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 188 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 193, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 188 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 193, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 198 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 203, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 198 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 203, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 208 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 213, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 208 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 213, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

The disclosure also provides vectors comprising any nucleic acid of the disclosure. In some embodiments, the nucleic acid of the vector comprises any one or more of the nucleic acid sequences provided in Tables 5A-5B. In some embodiments, the vector is an expression vector or an expression construct. In some embodiments, the vector is a mammalian vector. In some embodiments, the vector is a viral vector.

In some embodiments, the Protein S antibodies provided herein are produced by culturing a cell under suitable conditions for leading to the expression of the Protein S antibody, wherein the cell comprises a vector.

II. Uses of Protein S Antibodies

A. Therapeutic Protein S Antibodies

Provided herein are antibodies that recognize and selectively and/or specifically bind to Protein S, including Protein S fragments. The antibodies disclosed herein may be used for therapeutics in a subject. In some embodiments, the subject is a mammalian subject. In some embodiments, the mammalian subject is a human subject. In some embodiments, the mammalian subject is a non-human primate, e.g. a cynomolgus monkey.

In some embodiments, the Protein S antibodies provided herein are useful for treating a condition in a subject, wherein the condition is associated with the coagulation cascade. In some embodiments, the Protein S antibodies provided herein are useful for reducing an ability of Protein S to act as a cofactor within the coagulation cascade for the treatment of a condition in a subject.

In some embodiments, the Protein S antibodies provided herein are useful for reducing an ability of Protein S to act as a cofactor for APC, TFPI, or APC and TFPI for the treatment of a bleeding disorder or other diseases, e.g., a platelet disorder.

In some embodiments, provided herein is a method of promoting the coagulation of blood, the method comprising contacting any one of the Protein S antibodies disclosed herein with Protein S. In some embodiments, the contacting takes place in plasma. In some embodiments, the method is in vitro. In some embodiments, the method is in vivo. In some embodiments, the method is in vivo, and the method further comprises administering any one of the Protein S antibodies disclosed herein to a subject in need thereof.

In some embodiments, provided herein is a method of promoting the coagulation of blood, the method comprising contacting any one of the Protein S antibodies disclosed herein with a blood sample. Exemplary antibodies that may be used in a method for promoting the coagulation of blood include, but are not limited to, antibodies that (a) comprise the light chain variable domain comprising the amino acid sequence of SEQ ID NO: 71 and the heavy chain variable domain comprising the amino acid sequence of SEQ ID NO: 72, (b) comprise the light and heavy CDR amino acid sequences of SEQ ID NO: 2, SEQ ID NO: 13, SEQ ID NO: 22, SEQ ID NO: 34, SEQ ID NO: 46, and SEQ ID NO: 58, (c) comprise the amino acid sequence of SEQ ID NO: 75 and the heavy chain variable domain comprising the amino acid sequence of SEQ ID NO: 76, (d) comprise the light and heavy CDR amino acid sequences of SEQ ID NO: 1, SEQ ID NO: 15, SEQ ID NO: 24, SEQ ID NO: 36, SEQ ID NO: 48, and SEQ ID NO: 60, (e) comprise the amino acid sequence of SEQ ID NO: 69 and the heavy chain variable domain comprising the amino acid sequence of SEQ ID NO: 70, (f) comprise the light and heavy CDR amino acid sequences of SEQ ID NO: 1, SEQ ID NO: 12, SEQ ID NO: 21, SEQ ID NO: 33, SEQ ID NO: 45, and SEQ ID NO: 57, (g) comprise the amino acid sequence of SEQ ID NO: 89 and the heavy chain variable domain comprising the amino acid sequence of SEQ ID NO: 90, and (h) comprise the light and heavy CDR amino acid sequences of SEQ ID NO: 10, SEQ ID NO: 16, SEQ ID NO: 31, SEQ ID NO: 43, SEQ ID NO: 55, and SEQ ID NO: 67.

In some embodiments, the coagulation of blood is marked by an increase in thrombin generation. Exemplary antibodies wherein use of the antibodies in the method for promoting the coagulation of blood, and wherein the coagulation of blood is marked by an increase in thrombin generation, include, but are not limited to antibodies that (a) comprise the light chain variable domain comprising the amino acid sequence of SEQ ID NO: 71 and the heavy chain variable domain comprising the amino acid sequence of SEQ ID NO: 72, (b) comprise the light and heavy CDR amino acid sequences of SEQ ID NO: 2, SEQ ID NO: 13, SEQ ID NO: 22, SEQ ID NO: 34, SEQ ID NO: 46, and SEQ ID NO: 58, (c) comprise the amino acid sequence of SEQ ID NO: 75 and the heavy chain variable domain comprising the amino acid sequence of SEQ ID NO: 76, (d) comprise the light and heavy CDR amino acid sequences of SEQ ID NO: 1, SEQ ID NO: 15, SEQ ID NO: 24, SEQ ID NO: 36, SEQ ID NO: 48, and SEQ ID NO: 60, (e) comprise the amino acid sequence of SEQ ID NO: 69 and the heavy chain variable domain comprising the amino acid sequence of SEQ ID NO: 70, (f) comprise the light and heavy CDR amino acid sequences of SEQ ID NO: 1, SEQ ID NO: 12, SEQ ID NO: 21, SEQ ID NO: 33, SEQ ID NO: 45, and SEQ ID NO: 57, (g) comprise the amino acid sequence of SEQ ID NO: 89 and the heavy chain variable domain comprising the amino acid sequence of SEQ ID NO: 90, and (h) comprise the light and heavy CDR amino acid sequences of SEQ ID NO: 10, SEQ ID NO: 16, SEQ ID NO: 31, SEQ ID NO: 43, SEQ ID NO: 55, and SEQ ID NO: 67.

In some embodiments, the coagulation of blood is marked by an increase in fibrin generation. Exemplary antibodies wherein use of the antibodies in the method of promoting the coagulation of blood, and wherein the coagulation of blood is marked by an increase in fibrin generation include, but are not limited to antibodies that (a) comprise the light chain variable domain comprising the amino acid sequence of SEQ ID NO: 71 and the heavy chain variable domain comprising the amino acid sequence of SEQ ID NO: 72, (b) comprise the light and heavy CDR amino acid sequences of SEQ ID NO: 2, SEQ ID NO: 13, SEQ ID NO: 22, SEQ ID NO: 34, SEQ ID NO: 46, and SEQ ID NO: 58, (c) comprise the amino acid sequence of SEQ ID NO: 75 and the heavy chain variable domain comprising the amino acid sequence of SEQ ID NO: 76, (d) comprise the light and heavy CDR amino acid sequences of SEQ ID NO: 1, SEQ ID NO: 15, SEQ ID NO: 24, SEQ ID NO: 36, SEQ ID NO: 48, and SEQ ID NO: 60, (e) comprise the amino acid sequence of SEQ ID NO: 69 and the heavy chain variable domain comprising the amino acid sequence of SEQ ID NO: 70, (f) comprise the light and heavy CDR amino acid sequences of SEQ ID NO: 1, SEQ ID NO: 12, SEQ ID NO: 21, SEQ ID NO: 33, SEQ ID NO: 45, and SEQ ID NO: 57, (g) comprise the amino acid sequence of SEQ ID NO: 89 and the heavy chain variable domain comprising the amino acid sequence of SEQ ID NO: 90, and (h) comprise the light and heavy CDR amino acid sequences of SEQ ID NO: 10, SEQ ID NO: 16, SEQ ID NO: 31, SEQ ID NO: 43, SEQ ID NO: 55, and SEQ ID NO: 67.

In some embodiments, the coagulation of blood is marked by an increase in D-dimer.

In some embodiments, the blood sample is obtained from a subject having a coagulation factor deficiency or von Willebrand disease (vWD), or a platelet disorder. In some embodiments, the vWD is a subtype selected from: vWD Type 1, vWD Type 2A, vWD Type 2B, vWD Type 2N, vWD Type 2M, vWD Type 3, and acquired vWD. Exemplary antibodies wherein use of the antibodies for a method for promoting coagulation of blood, and wherein the blood is a blood sample obtained from a subject having a coagulation factor deficiency (e.g. such as Factor VII deficiency, Factor VIII deficiency, Factor IX deficiency, Factor XI deficiency) or von Willebrand disease may comprise the light chain variable domain comprising the amino acid sequence of SEQ ID NO: 75 and the heavy chain variable domain comprising the amino acid sequence of SEQ ID NO: 76, or may comprise the light and heavy CDR amino acid sequences of SEQ ID NO: 1, SEQ ID NO: 15, SEQ ID NO: 24, SEQ ID NO: 36, SEQ ID NO: 48, and SEQ ID NO: 60.

In some embodiments, provided herein is a method of promoting the coagulation of blood in a subject in need thereof, the method comprising administering to the subject any one of the Protein S antibodies disclosed herein, or any one of the pharmaceutical compositions disclosed herein. In some embodiments, the antibody remains active in the subject for a period of time, wherein the period of time is antibody dose-dependent. In some embodiments, the period of time is about 50 hours to about 170 hours. Exemplary antibodies wherein use of the antibodies for a method of promoting the coagulation of blood in a subject in need thereof, wherein the activity of the antibody is dose-dependent, may comprise the light chain variable domain comprising the amino acid sequence of SEQ ID NO: 71 and the heavy chain variable domain comprising the amino acid sequence of SEQ ID NO: 72, or may comprise the light and heavy CDR amino acid sequences of SEQ ID NO: 2, SEQ ID NO: 13, SEQ ID NO: 22, SEQ ID NO: 34, SEQ ID NO: 46, and SEQ ID NO: 58.

In some embodiments, provided herein is a method of promoting generation of thrombin in a subject in need thereof, the method comprising administering to the subject any one of the Protein S antibodies disclosed herein, or any one of the pharmaceutical compositions disclosed herein. In some embodiments, the subject suffers from a disease or condition selected from the group consisting of bleeding disorders, and platelet disorders. In some embodiments, the subject suffers from trauma and/or bleeding resulting from a surgery or a medical procedure. For example, the medical procedure may be a procedure in which bleeding may occur, but not necessarily so. In some embodiments, the medical procedure is a dental procedure. Exemplary antibodies that may be used in a method of promoting generation of thrombin in a subject in need thereof may comprise the light and heavy CDR amino acid sequences of SEQ ID NO: 2, SEQ ID NO: 13, SEQ ID NO: 22, SEQ ID NO: 34, SEQ ID NO: 46, and SEQ ID NO: 58, or may comprise the amino acid sequence of SEQ ID NO: 75 and the heavy chain variable domain comprising the amino acid sequence of SEQ ID NO: 76, or may comprise the light and heavy CDR amino acid sequences of SEQ ID NO: 1, SEQ ID NO: 15, SEQ ID NO: 24, SEQ ID NO: 36, SEQ ID NO: 48, and SEQ ID NO: 60, or may comprise the amino acid sequence of SEQ ID NO: 69 and the heavy chain variable domain comprising the amino acid sequence of SEQ ID NO: 70, and may comprise the light and heavy CDR amino acid sequences of SEQ ID NO: 1, SEQ ID NO: 12, SEQ ID NO: 21, SEQ ID NO: 33, SEQ ID NO: 45, and SEQ ID NO: 57.

In some embodiments, provided herein is a method of treating a condition in a subject in need thereof, wherein the disease is selected from the group consisting of bleeding disorders, and platelet disorders, and the method comprises administering to the subject any one of the Protein S antibodies disclosed herein, or any one of the pharmaceutical compositions disclosed herein. In some embodiments, the condition is a bleeding disorder. In some embodiments, the bleeding disorder is selected from the group consisting of hemophilia A, hemophilia B, von Willebrand disease (vWD, which may be a subtype selected from: vWD Type 1, vWD Type 2A, vWD Type 2B, vWD Type 2N, vWD Type 2M, vWD Type 3, and acquired vWD), menorrhagia including menorrhagia due to a congenital or acquired factor deficiency, Factor I deficiency, Factor II deficiency, Factor V deficiency, Factor VII deficiency, Factor X deficiency, Factor XI deficiency (hemophilia C), Factor VIII deficiency (hemophilia A), Factor IX deficiency (hemophilia B), trauma, and hereditary hemorrhagic telangiectasia. In some embodiments, the bleeding is associated with surgery, e.g. in a subject with a type of hemophilia. In some embodiments, the bleeding is associated with a medical procedure, e.g., a dental procedure. In some embodiments, the bleeding disorder is vWD, and the subject also suffers from menorrhagia. In some embodiments, the bleeding disorder is vWD, and the subject is undergoing a prophylactic treatment. In some embodiments, the subject suffers from menorrhagia associated with any one or more bleeding disorders and/or platelet disorders. In some embodiments, the subject is a hemophilia carrier. In some embodiments, the subject is a hemophilia carrier, and suffers from menorrhagia. In some embodiments, the condition is a platelet disorder. In some embodiments, the platelet disorder includes but is not limited to Bernard-Soulier syndrome, Glanzmann's thrombasthenia, and platelet storage pool deficiencies.

In some embodiments, the platelet disorder is a platelet storage pool deficiency. In some embodiments, the platelet storage pool deficiency includes but is not limited to: Gray platelet syndrome, Quebec platelet disorder, and MYH9-related thrombocytopenia (MYH9RD). In some embodiments, the subject has a bleeding disorder, and has inhibitors. In some embodiments, the bleeding disorder is hemophilia A or hemophilia B, wherein the subject has inhibitors. In some embodiments, the bleeding disorder is vWD. For example, the inhibitors may be developed in the subject as a response to factor replacement therapy. Exemplary antibodies that may be used for a method of treating a condition in a subject in need thereof, wherein the disease is selected from the group consisting of bleeding disorders, and platelet disorders, include, but are not limited to antibodies that (a) comprise the light chain variable domain comprising the amino acid sequence of SEQ ID NO: 71 and the heavy chain variable domain comprising the amino acid sequence of SEQ ID NO: 72, (b) comprise the light and heavy CDR amino acid sequences of SEQ ID NO: 2, SEQ ID NO: 13, SEQ ID NO: 22, SEQ ID NO: 34, SEQ ID NO: 46, and SEQ ID NO: 58, (c) comprise the amino acid sequence of SEQ ID NO: 75 and the heavy chain variable domain comprising the amino acid sequence of SEQ ID NO: 76, (d) comprise the light and heavy CDR amino acid sequences of SEQ ID NO: 1, SEQ ID NO: 15, SEQ ID NO: 24, SEQ ID NO: 36, SEQ ID NO: 48, and SEQ ID NO: 60, (e) comprise the amino acid sequence of SEQ ID NO: 69 and the heavy chain variable domain comprising the amino acid sequence of SEQ ID NO: 70, (f) comprise the light and heavy CDR amino acid sequences of SEQ ID NO: 1, SEQ ID NO: 12, SEQ ID NO: 21, SEQ ID NO: 33, SEQ ID NO: 45, and SEQ ID NO: 57, (g) comprise the amino acid sequence of SEQ ID NO: 89 and the heavy chain variable domain comprising the amino acid sequence of SEQ ID NO: 90, and (h) comprise the light and heavy CDR amino acid sequences of SEQ ID NO: 10, SEQ ID NO: 16, SEQ ID NO: 31, SEQ ID NO: 43, SEQ ID NO: 55, and SEQ ID NO: 67.

In some embodiments, a subject in need thereof may be treated with any of the Protein S antibodies provided herein, wherein the treatment is a routine prophylaxis to prevent or reduce the frequency of bleeding episodes. In some embodiments, a subject in need thereof may be treated with any of the Protein S antibodies provided herein, wherein the treatment is an on-demand treatment used for the control of bleeding episodes. In some embodiments, a subject in need thereof may be treated with any of the Protein S antibodies provided herein, wherein the treatment is a perioperative management of bleeding. For example, a perioperative management treatment may be used for treating a subject prior to, during, and/or after surgery or other medical procedure, or prior to, during, and/or after trauma.

In some embodiments, the treatment with any of the Protein S antibodies provided herein is provided as a chronic therapy, with dosing occurring continuously over time. In some embodiments, the treatment with any of the Protein S antibodies provided herein is provided as an intermittent therapy, with dosing occurring at irregular intervals. As an example, such an intermittent therapy can be used for a subject having menorrhagia. In some embodiments, the treatment with any of the Protein S antibodies provided herein is provided as an acute therapy, with dosing occurring for a short finite period of time. For example, the acute therapy may be administered for spontaneous bleeding episodes, or in conjunction with a surgery or other medical procedure, or after experiencing a trauma.

In some embodiments, the method of treatment of a subject may be a combination one of the above, e.g., the method of treatment may be prophylactic, and on-demand. In some embodiments, a prophylactic method of treatment may be a chronic therapy. In some embodiments, a prophylactic method of treatment may be an acute therapy. In some embodiments, a prophylactic method of treatment may be an intermittent therapy. In some embodiments, an on-demand treatment may be an acute therapy. In some embodiments, an on-demand treatment may be an intermittent treatment.

In some embodiments, treatment of a subject in need thereof comprises administering to the subject any of the Protein S antibodies provided herein, wherein the Protein S antibodies provided herein are Fab fragments. Without being bound to any theory, in some embodiments a shorter half-life of a Fab fragment, in relation to a full-length antibody with the same VH/VL may be beneficial for an acute treatment or on-demand. In some embodiments, the Fab fragment Protein S antibodies are administered to a subject in need thereof to reduce risk of bleeding.

B. Combination Therapies

The administration of any one of the therapeutic Protein S antibodies provided herein may be a monotherapy, or may be in combination with any other known drugs or treatments for diseases or conditions. In some embodiments, the other known drugs or treatments are useful for treating disorders, diseases, or conditions associated with reduced or impaired clotting. In some embodiments, the disorder, condition is a bleeding disorder. In some embodiments, the disorder, disease, or condition is a bleeding disorder or a platelet disorder.

In some embodiments, the administration of any of the therapeutic Protein S antibodies provided herein may be with a factor replacement therapy. In some embodiments, the administration of any of the therapeutic Protein S antibodies provided herein may be with the administration of a recombinant Factor VII.

C. Administration of Therapeutic Protein S Antibodies

The in vivo administration of the therapeutic Protein S antibodies described herein may be carried out intravenously, intramuscularly, subcutaneously, topically, orally, transdermally, intraperitoneally, intraorbitally, intrathecally, intraventricularly, intranasally, transmucosally, through implantation, or through inhalation. Administration of the therapeutic Protein S antibodies may be performed with any suitable excipients, carriers, or other agents to provide suitable or improved tolerance, transfer, delivery, and the like.

In some embodiments, the in vivo administration of any of the therapeutic Protein S antibodies provided herein may be an intravenous administration. In some embodiments, the intravenous administration may be provided as a prophylactic treatment. In some embodiments, the prophylactic treatment may be a routine prophylaxis. In some embodiments, the routine prophylaxis may have a regular dosing schedule. In some exemplary embodiments, the regular dosing schedule may be once weekly, twice weekly, once monthly, twice monthly, or three times monthly. In some embodiments, the intravenous administration may be provided as an on-demand treatment. In some embodiments, the intravenous administration may be provided as a chronic therapy. In some embodiments, the intravenous administration may be provided as an intermittent therapy. In some embodiments, the intravenous administration may be provided as an acute therapy. In some embodiments, an intermittent therapy may have a regular dosing schedule for the duration of the intermittent therapy. In some embodiments, an acute therapy may have a regular dosing schedule for the duration of the acute therapy. For example, administration of any of the therapeutic Protein S antibodies provided herein for an acute therapy by intravenous administration may occur on a regular dosing schedule for a predetermined duration of days, e.g., 7 days, 14 days, or more. Exemplary antibodies that may be used for an in vivo intravenous administration include, but are not limited to antibodies that (a) comprise the light chain variable domain comprising the amino acid sequence of SEQ ID NO: 71 and the heavy chain variable domain comprising the amino acid sequence of SEQ ID NO: 72, (b) comprise the light and heavy CDR amino acid sequences of SEQ ID NO: 2, SEQ ID NO: 13, SEQ ID NO: 22, SEQ ID NO: 34, SEQ ID NO: 46, and SEQ ID NO: 58, (c) comprise the amino acid sequence of SEQ ID NO: 75 and the heavy chain variable domain comprising the amino acid sequence of SEQ ID NO: 76, (d) comprise the light and heavy CDR amino acid sequences of SEQ ID NO: 1, SEQ ID NO: 15, SEQ ID NO: 24, SEQ ID NO: 36, SEQ ID NO: 48, and SEQ ID NO: 60, (e) comprise the amino acid sequence of SEQ ID NO: 69 and the heavy chain variable domain comprising the amino acid sequence of SEQ ID NO: 70, (f) comprise the light and heavy CDR amino acid sequences of SEQ ID NO: 1, SEQ ID NO: 12, SEQ ID NO: 21, SEQ ID NO: 33, SEQ ID NO: 45, and SEQ ID NO: 57, (g) comprise the amino acid sequence of SEQ ID NO: 89 and the heavy chain variable domain comprising the amino acid sequence of SEQ ID NO: 90, and (h) comprise the light and heavy CDR amino acid sequences of SEQ ID NO: 10, SEQ ID NO: 16, SEQ ID NO: 31, SEQ ID NO: 43, SEQ ID NO: 55, and SEQ ID NO: 67.

In some embodiments, the in vivo administration of any of the therapeutic Protein S antibodies provided herein may be a subcutaneous administration. In some embodiments, the subcutaneous administration may be provided as a prophylactic treatment. In some embodiments, the prophylactic treatment may be a routine prophylaxis. In some embodiments, the routine prophylaxis may have a regular dosing schedule. In some exemplary embodiments, the regular dosing schedule may be once weekly, twice weekly, once monthly, twice monthly, or three times monthly. In some embodiments, the subcutaneous administration may be provided as an on-demand treatment. In some embodiments, the subcutaneous administration may be provided as a chronic therapy. In some embodiments, the subcutaneous administration may be provided as an intermittent therapy. In some embodiments, the subcutaneous administration may be provided as an acute therapy. In some embodiments, an intermittent therapy may have a regular dosing schedule for the duration of the intermittent therapy. In some embodiments, an acute therapy may have a regular dosing schedule for the duration of the acute therapy. For example, administration of any of the therapeutic Protein S antibodies provided herein for an acute therapy by subcutaneous administration may occur on a regular dosing schedule for a predetermined duration of days, e.g., 7 days, 14 days, or more. Exemplary antibodies that may be used for an in vivo subcutaneous administration include, but are not limited to antibodies that (a) comprise the light chain variable domain comprising the amino acid sequence of SEQ ID NO: 71 and the heavy chain variable domain comprising the amino acid sequence of SEQ ID NO: 72, (b) comprise the light and heavy CDR amino acid sequences of SEQ ID NO: 2, SEQ ID NO: 13, SEQ ID NO: 22, SEQ ID NO: 34, SEQ ID NO: 46, and SEQ ID NO: 58, (c) comprise the amino acid sequence of SEQ ID NO: 75 and the heavy chain variable domain comprising the amino acid sequence of SEQ ID NO: 76, (d) comprise the light and heavy CDR amino acid sequences of SEQ ID NO: 1, SEQ ID NO: 15, SEQ ID NO: 24, SEQ ID NO: 36, SEQ ID NO: 48, and SEQ ID NO: 60, (e) comprise the amino acid sequence of SEQ ID NO: 69 and the heavy chain variable domain comprising the amino acid sequence of SEQ ID NO: 70, (f) comprise the light and heavy CDR amino acid sequences of SEQ ID NO: 1, SEQ ID NO: 12, SEQ ID NO: 21, SEQ ID NO: 33, SEQ ID NO: 45, and SEQ ID NO: 57, (g) comprise the amino acid sequence of SEQ ID NO: 89 and the heavy chain variable domain comprising the amino acid sequence of SEQ ID NO: 90, and (h) comprise the light and heavy CDR amino acid sequences of SEQ ID NO: 10, SEQ ID NO: 16, SEQ ID NO: 31, SEQ ID NO: 43, SEQ ID NO: 55, and SEQ ID NO: 67.

In some embodiments, the Protein S antibodies provided herein may be provided in a small volume amenable for injection, such as for subcutaneous administration. In some embodiments, the Protein S antibodies provided herein may be provided in a small volume amenable for injection by use of a pen-like auto-injector device. In some embodiments, the device is a syringe, for example a pre-filled syringe.

In some embodiments provided herein are single-dose vials useful for either subcutaneous or intravenous administration.

Accordingly, a therapeutically effective amount of the Protein S antibodies provided herein may be provided in a small volume for subcutaneous administration to a subject in need thereof. In some embodiments, the Protein S antibodies provided herein may be provided in a large volume amenable for administration by a subcutaneous infusion device, for subcutaneous infusion to a subject in need thereof.

D. Pharmaceutical Compositions

The disclosure also provides pharmaceutical compositions comprising any one of the Protein S antibodies disclosed herein, and optionally a pharmaceutical acceptable excipient or carrier. In some embodiments, the pharmaceutical composition is sterile. The pharmaceutical compositions may be formulated to be compatible with their intended routes of administration.

In some embodiments, the pharmaceutical compositions of the disclosure are suitable for administration to a human subject.

E. Diagnostic Antibodies

The antibodies provided herein may also be used for diagnostic purposes. For example, diagnostic antibodies could be used for detecting protein S deficiencies, or for detecting protein S levels in plasma prior to dosing (e.g. as a companion diagnostic).

Accordingly, in some embodiments, a Protein S antibody of the disclosure is conjugated to a label, for example a detectable label, a spin label, a colorimetric label, a radioactive label, an enzymatic label, a fluorescent label, or a magnetic label. The label may be detectable by spectroscopic, photochemical, biochemical, immunochemical, fluorescent, electrical, optical or chemical methods. Useful labels include, but are not limited to, magnetic beads (e.g. DYNABEADS®), fluorescent dyes (e.g., fluorescein isothiocyanate, red, rhodamine, and the like), radiolabels (e.g., 3H, 125I, 35S, 14C, or 32P), enzymes (e.g., LacZ, CAT, horseradish peroxidase, alkaline phosphatase and others, commonly used as detectable enzymes, either as marker gene products or in an ELISA), biotin, avidin, or streptavidin and colorimetric labels such as colloidal gold colored glass or plastic (e.g. polystyrene, polypropylene, latex, etc.) beads, and nanoparticles. In some embodiments, provided herein are substrates to which one or more Protein S antibodies of the disclosure is attached.

Detection may be carried out on any biological sample obtained from a subject. Biological samples include, but are not limited to whole blood, plasma, serum, saliva, urine, feces, synovial fluid, cerebrospinal fluid, bronchial lavage, ascites fluid, bone marrow aspirate, pleural effusion, tissue, cells, a biopsy, interstitial fluid, lymphatic fluid, or fractions thereof derived from a subject. In some embodiments, the biological sample comprises cells and the cells are in culture, in a suspension, on a slide, in intact tissue, or in preparation ready for a FACs analysis.

III. Kits and Articles of Manufacture

The disclosure also provides a kit or article of manufacture comprising any one of the antibodies disclosed herein, or any pharmaceutical composition disclosed herein. In some embodiments, the kits may further include instructional materials for carrying out any of the methods disclosed herein. In some embodiments, the kits may further include sterile containers or vials for holding the antibodies and/or pharmaceutical compositions disclosed herein. In some embodiments, the kits may further include sterile delivery devices for administering the antibodies and/or pharmaceutical compositions disclosed herein. In some embodiments, an article of manufacture comprises any pharmaceutical composition of the disclosure.

IV. Exemplary Enumerated Embodiments

Exemplary enumerated embodiments of the disclosure are as follows.

1. An antibody that binds Protein S, wherein the antibody is an inhibitor of the cofactor activity of Protein S for activated Protein C (APC), an inhibitor of the cofactor activity of Protein S for tissue factor pathway inhibitor (TFPI), or an inhibitor of the cofactor activity of Protein S for both APC and TFPI, and wherein the antibody is human, humanized, or chimeric.

2. An antibody that binds Protein S, wherein the antibody is capable of promoting coagulation and/or modulating a component in the coagulation cascade.

3. The antibody of any one of Enumerated Embodiments 1-2, wherein the antibody is an inhibitor for the cofactor activity of Protein S for APC.

4. The antibody of any one of Enumerated Embodiments 1-2, wherein the antibody is an inhibitor for the cofactor activity of Protein S for TFPI.

5. The antibody of any one of Enumerated Embodiments 1-2, wherein the antibody is an inhibitor for the cofactor activity of Protein S for both APC and TFPI.

6. The antibody of Enumerated Embodiment 3, wherein the capability of the antibody for inhibiting the cofactor activity of Protein S for TFPI is negligible.

7. The antibody of Enumerated Embodiment 4, wherein the capability of the antibody for inhibiting the cofactor activity of Protein S for APC is negligible.

8. The antibody of any one of Enumerated Embodiments 1-7, wherein the antibody binds to the C-terminus of Protein S.

9. The antibody of any one of Enumerated Embodiments 1-7, wherein the antibody binds to the N-terminus of Protein S.

10. The antibody of any one of Enumerated Embodiments 1-9, wherein the antibody binds to a thrombin-sensitive region of the Protein S.

11. The antibody of any one of Enumerated Embodiments 1-9, wherein the antibody binds to an EGF region of the Protein S.

12. The antibody of any one of Enumerated Embodiments 1-9, wherein the antibody binds to an SHBG region of Protein S.

13. The antibody of any one of Enumerated Embodiments 1-12, wherein the antibody is capable of promoting generation of a marker associated with coagulation activity.

14. The antibody of any one of Enumerated Embodiments 1-13, wherein the antibody is capable of promoting thrombin generation.

15. The antibody of any one of Enumerated Embodiments 1-14, wherein the antibody is capable of promoting D-dimer levels.

16. The antibody of any one of Enumerated Embodiments 1-15, wherein the antibody is capable of promoting fibrin generation.

17. The antibody of any one of Enumerated Embodiments 1-16, wherein activity of the antibody is dose-dependent.

18. The antibody of any one of Enumerated Embodiments 1-17, wherein activity of the antibody is measured in vitro.

19. The antibody of any one of Enumerated Embodiments 1-17, wherein activity of the antibody is measured in vivo.

20. The antibody of any one of Enumerated Embodiments 1-19, wherein the binding affinity of the antibody to Protein S is calcium-dependent.

21. The antibody of any one of Enumerated Embodiments 1-19, wherein the binding affinity of the antibody to Protein S is calcium-independent.

22. The antibody of any one of Enumerated Embodiments 1-21, wherein the antibody binds to free Protein S.

23. The antibody of any one of Enumerated Embodiments 1-21, wherein the antibody binds to complexed Protein S.

24. The antibody of Enumerated Embodiment 23, wherein the Protein S is complexed with C4BP.

25. The antibody of Enumerated Embodiment 23, wherein the Protein S is complexed with TFPI.

26. The antibody of any one of Enumerated Embodiments 1-25, wherein the antibody is a monoclonal antibody.

27. The antibody of any one of Enumerated Embodiments 1-26, wherein the antibody is a full-length antibody.

28. The antibody of any one of Enumerated Embodiments 1-26, wherein the antibody is an antibody fragment.

29. The antibody of any one of Enumerated Embodiments 1-28, wherein the antibody is a humanized antibody.

30. The antibody of any of Enumerated Embodiments 1-29, wherein the antibody comprises a Fc domain.

31. The antibody of Enumerated Embodiment 30, wherein the Fc domain is human.

32. The antibody of Enumerated Embodiment 31, wherein the human Fc domain is IgG1, IgG2, IgG3, or IgG4.

33. The antibody of Enumerated Embodiment 32, wherein the Fc domain of the antibody is human IgG4, optionally SEQ ID NO: 218, and comprises at least one amino acid substitution at a position selected from the group consisting of: 215, 221, 222, 228, 234, 235, 236, 239, 240, 241, 243, 244, 245, 247, 250, 252, 254, 256, 262, 263, 264, 265, 266, 267, 268, 269, 270, 292, 296, 297, 298, 299, 300, 305, 313, 324, 325, 326, 327, 328, 329, 330, 332, 333, 334, 345, 396, 428, 430, 433, 434, and 440, or comprises one or more of the substitutions selected from the group consisting of: T250Q/M428L, M252Y/S254T/T256E, M428L/N434S, S267E/L328F, N325S/L328F, and H433K/N434F, wherein the position numbers of the amino acid residues are of the EU numbering scheme.

34. The antibody of Enumerated Embodiment 27, wherein the antibody is a human antibody.

35. The antibody of Enumerated Embodiment 27, wherein the antibody is a chimeric antibody.

36. The antibody of any one of Enumerated Embodiments 1-35, wherein the antibody is conjugated.

37. The antibody of Enumerated Embodiment 36, wherein the antibody is conjugated to a label.

38. The antibody of any one of Enumerated Embodiments 1-37, wherein the antibody comprises any one or more of the amino acid sequences of the CDR sequences provided in Tables 1A, 1B, 1C, 2A, 2B, and 2C.

39. The Protein S antibody of any one of Enumerated Embodiments 1-38, wherein the antibody comprises:
   (a) any one of the CDR-L1 amino acid sequences of Table 1A;
   (b) any one of the CDR-L2 amino acid sequences of Table 1B;
   (c) any one of the CDR-L3 amino acid sequences of Table 1C;
   (d) any one of the CDR-H1 amino acid sequences of Table 2A;
   (e) any one of the CDR-H2 amino acid sequences of Table 2B; and
   (f) any one of the CDR-H3 amino acid sequences of Table 2C.

40. The Protein S antibody of any one of Enumerated Embodiments 1-39, wherein the light chain variable domain of the antibody comprises:
   (a) a CDR-L1 comprising the amino acid sequence of any one of SEQ ID NOs: 1-6, 9-11, 117, 127, 136, 141, 174, 184, 194, and 204;
   (b) a CDR-L2 comprising the amino acid sequence of any one of SEQ ID NOs: 12-20, 118, 128, 142, 175, 185, 195, and 205; and
   (c) a CDR-L3 comprising the amino acid sequence of any one of SEQ ID NOs: 21-27, 30-32, 119, 123, 129, 137, 143, 176, 186, 196, and 206.

41. The Protein S antibody of any one of Enumerated Embodiments 1-40, wherein the heavy chain variable domain of antibody comprises:
   (a) a CDR-H1 comprising the amino acid sequence of any one of SEQ ID NOs: 33-39, 42-44, 120, 124, 130, 138, 144, 179, 189, 199, and 209;
   (b) a CDR-H2 comprising the amino acid sequence of any one of SEQ ID NOs: 45-51, 54-56, 121, 125, 139, 145, 180, 190, 200, and 210; and
   (c) a CDR-H3 comprising the amino acid sequence of any one of SEQ ID NOs: 57-63, 66-68, 122, 126, 131, 140, 146, 181, 191, 201, and 211.

42. The Protein S antibody of any one of Enumerated Embodiments 1-41, wherein the light chain variable domain of the antibody comprises:
   (a) a CDR-L1 comprising the amino acid sequence of SEQ ID NO: 1;
   (b) a CDR-L2 comprising the amino acid sequence of SEQ ID NO: 12; and
   (c) a CDR-L3 comprising the amino acid sequence of SEQ ID NO: 21.

43. The Protein S antibody of any one of Enumerated Embodiments 1-41, wherein the light chain variable domain of the antibody comprises:
- (a) a CDR-L1 comprising the amino acid sequence of SEQ ID NO: 2;
- (b) a CDR-L2 comprising the amino acid sequence of SEQ ID NO: 13; and
- (c) a CDR-L3 comprising the amino acid sequence of SEQ ID NO: 22.

44. The Protein S antibody of any one of Enumerated Embodiments 1-41, wherein the light chain variable domain of the antibody comprises:
- (a) a CDR-L1 comprising the amino acid sequence of SEQ ID NO: 3;
- (b) a CDR-L2 comprising the amino acid sequence of SEQ ID NO: 14; and
- (c) a CDR-L3 comprising the amino acid sequence of SEQ ID NO: 23.

45. The Protein S antibody of any one of Enumerated Embodiments 1-41, wherein the light chain variable domain of the antibody comprises:
- (a) a CDR-L1 comprising the amino acid sequence of SEQ ID NO: 1;
- (b) a CDR-L2 comprising the amino acid sequence of SEQ ID NO: 15; and
- (c) a CDR-L3 comprising the amino acid sequence of SEQ ID NO: 24.

46. The Protein S antibody of any one of Enumerated Embodiments 1-41, wherein the light chain variable domain of the antibody comprises:
- (a) a CDR-L1 comprising the amino acid sequence of SEQ ID NO: 4;
- (b) a CDR-L2 comprising the amino acid sequence of SEQ ID NO: 16; and
- (c) a CDR-L3 comprising the amino acid sequence of SEQ ID NO: 25.

47. The Protein S antibody of any one of Enumerated Embodiments 1-41, wherein the light chain variable domain of the antibody comprises:
- (a) a CDR-L1 comprising the amino acid sequence of SEQ ID NO: 5;
- (b) a CDR-L2 comprising the amino acid sequence of SEQ ID NO: 17; and
- (c) a CDR-L3 comprising the amino acid sequence of SEQ ID NO: 26.

48. The Protein S antibody of any one of Enumerated Embodiments 1-41, wherein the light chain variable domain of the antibody comprises:
- (a) a CDR-L1 comprising the amino acid sequence of SEQ ID NO: 6;
- (b) a CDR-L2 comprising the amino acid sequence of SEQ ID NO: 18; and
- (c) a CDR-L3 comprising the amino acid sequence of SEQ ID NO: 27.

49. The Protein S antibody of any one of Enumerated Embodiments 1-41, wherein the light chain variable domain of the antibody comprises:
- (a) a CDR-L1 comprising the amino acid sequence of SEQ ID NO: 9;
- (b) a CDR-L2 comprising the amino acid sequence of SEQ ID NO: 19; and
- (c) a CDR-L3 comprising the amino acid sequence of SEQ ID NO: 30.

50. The Protein S antibody of any one of Enumerated Embodiments 1-41, wherein the light chain variable domain of the antibody comprises:
- (a) a CDR-L1 comprising the amino acid sequence of SEQ ID NO: 10;
- (b) a CDR-L2 comprising the amino acid sequence of SEQ ID NO: 16; and
- (c) a CDR-L3 comprising the amino acid sequence of SEQ ID NO: 31.

51. The Protein S antibody of any one of Enumerated Embodiments 1-41, wherein the light chain variable domain of the antibody comprises:
- (a) a CDR-L1 comprising the amino acid sequence of SEQ ID NO: 11;
- (b) a CDR-L2 comprising the amino acid sequence of SEQ ID NO: 20; and
- (c) a CDR-L3 comprising the amino acid sequence of SEQ ID NO: 32.

52. The Protein S antibody of any one of Enumerated Embodiments 1-41, wherein the light chain variable domain of the antibody comprises:
- (a) a CDR-L1 comprising the amino acid sequence of SEQ ID NO: 117;
- (b) a CDR-L2 comprising the amino acid sequence of SEQ ID NO: 118; and
- (c) a CDR-L3 comprising the amino acid sequence of SEQ ID NO: 119.

53. The Protein S antibody of any one of Enumerated Embodiments 1-41, wherein the light chain variable domain of the antibody comprises:
- (a) a CDR-L1 comprising the amino acid sequence of SEQ ID NO: 117;
- (b) a CDR-L2 comprising the amino acid sequence of SEQ ID NO: 118; and
- (c) a CDR-L3 comprising the amino acid sequence of SEQ ID NO: 123.

54. The Protein S antibody of any one of Enumerated Embodiments 1-41, wherein the light chain variable domain of the antibody comprises:
- (a) a CDR-L1 comprising the amino acid sequence of SEQ ID NO: 127;
- (b) a CDR-L2 comprising the amino acid sequence of SEQ ID NO: 128; and
- (c) a CDR-L3 comprising the amino acid sequence of SEQ ID NO: 129.

55. The Protein S antibody of any one of Enumerated Embodiments 1-41, wherein the light chain variable domain of the antibody comprises:
- (a) a CDR-L1 comprising the amino acid sequence of SEQ ID NO: 136;
- (b) a CDR-L2 comprising the amino acid sequence of SEQ ID NO: 17; and
- (c) a CDR-L3 comprising the amino acid sequence of SEQ ID NO: 137.

56. The Protein S antibody of any one of Enumerated Embodiments 1-41, wherein the light chain variable domain of the antibody comprises:
- (a) a CDR-L1 comprising the amino acid sequence of SEQ ID NO: 141;
- (b) a CDR-L2 comprising the amino acid sequence of SEQ ID NO: 142; and
- (c) a CDR-L3 comprising the amino acid sequence of SEQ ID NO: 143.

57. The Protein S antibody of any one of Enumerated Embodiments 1-41, wherein the light chain variable domain of the antibody comprises:
- (a) a CDR-L1 comprising the amino acid sequence of SEQ ID NO: 174;
- (b) a CDR-L2 comprising the amino acid sequence of SEQ ID NO: 175; and (c) a CDR-L3 comprising the amino acid sequence of SEQ ID NO: 176.

58. The Protein S antibody of any one of Enumerated Embodiments 1-41, wherein the light chain variable domain of the antibody comprises:
(a) a CDR-L1 comprising the amino acid sequence of SEQ ID NO: 184;
(b) a CDR-L2 comprising the amino acid sequence of SEQ ID NO: 185; and
(c) a CDR-L3 comprising the amino acid sequence of SEQ ID NO: 186.

59. The Protein S antibody of any one of Enumerated Embodiments 1-41, wherein the light chain variable domain of the antibody comprises:
(a) a CDR-L1 comprising the amino acid sequence of SEQ ID NO: 194;
(b) a CDR-L2 comprising the amino acid sequence of SEQ ID NO: 195; and
(c) a CDR-L3 comprising the amino acid sequence of SEQ ID NO: 196.

60. The Protein S antibody of any one of Enumerated Embodiments 1-41, wherein the light chain variable domain of the antibody comprises:
(a) a CDR-L1 comprising the amino acid sequence of SEQ ID NO: 204;
(b) a CDR-L2 comprising the amino acid sequence of SEQ ID NO: 205; and
(c) a CDR-L3 comprising the amino acid sequence of SEQ ID NO: 206.

61. The Protein S antibody of any one of Enumerated Embodiments 1-60, wherein the heavy chain variable domain of the antibody comprises:
(a) a CDR-H1 comprising the amino acid sequence of SEQ ID NO: 33;
(b) a CDR-H2 comprising the amino acid sequence of SEQ ID NO: 45; and
(c) a CDR-H3 comprising the amino acid sequence of SEQ ID NO: 57.

62. The Protein S antibody of any one of Enumerated Embodiments 1-60, wherein the heavy chain variable domain of the antibody comprises:
(a) a CDR-H1 comprising the amino acid sequence of SEQ ID NO: 34;
(b) a CDR-H2 comprising the amino acid sequence of SEQ ID NO: 46; and
(c) a CDR-H3 comprising the amino acid sequence of SEQ ID NO: 58.

63. The Protein S antibody of any one of Enumerated Embodiments 1-60, wherein the heavy chain variable domain of the antibody comprises:
(a) a CDR-H1 comprising the amino acid sequence of SEQ ID NO: 35;
(b) a CDR-H2 comprising the amino acid sequence of SEQ ID NO: 47; and
(c) a CDR-H3 comprising the amino acid sequence of SEQ ID NO: 59.

64. The Protein S antibody of any one of Enumerated Embodiments 1-60, wherein the heavy chain variable domain of the antibody comprises:
(a) a CDR-H1 comprising the amino acid sequence of SEQ ID NO: 36;
(b) a CDR-H2 comprising the amino acid sequence of SEQ ID NO: 48; and
(c) a CDR-H3 comprising the amino acid sequence of SEQ ID NO: 60.

65. The Protein S antibody of any one of Enumerated Embodiments 1-60, wherein the heavy chain variable domain of the antibody comprises:
(a) a CDR-H1 comprising the amino acid sequence of SEQ ID NO: 37;
(b) a CDR-H2 comprising the amino acid sequence of SEQ ID NO: 49; and
(c) a CDR-H3 comprising the amino acid sequence of SEQ ID NO: 61.

66. The Protein S antibody of any one of Enumerated Embodiments 1-60, wherein the heavy chain variable domain of the antibody comprises:
(a) a CDR-H1 comprising the amino acid sequence of SEQ ID NO: 38;
(b) a CDR-H2 comprising the amino acid sequence of SEQ ID NO: 50; and
(c) a CDR-H3 comprising the amino acid sequence of SEQ ID NO: 62.

67. The Protein S antibody of any one of Enumerated Embodiments 1-60, wherein the heavy chain variable domain of the antibody comprises:
(a) a CDR-H1 comprising the amino acid sequence of SEQ ID NO: 39;
(b) a CDR-H2 comprising the amino acid sequence of SEQ ID NO: 51; and
(c) a CDR-H3 comprising the amino acid sequence of SEQ ID NO: 63.

68. The Protein S antibody of any one of Enumerated Embodiments 1-60, wherein the heavy chain variable domain of the antibody comprises:
(a) a CDR-H1 comprising the amino acid sequence of SEQ ID NO: 42;
(b) a CDR-H2 comprising the amino acid sequence of SEQ ID NO: 54; and
(c) a CDR-H3 comprising the amino acid sequence of SEQ ID NO: 66.

69. The Protein S antibody of any one of Enumerated Embodiments 1-60, wherein the heavy chain variable domain of the antibody comprises:
(a) a CDR-H1 comprising the amino acid sequence of SEQ ID NO: 43;
(b) a CDR-H2 comprising the amino acid sequence of SEQ ID NO: 55; and
(c) a CDR-H3 comprising the amino acid sequence of SEQ ID NO: 67.

70. The Protein S antibody of any one of Enumerated Embodiments 1-60, wherein the heavy chain variable domain of the antibody comprises:
(a) a CDR-H1 comprising the amino acid sequence of SEQ ID NO: 44;
(b) a CDR-H2 comprising the amino acid sequence of SEQ ID NO: 56; and
(c) a CDR-H3 comprising the amino acid sequence of SEQ ID NO: 68.

71. The Protein S antibody of any one of Enumerated Embodiments 1-60, wherein the heavy chain variable domain of the antibody comprises:
(a) a CDR-H1 comprising the amino acid sequence of SEQ ID NO: 120;
(b) a CDR-H2 comprising the amino acid sequence of SEQ ID NO: 121; and
(c) a CDR-H3 comprising the amino acid sequence of SEQ ID NO: 122.

72. The Protein S antibody of any one of Enumerated Embodiments 1-60, wherein the heavy chain variable domain of the antibody comprises:
- (a) a CDR-H1 comprising the amino acid sequence of SEQ ID NO: 124;
- (b) a CDR-H2 comprising the amino acid sequence of SEQ ID NO: 125; and
- (c) a CDR-H3 comprising the amino acid sequence of SEQ ID NO: 126.

73. The Protein S antibody of any one of Enumerated Embodiments 1-60, wherein the heavy chain variable domain of the antibody comprises:
- (a) a CDR-H1 comprising the amino acid sequence of SEQ ID NO: 130;
- (b) a CDR-H2 comprising the amino acid sequence of SEQ ID NO: 50; and
- (c) a CDR-H3 comprising the amino acid sequence of SEQ ID NO: 131.

74. The Protein S antibody of any one of Enumerated Embodiments 1-60, wherein the heavy chain variable domain of the antibody comprises:
- (a) a CDR-H1 comprising the amino acid sequence of SEQ ID NO: 138;
- (b) a CDR-H2 comprising the amino acid sequence of SEQ ID NO: 139; and
- (c) a CDR-H3 comprising the amino acid sequence of SEQ ID NO: 140.

75. The Protein S antibody of any one of Enumerated Embodiments 1-60, wherein the heavy chain variable domain of the antibody comprises:
- (a) a CDR-H1 comprising the amino acid sequence of SEQ ID NO: 144;
- (b) a CDR-H2 comprising the amino acid sequence of SEQ ID NO: 145; and
- (c) a CDR-H3 comprising the amino acid sequence of SEQ ID NO: 146.

76. The Protein S antibody of any one of Enumerated Embodiments 1-60, wherein the heavy chain variable domain of the antibody comprises:
- (a) a CDR-H1 comprising the amino acid sequence of SEQ ID NO: 179;
- (b) a CDR-H2 comprising the amino acid sequence of SEQ ID NO: 180; and
- (c) a CDR-H3 comprising the amino acid sequence of SEQ ID NO: 181.

77. The Protein S antibody of any one of Enumerated Embodiments 1-60, wherein the heavy chain variable domain of the antibody comprises:
- (a) a CDR-H1 comprising the amino acid sequence of SEQ ID NO: 189;
- (b) a CDR-H2 comprising the amino acid sequence of SEQ ID NO: 190; and
- (c) a CDR-H3 comprising the amino acid sequence of SEQ ID NO: 191.

78. The Protein S antibody of any one of Enumerated Embodiments 1-60, wherein the heavy chain variable domain of the antibody comprises:
- (a) a CDR-H1 comprising the amino acid sequence of SEQ ID NO: 199;
- (b) a CDR-H2 comprising the amino acid sequence of SEQ ID NO: 200; and
- (c) a CDR-H3 comprising the amino acid sequence of SEQ ID NO: 201.

79. The Protein S antibody of any one of Enumerated Embodiments 1-60, wherein the heavy chain variable domain of the antibody comprises:
- (a) a CDR-H1 comprising the amino acid sequence of SEQ ID NO: 209;
- (b) a CDR-H2 comprising the amino acid sequence of SEQ ID NO: 210; and
- (c) a CDR-H3 comprising the amino acid sequence of SEQ ID NO: 211.

80. The Protein S antibody of any one of Enumerated Embodiments 1-41, wherein the antibody comprises the light and heavy CDR amino acid sequences of SEQ ID NO: 1, SEQ ID NO: 12, SEQ ID NO: 21, SEQ ID NO: 33, SEQ ID NO: 45, and SEQ ID NO: 57.

81. The Protein S antibody of any one of Enumerated Embodiments 1-41, wherein the antibody comprises the light and heavy CDR amino acid sequences of SEQ ID NO: 2, SEQ ID NO: 13, SEQ ID NO: 22, SEQ ID NO: 34, SEQ ID NO: 46, and SEQ ID NO: 58.

82. The Protein S antibody of any one of Enumerated Embodiments 1-41, wherein the antibody comprises the light and heavy CDR amino acid sequences of SEQ ID NO: 3, SEQ ID NO: 14, SEQ ID NO: 23, SEQ ID NO: 35, SEQ ID NO: 47, and SEQ ID NO: 59.

83. The Protein S antibody of any one of Enumerated Embodiments 1-41, wherein the antibody comprises the light and heavy CDR amino acid sequences of SEQ ID NO: 1, SEQ ID NO: 15, SEQ ID NO: 24, SEQ ID NO: 36, SEQ ID NO: 48, and SEQ ID NO: 60.

84. The Protein S antibody of any one of Enumerated Embodiments 1-41, wherein the antibody comprises the light and heavy amino acid sequences of SEQ ID NO: 4, SEQ ID NO: 16, SEQ ID NO: 25, SEQ ID NO: 37, SEQ ID NO: 49, and SEQ ID NO: 61.

85. The Protein S antibody of any one of Enumerated Embodiments 1-41, wherein the antibody comprises the light and heavy CDR amino acid sequences of SEQ ID NO: 5, SEQ ID NO: 17, SEQ ID NO: 26, SEQ ID NO: 38, SEQ ID NO: 50, and SEQ ID NO: 62.

86. The Protein S antibody of any one of Enumerated Embodiments 1-41, wherein the antibody comprises the light and heavy CDR amino acid sequences of SEQ ID NO: 6, SEQ ID NO: 18, SEQ ID NO: 27, SEQ ID NO: 39, SEQ ID NO: 51, and SEQ ID NO: 63.

87. The Protein S antibody of any one of Enumerated Embodiments 1-41, wherein the antibody comprises the light and heavy CDR amino acid sequences of SEQ ID NO: 9, SEQ ID NO: 19, SEQ ID NO: 30, SEQ ID NO: 42, SEQ ID NO: 54, and SEQ ID NO: 66.

88. The Protein S antibody of any one of Enumerated Embodiments 1-41, wherein the antibody comprises the light and heavy CDR amino acid sequences of SEQ ID NO: 10, SEQ ID NO: 16, SEQ ID NO: 31, SEQ ID NO: 43, SEQ ID NO: 55, and SEQ ID NO: 67.

89. The Protein S antibody of any one of Enumerated Embodiments 1-41, wherein the antibody comprises the light and heavy CDR amino acid sequences of SEQ ID NO: 11, SEQ ID NO: 20, SEQ ID NO: 32, SEQ ID NO: 44, SEQ ID NO: 56, and SEQ ID NO: 68.

90. The Protein S antibody of any one of Enumerated Embodiments 1-41, wherein the antibody comprises the light and heavy CDR amino acid sequences of SEQ ID NO: 117, SEQ ID NO: 118, SEQ ID NO: 119, SEQ ID NO: 120, SEQ ID NO: 121, and SEQ ID NO: 122.

91. The Protein S antibody of any one of Enumerated Embodiments 1-41, wherein the antibody comprises the light and heavy CDR amino acid sequences of SEQ ID NO: 117, SEQ ID NO: 118, SEQ ID NO: 123, SEQ ID NO: 124, SEQ ID NO: 125, and SEQ ID NO: 126.

92. The Protein S antibody of any one of Enumerated Embodiments 1-41, wherein the antibody comprises the light and heavy CDR amino acid sequences of SEQ ID NO: 127, SEQ ID NO: 128, SEQ ID NO: 129, SEQ ID NO: 130, SEQ ID NO: 50, and SEQ ID NO: 131.

93. The Protein S antibody of any one of Enumerated Embodiments 1-41, wherein the antibody comprises the light and heavy CDR amino acid sequences of SEQ ID NO: 136, SEQ ID NO: 17, SEQ ID NO: 137, SEQ ID NO: 138, SEQ ID NO: 139, and SEQ ID NO: 140.

94. The Protein S antibody of any one of Enumerated Embodiments 1-41, wherein the antibody comprises the light and heavy CDR amino acid sequences of SEQ ID NO: 141, SEQ ID NO: 142, SEQ ID NO: 143, SEQ ID NO: 144, SEQ ID NO: 145, and SEQ ID NO: 146.

95. The Protein S antibody of any one of Enumerated Embodiments 1-41, wherein the antibody comprises the light and heavy CDR amino acid sequences of SEQ ID NO: 174, SEQ ID NO: 175, SEQ ID NO: 176, SEQ ID NO: 179, SEQ ID NO: 180, and SEQ ID NO: 181.

96. The Protein S antibody of any one of Enumerated Embodiments 1-41, wherein the antibody comprises the light and heavy CDR amino acid sequences of SEQ ID NO: 184, SEQ ID NO: 185, SEQ ID NO: 186, SEQ ID NO: 189, SEQ ID NO: 190, and SEQ ID NO: 191.

97. The Protein S antibody of any one of Enumerated Embodiments 1-41, wherein the antibody comprises the light and heavy CDR amino acid sequences of SEQ ID NO: 194, SEQ ID NO: 195, SEQ ID NO: 196, SEQ ID NO: 199, SEQ ID NO: 200, and SEQ ID NO: 201.

98. The Protein S antibody of any one of Enumerated Embodiments 1-41, wherein the antibody comprises the light and heavy CDR amino acid sequences of SEQ ID NO: 204, SEQ ID NO: 205, SEQ ID NO: 206, SEQ ID NO: 209, SEQ ID NO: 210, and SEQ ID NO: 211.

99. The Protein S antibody of any one of Enumerated Embodiments 1-98, wherein the antibody comprises the variable chain amino acid sequence of any one of the amino acid sequences provided in Table 4A, and/or the variable chain amino acid sequence of any one of the amino acid sequences provided in Table 4B.

100. The Protein S antibody of any one of Enumerated Embodiments 1-99, wherein the antibody comprises the light and heavy variable chain amino acid sequence of any one of the amino acid sequence combinations provided in Table 4C.

101. The Protein S antibody of any one of Enumerated Embodiments 1-100, wherein the light chain variable domain of the antibody comprises the amino acid sequence of SEQ ID NO: 69 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and wherein the heavy chain variable domain of the antibody comprises the amino acid sequence of SEQ ID NO: 70, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

102. The Protein S antibody of one of Enumerated Embodiments 1-100, wherein the light chain variable domain of the antibody comprises the amino acid sequence of SEQ ID NO: 71 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 72, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

103. The Protein S antibody of any one of Enumerated Embodiments 1-100, wherein the light chain variable domain of the antibody comprises the amino acid sequence of SEQ ID NO: 73 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 74, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

104. The Protein S antibody of any one of Enumerated Embodiments 1-100, wherein the light chain variable domain of the antibody comprises the amino acid sequence of SEQ ID NO: 75 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 76, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

105. The Protein S antibody of any one of Enumerated Embodiments 1-100, wherein the light chain variable domain of the antibody comprises the amino acid sequence of SEQ ID NO: 77 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 78, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

106. The Protein S antibody of any one of Enumerated Embodiments 1-100, wherein the light chain variable domain of the antibody comprises the amino acid sequence of SEQ ID NO: 79 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 80, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

107. The Protein S antibody of any one of Enumerated Embodiments 1-100, wherein the light chain variable domain of the antibody comprises the amino acid sequence of SEQ ID NO: 81 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 82, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

108. The Protein S antibody of any one of Enumerated Embodiments 1-100, wherein the light chain variable domain of the antibody comprises the amino acid sequence of SEQ ID NO: 87 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 88, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

109. The Protein S antibody of any one of Enumerated Embodiments 1-100, wherein the light chain variable domain of the antibody comprises In some embodiments, provided herein are Protein S antibodies, wherein the light chain variable domain of the antibodies comprise the amino acid sequence of SEQ ID NO: 89 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 90, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

110. The Protein S antibody of any one of Enumerated Embodiments 1-100, wherein the light chain variable domain of the antibody comprises the amino acid sequence of SEQ ID NO: 91 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 92, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

111. The Protein S antibody of any one of Enumerated Embodiments 1-100, wherein the light chain variable domain of the antibody comprises the amino acid sequence of SEQ ID NO: 148 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 149, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

112. The Protein S antibody of any one of Enumerated Embodiments 1-100, wherein the light chain variable domain of the antibody comprises the amino acid sequence of SEQ ID NO: 150 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 151, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

113. The Protein S antibody of any one of Enumerated Embodiments 1-100, wherein the light chain variable domain of the antibody comprises the amino acid sequence of SEQ ID NO: 152 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 153, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

114. The Protein S antibody of any one of Enumerated Embodiments 1-100, wherein the light chain variable domain of the antibody comprises the amino acid sequence of SEQ ID NO: 156 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 157, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

115. The Protein S antibody of any one of Enumerated Embodiments 1-100, wherein the light chain variable domain of the antibody comprises the amino acid sequence of SEQ ID NO: 158 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 159, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

116. The Protein S antibody of any one of Enumerated Embodiments 1-100, wherein the light chain variable domain of the antibody comprises the amino acid sequence of SEQ ID NO: 177 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 182, or an amino acid sequence with at least 80%, 81%, 82%, $8^3$%, 84%, 85%, 86%, 87%, 88%, 89%, 90%, 91%, 92%, 93%, 94%, 95%, 96%, 97%, 98%, or 99% sequence identity thereto.

117. The Protein S antibody of any one of Enumerated Embodiments 1-100, wherein the light chain variable domain of the antibody comprises the amino acid sequence of SEQ ID NO: 187 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 192, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

118. The Protein S antibody of any one of Enumerated Embodiments 1-41, wherein the light chain variable domain of the antibody comprises the amino acid sequence of SEQ ID NO: 197 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 202, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

119. The Protein S antibody of any one of Enumerated Embodiments 1-100, wherein the light chain variable domain of the antibody comprises the amino acid sequence of SEQ ID NO: 207 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 212, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

120. The Protein S antibody of any one of Enumerated Embodiments 1-119, wherein the light chain comprises the amino acid sequence of SEQ ID NO: 214.

121. The Protein S antibody of any one of Enumerated Embodiments 1-119, wherein the light chain comprises the amino acid sequence of SEQ ID NO: 215.

122. A pharmaceutical composition comprising any one of the antibodies of Enumerated Embodiments 1-121, and optionally a pharmaceutically acceptable excipient.

123. A complex comprising Protein S and the antibody of any one of Enumerated Embodiments 1-119, wherein the antibody is bound to the Protein S, and the Protein S is free.

124. A complex comprising Protein S and the antibody of any one of Enumerated Embodiments 1-119, wherein the antibody is bound to the Protein S, and the Protein S is complexed.

125. The complex of Enumerated Embodiment 124, wherein the Protein S is bound to C4BP.

126. The complex of Enumerated Embodiment 124, wherein the Protein S is bound to TFPI.

127. A nucleic acid encoding for any one of the antibodies of Enumerated Embodiments 1-121.

128. The nucleic acid of Enumerated Embodiment 127, comprising any one of the nucleic acid sequences selected from Table 5A.

129. The nucleic acid of any one of Enumerated Embodiments 127-128, comprising any one of the nucleic acid sequences selected from Table 5B.

130. The nucleic acid of any one of Enumerated Embodiments 127-129, wherein the nucleic acid comprises the nucleic acid sequence of any one of the nucleic acid sequence combinations provided in Table 5C.

131. The nucleic acid of any one of Enumerated Embodiments 127-130, wherein the light chain variable domain of the Protein S antibody is encoded by the nucleic acid sequence of SEQ ID NO: 93 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 94, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

132. The nucleic acid of any one of Enumerated Embodiments 127-130, wherein the light chain variable domain of the Protein S antibody is encoded by the nucleic acid sequence of SEQ ID NO: 95 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 96, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

133. The nucleic acid of any one of Enumerated Embodiments 127-130, wherein the light chain variable domain of the Protein S antibody is encoded by the nucleic acid sequence of SEQ ID NO: 97 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 98, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

134. The nucleic acid of any one of Enumerated Embodiments 127-130, wherein the light chain variable domain of the Protein S antibody is encoded by the nucleic acid sequence of SEQ ID NO: 99 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 100, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

135. The nucleic acid of any one of Enumerated Embodiments 127-130, wherein the light chain variable domain of the Protein S antibody is encoded by the nucleic acid sequence of SEQ ID NO: 101 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 102, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

136. The nucleic acid of any one of Enumerated Embodiments 127-130, wherein the light chain variable domain of the Protein S antibody is encoded by the nucleic acid sequence of SEQ ID NO: 103 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 104, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

137. The nucleic acid of any one of Enumerated Embodiments 127-130, wherein the light chain variable domain of the Protein S antibody is encoded by the nucleic acid sequence of SEQ ID NO: 105 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 106, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

138. The nucleic acid of any one of Enumerated Embodiments 127-130, wherein the light chain variable domain of the Protein S antibody is encoded by the nucleic acid sequence of SEQ ID NO: 111 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 112, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

139. The nucleic acid of any one of Enumerated Embodiments 127-130, wherein the light chain variable domain of the Protein S antibody is encoded by the nucleic acid sequence of SEQ ID NO: 113 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 114, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

140. The nucleic acid of any one of Enumerated Embodiments 127-130, wherein the light chain variable domain of the Protein S antibody is encoded by the nucleic acid sequence of SEQ ID NO: 115 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 116, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

141. The nucleic acid of any one of Enumerated Embodiments 127-130, wherein the light chain variable domain of the Protein S antibody is encoded by the nucleic acid sequence of SEQ ID NO: 162 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 163, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

142. The nucleic acid of any one of Enumerated Embodiments 127-130, wherein the light chain variable domain of the Protein S antibody is encoded by the nucleic acid sequence of SEQ ID NO: 164 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 165, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

143. The nucleic acid of any one of Enumerated Embodiments 127-130, wherein the light chain variable domain of the Protein S antibody is encoded by the nucleic acid sequence of SEQ ID NO: 166 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 167, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

144. The nucleic acid of any one of Enumerated Embodiments 127-130, wherein the light chain variable domain of the Protein S antibody is encoded by the nucleic acid sequence of SEQ ID NO: 170 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 171, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

145. The nucleic acid of any one of Enumerated Embodiments 127-130, wherein the light chain variable domain of the Protein S antibody is encoded by the nucleic acid sequence of SEQ ID NO: 172 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 173, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

146. The nucleic acid of any one of Enumerated Embodiments 127-130, wherein the light chain variable domain of the Protein S antibody is encoded by the nucleic acid sequence of SEQ ID NO: 178 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 183, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

147. The nucleic acid of any one of Enumerated Embodiments 127-130, wherein the light chain variable domain of the Protein S antibody is encoded by the nucleic acid sequence of SEQ ID NO: 188 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 193, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

148. The nucleic acid of any one of Enumerated Embodiments 127-130, wherein the light chain variable domain of the Protein S antibody is encoded by the nucleic acid sequence of SEQ ID NO: 198 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 203, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

149. The nucleic acid of any one of Enumerated Embodiments 127-130, wherein the light chain variable domain of the Protein S antibody is encoded by the nucleic acid sequence of SEQ ID NO: 208 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 213, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

150. A vector comprising the nucleic acid of any one of Enumerated Embodiments 127-149.

151. An in vitro method of promoting the coagulation of blood, comprising contacting the antibody of any one of Enumerated Embodiments 1-121 with a blood sample.

152. The method of Enumerated Embodiment 151, wherein the blood sample comprises plasma.

153. The method of any one of Enumerated Embodiments 151-152, wherein a marker associated with coagulation activity is increased.

154. The method of any one of Enumerated Embodiments 151-153, wherein thrombin generation is promoted.

155. The method of any one of Enumerated Embodiments 151-154, wherein fibrin generation is promoted.

156. The method of any one of Enumerated Embodiments 151-155, wherein D-dimer levels are promoted.

157. The method of any one of Enumerated Embodiments 151-156, wherein the blood sample is obtained from a subject having a coagulation factor deficiency, von Willebrand disease, or a platelet disorder.

158. A method of promoting the coagulation of blood in a subject in need thereof, comprising administering to the subject the antibody of any one of Enumerated Embodiments 1-121 or the pharmaceutical composition of Enumerated Embodiment 122.

159. The method of Enumerated Embodiment 158, wherein a marker associated with coagulation activity is increased.

160. The method of any of Enumerated Embodiments 158-159, wherein thrombin generation is promoted in the subject.

161. The method of any of Enumerated Embodiments 158-160, wherein fibrin generation is promoted in the subject.

162. The method of any of Enumerated Embodiments 153-161, wherein D-dimer levels are increased in the subject.

163. The method of any of Enumerated Embodiments 153-162, wherein the antibody remains active in the subject for a period of time.

164. method of any of Enumerated Embodiments 151-163, wherein activity of the antibody is dose-dependent.

165. A method of promoting the generation of thrombin in a subject in need thereof, comprising administering to the subject the antibody of any one of Enumerated Embodiments 1-121 or the pharmaceutical composition of Enumerated Embodiment 122.

166. The method of Enumerated Embodiment 165, wherein the subject has a coagulation factor deficiency, von Willebrand disease, or a platelet disorder, and the antibody restores or promotes the generation of thrombin.

167. A method of treating a condition in a subject in need thereof, comprising administering to the subject the antibody of Enumerated Embodiments 1-121 or the pharmaceutical composition of Enumerated Embodiment 122, wherein the condition is selected from the group consisting of: bleeding disorders, platelet disorders, trauma, and bleeding resulting from a surgery or a medical procedure.

168. The method of Enumerated Embodiment 167, wherein the method of treating is prophylactic.

169. The method of Enumerated Embodiment 167, wherein the method of treating is on-demand.

170. The method of any one of Enumerated Embodiments 167-169, wherein the method is prophylactic and on-demand.

171. The method of any one of Enumerated Embodiments 168 or 170, wherein the prophylactic method of treating is a routine prophylaxis.

172. The method of any one of Enumerated Embodiments 167-171, wherein the administration of the antibody of any one of Enumerated Embodiments 1-119 is a subcutaneous administration.

173. The method of any one of Enumerated Embodiments 158-172, wherein the method of treating is acute.

174. The method of any one of Enumerated Embodiments 158-172, wherein the method of treating is chronic.

175. The method of any one of Enumerated Embodiments 158-172, wherein the method of treating is perioperative.

176. The method of any one of Enumerated Embodiments 158-172, wherein the method of treating is intermittent.

177. The method of any one of Enumerated Embodiments 158-176, wherein the antibody exhibits graded inhibition.

178. The method of any one of Enumerated Embodiments 158-176, wherein the antibody exhibits switch-like inhibition.

179. The method of any one of Enumerated Embodiments 167-178, wherein the subject suffers from two or more conditions selected from the group consisting of: bleeding disorders, platelet disorders, trauma, and bleeding resulting from a surgery or a medical procedure.

180. The method of any one of Enumerated Embodiments 165-179, wherein the subject suffers from a bleeding disorder selected from the group consisting of: hemophilia A, hemophilia B, von Willebrand disease (vWD) disease, menorrhagia, Factor I deficiency, Factor II deficiency, Factor V deficiency, Factor VII deficiency, Factor X deficiency, Factor XI deficiency, Factor VIII deficiency (hemophilia A), Factor IX deficiency (hemophilia B), trauma, and hereditary hemorrhagic telangiectasia.

181. The method of any one of Enumerated Embodiments 158-180, wherein the subject is a hemophilia carrier.

182. The method of any one of Enumerated Embodiments 165-181, wherein the subject suffers from menorrhagia.

183. The method of any one of Enumerated Embodiments 158-182, wherein the subject suffers from menorrhagia associated with one or more of the bleeding disorders or the platelet disorders.

184. The method of Enumerated Embodiment 180, wherein the bleeding disorder is vWD, and wherein the subject is undergoing a prophylactic treatment.

185. The method of Enumerated Embodiment 180, wherein the bleeding disorder is vWD, and the vWD is a subtype selected from: vWD Type 1, vWD Type 2A, vWD Type 2B, vWD Type 2N, vWD Type 2M, vWD Type 3, and acquired vWD.

186. The method of any one of Enumerated Embodiments 167-185, wherein the condition is a platelet disorder selected from the group consisting of: Bernard-Soulier syndrome, Glanzmann's thrombasthenia, and platelet storage pool deficiency.

187. The method of Enumerated Embodiment 186, wherein the platelet disorder is a platelet storage pool deficiency selected from the group consisting of: Gray platelet syndrome, Quebec platelet disorder, and MYH9-related thrombocytopenia (MYH9RD).

188. The method of Enumerated Embodiment 180, wherein the bleeding disorder is selected from Factor I deficiency, Factor II deficiency, Factor V deficiency, Factor VII deficiency, Factor X deficiency, Factor XI deficiency, Factor VIII deficiency (hemophilia A), Factor IX deficiency (hemophilia B), and vWD disease, and wherein the subject has inhibitors.

189. The method of any one of Enumerated Embodiments 167-188, wherein the antibody or the pharmaceutical composition is capable of promoting thrombin generation in the subject.

190. The method of any one of Enumerated Embodiments 165-166, wherein the thrombin generation does not exceed a predetermined threshold level.

191. The method of any one of Enumerated Embodiments 165-166 and 190, wherein the thrombin generation is antibody concentration-dependent.

193. A kit or article of manufacture comprising an antibody of any one of Enumerated Embodiments 1-121 or the pharmaceutical composition of Enumerated Embodiment 122.

193. Use of the antibody of any one of Enumerated Embodiments 1-121 or the pharmaceutical composition of Enumerated Embodiment 122 for the treatment of a condition in a subject in need thereof.

194. Use of the antibody of any one of Enumerated Embodiments 1-121 or the pharmaceutical composition of Enumerated Embodiment 122 for the manufacture of a medicament for the treatment of a condition in a subject in need thereof.

The present invention is not limited in scope by the specific embodiments described herein, which are intended as illustrations of individual aspects or embodiments of the invention. Functionally equivalent methods and components are within the scope of the invention. Various modifications of the invention, in addition to those described here, are apparent to those skilled in the art from the foregoing description and accompanying drawings. Such modifications fall within the scope of the invention.

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the antibodies of the present invention and practice the claimed methods. The following examples therefore, specifically point out the preferred embodiments of the present invention, and are not to be construed as limiting in any way the remainder of the disclosure.

EXAMPLES

Example 1: Generation of Protein S Antibodies

The Protein S antibodies of the disclosure were generated as follows. Animals (e.g., mice, rats) were immunized with a full-length purified human plasma Protein S. Three immunization campaigns were carried out and standard techniques were used to generate hybridoma libraries from the animals. Flow cytometry and single cell sorting was used to generate single cell clones. Supernatants from these single clones were then screened for binding to both human and cynomolgus monkey Protein S. Clones that exhibited binding to both human and cynomolgus monkey Protein S were selected for expanded growth. The expanded cultures were then purified over Protein G or Protein A Sepharose using standard techniques. These purified antibody preparations were used in subsequent functional assays. The selected Protein S antibodies had a human or mouse variable region and a rat Fc domain, or a mouse Fc domain.

Antibodies having a human variable region and a rat or mouse Fc domain were made into fully human antibodies maintaining the human variable domain as the parent antibody, but with a human IgG4 Fc domain. Table 6 below lists the Antibody number used to designate the human antibodies in the first column and the corresponding parental rodent antibodies (with the human variable region) in the second column. The second column also includes a single antibody with a mouse variable domain and a mouse Fc domain. The subsequent columns provide the variable light chain/variable heavy chain amino acid sequences and nucleic acid sequences, and the last column provides the amino acid sequences of the set of six CDRs that map to each Antibody.

TABLE 6

| Human Antibody: Protein S Antibody with Human Fc | Rat Antibody: Protein S Antibody with Rat Fc | Variable Light Chain, Variable Heavy Chain (Amino Acid Sequences) | Variable Light Chain, Variable Heavy Chain (Nucleic Acid Sequences) | CDR Combination (Amino Acid Sequences) |
|---|---|---|---|---|
| Antibody 1 | Antibody 13 | SEQ ID NO: 71, SEQ ID NO: 72 | SEQ ID NO: 95, SEQ ID NO: 96 | SEQ ID NO: 2, SEQ ID NO: 13, SEQ ID NO: 22, SEQ ID NO: 34, SEQ ID NO: 46, SEQ ID NO: 58 |
| Antibody 2 | Antibody 14 | SEQ ID NO: 73, SEQ ID NO: 74 | SEQ ID NO: 97, SEQ ID NO: 98 | SEQ ID NO: 3, SEQ ID NO: 14, SEQ ID NO: 23, SEQ ID NO: 35, SEQ ID NO: 47, SEQ ID NO: 59 |
| Antibody 3 | Antibody 15 | SEQ ID NO: 75, SEQ ID NO: 76 | SEQ ID NO: 99, SEQ ID NO: 100 | SEQ ID NO: 1, SEQ ID NO: 15, SEQ ID NO: 24, SEQ ID NO: 36, SEQ ID NO: 48, SEQ ID NO: 60 |

TABLE 6-continued

| Human Antibody: Protein S Antibody with Human Fc | Rat Antibody: Protein S Antibody with Rat Fc | Variable Light Chain, Variable Heavy Chain (Amino Acid Sequences) | Variable Light Chain, Variable Heavy Chain (Nucleic Acid Sequences) | CDR Combination (Amino Acid Sequences) |
|---|---|---|---|---|
| Antibody 4 | Antibody 16 | SEQ ID NO: 77, SEQ ID NO: 78 | SEQ ID NO: 101, SEQ ID NO: 102 | SEQ ID NO: 4, SEQ ID NO: 16, SEQ ID NO: 25, SEQ ID NO: 37, SEQ ID NO: 49, SEQ ID NO: 61 |
| Antibody 6 | Antibody 18 | SEQ ID NO: 91, SEQ ID NO: 92 | SEQ ID NO: 115, SEQ ID NO: 116 | SEQ ID NO: 11, SEQ ID NO: 20, SEQ ID NO: 32, SEQ ID NO: 44, SEQ ID NO: 56, SEQ ID NO: 68 |
| Antibody 7 | Antibody 19 | SEQ ID NO: 69, SEQ ID NO: 70 | SEQ ID NO: 93, SEQ ID NO: 94 | SEQ ID NO: 1, SEQ ID NO: 12, SEQ ID NO: 21, SEQ ID NO: 33, SEQ ID NO: 45, SEQ ID NO: 57 |
| Antibody 8 | Antibody 20 | SEQ ID NO: 79, SEQ ID NO: 80 | SEQ ID NO: 103, SEQ ID NO: 104 | SEQ ID NO: 5, SEQ ID NO: 17, SEQ ID NO: 26, SEQ ID NO: 38, SEQ ID NO: 50, SEQ ID NO: 62 |
| Antibody 9 | Antibody 21 | SEQ ID NO: 81, SEQ ID NO: 82 | SEQ ID NO: 105, SEQ ID NO; 106 | SEQ ID NO: 6, SEQ ID NO: 18, SEQ ID NO: 27, SEQ ID NO: 39, SEQ ID NO: 51, SEQ ID NO: 63 |
| Antibody 11 | Antibody 23 | SEQ ID NO: 87, SEQ ID NO: 88 | SEQ ID NO: 111, SEQ ID NO: 112 | SEQ ID NO: 9, SEQ ID NO: 19, SEQ ID NO: 30, SEQ ID NO: 42, SEQ ID NO: 54, SEQ ID NO: 66 |
| Antibody 12 | Antibody 24 | SEQ ID NO: 89, SEQ ID NO: 90 | SEQ ID NO: 113, SEQ ID NO: 114 | SEQ ID NO: 10, SEQ ID NO: 16, SEQ ID NO: 31, SEQ ID NO: 43, SEQ ID NO: 55, SEQ ID NO: 67 |
| Antibody 29 | Antibody 35 | SEQ ID NO: 148, SEQ ID NO: 149 | SEQ ID NO: 162, SEQ ID NO: 163 | SEQ ID NO: 117, SEQ ID NO: 118, SEQ ID NO: 119, SEQ ID NO: 120, SEQ ID NO: 121, SEQ ID NO: 122 |
| Antibody 30 | Antibody 36 | SEQ ID NO: 150, SEQ ID NO: 151 | SEQ ID NO: 164, SEQ ID NO: 165 | SEQ ID NO: 117, SEQ ID NO: 118, SEQ ID NO: 123, SEQ ID NO: 124, SEQ ID NO: 125, SEQ ID NO: 126 |
| Antibody 25 | Antibody 31 | SEQ ID NO: 152, SEQ ID NO: 153 | SEQ ID NO: 166, SEQ ID NO: 167 | SEQ ID NO: 127, SEQ ID NO: 128, SEQ ID NO: 129, SEQ ID NO: 130, SEQ ID NO: 50, SEQ ID NO: 131 |
| Antibody 27 | Antibody 33 | SEQ ID NO: 156, SEQ ID NO: 157 | SEQ ID NO: 170, SEQ ID NO: 171 | SEQ ID NO: 136, SEQ ID NO: 17, SEQ ID NO: 137, SEQ ID NO: 138, SEQ ID NO: 139, SEQ ID NO: 140 |
| Antibody 28 | Antibody 34* (*mouse variable region/mouse Fc) | SEQ ID NO: 158, SEQ ID NO: 159 | SEQ ID NO: 172, SEQ ID NO: 173 | SEQ ID NO: 141, SEQ ID NO: 142, SEQ ID NO: 143, SEQ ID NO: 144, SEQ ID NO: 145, SEQ ID NO: 146 |

TABLE 6-continued

| Human Antibody: Protein S Antibody with Human Fc | Rat Antibody: Protein S Antibody with Rat Fc | Variable Light Chain, Variable Heavy Chain (Amino Acid Sequences) | Variable Light Chain, Variable Heavy Chain (Nucleic Acid Sequences) | CDR Combination (Amino Acid Sequences) |
|---|---|---|---|---|
| Antibody 37 | Antibody 38 | SEQ ID NO: 177, SEQ ID NO: 182 | SEQ ID NO: 178, SEQ ID NO: 183 | SEQ ID NO: 174, SEQ ID NO: 175, SEQ ID NO: 176, SEQ ID NO: 179, SEQ ID NO: 180, SEQ ID NO: 181 |
| Antibody 39 | Antibody 40 | SEQ ID NO: 187, SEQ ID NO: 192 | SEQ ID NO: 188, SEQ ID NO: 193 | SEQ ID NO: 184, SEQ ID NO: 185, SEQ ID NO: 186, SEQ ID NO: 189, SEQ ID NO: 190, SEQ ID NO: 191 |
| Antibody 41 | Antibody 42 | SEQ ID NO: 197, SEQ ID NO: 202 | SEQ ID NO: 198, SEQ ID NO: 203 | SEQ ID NO: 194, SEQ ID NO: 195, SEQ ID NO: 196, SEQ ID NO: 199, SEQ ID NO: 200, SEQ ID NO: 201 |
| Antibody 43 | Antibody 44 | SEQ ID NO: 207, SEQ ID NO: 212 | SEQ ID NO: 208, SEQ ID NO: 213 | SEQ ID NO: 204, SEQ ID NO: 205, SEQ ID NO: 206, SEQ ID NO: 209, SEQ ID NO: 210, SEQ ID NO: 211 |

Example 2: Assessing Thrombin Generation in APC and TFPT Cofactor Activity Screening Assays Assessing APC and TFPI Cofactor Activity with Screening Assays FIGS. 2A-2B3 depict exemplary assays performed to assess APC and TFPI cofactor activity, respectively and demonstrate how a APC cofactor inhibitor and a TFPI cofactor inhibitor would behave in the assay.

Figure 2B:
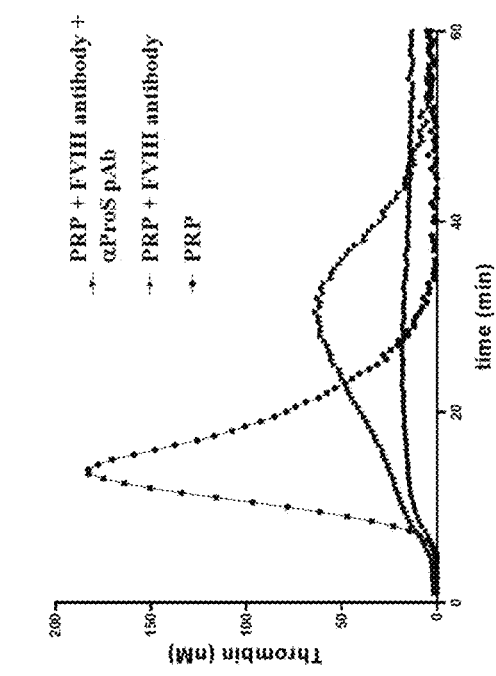
FIGS. 2A-2B depict the results of screening assays performed to assess APC and TFPI cofactor activity, respectively, using control Protein S antibodies. In this and subsequent figures, ProS=Protein S; mAb=monoclonal antibody; pAb=polyclonal antibody; PRP=platelet rich plasma.
Figure 2A:
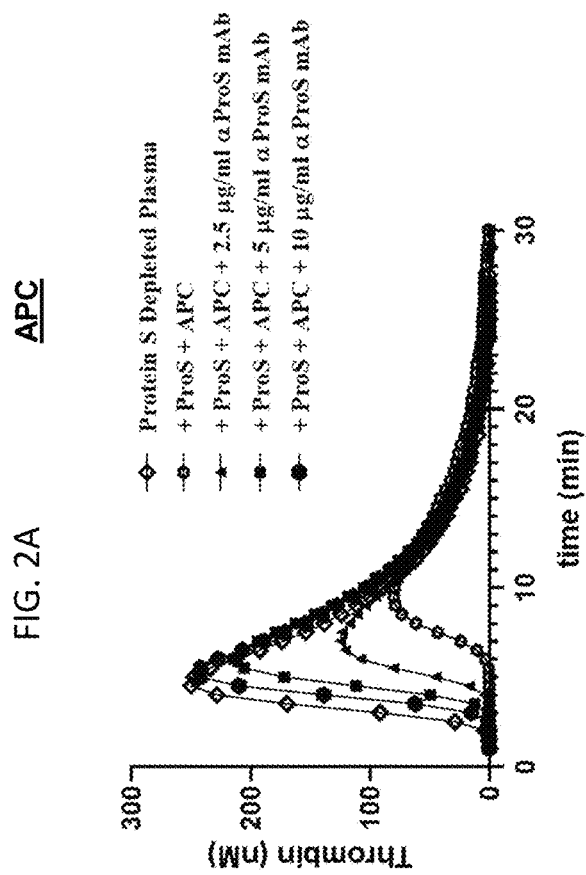
Figure 3:
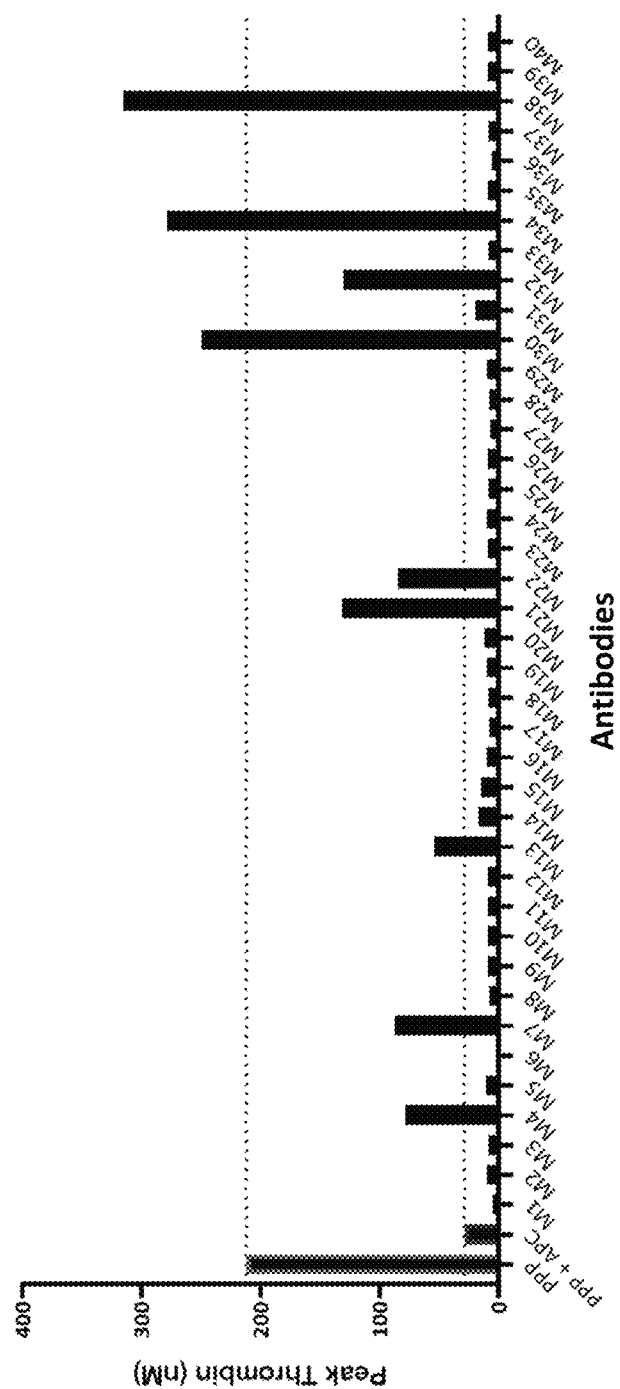
FIGS. 3-4 depict peak thrombin levels generated by Protein S monoclonal antibodies, identified from hybridoma libraries, in the APC cofactor and TFPI cofactor screening assays, respectively.

FIGS. 2A-2B depict assays performed to assess APC and TFPI cofactor activity, respectively. For the APC cofactor activity screening assay depicted in FIG. 2A, the following were tested: Protein S depleted platelet poor plasma, Protein S depleted plasma reconstituted with a Protein S and APC mixture, and Protein S depleted plasma reconstituted with a Protein S and APC mixture in the presence of varying concentrations of an anti-Protein S monoclonal antibody (mAb). The Protein S and APC mixture was made by pre-mixing Protein S and APC and adding to the Protein S depleted plasma to create a Protein S-dependent assay, due to APC not showing inhibition of thrombin generation in the absence of Protein S. As shown, the addition of the pre-mixed Protein S and APC mixture to Protein S depleted plasma shows significantly less tissue factor-induced thrombin generation than the Protein S depleted plasma alone. Addition of anti-Protein S mAbs to the Protein S depleted plasma+Protein S and APC mixture restored tissue factor-induced thrombin generation in a concentration-dependent manner.

For the TFPI cofactor activity screening assay depicted in FIG. 2B, the following were tested: platelet rich plasma with no treatment (also referred to herein as platelet-rich plasma, or PRP), a commercial Factor VIII (FVIII) neutralizing antibody, and a FVIII antibody and Protein S polyclonal antibody (pAB) mixture. The FVIII antibody acts as a neutralizing antibody and inhibits tissue factor induced thrombin generation. Addition of the neutralizing Protein S antibodies enhanced thrombin generation in the presence of the FVIII antibody. Neutralizing Protein C antibodies did not show an effect on thrombin generation in the TFPI cofactor activity assay, suggesting that endogenous Protein C or activated Protein C does not inhibit thrombin generation in this assay.

Figure 4:
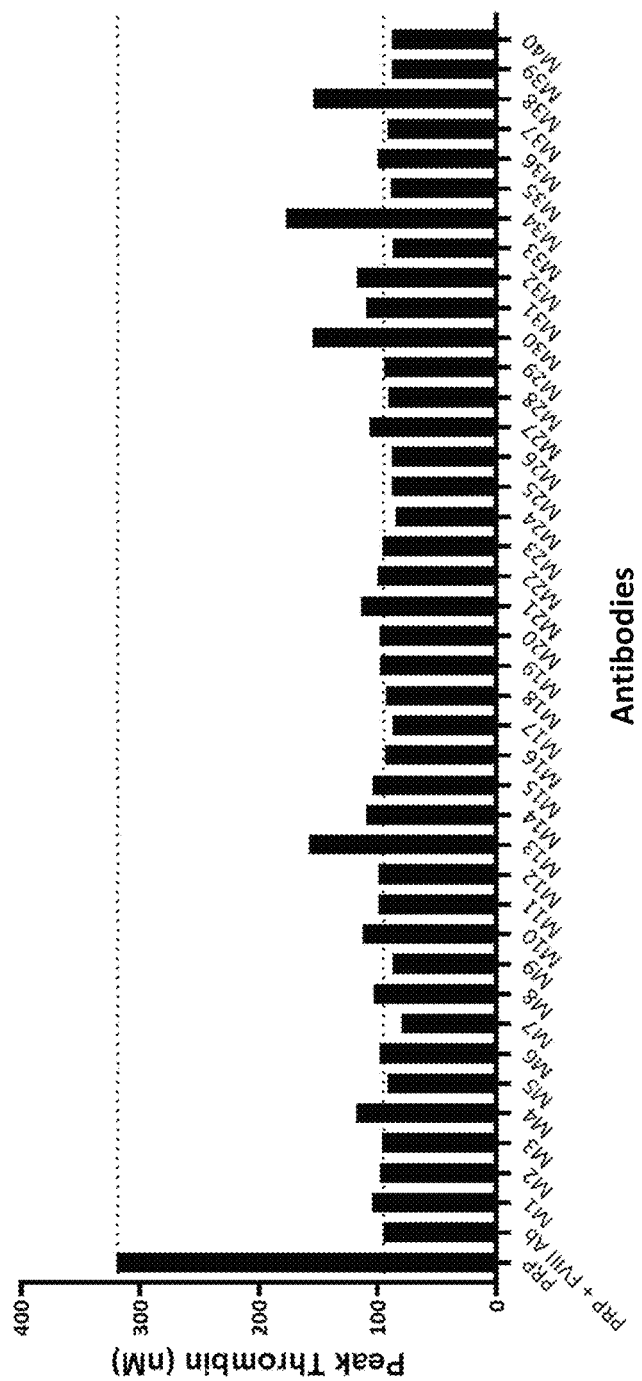

Clones M1-M40 were generated from a rat hybridoma library described in Example 1. The cofactor activity assays performed as described when referring to FIGS. 2A-2B were used to measure the amount of thrombin generation in the presence of clones M1-M40 generated from a rat hybridoma library. FIGS. 3-4 depict the peak thrombin levels generated from an APC cofactor screening assay (APC assay) and a TFPI cofactor screening assay, respectively, of the clones M1-M40. Controls used for the APC assay depicted in FIG. 3 were platelet-poor plasma ("PPP") alone and PPP with APC. Controls used for the TFPI assay depicted in FIG. 4 were platelet-rich plasma ("PRP") alone and PRP with a commercial neutralizing FVIII antibody.

Example 3: Characterization of Selected Protein S Antibodies

Characterization of Inhibitor Type by Cofactor Activity Assays

As a general matter, Protein S antibodies can be identified as either a dual inhibitor of Protein S cofactor activity for both APC and TFPI, for APC only (APC cofactor inhibitor), or for TFPI (TFPI cofactor inhibitor) only. The antibodies can be categorized by assessment of the thrombin generation profiles shown when assaying each antibody using the cofactor activity assays described in FIGS. 2A-2B.

Figure 5:
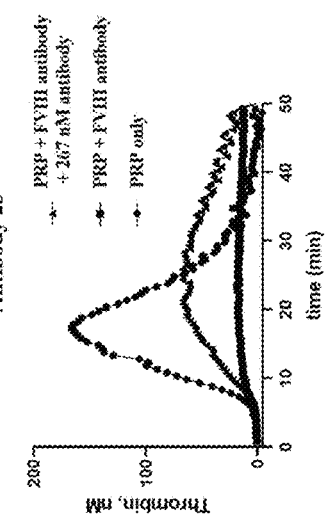
FIGS. 5-10 depict the prototypic thrombin generation profiles of a dual inhibitor of APC and TFPI (Antibody 13.
Figure 6:
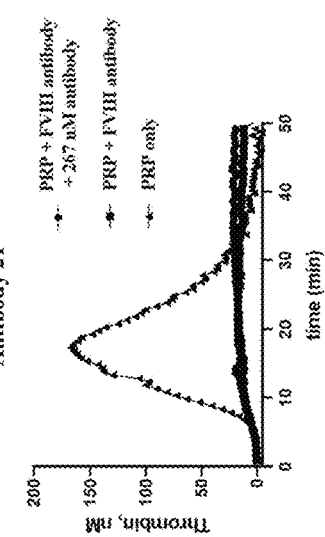

FIGS. 5-6 depict thrombin generation in the presence of Antibody 13 in the TFPI cofactor assay (FIG. 5) and the APC cofactor assay (FIG. 6). As shown in the TFPI cofactor activity assay using PRP, robust thrombin generation occurred in the absence of FVIII antibody and was reduced by addition of the FVIII antibody. Addition of 267 nM Antibody 13 promoted thrombin generation in the presence of the FVIII antibody. As shown in the APC cofactor activity assay, thrombin generation was reduced by addition of both APC and Protein S to Protein S depleted plasma. Addition of 267 nM Antibody 13 to Protein S depleted plasma containing APC and Protein S rescued thrombin generation. Since Antibody 13 induced thrombin generation in both the TFPI and APC cofactor assays, Antibody 13 was characterized as a dual inhibitor.

Protein S depleted plasma with APC+Protein S showed limited rescue of the thrombin generation. Since Antibody 23 induced thrombin generation in the TFPI cofactor assay but not in the APC cofactor assay, Antibody 23 was characterized as a TFPI cofactor inhibitor.

Characterization of Protein S Antibodies

The assay results depicted in FIGS. 11A-20H were used to characterize the exemplary Protein S antibodies provided herein. The antibodies were characterized as an inhibitor of APC cofactor activity (APC cofactor inhibitor), an inhibitor of TFPI cofactor activity (TFPI cofactor inhibitor), or a dual inhibitor. Binding regions and calcium dependence were also determined. The results of the characterization assays are summarized in Tables 7 and 8 below and described in further detail in the below sections.

TABLE 7

| Protein S Antibody | Fc | Pathway Inhibitor (APC, TFPI, or Dual) | IC50 APC (nM) | Hill Coefficient | IC50 TFPI (nM) | Hill Coefficient |
|---|---|---|---|---|---|---|
| Antibody 13 | Rat | Dual | 5.30E−09 | 2.56 | 5.11E−08 | 5.62 |
| Antibody 14 | Rat | Dual | 8.76E−09 | 2.26 | 7.33E−08 | 2.46 |
| Antibody 15 | Rat | Dual | 1.35E−08 | 2.80 | 7.73E−08 | 3.79 |
| Antibody 16 | Rat | Dual | 1.40E−08 | 2.69 | 4.63E−08 | 3.9 |
| Antibody 18 | Rat | APC | 1.28E−08 | 2.7 | N/A | N/A |
| Antibody 19 | Rat | Dual | 8.12E−08 | 1.06 | 1.05E−07 | 1.39 |
| Antibody 20 | Rat | Dual | 1.28E−08 | 2.70 | N/A | N/A |
| Antibody 21 | Rat | APC only | 6.23E−09 | 2.10 | N/A | N/A |
| Antibody 23 | Rat | TFPI only | N/A | N/A | <4.4E−09 | N/A |
| Antibody 24 | Rat | Dual | 1.79E−08 | 1.6 | 7.36E−08 | 1.59 |
| Antibody 31 | Rat | APC only | 9.90E−08 | 1.12 | N/A | N/A |
| Antibody 33 | Rat | Dual | 5.81E−08 | 2.48 | 3.4E−08 | 2.21 |
| Antibody 34 | Mouse | APC only | 9.58E−08 | 2.28 | N/A | N/A |
| Antibody 35 | Rat | APC only | 3.71E−07 | 0.68 | N/A | N/A |
| Antibody 36 | Rat | Dual | 1.53E−08 | 1.55 | 6.05E−09 | 3.53 |
| Antibody 38 | Rat | APC only | 8.40E−08 | 0.70 | N/A | N/A |
| Antibody 40 | Rat | APC only | 1.19E−08 | 2.82 | N/A | N/A |
| Antibody 42 | Rat | APC only | 2.15E−07 | 1.37 | N/A | N/A |
| Antibody 44 | Rat | APC only | 4.92E−07 | 0.87 | N/A | N/A |

Figure 7:
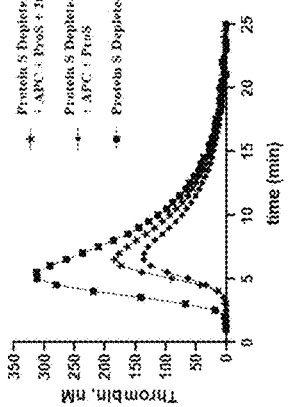
Figure 8:
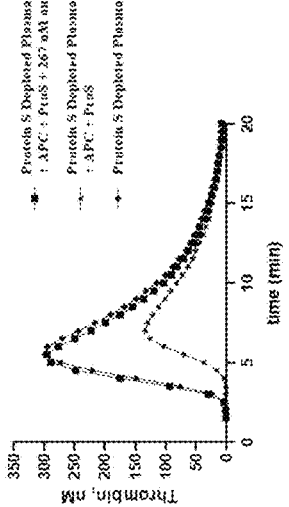

FIGS. 7-8 depict the thrombin generation of Antibody 21 when using a TFPI cofactor assay (FIG. 7) and an APC cofactor assay (FIG. 8). As shown in the TFPI cofactor activity assay depicted in FIG. 7, in PRP, robust thrombin generation occurred in the absence of FVIII antibody. Thrombin generation was reduced by addition of the FVIII antibody only. Addition of 267 nM Antibody 21 showed no rescue of the thrombin generation. As shown in the APC cofactor activity assay depicted in FIG. 8, thrombin generation was reduced by addition of a mixture of APC and Protein S, which was rescued by the addition of 267 nM Antibody 21. Because Antibody 21 did not induce thrombin generation in the TFPI cofactor assay but did rescue thrombin generation in the APC cofactor assay, Antibody 21 was characterized as an APC cofactor inhibitor.

Figure 9:
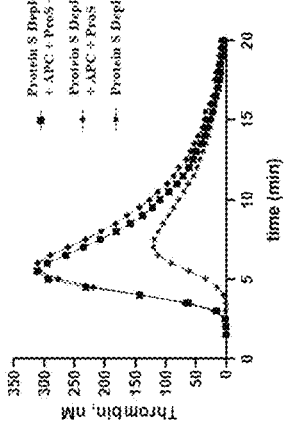
Figure 10:
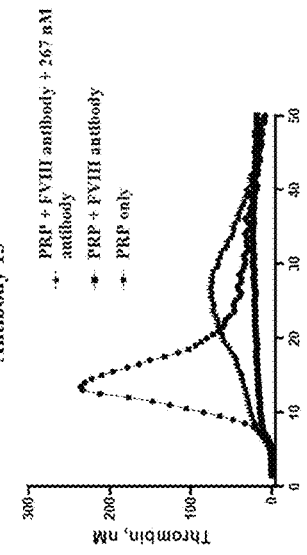

FIGS. 9-10 depict the thrombin generation of Antibody 23 when using a TFPI cofactor assay (FIG. 9) and an APC cofactor assay (FIG. 10). As shown in the TFPI cofactor activity assay depicted in FIG. 9, in PRP, robust thrombin generation occurred in the absence of FVIII antibody. Thrombin generation was reduced by addition of the FVIII antibody only. Addition of 267 nM Antibody 23 promoted thrombin generation. As shown in the APC cofactor activity assay depicted in FIG. 10, in Protein S depleted plasma, thrombin generation was reduced by addition of a mixture of APC and Protein S. Addition of 267 nM Antibody 23 to

TABLE 8

| Protein S Antibody with Rat Fc | Pathway Inhibitor | Binds Heavy Chain | Calcium-Dependent Binding | Binds Thrombin-Sensitive Region of Protein S |
|---|---|---|---|---|
| Antibody 13 | Dual | Yes | No | No |
| Antibody 14 | Dual | Yes | No | No |
| Antibody 15 | Dual | Yes | Yes | Yes |
| Antibody 16 | Dual | Yes | Yes | No |
| Antibody 19 | Dual | Yes | Yes | Yes |
| Antibody 20 | Dual | Yes | Yes | No |
| Antibody 24 | Dual | Yes | Yes | Yes |
| Antibody 18 | APC | Yes | Yes | No |
| Antibody 21 | APC | Yes | No | No |
| Antibody 23 | TFPI | No | No | No |
| Antibody 31 | APC | No | No | No |
| Antibody 33 | Dual | No | Yes | No |
| Antibody 34 | APC | No | Yes | No |
| Antibody 35 | APC | No | Yes | No |
| Antibody 36 | Dual | No | Yes | No |
| Antibody 38 | APC | No | Yes | No |
| Antibody 40 | APC | No | Yes | No |
| Antibody 42 | APC | No | No | No |
| Antibody 44 | APC | Yes | No | No |

Binding characteristics of the Protein S antibodies were also determined. Binding interaction analysis was obtained by Surface Plasmon Resonance in a Biacore X100 instrument. The human anti-IgG (Fc) antibody was immobilized to the carboxymethylated dextran membrane on the sensor chip surface (CM5) via the free amine method for a contact time of 420 seconds. Human anti-IgG antibody at 25 μg/mL in 0.15 M NaCl was immobilized to 9,785 RU in 10 mM sodium acetate pH 5.0. Each tested monoclonal antibody (Antibody 1-12) was captured at a fixed concentration (0.25 μg/mL) with immobilized human anti-IgG antibody. Experimentally, the capture ligand level for the antibodies tested was determined to be 66-99 RL, corresponding to a $R_{max}$ of 61-91 RU. No signs of mass transport limitation were observed.

The following experimental conditions were used: purified Protein S was injected at concentrations: 2-128 nM, 1:2-fold dilution. Dilution and running buffer were as follows: Hbs-EP+5 mM $CaCl_2$). Regeneration was obtained by 3 M $MgCl_2$. Binding constants (ka, kd, and KD) were determined using the Biacore X100 evaluation software, assuming a 1:1 interaction of Protein S and the tested monoclonal antibody under investigation. The resulting data are presented in Table 9 below.

TABLE 9

|  | Ka (1/MS) | Kd (1/S) | KD nM |
|---|---|---|---|
| Antibody 1 | 2.90E+05 | 3.90E−04 | 1.33 |
| Antibody 2 | 3.46E+05 | 5.60E−04 | 1.63 |
| Antibody 3 | 2.53E+05 | 5.69E−04 | 2.24 |
| Antibody 4 | 3.99E+05 | 1.65E−03 | 4.13 |
| Antibody 6 | 2.80E+05 | 1.60E−03 | 5.79 |
| Antibody 7 | 2.52E+05 | 5.00E−03 | 20.00 |
| Antibody 8 | 1.32E+05 | 8.23E−04 | 6.25 |
| Antibody 9 | 2.12E+05 | 3.36E−03 | 15.90 |
| Antibody 11 | 1.16E+05 | 1.13E−03 | 9.60 |
| Antibody 12 | 6.57E+05 | 9.47E−03 | 14.40 |

Binding characteristics of the Protein S antibodies were also further characterized using Octet. Using the Octet System (Sartorius), the binding of each antibody to both human and cynomolgus monkey ("cyno" in Table 10) Protein S was determined. The human Fc antibodies were immobilized onto anti-human Fc capture probes by placing the probes into 10 g/ml antibody solution in 10 mg/ml bovine serum albumin, 20 mE Tris pH 7.0, 150 mM NaCl, and 4 mM calcium chloride. Next, the bound antibodies were placed into solutions containing 500 nM, 250 nM, 125 nM 62.5 nM, 31.25 nM, 15.625 nM and 7.81 nM Protein S and the association rates were measured. Next, the probes were placed into buffer and the dissociation rates were measured. A summary of the resulting data is provided in Table 10 below.

TABLE 10

| Antibody | $k_{on}$ (l/Ms) | kdis (1/s) | KD (human) (M) | $k_{on}$ (1/Ms) | kdis (1/s) | KD (cyno) (M) |
|---|---|---|---|---|---|---|
| Antibody 1 | 1.69E+05 | <1.0E−07 | <1.0E−12 | 1.39E+05 | <1.0E−07 | <1.0E−12 |
| Antibody 2 | 2.07E+05 | <1.0E−07 | <1.0E−12 | 1.54E+05 | <1.0E−07 | <1.0E−12 |
| Antibody 3 | 1.64E+05 | 8.86E−06 | 5.42E−11 | 1.27E+05 | <1.0E−07 | <1.0E−12 |
| Antibody 4 | 2.71E+05 | 7.08E−04 | 2.62E−09 | 2.01E+05 | 3.08E−03 | 1.53E−08 |
| Antibody 6 | 2.26E+05 | 3.32E−04 | 1.47E−09 | 1.40E+05 | 3.94E−04 | 2.81E−09 |
| Antibody 7 | 1.72E+05 | 1.41E−03 | 8.18E−09 | 1.37E+05 | 2.32E−03 | 1.69E−08 |
| Antibody 8 | 1.31E+05 | 6.70E−05 | 5.14E−10 | 8.58E+04 | 1.33E−04 | 1.55E−09 |
| Antibody 9 | 3.04E+05 | 1.62E−04 | 5.33E−10 | 1.66E+05 | 4.42E−05 | 2.66E−10 |
| Antibody 11 | 8.52E+04 | 3.40E−05 | 3.99E−10 | 8.21E+04 | <1.0E−07 | <1.0E−12 |
| Antibody 12 | 3.09E+05 | 2.32E−03 | 7.49E−09 | 2.58E+05 | 2.91E−03 | 1.13E−08 |
| Antibody 25 | 1.43E+05 | <1.0E−07 | <1.0E−12 | 1.24E+05 | <1.0E−07 | <1.0E−12 |
| Antibody 27 | 2.77E+05 | 1.59E−04 | 5.74E−10 | 6.79E+04 | 2.33E−03 | 3.43E−08 |
| Antibody 28 | 1.56E+05 | 1.06E−03 | 6.78E−09 | 1.09E+05 | 1.06E−03 | 9.81E−09 |
| Antibody 29 | 8.19E+04 | 1.73E−03 | 2.11E−08 | 8.82E+04 | 1.77E−03 | 2.00E−08 |
| Antibody 30 | 2.42E+04 | 2.79E−04 | 1.15E−08 | 3.50E+04 | 7.30E−04 | 2.09E−08 |
| Antibody 37 | 2.18E+05 | 8.32E−05 | 3.82E−10 | 1.77E+04 | 1.19E−04 | 6.72E−10 |
| Antibody 39 | 2.34E+05 | 5.84E−05 | 2.50E−10 | 1.91E+05 | 8.02E−05 | 4.19E−10 |
| Antibody 41 | 8.00E+04 | 1.10E−03 | 1.38E−08 | 9.64E+04 | 1.88E−03 | 1.95E−08 |
| Antibody 43 | 3.20E+05 | 6.36E−04 | 1.99E−09 | 2.68E+05 | 1.04E−03 | 3.88E−09 |

Antibody 19 and Antibody 7

FIGS. 11A-11H depict the characterization of Antibody 19 and Antibody 7. Antibody 19 and Antibody 7 both comprise the same human variable regions, while Antibody 19 comprises a rat Fc domain and Antibody 7 comprises a human IgG4 Fc domain.

FIG. 11A depicts a Western blot showing that Antibody 19 binds Protein S in the Thrombin Sensitive Region (TSR) of Protein S. A full-length human Protein S protein (Reduced (Red) and Non-reduced (NR)) and a thrombin-cleaved Protein S fragment (cleaved in the Thrombin Sensitive Region (TSR), NR and Red) were used. By Western blot, Antibody 19 bound the full Protein S, but not the thrombin-cleaved Protein S, indicating that Antibody 19 binds at the TSR. Because no signal was observed with the reduced Protein S, the epitope for this antibody is not a linear epitope.

Binding to the heavy chain of Protein S was determined using an ELISA based method. Briefly, high binding ELISA plates were coated with recombinant heavy chain Protein S expressed and purified from HEK293 cells. The "heavy chain" of Protein S represents a fragment of Protein S spanning amino acids 42-296. The coated plate was blocked with 1% casein solution. Then, buffer containing 1 μg/ml of antibody was applied to the well with buffer containing 1 mM calcium chloride. For antibodies that bound this fragment of Protein S, it was concluded that the epitope on Protein S for that antibody is between amino acids 42-296 of Protein S. Table 11 below summarizes the results of the heavy chain binding assay for all Antibodies. (antibodies that do bind this region have ODs greater than about 0.48 OD).

TABLE 11

| Antibody | Binding to heavy chain (OD) |
|---|---|
| Antibody 13 | 1.63 |
| Antibody 14 | 2.03 |
| Antibody 15 | 1.78 |
| Antibody 16 | 1.67 |
| Antibody 18 | 0.60 |

TABLE 11-continued

| Antibody | Binding to heavy chain (OD) |
|---|---|
| Antibody 19 | 0.61 |
| Antibody 20 | 1.54 |
| Antibody 21 | 1.58 |
| Antibody 23 | 0.10 |
| Antibody 24 | 0.71 |
| Antibody 31 | 0.13 |
| Antibody 33 | 0.11 |
| Antibody 34 | 0.16 |
| Antibody 35 | 0.08 |
| Antibody 36 | 0.08 |
| Antibody 38 | 0.10 |
| Antibody 40 | 0.11 |
| Antibody 42 | 0.11 |
| Antibody 44 | 0.48 |

Calcium dependence of binding was determined using an ELISA based method. Briefly, high binding ELISA plates were coated with human Protein S. Then, buffer containing 1 μg/ml of antibody was applied to the well with either buffer containing 1 mM EDTA or 1 mM calcium chloride. If the level of binding of Protein S was reduced dramatically (greater than 85% of the absorbance observed in the presence of calcium) when EDTA was added, it was concluded that the binding was calcium-dependent. Table 12 summarizes the results of the calcium dependence assay for all Antibodies.

TABLE 12

| | Binding to Protein S in EDTA (OD) | Binding to Protein S in CaCl2 (OD) |
|---|---|---|
| Antibody 13 | 0.48 | 1.77 |
| Antibody 14 | 0.75 | 2.03 |
| Antibody 15 | 0.07 | 1.86 |
| Antibody 16 | 0.17 | 1.95 |
| Antibody 18 | 0.10 | 1.96 |
| Antibody 19 | 0.06 | 1.68 |
| Antibody 20 | 0.26 | 1.93 |
| Antibody 21 | 1.40 | 1.92 |
| Antibody 23 | 0.26 | 0.57 |
| Antibody 24 | 0.06 | 1.72 |
| Antibody 31 | 0.63 | 1.03 |
| Antibody 33 | 0.20 | 1.23 |
| Antibody 34 | 0.06 | 0.51 |
| Antibody 35 | 0.11 | 0.96 |
| Antibody 36 | 0.03 | 0.60 |
| Antibody 38 | 0.09 | 1.38 |
| Antibody 40 | 0.11 | 0.51 |
| Antibody 42 | 0.53 | 0.67 |
| Antibody 44 | 0.89 | 1.17 |

FIGS. 11B-11D depict the results of an APC cofactor assay for Antibody 19 using PP-3T Protein S deficient human PPP, cynomolgus monkey PPP, and a TFPI cofactor assay using human PRP, respectively.

Figure 11F:
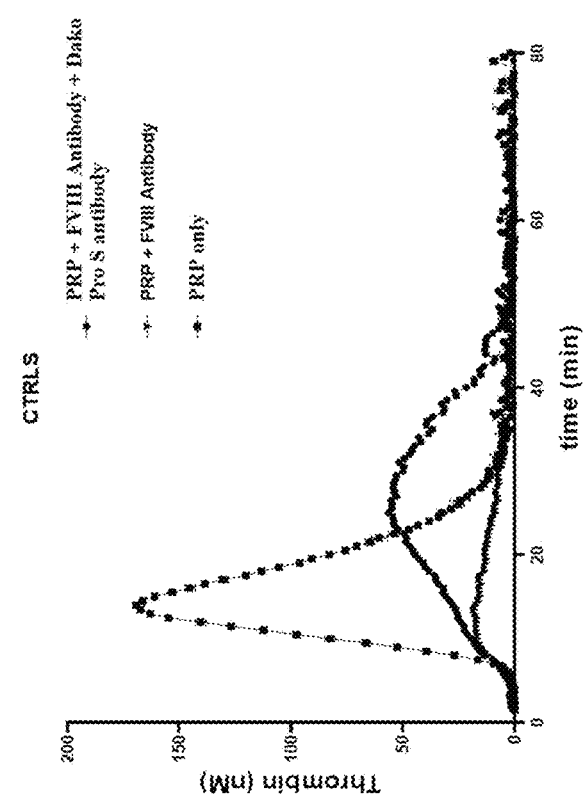
Figure 11E:
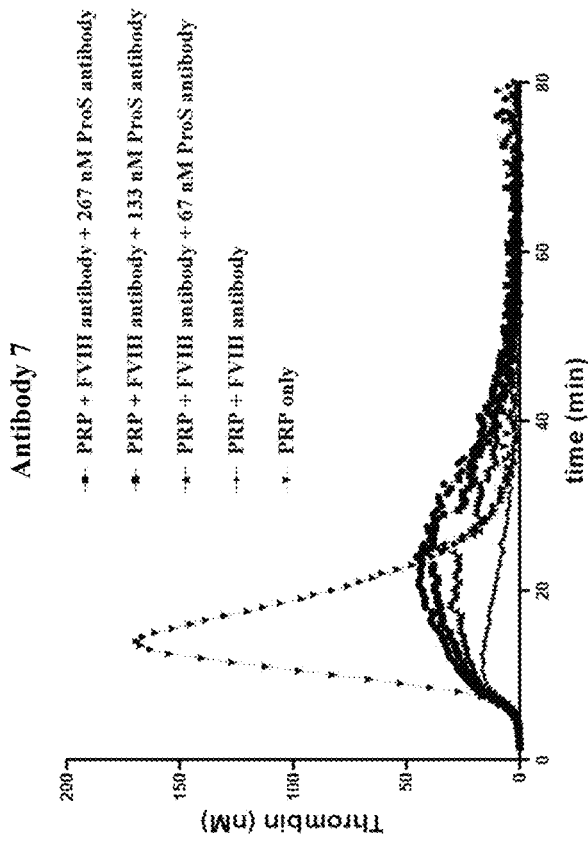

FIGS. 11E and 11F depict the results of a TFPI cofactor assay in human PRP using Antibody 7 and controls, respectively. A rabbit polyclonal human Protein S antibody labeled Dako was used as a positive control.

Figure 11H:
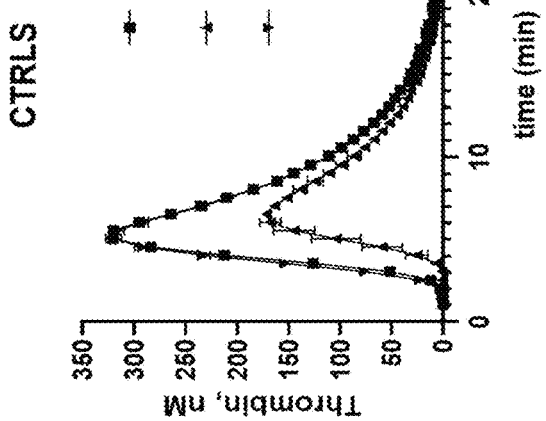
Figure 11G:
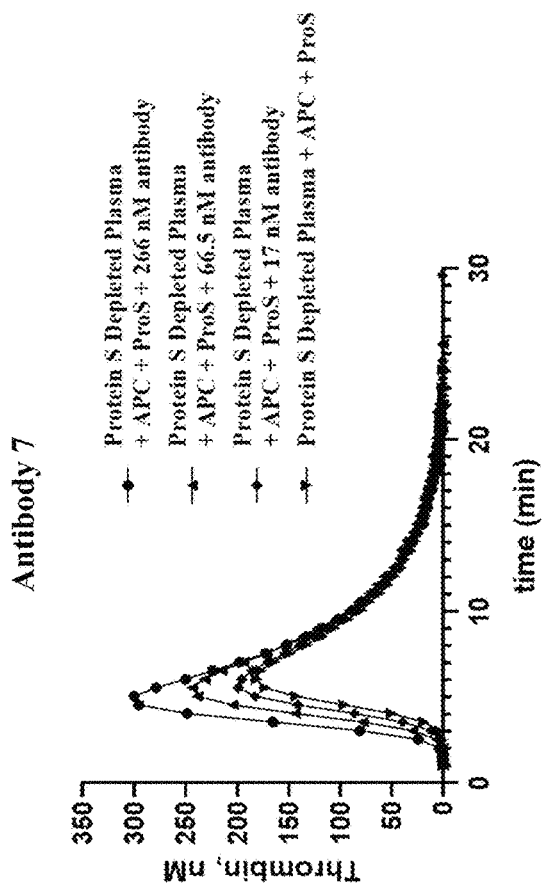

FIGS. 11G-11H depict the results of a PPP with APC assay performed with Antibody 7, and controls, respectively.

These results indicate that Antibody 19 and Antibody 7 are dual inhibitors.

Antibody 13 and Antibody 1

FIGS. 12A-12H depict the characterization of Antibody 13 and Antibody 1, antibodies sharing the same human variable region, and are characterized as dual inhibitors.

FIG. 12A depicts a Western blot showing that Antibody 13 does not bind to Protein S in the TSR of Protein S. The Western blot was carried out as described for FIG. 11A. By Western blot, Antibody 13 bound the full Protein S, the thrombin-cleaved Protein S, the reduced Protein S, and the reduced thrombin-cleaved Protein S, indicating that Antibody 13 does not bind Protein S at the TSR. Binding to reduced Protein S showed that the epitope for Antibody 13 is a linear epitope.

Binding to the heavy chain of Protein S was determined using an ELISA based method, as described herein. Antibody 13 was determined to bind to the heavy chain of Protein S. Calcium dependence was determined, also as described above, and Antibody 13 showed calcium-independent binding.

FIGS. 12B-12D depict the results of an APC cofactor assay for Antibody 13 using Protein S deficient human PPP, cynomolgus monkey PPP, and a TFPI cofactor assay using human PRP, respectively.

Figure 12F:
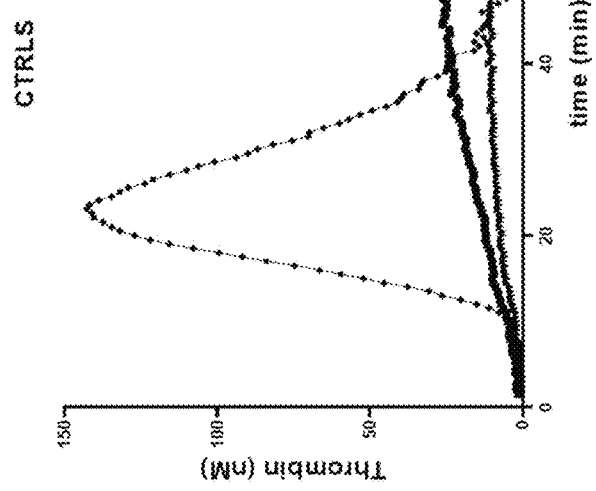
Figure 12E:
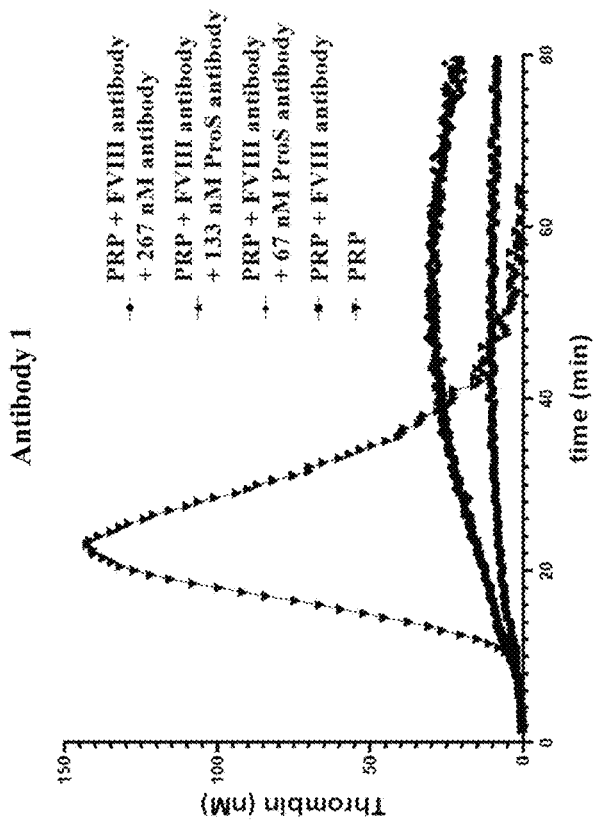

FIGS. 12E and 12F depict the results of a TFPI cofactor assay in human PRP using Antibody 1 and controls, respectively. A rabbit polyclonal human Protein S antibody labeled Dako was used as a positive control.

Figure 12H:
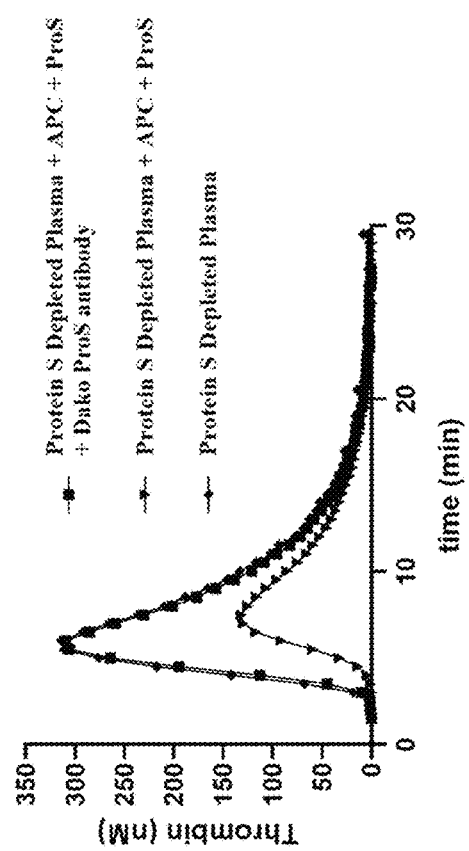
Figure 12G:
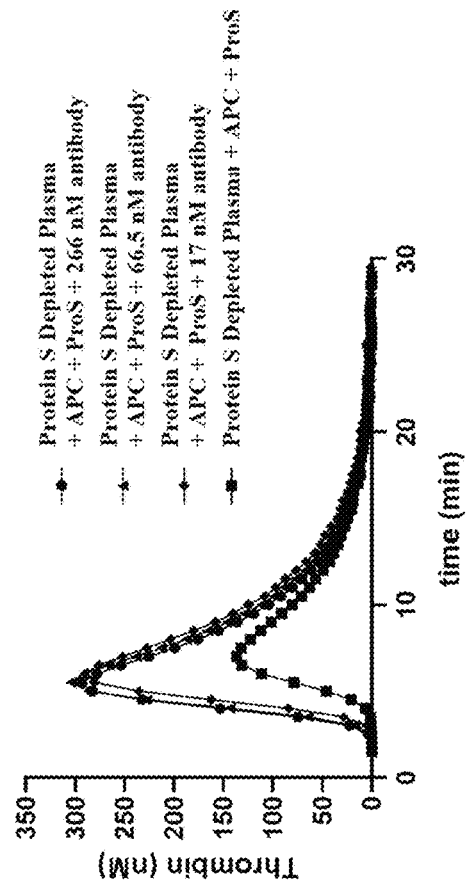

FIGS. 12G-12H depict the results of the APC cofactor assay performed with Antibody 1, and controls, respectively.

These results indicate that Antibody 13 and Antibody 1 are dual inhibitors.

Antibody 14 and Antibody 2

FIGS. 13A-13H depict the characterization of Antibody 14 and Antibody 2, antibodies sharing the same human variable region, and are characterized as dual inhibitors.

Figure 13B:
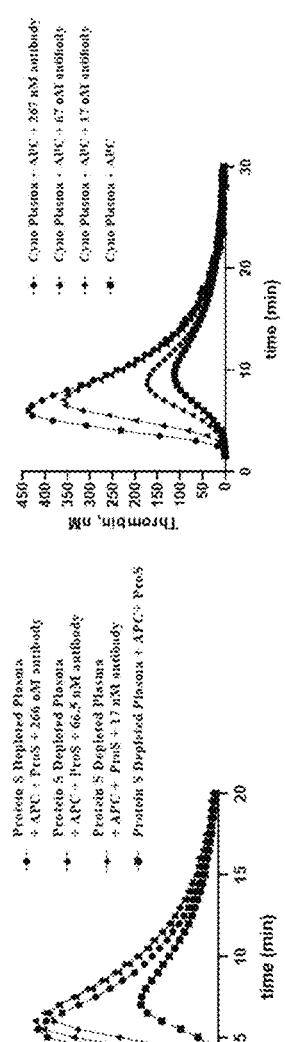
FIGS. 13A-13H depict the characterization of Antibody 14 and Antibody 2, antibodies sharing the same human variable region, and are characterized as dual inhibitors.
Figure 13C:
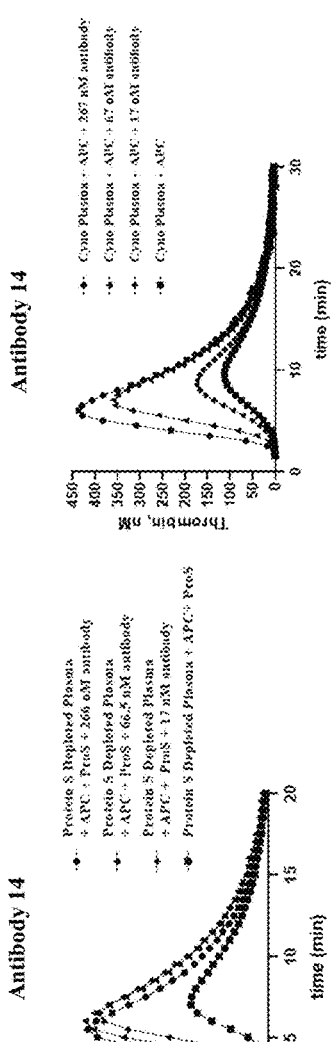
Figure 13D:
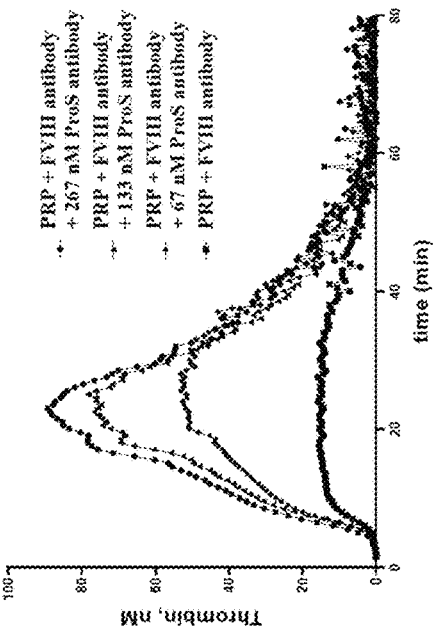
Figure 13A:
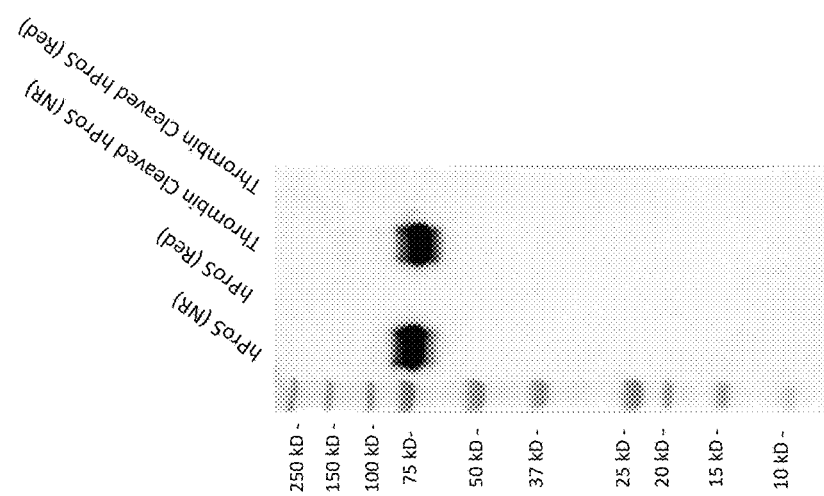

FIG. 13A depicts a Western blot showing that Antibody 14 does not bind Protein S in the TSR of Protein S. The Western blot was carried out as described for FIG. 11A. By Western blot, Antibody 14 bound the full Protein S and the thrombin-cleaved Protein S, but did not bind the reduced Protein S, and the reduced thrombin-cleaved Protein S. These results indicate that Antibody 14 does not bind Protein S at the TSR, and the lack of signal observed with the reduced Protein S showed that the epitope for this antibody is not a linear epitope.

Binding to the heavy chain of Protein S was determined using an ELISA based method, as described herein. Antibody 14 was determined to bind to the heavy chain of Protein S. Calcium dependence was determined, also as described above, and Antibody 14 showed binding that was calcium-independent.

FIGS. 13B-13D depict the results of an APC cofactor assay for Antibody 14 using Protein S deficient human PPP, cynomolgus monkey PPP, and a TFPI cofactor assay using human PRP, respectively.

Figure 13E:
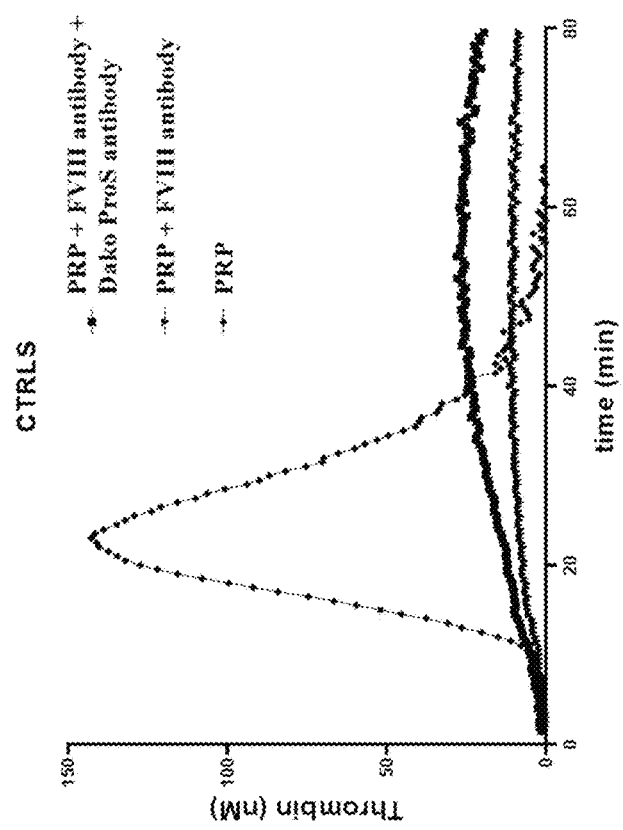
Figure 13F:
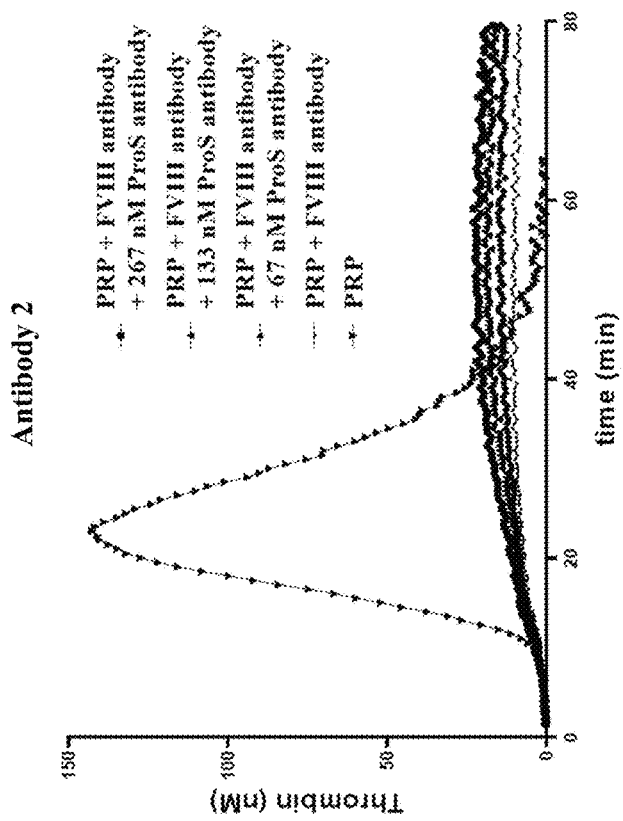

FIGS. 13E and 13F depict the results of a TFPI cofactor assay in human PRP using Antibody 2 and controls, respectively. A rabbit polyclonal human Protein S antibody labeled Dako was used as a positive control.

Figure 13G:
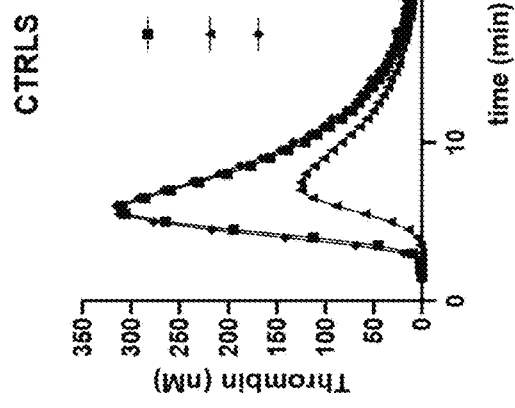
Figure 13H:
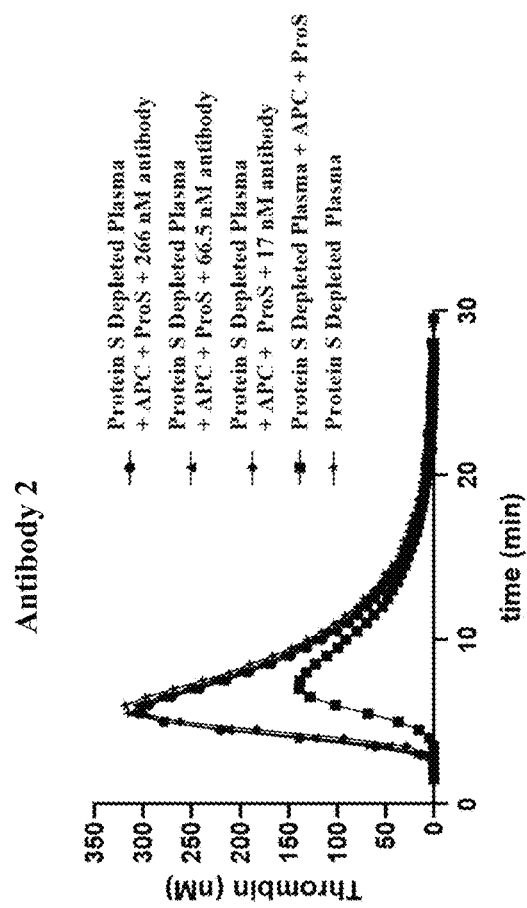

FIGS. 13G-13H depict the results of the APC cofactor assay performed with Antibody 2 and controls, respectively.

These results indicate that Antibody 14 and Antibody 2 are dual inhibitors.

Antibody 15 and Antibody 3

FIGS. 14A-14H depict the characterization of Antibody 15 and Antibody 3, antibodies sharing the same human variable region, and are characterized as dual inhibitors.

FIG. 14A depicts a Western blot showing that Antibody 15 binds Protein S in the TSR region of Protein S. The Western blot was carried out as described for FIG. 11A. By Western blot, Antibody 15 bound the full Protein S and showed a small band for the thrombin-cleaved Protein S, but did not bind the reduced Protein S, and the reduced thrombin-cleaved Protein S. These results indicate that Antibody 15 binds Protein S at the TSR, and the lack of signal observed with the reduced Protein S showed that the epitope for this antibody is not a linear epitope.

Binding to the heavy chain of Protein S was determined using an ELISA based method, as described above. Antibody 15 was determined to bind to the heavy chain of Protein S. Calcium dependence was determined, also as described above, and Antibody 15 showed binding that was calcium-dependent.

FIGS. 14B-14D depict the results of an APC cofactor assay for Antibody 15 using Protein S deficient human PPP, cynomolgus monkey PPP, and a TFPI cofactor assay using human PRP, respectively.

Figure 14E:
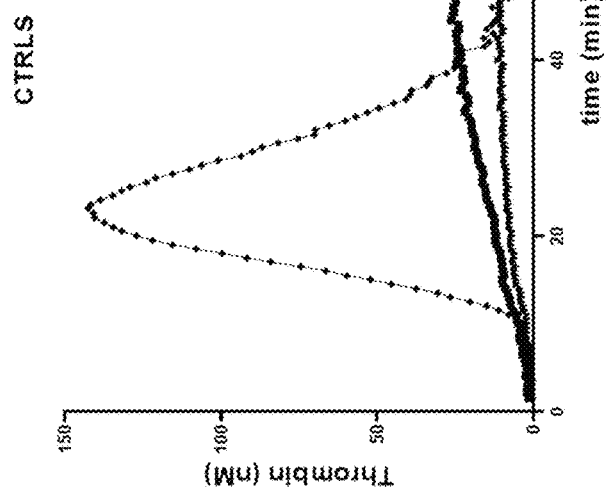
Figure 14F:
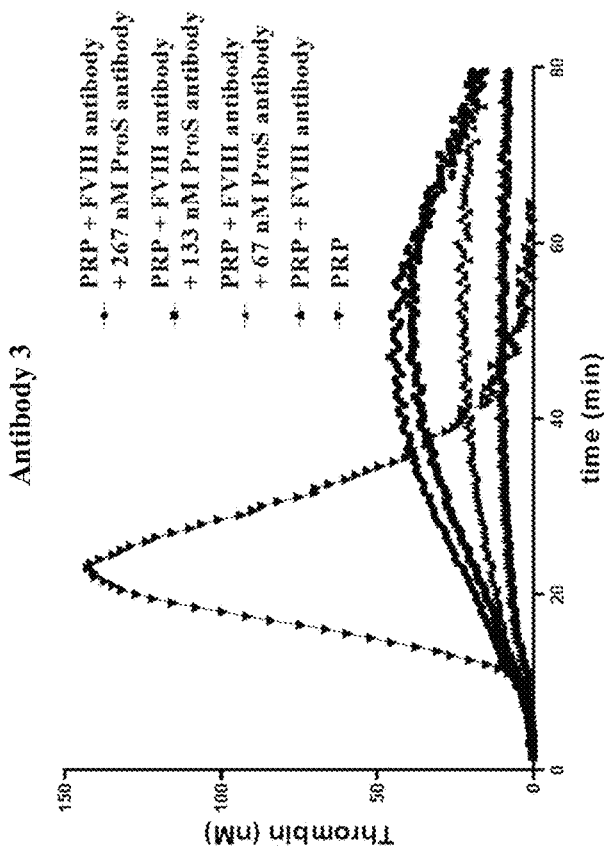

FIGS. 14E and 14F depict the results of a TFPI cofactor assay in human PRP using Antibody 3 and controls, respectively. A rabbit polyclonal human Protein S antibody labeled Dako was used as a positive control.

Figure 14H:
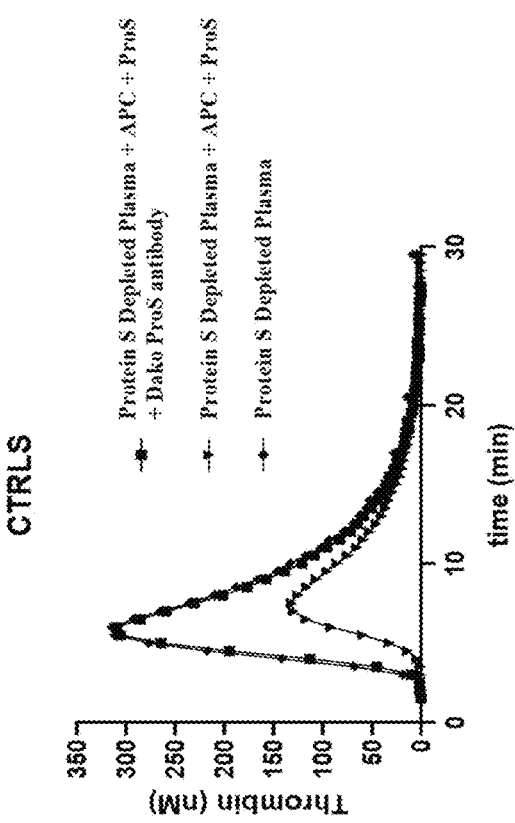
Figure 14G:
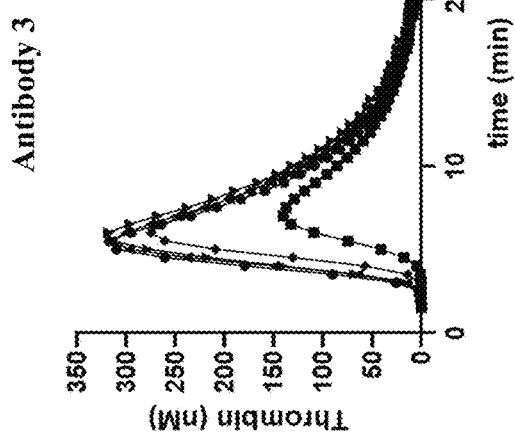

FIGS. 14G-14H depict the results of the APC cofactor assay performed with Antibody 3 and controls, respectively.

These results indicate that Antibody 15 and Antibody 3 are dual inhibitors.

Antibody 16 and Antibody 4

FIGS. 15A-15H depict the characterization of Antibody 16 and Antibody 4, antibodies sharing the same human variable region, and are characterized as dual inhibitors.

FIG. 15A depicts a Western blot showing that Antibody 16 binds Protein S in the Gla-domain of Protein S. The Western blot was carried out as described for FIG. 11A. By Western blot, Antibody 16 bound the full Protein S, the thrombin-cleaved Protein S, the reduced Protein S, but did not bind the reduced thrombin-cleaved Protein S. These results indicate that Antibody 16 binds Protein S at the Gla-domain, and the signal observed with the reduced Protein S showed that the epitope for this antibody is a linear epitope.

Binding to the heavy chain of Protein S was determined using an ELISA based method, as described herein. Antibody 16 was determined to bind to the heavy chain of Protein S. Calcium dependence was determined, also as described herein, and Antibody 16 showed binding that was calcium-dependent.

FIGS. 15B-15D depict the results of an APC cofactor assay for Antibody 16 using Protein S deficient human PPP, cynomolgus monkey PPP, and a TFPI cofactor assay using human PRP, respectively.

Figure 15E:
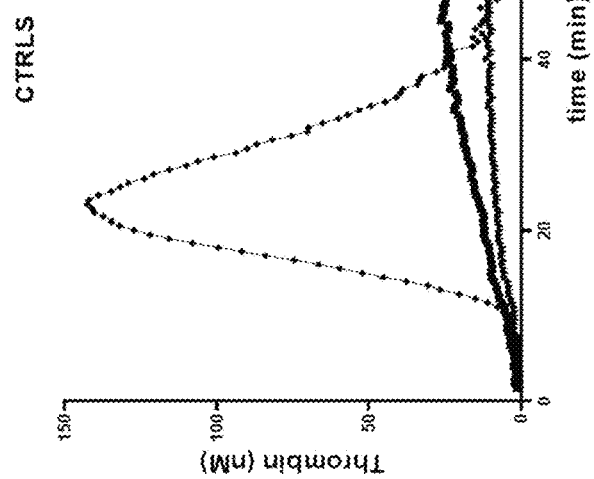
Figure 15F:
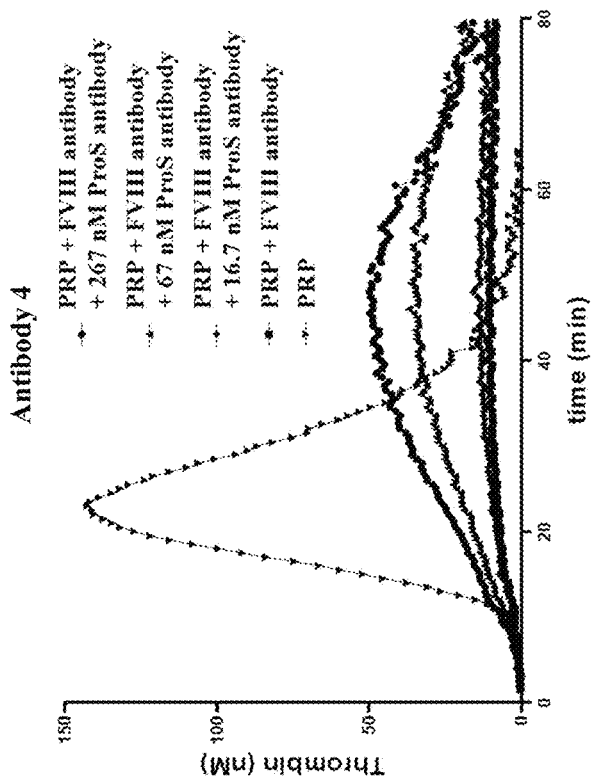

FIGS. 15E and 15F depict the results of a TFPI cofactor assay in human PRP using Antibody 4 and controls, respectively. A rabbit polyclonal human Protein S antibody labeled Dako was used as a positive control.

Figure 15H:
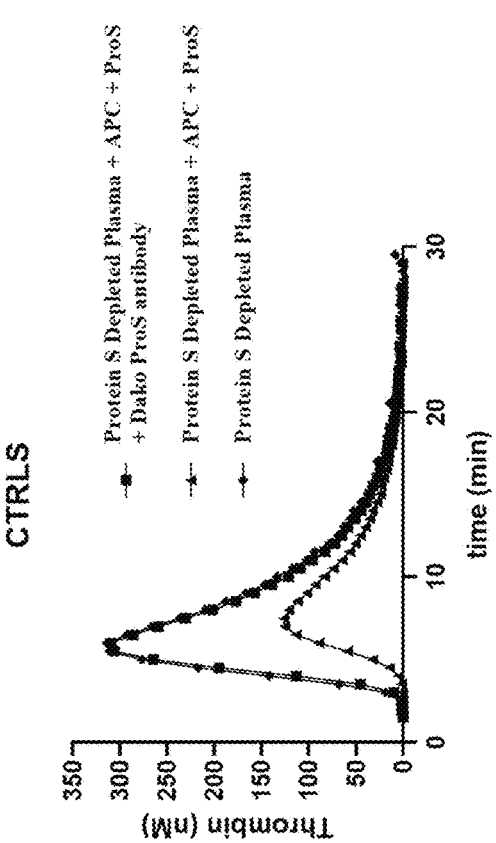
Figure 15G:
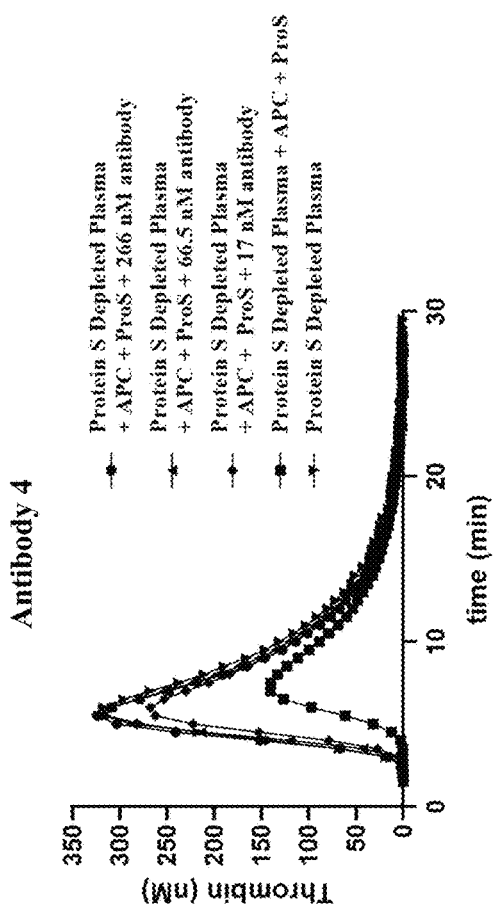

FIGS. 15G-15H depict the results of the APC cofactor assay performed with Antibody 4, and controls, respectively.

These results indicate that Antibody 16 and Antibody 4 are dual inhibitors.

Antibody 20 and Antibody 8

FIGS. 16A-16H depict the characterization of Antibody 20 and Antibody 8, antibodies sharing the same human variable region, and are characterized as dual inhibitors.

FIG. 16A depicts a Western blot showing that Antibody 20 does not bind Protein S in the TSR of Protein S. The Western blot was carried out as described for FIG. 11A. By Western blot, Antibody 20 bound the full Protein S and the thrombin-cleaved Protein S, but did not bind the reduced Protein S or the reduced thrombin-cleaved Protein S. These results indicate that Antibody 20 does not bind Protein S at the TSR, and the lack of signal observed with the reduced Protein S showed that the epitope for this antibody is not a linear epitope.

Binding to the heavy chain of Protein S was determined using an ELISA based method, as described herein. Antibody 20 was determined to bind to the heavy chain of Protein S. Calcium dependence was determined, also as described herein, and Antibody 20 showed binding that was calcium-dependent.

FIGS. 16B-16D depict the results of an APC cofactor assay for Antibody 20 using Protein S deficient human PPP, cynomolgus monkey PPP, and a TFPI cofactor assay using human PRP, respectively.

Figure 16F:
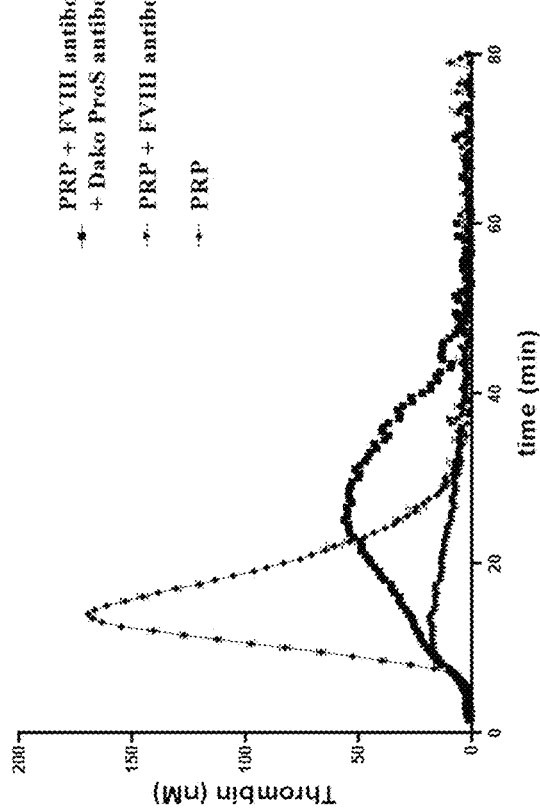
Figure 16E:
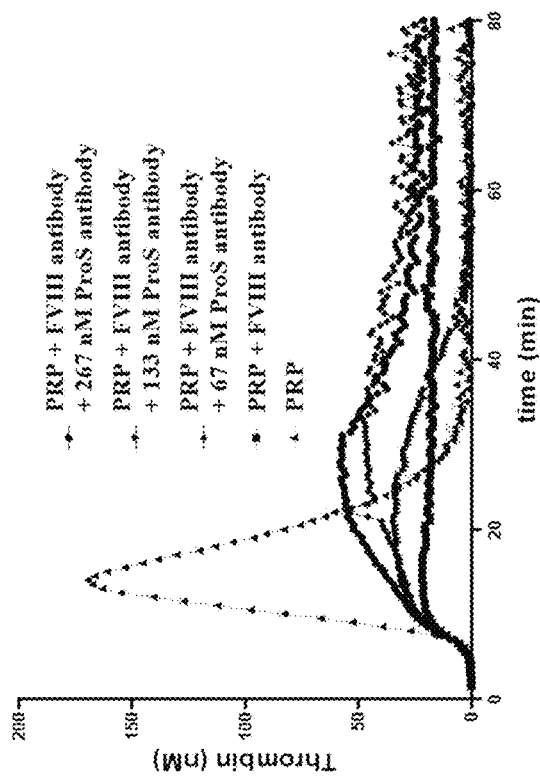

FIGS. 16E and 16F depict the results of a TFPI cofactor assay in human PRP using Antibody 8 and controls, respectively. A rabbit polyclonal human Protein S antibody labeled Dako was used as a positive control.

Figure 16H:
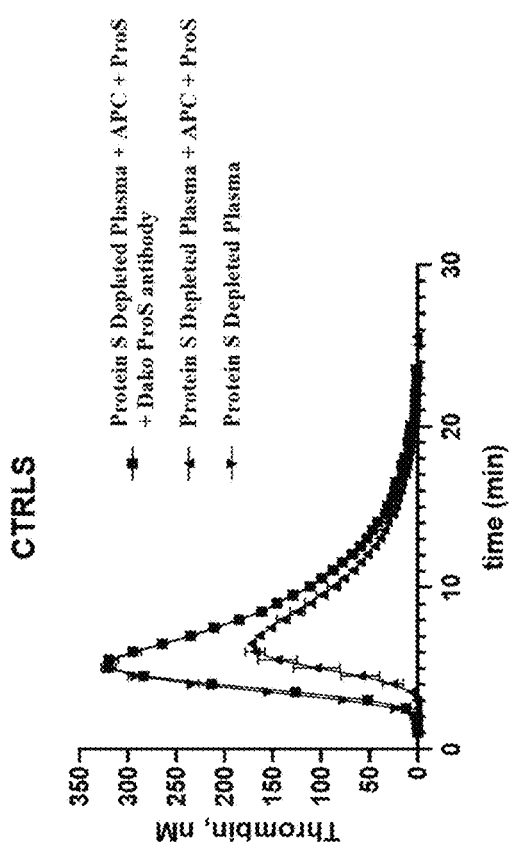
Figure 16G:
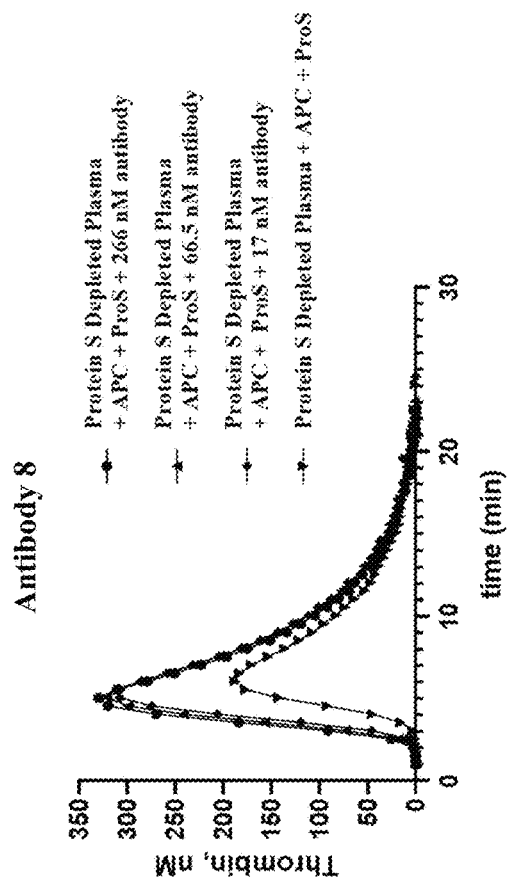

FIGS. 16G-16H depict the results of the APC cofactor assay performed with Antibody 8 and controls, respectively.

These results indicate that Antibody 20 and Antibody 8 are dual inhibitors.

Antibody 21 and Antibody 9

FIGS. 17A-17H depict the characterization of Antibody 21 and Antibody 9, antibodies sharing the same human variable region, and are characterized as APC cofactor inhibitors.

Figure 17B:
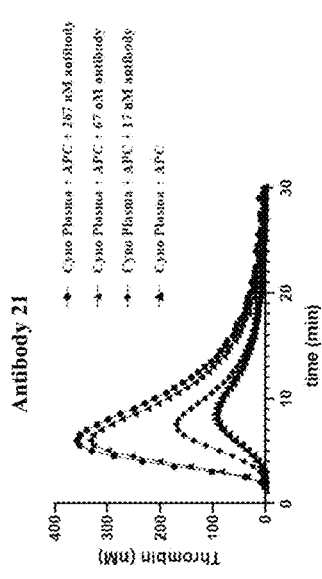
FIGS. 17A-17H depict the characterization of Antibody 21 and Antibody 9, antibodies sharing the same human variable region, and are characterized as APC cofactor inhibitors.
Figure 17B:
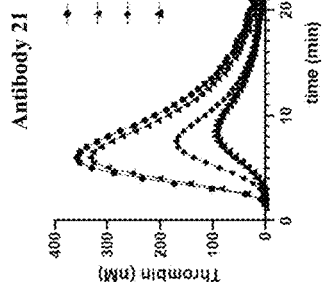
Figure 17A:
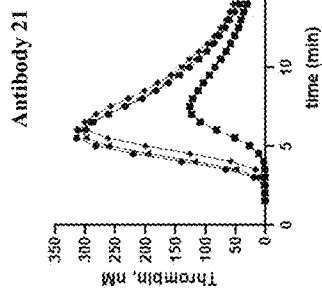

FIG. 17A depicts a Western blot showing that Antibody 21 does not bind Protein S in the TSR of Protein S. The Western blot was carried out as described for FIG. 11A. By Western blot, Antibody 21 bound the full Protein S and the thrombin-cleaved Protein S, but did not bind the reduced Protein S or the reduced thrombin-cleaved Protein S. These results indicate that Antibody 21 does not bind Protein S at the TSR, and the lack of signal observed with the reduced Protein S showed that the epitope for this antibody is not a linear epitope.

Binding to the heavy chain of Protein S was determined using an ELISA based method, as described herein. Antibody 21 was determined to bind to the heavy chain of Protein S. Calcium dependence was determined, also as described herein, and Antibody 21 showed binding that was calcium-independent.

Figure 17C:
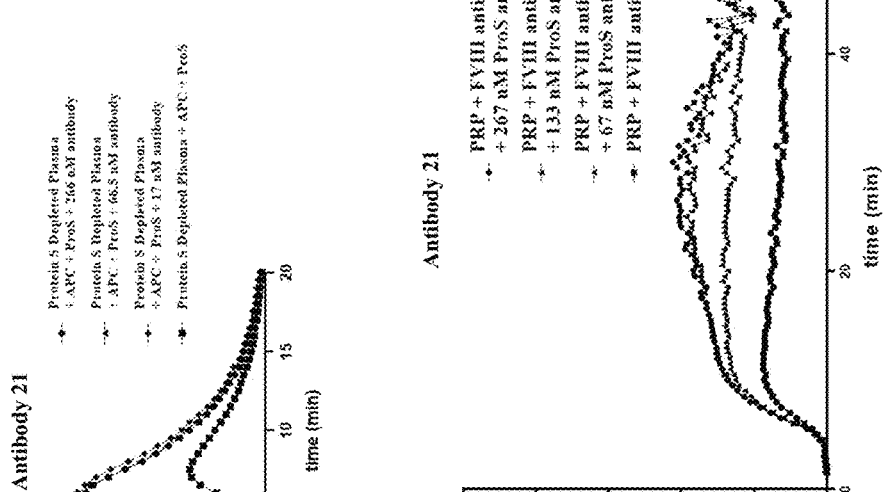
Figure 17D:
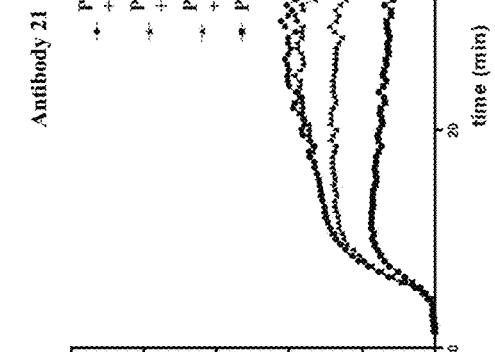
Figure 17D:
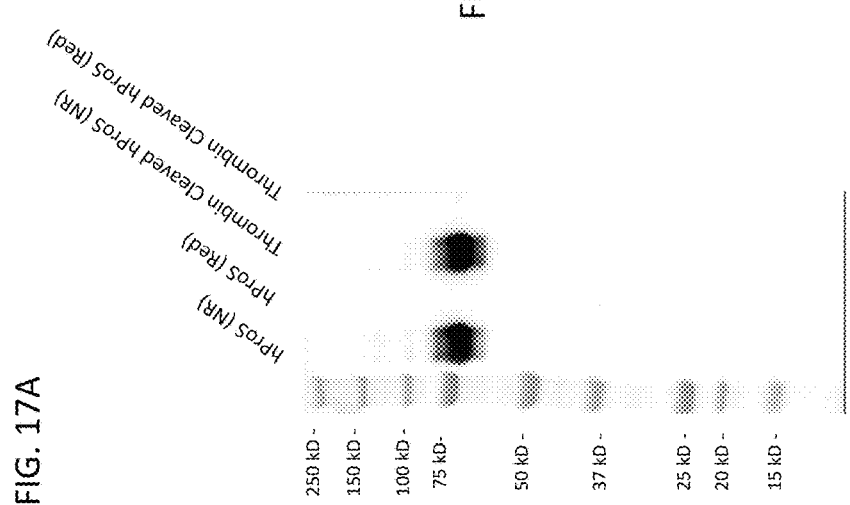

FIGS. 17B-17D depict the results of an APC cofactor assay for Antibody 21 using Protein S deficient human PPP, cynomolgus monkey PPP, and a TFPI cofactor assay using human PRP, respectively.

Figure 17E:
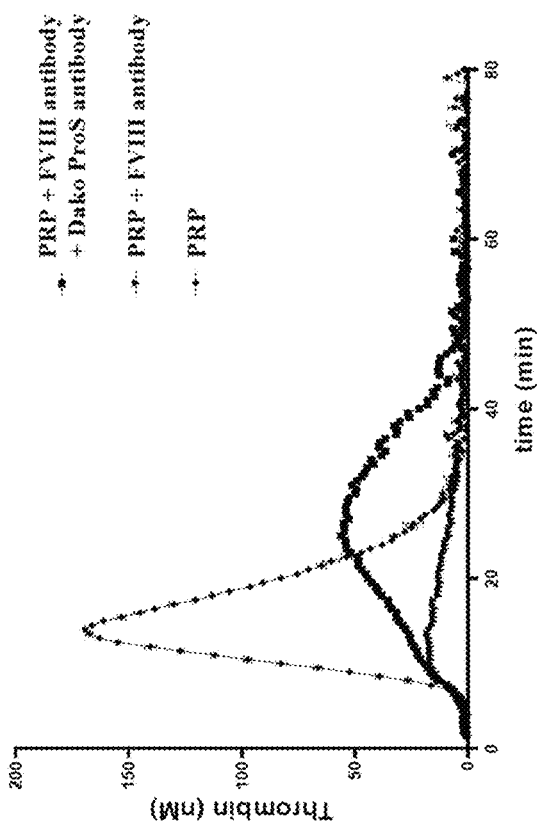
Figure 17F:
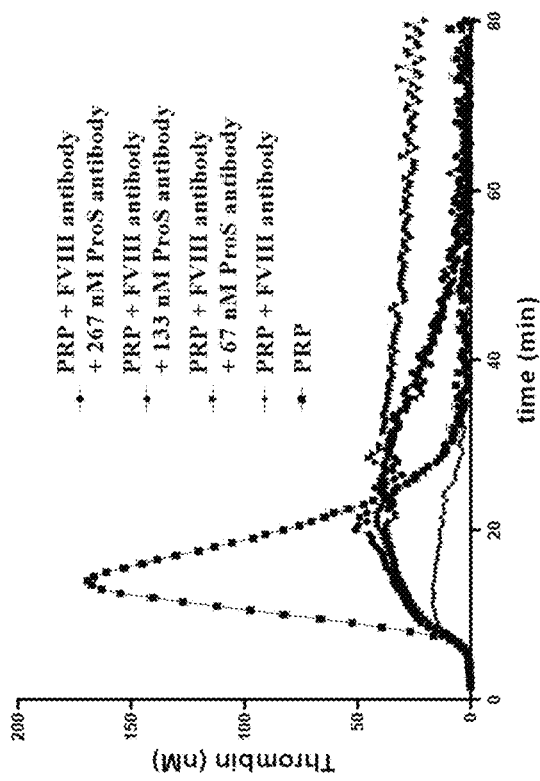

FIGS. 17E and 17F depict the results of a TFPI cofactor assay in human PRP using Antibody 9 and controls, respectively. A rabbit polyclonal human Protein S antibody labeled Dako was used as a positive control.

Figure 17H:
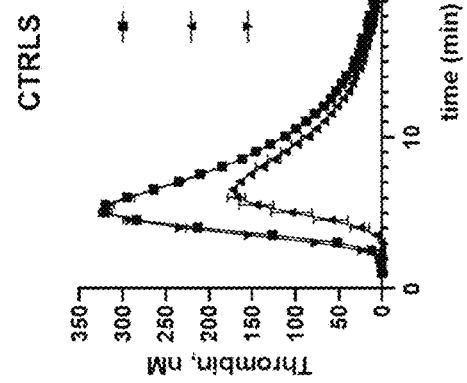
Figure 17G:
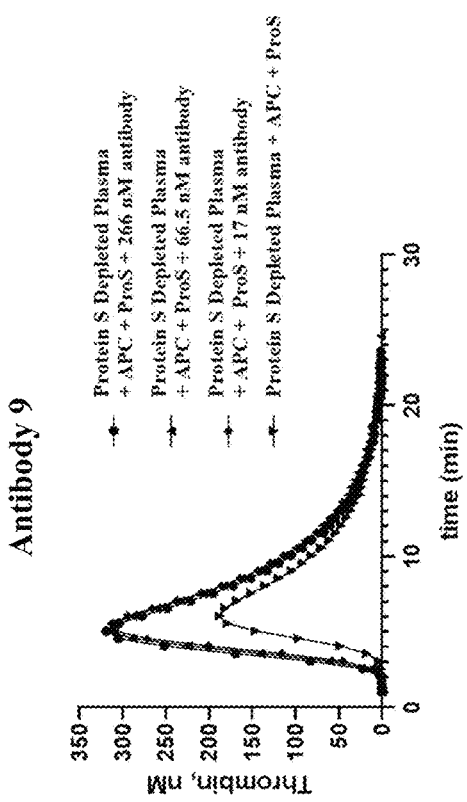

FIGS. 17G-17H depict the results of the APC cofactor assay performed with Antibody 9 and controls, respectively.

These results indicate that Antibody 21 and Antibody 9 are APC cofactor inhibitors.

Antibody 23 and Antibody 11

FIGS. 18A-18G depict the characterization of Antibody 23 and Antibody 11, antibodies sharing the same human variable region, and are characterized as TFPI cofactor inhibitors.

Binding to the heavy chain of Protein S was determined using an ELISA based method, as described herein. Antibody 23 was determined to not bind to the heavy chain of Protein S. Calcium dependence was determined, also as described herein, and Antibody 23 showed binding that was calcium-independent.

Figure 18A:
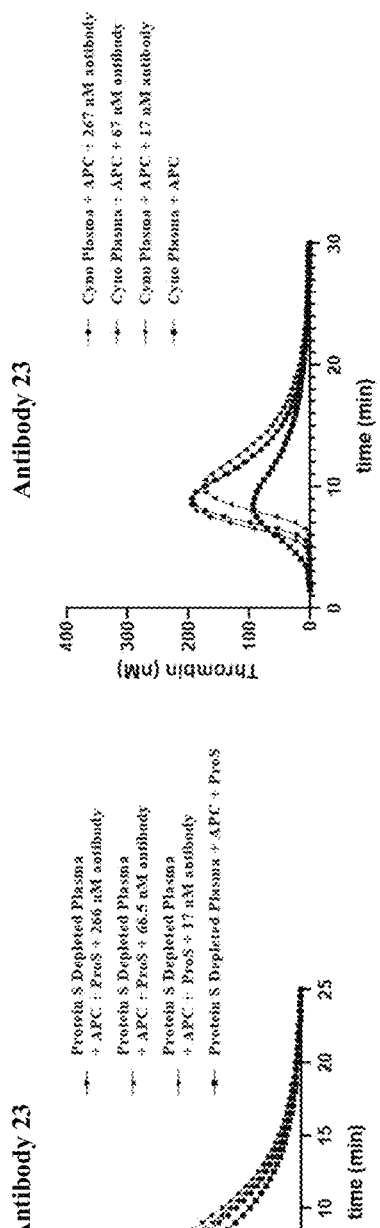
FIGS. 18A-18G depict the characterization of Antibody 23 and Antibody 11, antibodies sharing the same human variable region, and are characterized as TFPI cofactor inhibitors.
Figure 18B:
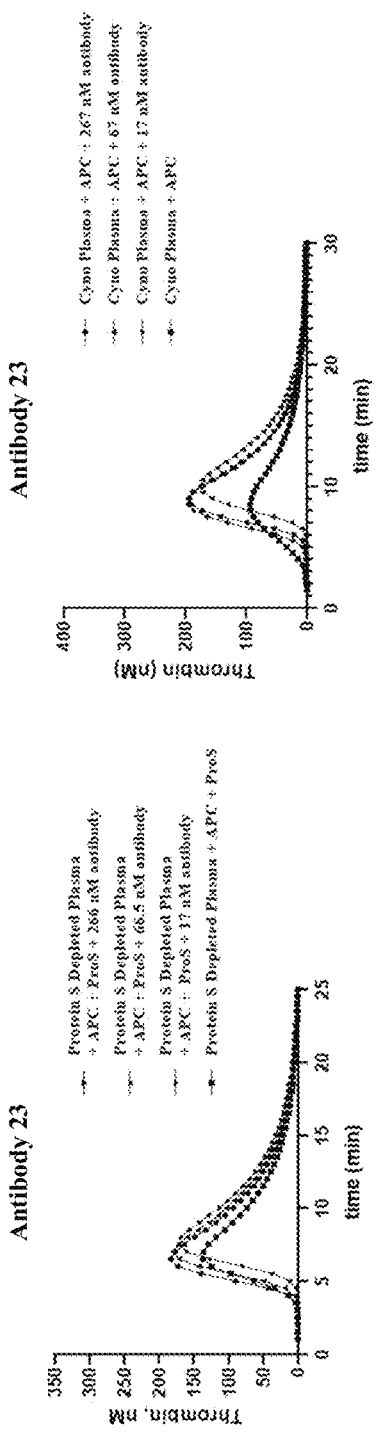
Figure 18C:
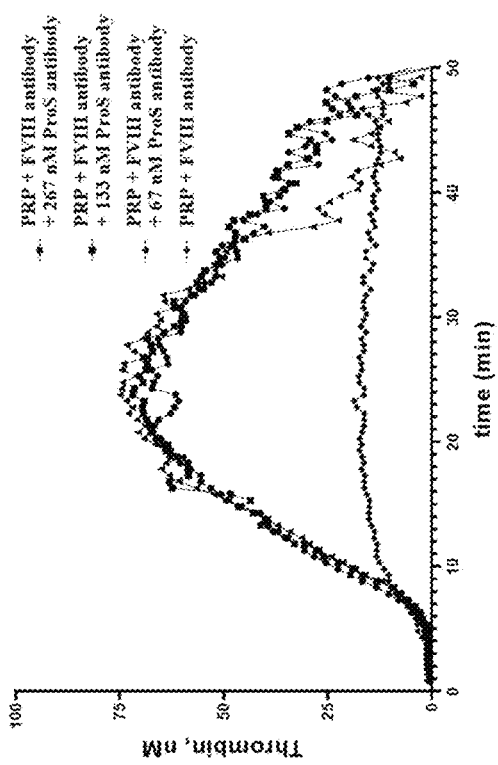

FIGS. 18A-18C depict the results of a APC cofactor assay for Antibody 23 using Protein S deficient human PPP, cynomolgus monkey PPP, and a TFPI cofactor assay using human PRP, respectively.

Figure 18E:
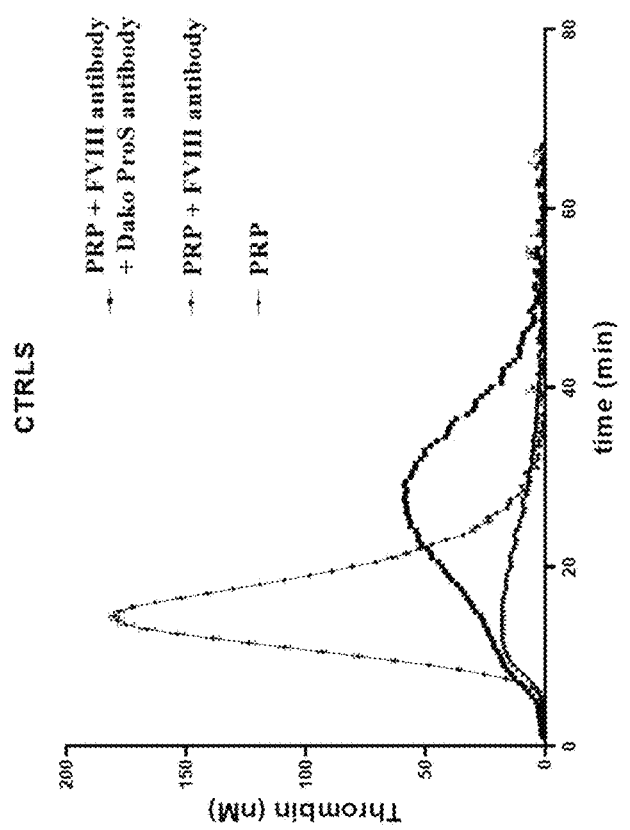
Figure 18D:
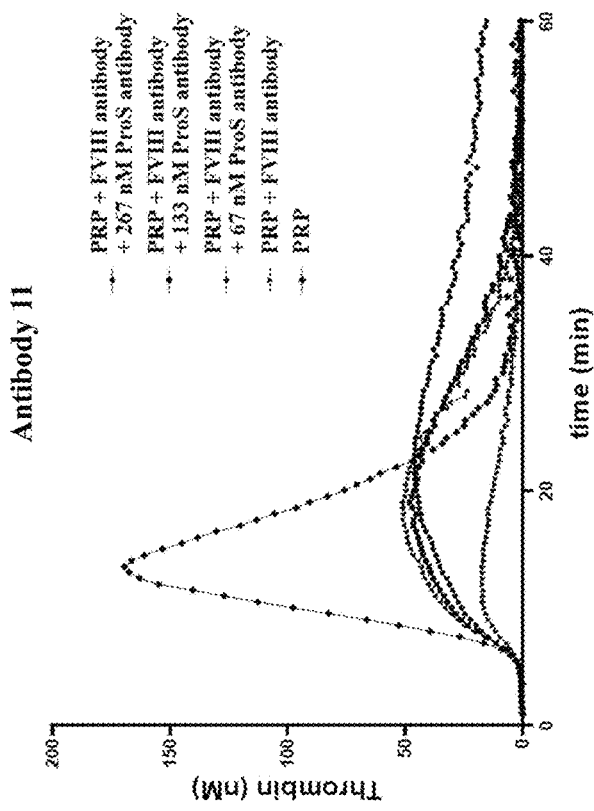

FIGS. 18D and 18E depict the results of a TFPI cofactor assay in human PRP using Antibody 11 and controls, respectively.

Figure 18G:
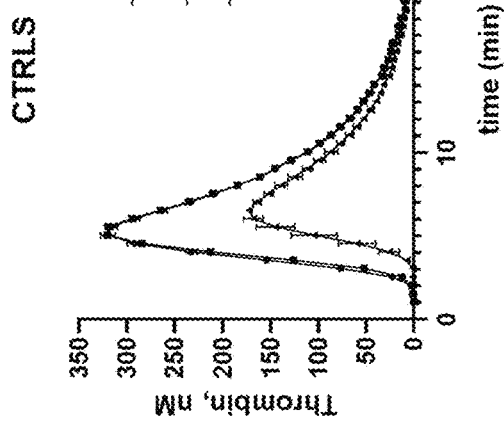
Figure 18F:
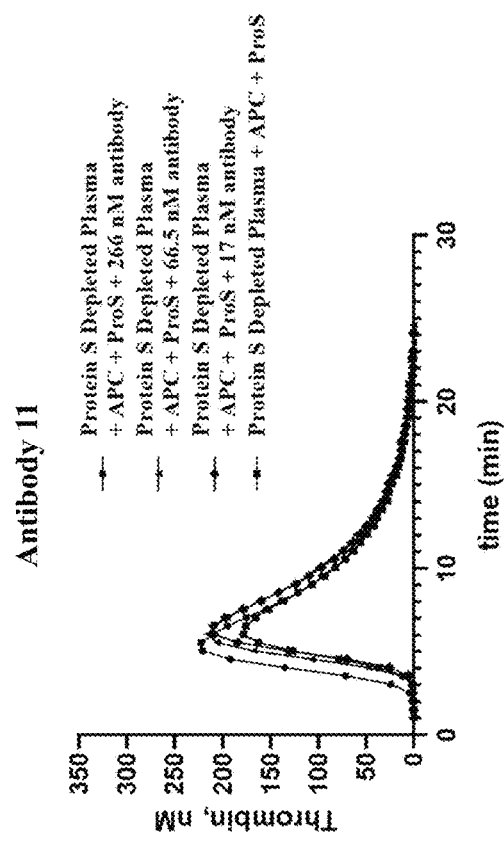

FIGS. 18F and 18G depict the results of a APC cofactor assay with Antibody 11 and controls, respectively.

These results indicate that Antibody 23 and Antibody 11 are TFPI cofactor inhibitors.

Antibody 24 and Antibody 12

FIGS. 19A-19H depict the characterization of Antibody 24 and Antibody 12, antibodies sharing the same human variable region, and are characterized as dual inhibitors.

FIG. 19A depicts a Western blot showing that Antibody 24 binds Protein S in the TSR of Protein S. The Western blot was carried out as described for FIG. 11A. By Western blot, Antibody 24 bound the full Protein S but did not bind the thrombin-cleaved Protein S. Antibody 24 did not bind the reduced Protein S or the reduced thrombin-cleaved Protein S. These results indicate that Antibody 24 binds Protein S at the TSR, and the lack of signal observed with the reduced Protein S showed that the epitope for this antibody is not a linear epitope.

Binding to the heavy chain of Protein S was determined using an ELISA based method, as described herein. Antibody 24 was determined to bind to the heavy chain of Protein S. Calcium dependence was determined, also as described herein, and Antibody 24 showed binding that was calcium-dependent.

FIGS. 19B-19D depict the results of a APC cofactor assay for Antibody 24 using Protein S deficient human PPP, cynomolgus monkey PPP, and a TFPI cofactor assay using human PRP, respectively.

Figure 19F:
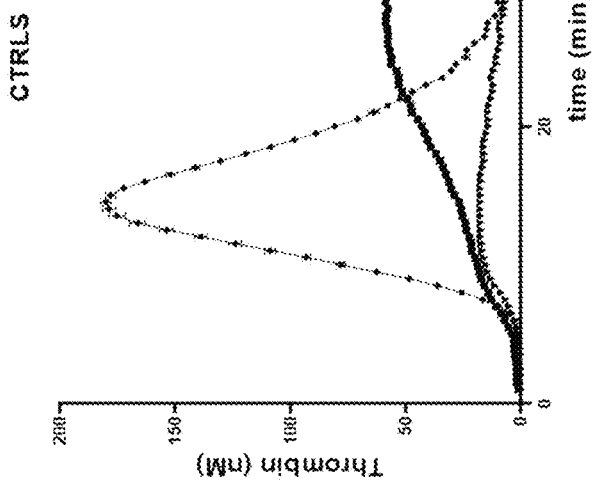
Figure 19E:
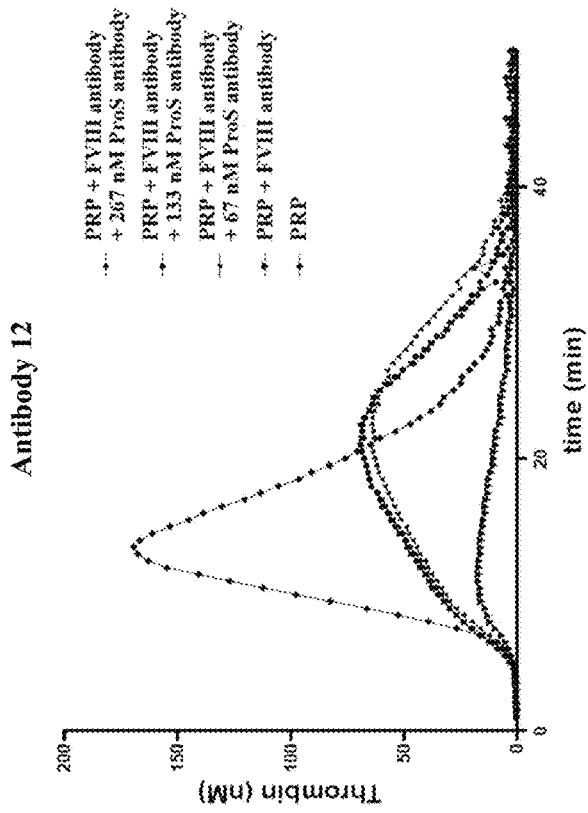

FIGS. 19E and 19F depict the results of a TFPI cofactor assay in human PRP using Antibody 12 and controls, respectively.

Figure 19G:
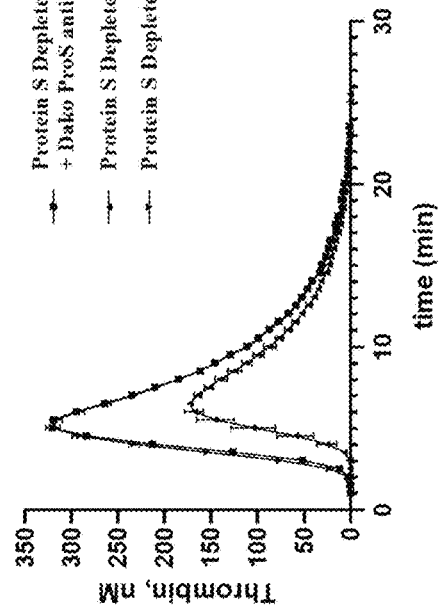
Figure 19H:
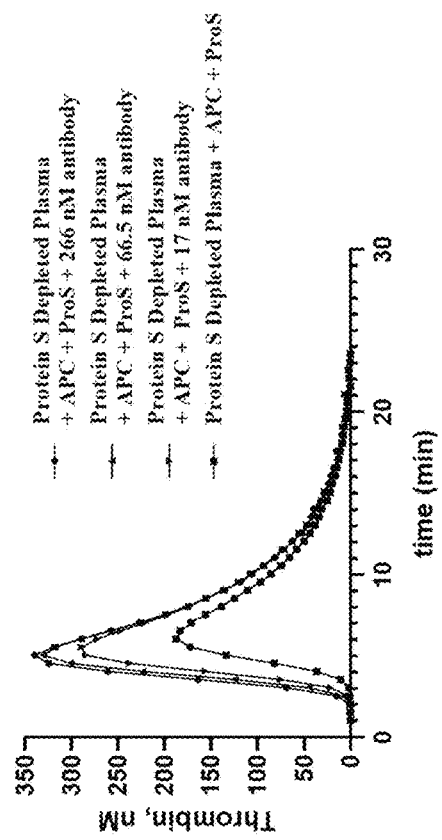

FIGS. 19G and 19H depict the results of a APC cofactor assay with Antibody 12 and controls, respectively.

These results indicate that Antibody 24 and Antibody 12 are dual inhibitors.

Antibody 18 and Antibody 6

FIGS. 20A-20H depict the characterization of Antibody 18 and Antibody 6, antibodies sharing the same human variable region, and are characterized as APC cofactor inhibitors.

FIG. 20A depicts a Western blot showing that Antibody 18 does not bind Protein S in the TSR of Protein S. The Western blot was carried out as described for FIG. 20A. By Western blot, Antibody 18 bound the full Protein S and the thrombin-cleaved Protein S, but did not bind the reduced Protein S or the reduced thrombin-cleaved Protein S. These results indicate that Antibody 18 does not bind Protein S at the TSR, and the lack of signal observed with the reduced Protein S showed that the epitope for this antibody is not a linear epitope.

Binding to the heavy chain of Protein S was determined using an ELISA based method, as described herein. Antibody 18 was determined to bind to the heavy chain of Protein S. Calcium dependence was determined, also as described herein, and Antibody 18 showed binding that was calcium-dependent.

FIGS. 20B-20D depict the results of a APC cofactor assay for Antibody 18 using Protein S deficient human PPP, cynomolgus monkey PPP, and a TFPI cofactor assay using human PRP, respectively.

Figure 20F:
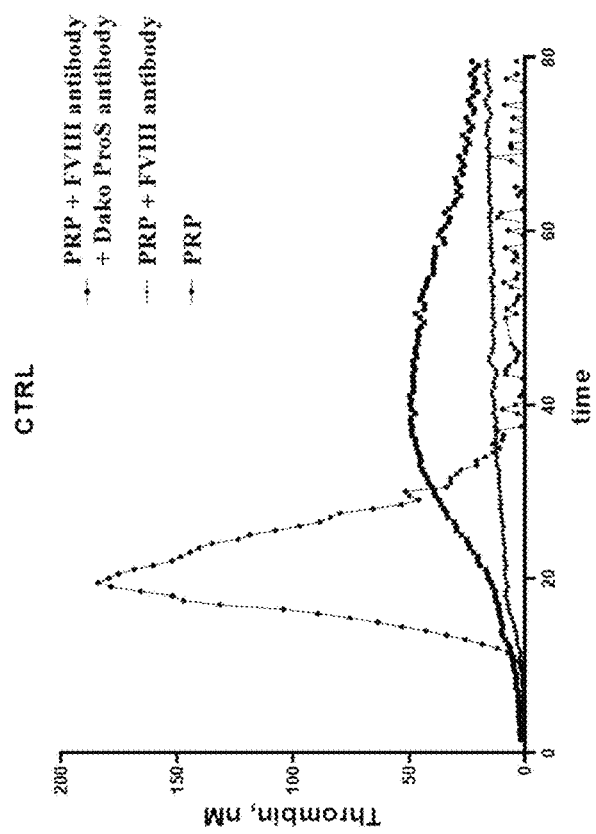
Figure 20E:
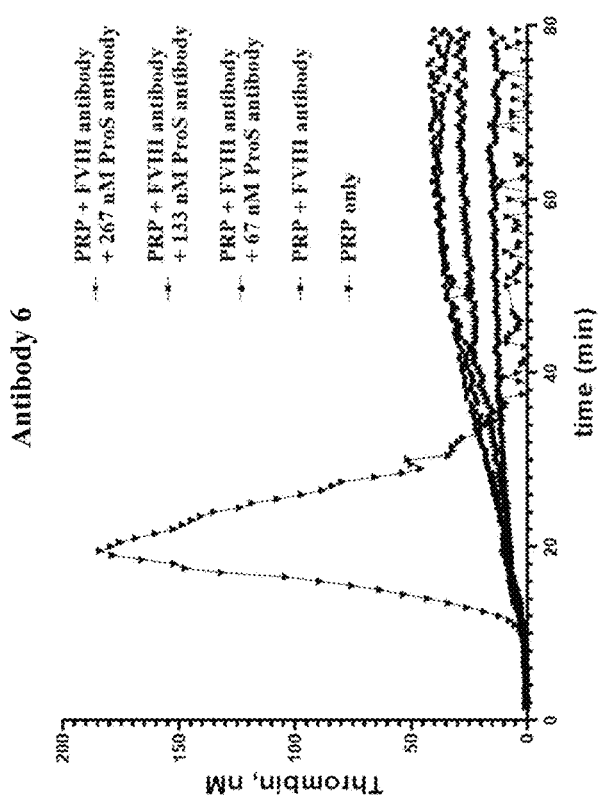

FIGS. 20E and 20F depict the results of a TFPI cofactor assay in human PRP using Antibody 6 and controls, respectively.

Figure 20G:
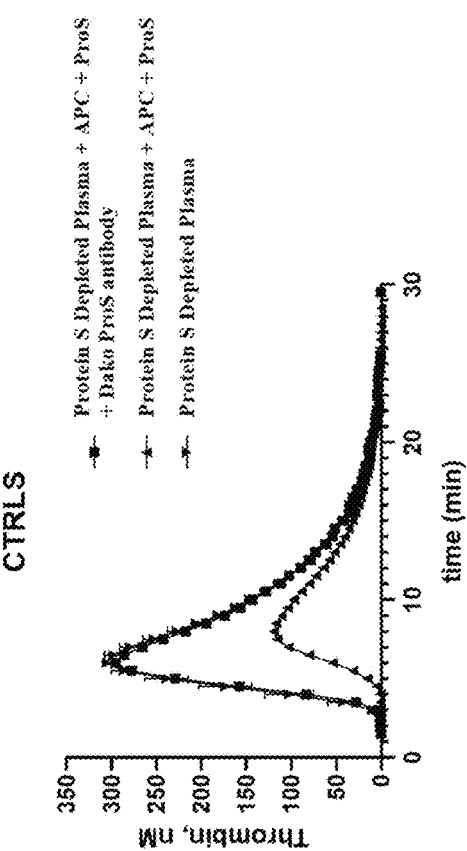
Figure 20H:
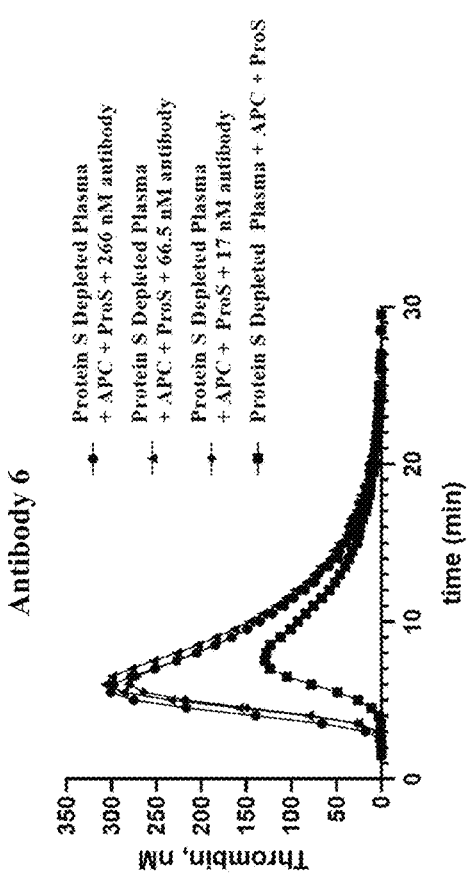

FIGS. 20G and 20H depict the results of a APC cofactor assay with Antibody 6 and controls, respectively.

These results indicate that Antibody 18 and Antibody 6 are APC cofactor inhibitors.

A summary of the characterizations exemplified above is presented in Table 13 below.

TABLE 13

| Human Antibody: Corresponding Protein S Antibody with Human Fc | Rat Antibody: Protein S Antibody with Rat Fc | Inhibitor Type |
|---|---|---|
| Antibody 1 | Antibody 13 | Dual |
| Antibody 2 | Antibody 14 | Dual |
| Antibody 3 | Antibody 15 | Dual |
| Antibody 4 | Antibody 16 | Dual |
| Antibody 6 | Antibody 18 | APC cofactor |
| Antibody 7 | Antibody 19 | Dual |
| Antibody 8 | Antibody 20 | Dual |
| Antibody 9 | Antibody 21 | APC cofactor |
| Antibody 11 | Antibody 23 | TFPI cofactor |
| Antibody 12 | Antibody 24 | Dual |

Example 4: Thrombin Generation Improvement in Plasma Samples from Patients with Various Factor Deficiencies and von Willebrand Disease FIGS. 21A-21G depict enhanced thrombin generation when Antibody 15 is added to various samples of congenital factor deficient plasma containing soluble thrombomodulin, a cofactor of thrombin that is involved in conversion of thrombin to an anti-coagulant enzyme. Plasma samples were taken from patients having various factor deficiencies and conditions: Factor VII, Factor VIII, Factor IX, or Factor XI deficiencies, and von Willebrand disease (vWD) type 1, 2, or 3.

Figure 21A:
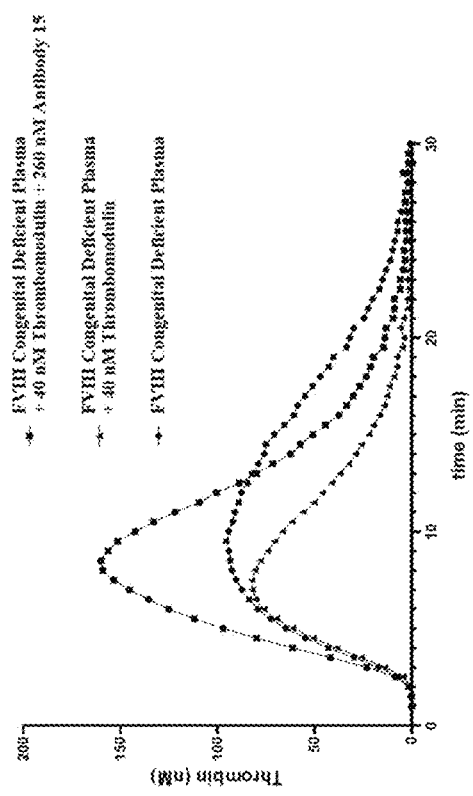
FIGS. 21A-21G depict enhanced thrombin generation when Antibody 15 is added to various samples of congenital factor deficient plasma containing soluble thrombomodulin.
Figure 21B:
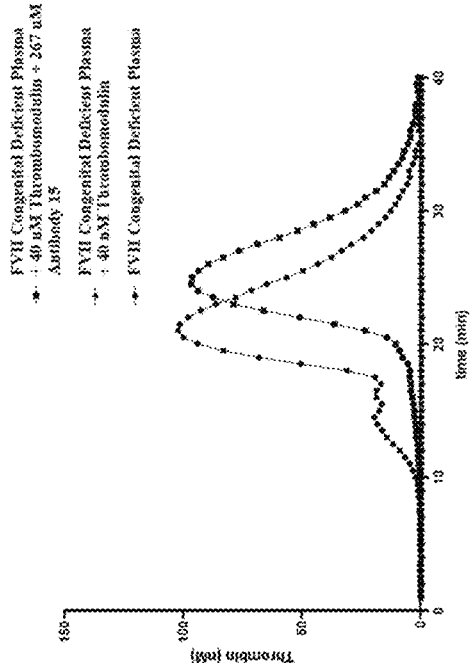
Figure 21C:
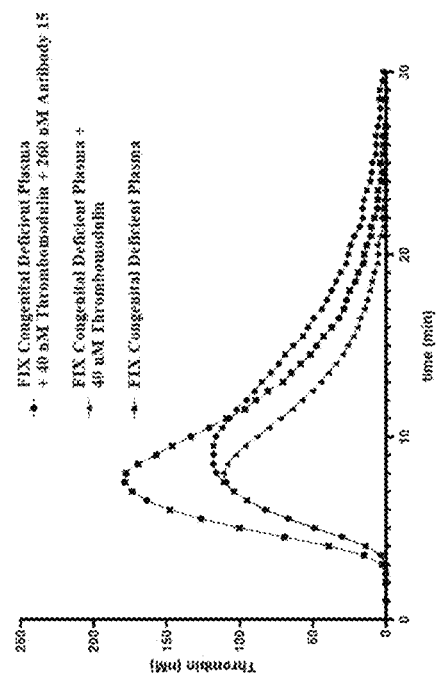
Figure 21E:
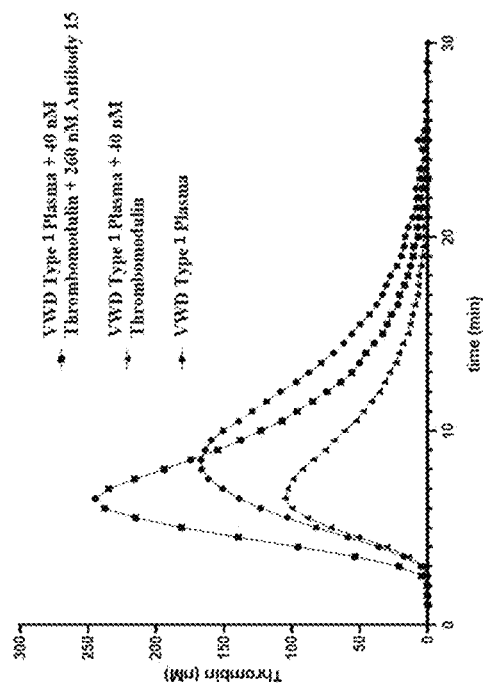
Figure 21D:
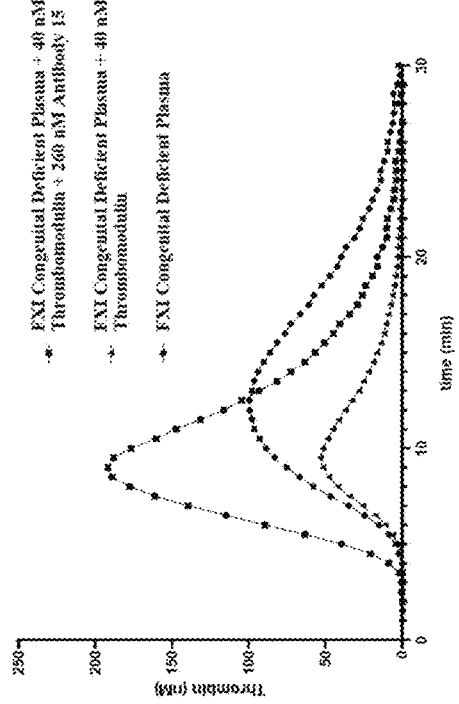
Figure 21F:
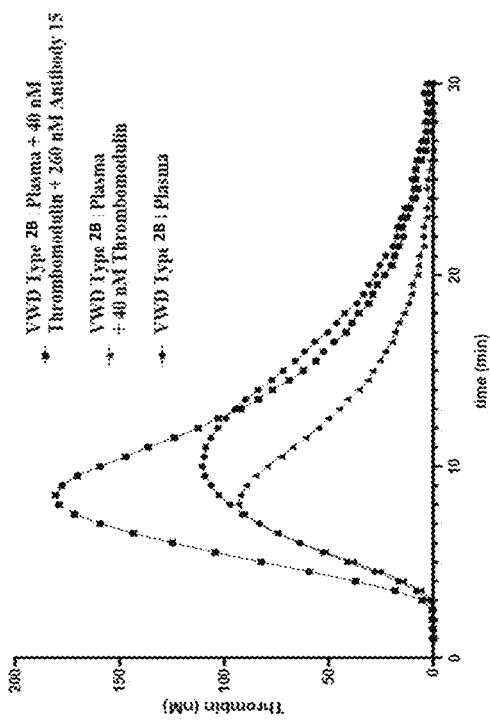
Figure 21G:
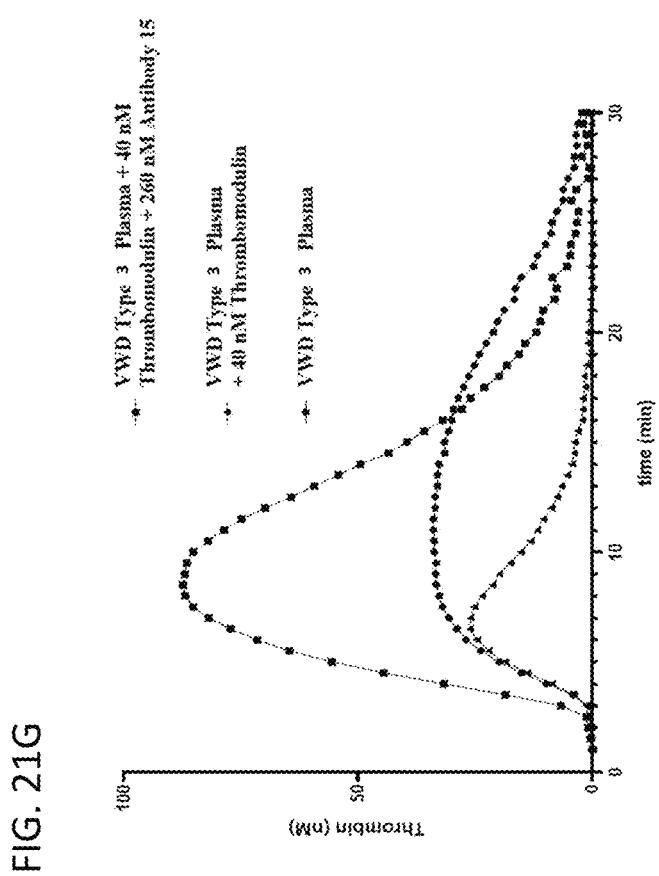
Figure 22A:
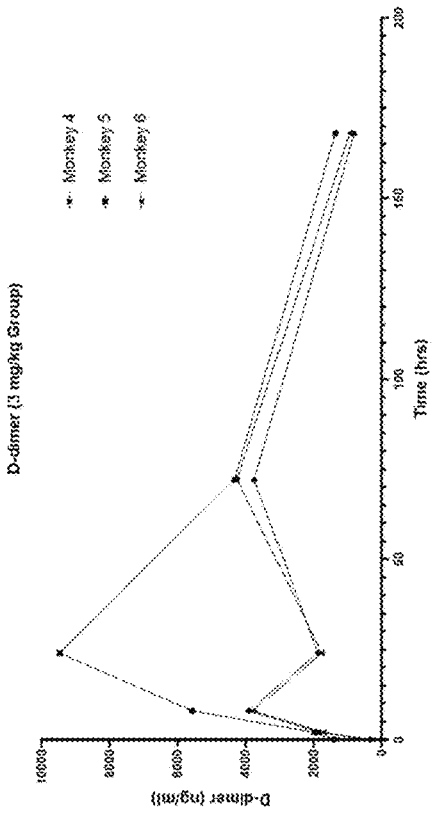
FIGS. 22A-22B depict the levels of D-dimer, as a marker of coagulation activity, observed over time in cynomolgus monkeys injected with either 1 mg/kg or 3 mg/kg of Antibody 1.
Figure 22B:
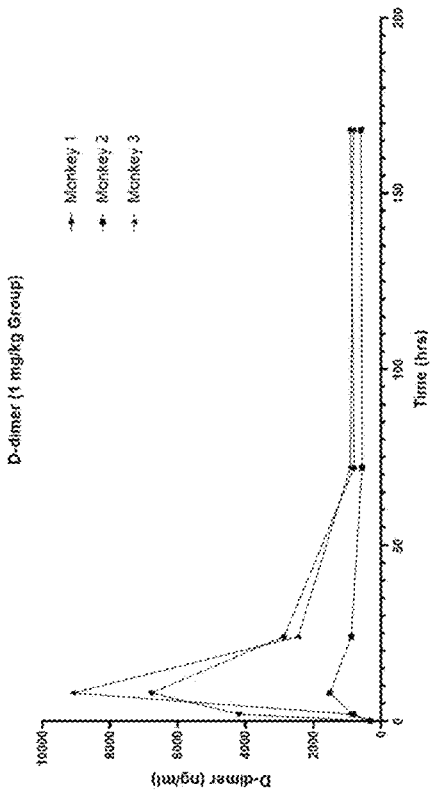

FIG. 21A depicts soluble tissue factor added to congenital Factor VII deficient plasma in the presence or absence of 40 nM soluble thrombomodulin. The level of thrombin generated is measured over time. When Antibody 15 is added to the deficient plasma containing thrombomodulin, increased thrombin was observed. FIGS. 21B-21G depict data generated from experiments performed in a similar manner, but using congenital Factor VIII deficient plasma, congenital Factor IX deficient plasma, congenital Factor XI deficient plasma, vWD type 1 plasma, vWD type 2B plasma or vWD type 3 plasma, respectively. These results show that the tested antibodies were able to promote thrombin generation in samples having a factor deficiency or vWD disease.

Example 5: Activity of Protein S Antibodies Post-Treatment in Cynomolgus Monkeys Using D-Dimer as a Marker

FIGS. 22A and 22B depict D-dimer levels observed in cynomolgus monkeys treated with 1 mg/kg or 3 mg/kg, respectively, of Antibody 1. At varying times post-injection of the antibody, blood was collected in sodium citrate tubes. Plasma samples were analyzed for the presence of D-dimer, a fibrin degradation product which acts as a marker of coagulation. Increases in the levels of D-dimer indicated that the tested antibodies activate the coagulation cascade and remain active in vivo for a period of time after treatment. FIG. 22A shows that treatment with 1 mg/kg of Antibody 1 showed activity for approximately 70 hours after treatment, and FIG. 22B shows that treatment with 3 mg/kg of Antibody 1 showed activity for approximately 105-110 hours after treatment.

Example 6: Restoration of Fibrin Deposition by Protein S Antibodies

Figure 23A:
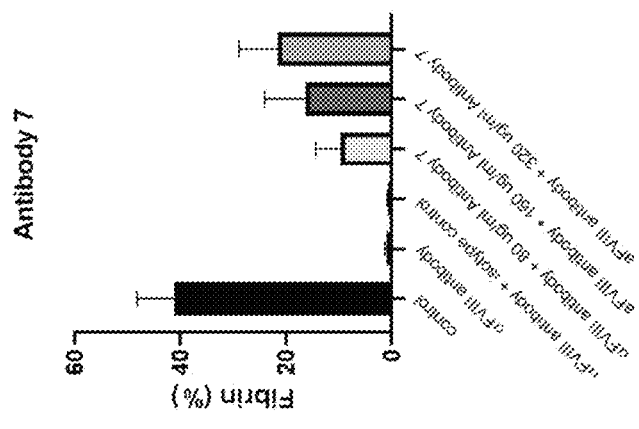
FIGS. 23A-23C depict the level of fibrin deposited onto collagen coated spots in Factor VIII (FVIII) neutralized blood treated with various Protein S antibodies, showing a restoration of fibrin deposition activity by the Protein S antibodies in the FVIII neutralized blood.
Figure 23B:
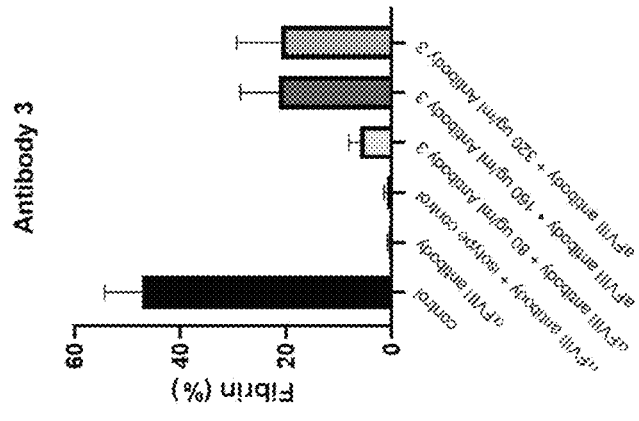
Figure 23C:
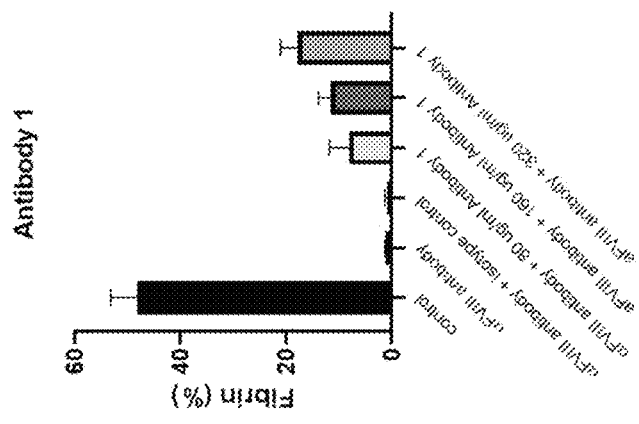

FIGS. 23A-23C depict the level of fibrin deposited onto collagen spots in a microfluidic system. Certain coagulation factor deficiencies can cause fibrin deposition to be at levels lower than that of subjects not having a factor deficiency. The microfluidic system can allow measurement of coagulation occurring during flow of blood.

Normal human blood, from a patient without any factor deficiencies, was untreated or treated with Factor VIII (FVIII) neutralizing antibody. This was then passed over collagen spots in a microfluidic system. Strong fibrin deposition was observed in untreated blood, but not in treated blood. When Antibodies 1, 3 and 7 were added to the treated blood, fibrin deposition was restored in a dose dependent manner. These results show that in blood neutralized with FVIII antibody, the Protein S antibodies disclosed herein may be used for restoration of fibrin formation or deposition, which may serve as a desired marker for coagulation activity.

Example 7: Binding of Protein S Antibodies to the Protein S-C4BP Complex

The Octet assay was used to determine the capability of the Protein S antibodies provided herein to bind to Protein S either alone, or when complexed to C4BP. A summary of the binding to Protein S or the Protein S-C4BP complex is provided in Table 14. Table 14 presents an X where a tested antibody was able to bind to either the Protein S-C4BP Complex, and/or the Protein S alone. A dash indicates that the binding did not occur.

Using the Octet System (Sartorius), the binding of each antibody to both Protein S and Protein S in complex with C4BP was determined. It had previously been determined that the C4BP preparation from Complement Technologies contains Protein S precomplexed to human C4BP. Therefore, this preparation represented the Protein S-C4BP complex and plasma purified Protein S from Haematologic Technologies was used as the source of free Protein S. The human Fc antibodies were immobilized onto anti-human Fc capture probes by placing the probes into 10 µg/ml antibody solution in 10 mg/ml bovine serum albumin, 20 mM Tris pH 7.0, 150 mM NaCl, and 4 mM calcium chloride. Then the bound antibodies were placed into solutions containing either 75 µg/ml Protein S or 100 µg/ml C4BP (C4BP-Protein S complex). With antibodies that do not bind Protein S in complex with C4BP, no binding is observed. With antibodies that bind Protein S in free form or in complex with C4BP, an association is observed under both conditions. All antibodies tested bound free Protein S, as depicted in Table 14.

TABLE 14

| Antibody with Human Fc | Binding to ProS-C4BP Complex | Binding to ProS |
| --- | --- | --- |
| Antibody 1 | X | X |
| Antibody 2 | X | X |
| Antibody 3 | X | X |
| Antibody 4 | X | X |
| Antibody 6 | X | X |
| Antibody 7 | X | X |
| Antibody 8 | X | X |
| Antibody 9 | X | X |
| Antibody 11 | — | X |
| Antibody 12 | X | X |
| Antibody 25 | — | X |
| Antibody 27 | X | X |
| Antibody 28 | X | X |
| Antibody 29 | — | X |
| Antibody 30 | — | X |
| Antibody 37 | — | X |
| Antibody 39 | — | X |
| Antibody 41 | — | X |
| Antibody 43 | X | X |

Example 8: Effects of Protein S Antibodies on Fibrin Deposition

These experiments were carried out as follows. Bioflux 1000z 48-well high shear microfluidics plates (0-200 dynes/cm2) employed in the experiments were purchased from Bioflux. The device has the #1.5 borosilicate glass coverslip which forms the floor of the microfluidic channel engineer to facilitate the coated of collagen. Collagen type 1 was purchase from Chrono-Par collagen (chrono-Log Corp, Havertown, PA). Collagen was perfused from the wells at room temperature and incubated for 1 hour. Precoated plates with collagen type 1 were rinsed with PBS and channels were blocked with 0.5% (v/v) BSA for 10 min in PBS prior to the addition of the labeled blood to the wells. Sodium citrate anti-coagulated whole human blood (ALLCells, Oakland, CA) was used within 4-8 h of collection. Whole blood was incubated for 1 hour with 100 µg/mL Sheep anti-Human Factor VIII (Haematologic Technologies, Essex, VT). The antibodies were added and incubated with whole blood. Fibrinogen from human plasma, Alexa Fluor 546 (Invitrogen, Carlsbad, CA) was added at a final concentration of 50 µg/mL prior to biological experiments. Whole blood was added to the input wells and perfused at 30 dyn/cm2 using the BioFlux Controller and software. The samples were illuminated for no more than 30 ms for each capture. The BioFlux software imaging module was used to control the image acquisition settings and to process the fluorescence intensity measurements. Fluorescent micrographs were captured with the blood under flow using an inverted microscope (ZEISS Axio Observer 7) and sCMOS Camera. Images were timelapse recorded using the BioFlux 1000 imaging system (Fluxion Biosciences). Data was processed using BioFlux Montage Software.

Figure 25A:
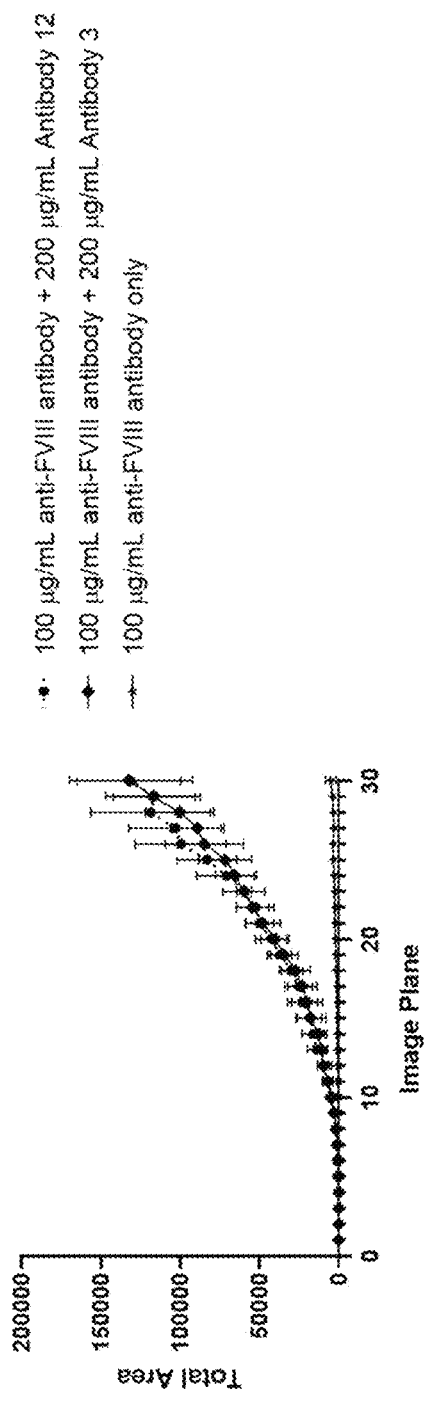
FIGS. 25A-25B depict the effect of selected Protein S antibodies on fibrin deposition.
Figure 25B:
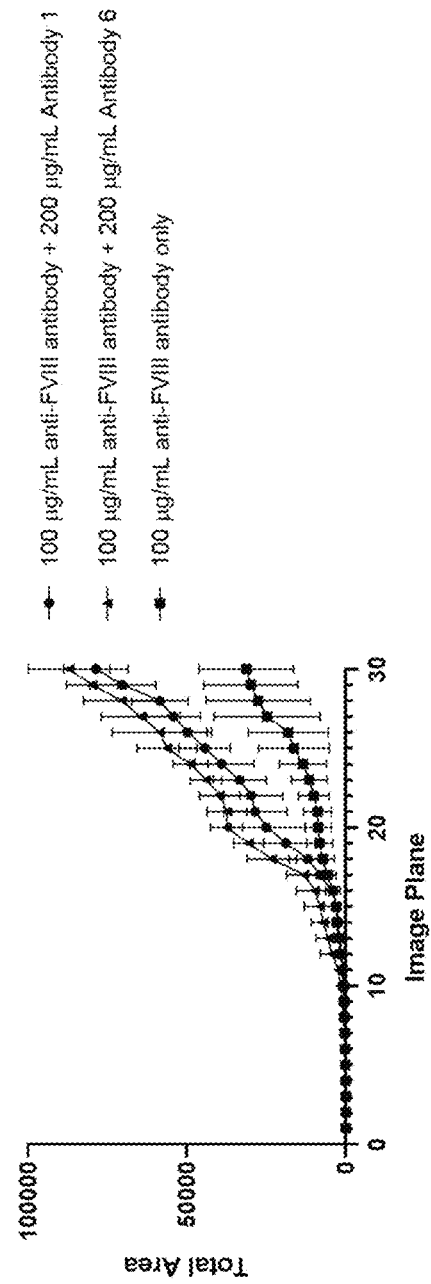

FIGS. 25A-25B depict the level of fibrin deposition resulting from the Protein S antibodies added to whole blood treated with Factor VIII neutralizing antibodies. This experiment tests the ability of the Protein S antibodies to restore or increase fibrin deposition in an in vitro microfluidic Hemophilia A model. Whole blood was treated with Factor VIII antibody to decrease fibrin deposition. FIG. 25A depicts the effects of Antibodies 12, and 3, and a control on fibrin deposition in anti-FVIII treated human plasma, and FIG. 25B depicts the effects of Antibodies 1 and 6 and a control on fibrin deposition in anti-FVIII treated human plasma. These results demonstrate that the Protein S antibodies 12, 3, 1 and 6 could restore or increase fibrin deposition in an in vitro microfluidic Hemophilia A model.

Example 9: Effect of Protein S Antibodies in an In Vitro Microfluidics Hemophilia A Bleeding Model These experiments were carried out using a fully endothelialized microfluidic system that was coupled to a microengineered pneumatic valve that mimics vascular damage (Sakurai, et al. Nature Communications 2018). Briefly, whole blood collected from healthy volunteers were treated with a sheep anti-human FVIII antibody to mimic whole blood from a hemophilia A patient. After treatment, the whole blood was perfused into the microfluidics system at which time an "injury" was introduced using the pneumatic valve. The localization of both platelets and fibrin at the site of "injury" was monitored and the time to cessation of "bleeding" was measured.

Figure 26B:
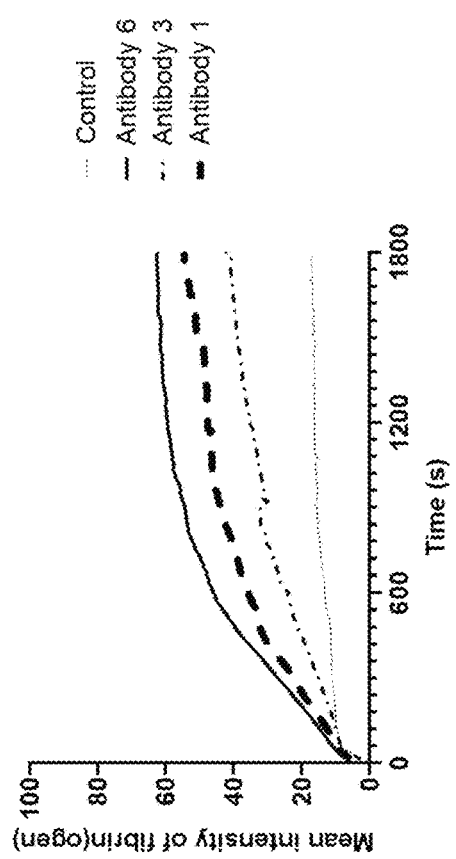
FIGS. 26A-26B depict the effects of Protein S antibodies in an in vitro microfluidic Hemophilia A bleeding model.
Figure 26A:
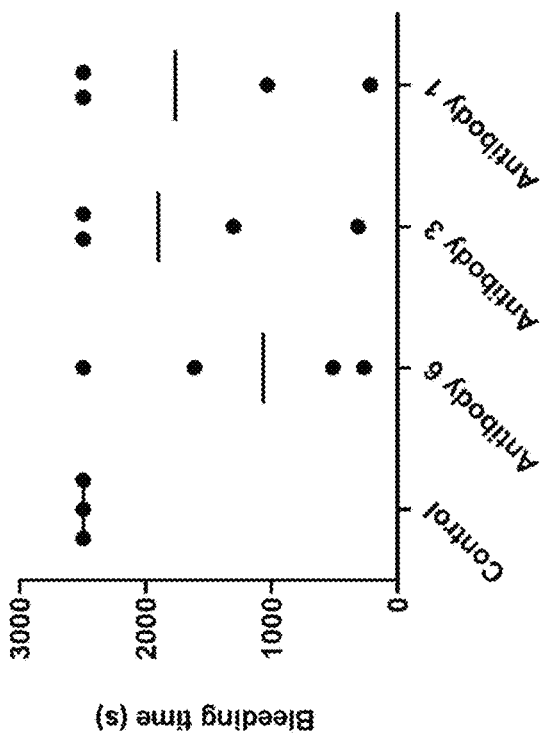

FIGS. 26A-26B depict the effects of Protein S antibodies in an in vitro microfluidics Hemophilia A bleeding model, measured by microfluidics experiments. These experiments were performed to measure the time of various Protein S antibodies to stop bleeding, and to determine the extent to which these antibodies induced fibrin deposition, respectively, in a microengineered, vascularized Hemophilia A bleeding model. The tested antibodies were Antibodies 6, 3, and 1. These results demonstrate that the antibodies were able to restore or increase fibrin deposition in a Hemophilia A bleeding model and therefore stop bleeding.

Example 10: Effect of Protein S Antibodies on Thrombin Generation

These experiments were carried out as follows. The Thrombin Generation Assay (TGA) was performed using a Thermo Fluoroskan Ascent Microplate Fluorometer and Thrombinoscope software. The PPP low reagent (Diagnostica Stago) was used in this experiment. Briefly, plasma from von Willebrand diseased patients was mixed with increasing levels of Protein S antibodies and incubated at room temperature. Then soluble human thrombomodulin was added prior to initiation of the reaction. To start the reaction, PPP low reagent was added along with calcium and the thrombin substrate. The levels of thrombin were then monitored.

FIGS. 27A-27F depict various results of enhanced dose-dependent thrombin generation when Protein S antibodies were added to plasma obtained from patients with various types of von Willebrand disease, with thrombomodulin added. These results demonstrate that the Protein S antibodies could effectively increase thrombin generation in a dose-dependent manner, and that different Protein S antibodies were more efficacious for different types of von Willebrand disease. Generally, the tested antibodies were more effective at increasing thrombin generation for Type 1 than Types 2A, 2B, and 3.

Figure 27B:
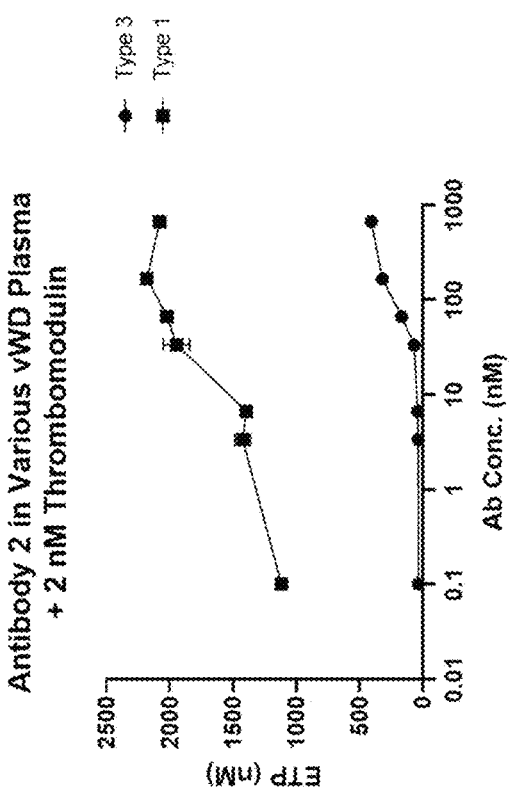
FIGS. 27A-27F depict the effect of selected Protein S antibodies on enhanced dose-dependent thrombin generation, wherein the Protein S antibodies were added to plasma obtained from patients with various types of von Willebrand disease.
Figure 27A:
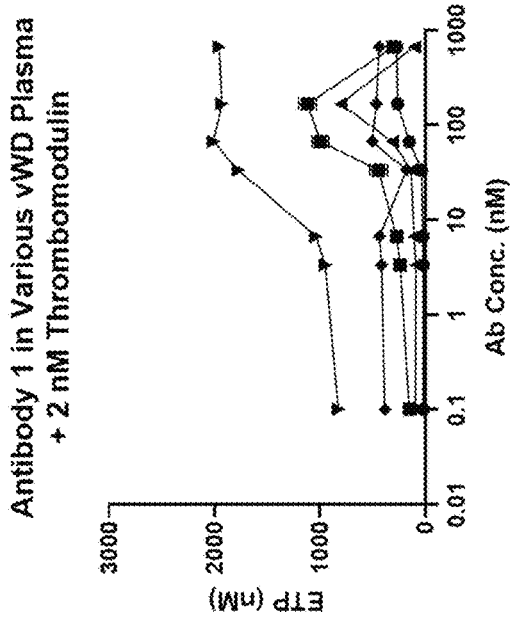
Figure 27D:
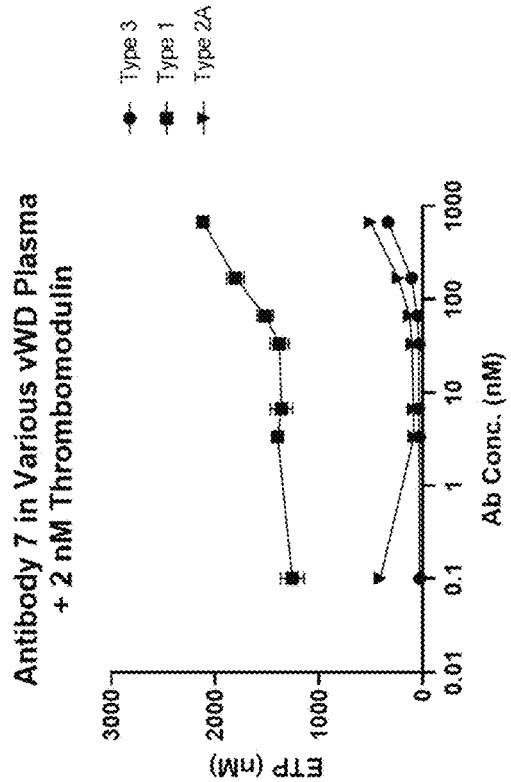
Figure 27C:
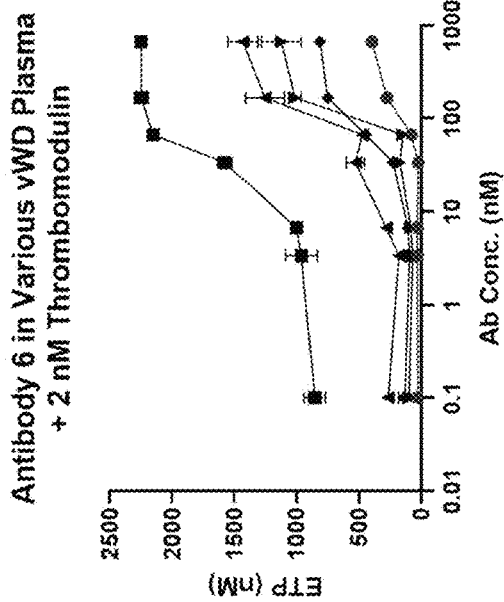
Figure 27E:
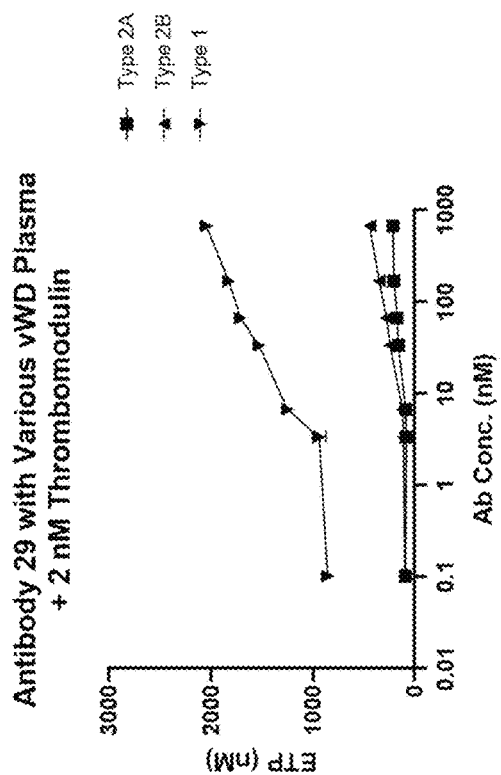
Figure 27F:
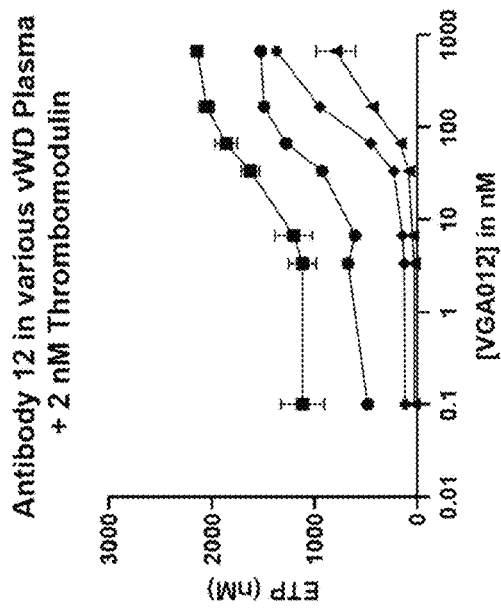

FIGS. 27A-27B depict enhanced dose-dependent thrombin generation when Antibodies 1 and 2 were added to plasma obtained from patients with various types of von Willebrand disease. FIGS. 27C-27D depict enhanced dose-dependent thrombin generation when Antibodies 6 and 7 were added to plasma obtained from patients with various types of von Willebrand disease, with thrombomodulin added. FIGS. 27E-27F depict enhanced dose-dependent thrombin generation when Antibodies 12 and 29 were added to plasma obtained from patients with various types of von Willebrand disease, with thrombomodulin added.

Example 11: APC Cofactor Assay in Cynomolgus Monkeys with Subcutaneous and Intravenous Injection The APC cofactor assay was performed using a Thermo Fluoroskan Ascent Microplate Fluorometer and Thrombinoscope software. The PPP reagent (Diagnostica Stago) was used in this experiment. Briefly, cynomolgus monkey plasma was mixed with PPP reagent and 5 µg/ml of activated Protein C along with calcium and substrate and the levels of thrombin generation was monitored over 1 hour. The PK assay was performed by incubating diluted cynomolgus monkey plasma onto plates immobilized with human Protein S. The plates used were MSD 96-well plates. 30 µl of 2 µg/ml plasma purified Protein S in Tris buffer containing calcium was used to coat the plate overnight. After blocking, the wells were incubated with samples, standards and QCs. 25 µl per well of 2 µg/ml sulfo-tagged goat anti-human IgG, monkey ads and incubated at room temperature for 1 hr. After washing, 150 µl of 1λ MSD Read Buffer T in water was added to each well and the plate was read on a MSD plate reader. The levels of D-dimer were measured using the D-dimer assay kit from Diagnostica Stago following manufacturer's recommended protocol.

Figure 28A:
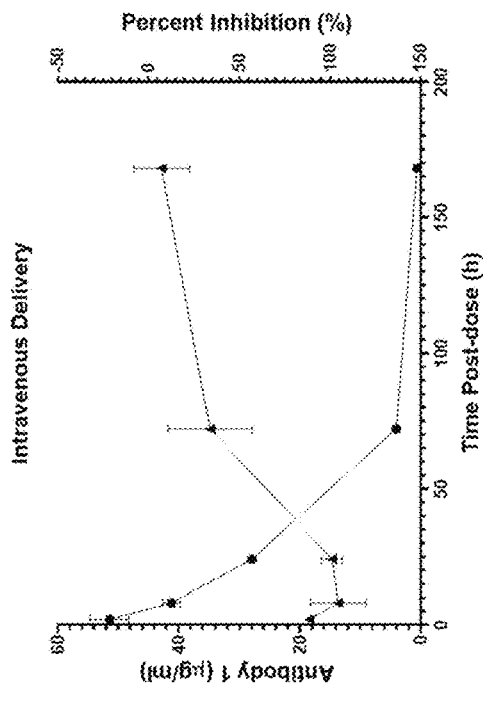
FIGS. 28A-28N depict the results of thrombin generation assays (ex vivo pharmacodynamic assay) as well as pharmacokinetic assays used to measure free antibody, in cynomolgus monkeys injected subcutaneously or intravenously with Protein S antibodies. These figures also depict levels of D-dimer, used as a marker of coagulation activity, observed in the monkeys.
Figure 28B:
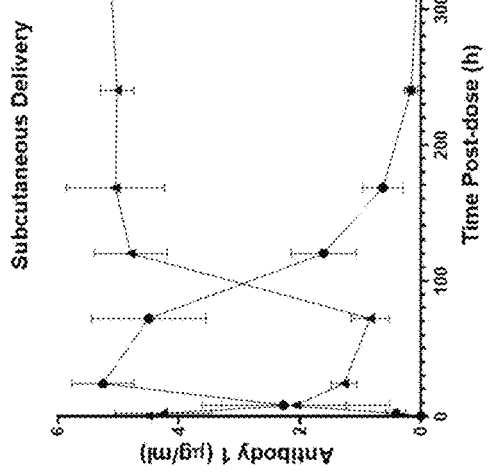
Figure 28C:
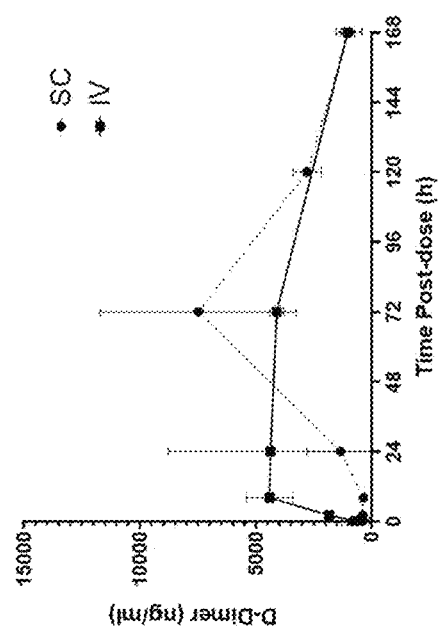
Figure 28E:
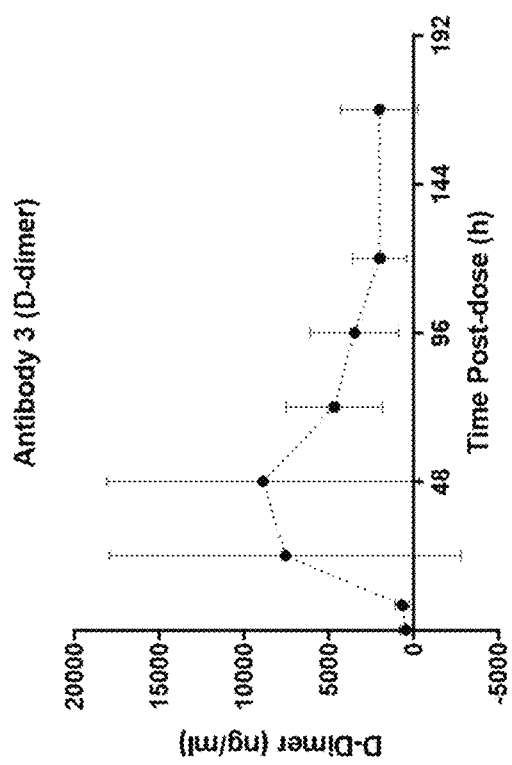
Figure 28D:
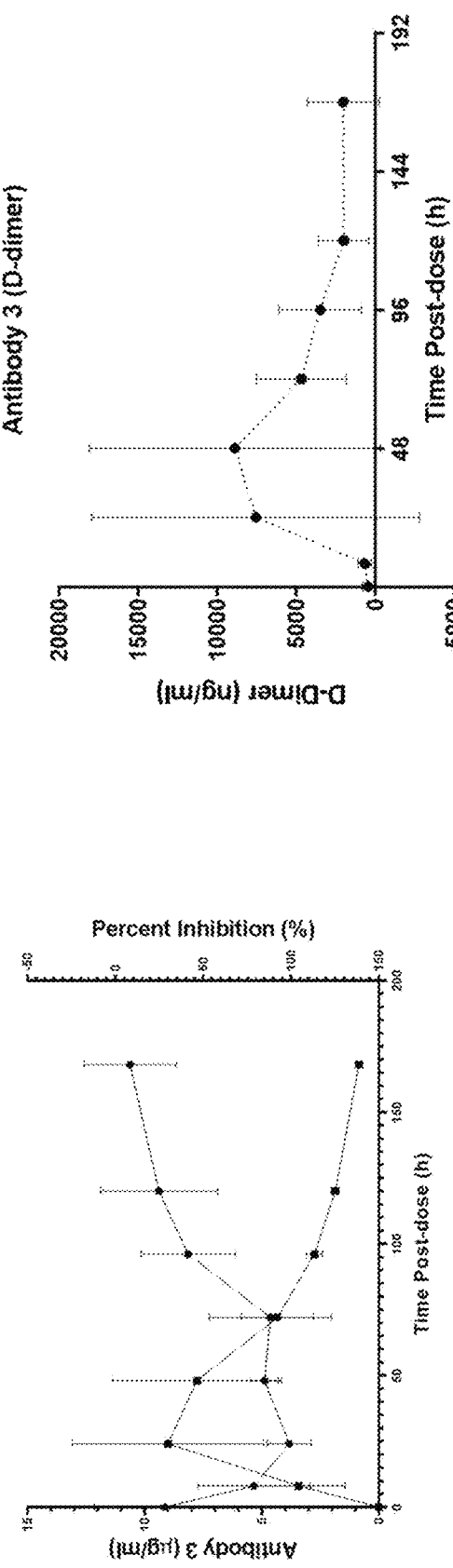
Figure 28G:
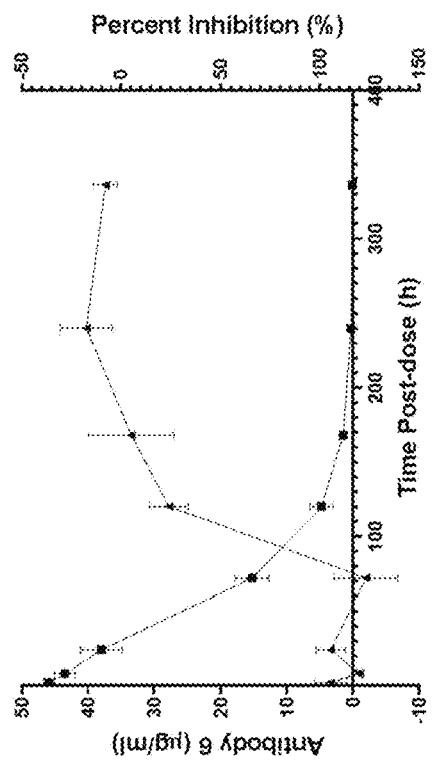
Figure 28F:
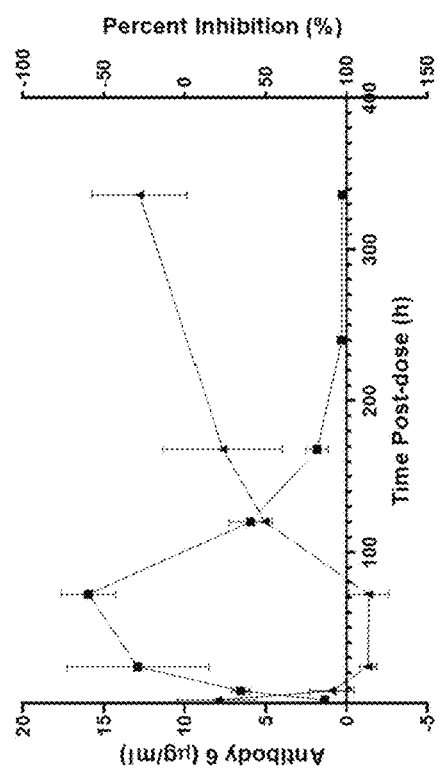
Figure 28H:
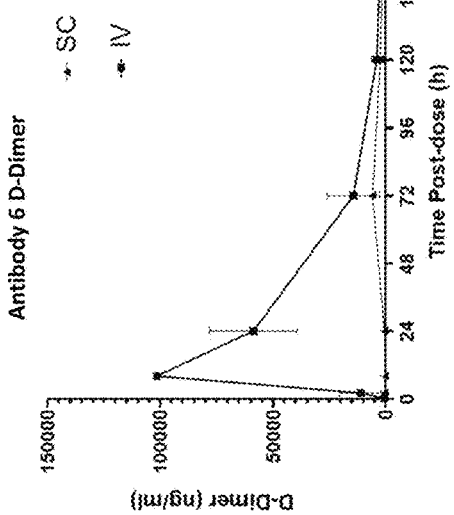
Figure 28J:
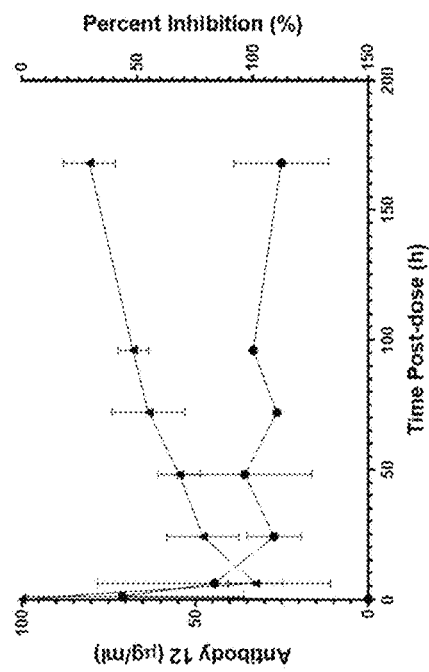
Figure 28I:
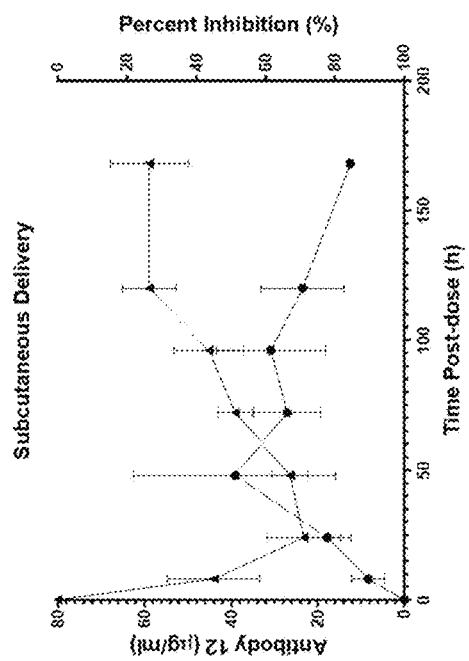
Figure 28K:
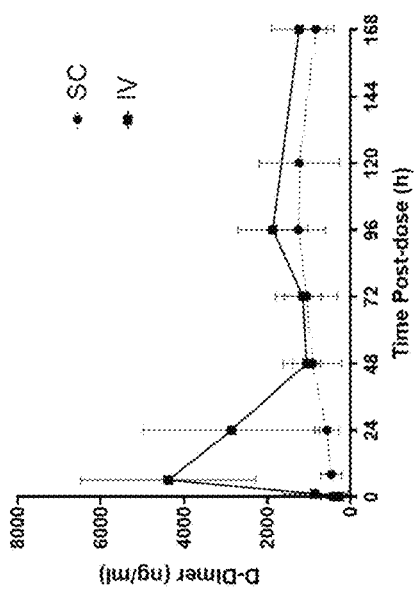
Figure 28M:
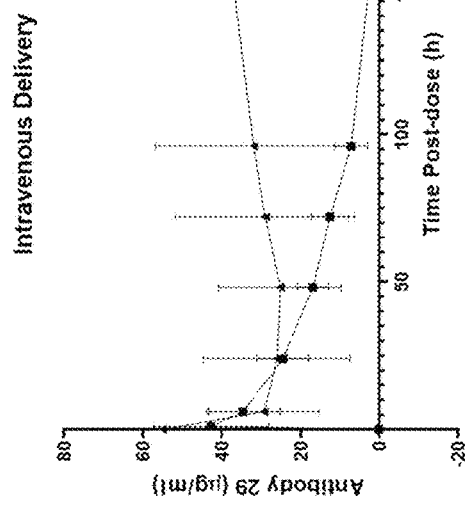
Figure 28L:
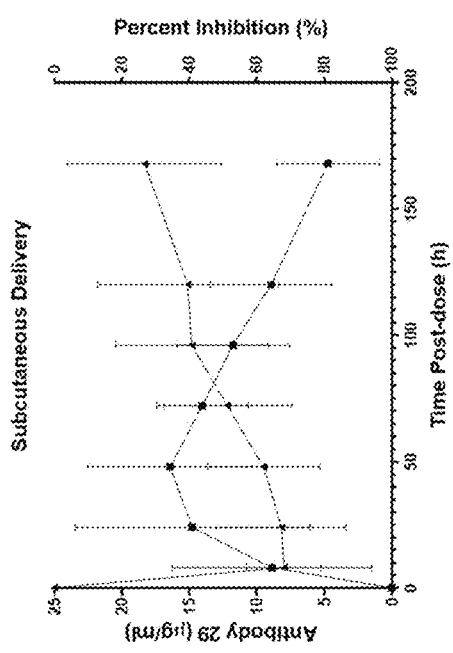
Figure 28N:
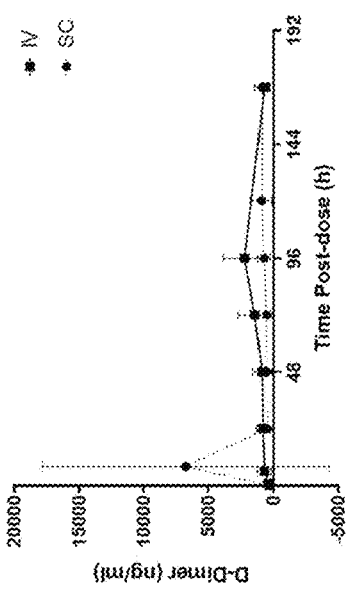
Figure 29:
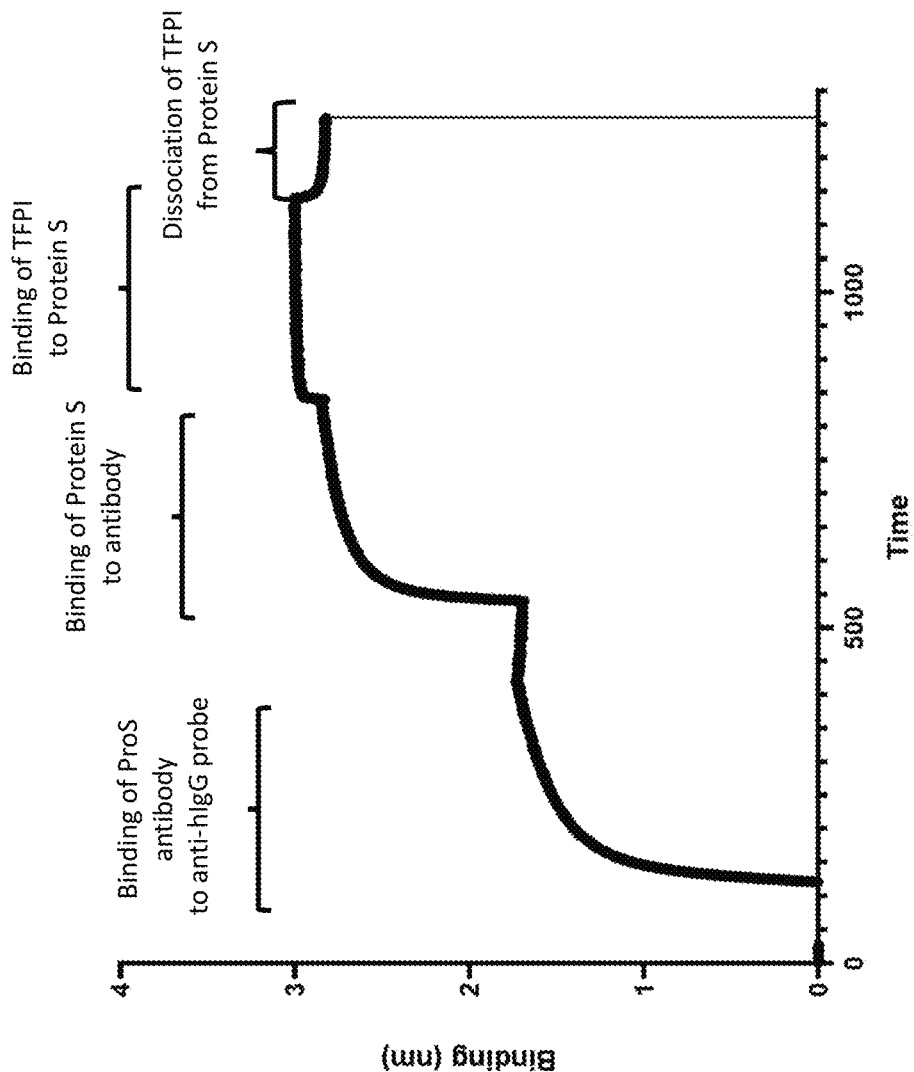
FIG. 29 depicts the effect of Antibody 2 on the ability of Protein S to bind TFPI.

FIGS. 28A-28N depict the results of APC cofactor assays, PK assays, and D-dimer assays for plasma samples collected after administration of Protein S antibodies into cynomolgus monkeys at 3 mg/kg subcutaneously and intravenously. The APC cofactor assay was used to measure the pharmacodynamic activity of the administered Protein S antibodies at the various times. In addition, FIGS. 28A-28N also show the levels of free antibody which was measured using an ELISA assay. And finally, elevated D-dimer, which was used as a biomarker of Protein S antibody induced coagulation activity, was observed in the monkeys and the data shown.

Specifically, FIGS. 28A-28B depict the levels of free antibody (left axis, filled circles) and percent inhibition in an APC cofactor assay (right axis, filled triangles) when Antibody 1 was administered to cynomolgus monkeys at 3 mg/kg subcutaneously and intravenously, respectively.

FIG. 28C depicts levels of D-dimer, as a marker of coagulation activity, measured over time in cynomolgus monkeys injected with Antibody 1, subcutaneously (SC) and intravenously (IV).

FIG. 28D depicts the levels of free antibody (left axis, filled squares) and percent inhibition in an APC cofactor assay (right axis, filled circles) when Antibody 3 was administered to cynomolgus monkeys at 3 mg/kg subcutaneously.

FIG. 28E depicts levels of D-dimer, as a marker of coagulation activity, measured over time in cynomolgus monkeys injected with Antibody 3.

FIGS. 28F-28G depict the levels of free antibody (left axis, filled squares) and percent inhibition in an APC cofactor assay (right axis, filled triangles) when Antibody 6 was administered to cynomolgus monkeys at 3 mg/kg subcutaneously and intravenously, respectively.

FIG. 28H depicts levels of D-dimer, as a marker of coagulation activity, measured over time in cynomolgus monkeys injected with Antibody 6.

FIGS. 28I-28J depict the levels of free antibody (left axis, filled circles) and percent inhibition in an APC cofactor assay (right axis, filled triangles) when Antibody 12 was administered to cynomolgus monkeys at 3 mg/kg subcutaneously and intravenously, respectively.

FIG. 28K depicts levels of D-dimer, as a marker of coagulation activity, measured over time in cynomolgus monkeys injected with Antibody 12.

FIGS. 28L-28M depict the levels of free antibody (left axis, filled squares) and percent inhibition in an APC cofactor assay (right axis, filled triangles) when Antibody 29 was administered to cynomolgus monkeys at 3 mg/kg subcutaneously and intravenously, respectively.

FIG. 28N depicts levels of D-dimer, as a marker of coagulation activity, measured over time in cynomolgus monkeys injected with Antibody 29.

Example 12: Effects of Protein S Antibodies on the Binding of Protein S to TFPI

The effect of the antibodies of the disclosure on the binding of Protein S to TFPI was measured.

Using the Octet System (Sartorius), an assay to measure the binding of TFPI to Protein S was developed. Briefly, the human Fc antibodies were immobilized onto anti-human Fc capture probes by placing the probes into 10 µg/ml antibody solution in 10 mg/ml bovine serum albumin, 20 mM Tris pH 7.0, 150 mM NaCl, and 4 mM calcium chloride. Then the bound antibodies were placed into a solution containing 10 µg/ml human Protein S followed by a 10 µg/ml solution containing human TFPI. Finally, the probe was placed into a buffer solution (wash) to observe the dissociation of TFPI from Protein S. The kinetics of association and dissociation of TFPI to Protein S were measured.

FIG. 31 depicts the binding of human TFPI to Protein S after the binding of Protein S to Antibody 2. These results demonstrate that Antibody 2 does not block the binding of TFPI to Protein S.

Figure 30B:
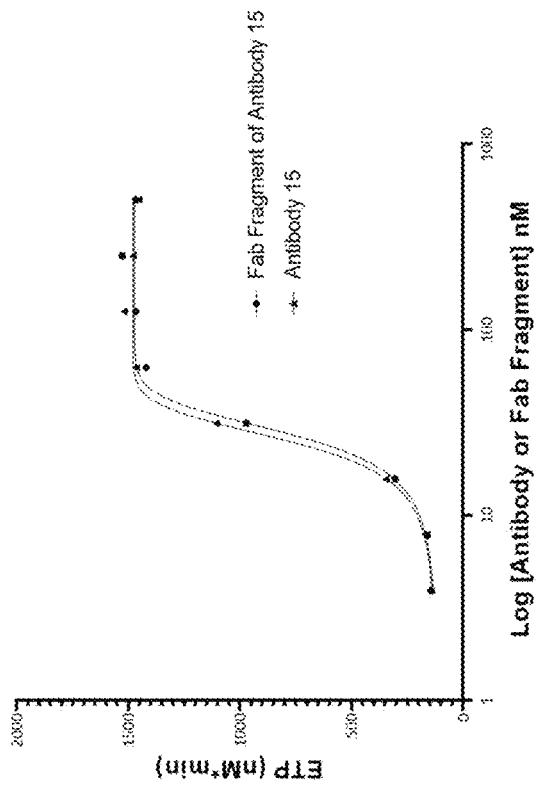
FIGS. 30A-30B depict similar dose-titration curves resulting from a full-length antibody or a Fab fragment of the same antibody in an APC cofactor assay.
Figure 30A:
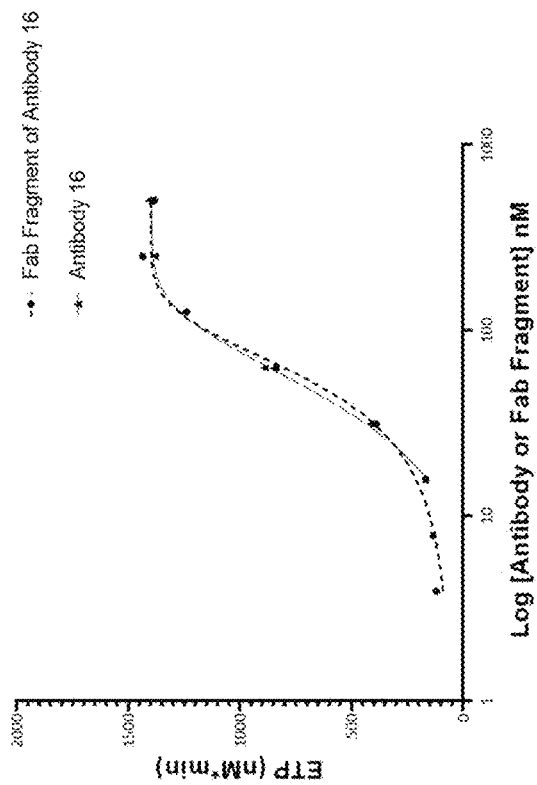

Example 13: Full-Length and Fab Fragments of Protein S Antibodies in APC Cofactor Assays FIGS. 30A-30B depict similar dose-titration curves resulting from a full-length antibody or a Fab fragment of the same antibody in an APC cofactor assay. FIG. 30A shows the results using the full-length and Fab fragment of Antibody 15, and FIG. 30B shows the results using the full-length and Fab fragment of Antibody 16. These results demonstrate that both the full-length and the Fab fragments of the antibodies tested gave similar results in the APC cofactor assay.

The invention claimed is:

1. A method of prophylactically treating a bleeding disorder in a subject in need thereof, comprising administering to the subject an antibody that binds Protein S, wherein the bleeding disorder is selected from the group consisting of hemophilia A, hemophilia B, von Willebrand disease (vWD) disease, menorrhagia, Factor I deficiency, Factor II deficiency, Factor VII deficiency, Factor XI deficiency, Factor VIII deficiency, Factor IX deficiency, trauma, and hereditary hemorrhagic telangiectasia, wherein the antibody comprises a heavy chain variable region (VH) and a light chain variable region (VL), and wherein the VH and VL comprise a combination of six complementarity determining regions (CDRs), whose amino acid sequences are selected from the group consisting of:
   a. a CDR-L1 comprising the sequence of SEQ ID NO: 1, a CDR-L2 comprising an amino acid sequence of QNS, a CDR-L3 comprising the sequence of SEQ ID NO: 24, a CDR-H1 comprising the sequence of SEQ ID NO: 36, a CDR-H2 comprising the sequence of SEQ ID NO: 48, and a CDR-H3 comprising the sequence of SEQ ID NO: 60; and
   b. a CDR-L1 comprising the sequence of SEQ ID NO: 10, a CDR-L2 comprising an amino acid sequence of DAS, a CDR-L3 comprising the sequence of SEQ ID NO: 31, a CDR-H1 comprising the sequence of SEQ ID NO: 43, a CDR-H2 comprising the sequence of SEQ ID NO: 55, and a CDR-H3 comprising the sequence of SEQ ID NO: 67.

2. The method of claim 1, wherein the subject has inhibitors against factor replacement therapy.

3. The method of claim 1, wherein the bleeding disorder is vWD, and wherein the subject is undergoing an additional prophylactic treatment.

4. The method of claim 1, wherein the bleeding disorder is a vWD subtype selected from the group consisting of vWD Type 1, vWD Type 2A, vWD Type 2B, vWD Type 2N, vWD Type 2M, vWD Type 3, and acquired vWD.

5. The method of claim 1, wherein the subject is a hemophilia carrier.

6. The method of claim 1, wherein the prophylactic treatment is a routine prophylaxis.

7. The method of claim 1, wherein the administration of the antibody is a subcutaneous administration.

8. The method of claim 1, wherein the treatment is acute.

9. The method of claim 1, wherein the treatment is chronic.

10. The method of claim 1, wherein treatment is perioperative.

11. The method of claim 1, wherein treatment is intermittent.

12. The method of claim 1, wherein the antibody comprises:
   a. a VH comprising the amino acid sequence of SEQ ID NO: 76 or an amino acid sequence with at least 80% sequence identity thereto; and a VL comprising the amino acid sequence of SEQ ID NO: 75 or an amino acid sequence with at least 80% sequence identity thereto; and/or
   b. a VH comprising the amino acid sequence of SEQ ID NO: 90 or an amino acid sequence with at least 80% sequence identity thereto; and a VL comprising the amino acid sequence of SEQ ID NO: 89 or an amino acid sequence with at least 80% sequence identity thereto.

13. The method of claim 1, wherein the antibody is:
   a. a monoclonal antibody;
   b. a full-length antibody;
   c. an antibody fragment; or
   d. a humanized antibody.

14. The method of claim 1, wherein the antibody comprises an Fc domain selected from the group consisting of human IgG1, human IgG2, human IgG3, and human IgG4.

15. The method of claim 14, wherein the domain comprises an amino acid sequence of SEQ ID NO: 218, and wherein the amino acid sequence comprises at least one amino acid substitution at a position selected from the group consisting of: 215, 221, 222, 228, 234, 235, 236, 239, 240, 241, 243, 244, 245, 247, 250, 252, 254, 256, 262, 263, 264, 265, 266, 267, 268, 269, 270, 292, 296, 297, 298, 299, 300, 305, 313, 324, 325, 326, 327, 328, 329, 330, 332, 333, 334, 345, 396, 428, 430, 433, 434, and 440.

16. The method of claim 14, wherein the Fc domain of the antibody comprises one or more of the substitutions selected from the group consisting of T250Q/M428L, M252Y/S254T/T256E, M428L/N434S, S267E/L328F, N325S/L328F, and H433K/N434F, wherein the position numbers of the amino acid residues are of the EU numbering scheme.

17. The method of claim 1, wherein the antibody is capable of promoting thrombin generation, D-dimer levels, fibrin generation, or generation of a marker associated with coagulation activity.

18. The method of claim 17, wherein the thrombin generation does not exceed a predetermined threshold level.

19. The method of claim 17, wherein the thrombin generation is antibody concentration-dependent.

20. The method of claim 1, wherein the antibody exhibits graded inhibition.

21. The method of claim 1, wherein the antibody exhibits switch-like inhibition.

* * * * *

```
                          SEQUENCE LISTING

Sequence total quantity: 218
SEQ ID NO: 1            moltype = AA  length = 6
FEATURE                 Location/Qualifiers
REGION                  1..6
                        note = Protein S antibody CDR-L1 sequence
source                  1..6
                        mol_type = protein
                        organism = synthetic construct
SEQUENCE: 1
KLGDKY                                                                      6

SEQ ID NO: 2            moltype = AA  length = 6
FEATURE                 Location/Qualifiers
REGION                  1..6
                        note = Protein S antibody CDR-L1 sequence
source                  1..6
                        mol_type = protein
                        organism = synthetic construct
SEQUENCE: 2
SLRNYY                                                                      6

SEQ ID NO: 3            moltype = AA  length = 9
FEATURE                 Location/Qualifiers
REGION                  1..9
                        note = Protein S antibody CDR-L1 sequence
source                  1..9
                        mol_type = protein
                        organism = synthetic construct
SEQUENCE: 3
SSDVGGYEF                                                                   9

SEQ ID NO: 4            moltype = AA  length = 6
FEATURE                 Location/Qualifiers
REGION                  1..6
                        note = Protein S antibody CDR-L1 sequence
source                  1..6
                        mol_type = protein
                        organism = synthetic construct
SEQUENCE: 4
QSVSIY                                                                      6

SEQ ID NO: 5            moltype = AA  length = 6
FEATURE                 Location/Qualifiers
REGION                  1..6
                        note = Protein S antibody CDR-L1 sequence
source                  1..6
                        mol_type = protein
                        organism = synthetic construct
SEQUENCE: 5
QRINSN                                                                      6

SEQ ID NO: 6            moltype = AA  length = 11
FEATURE                 Location/Qualifiers
REGION                  1..11
                        note = Protein S antibody CDR-L1 sequence
source                  1..11
```

```
                        mol_type = protein
                        organism = synthetic construct
SEQUENCE: 6
QSLLHSNGYN Y                                                        11

SEQ ID NO: 7            moltype =    length =
SEQUENCE: 7
000

SEQ ID NO: 8            moltype =    length =
SEQUENCE: 8
000

SEQ ID NO: 9            moltype = AA   length = 9
FEATURE                 Location/Qualifiers
REGION                  1..9
                        note = Protein S antibody CDR-L1 sequence
source                  1..9
                        mol_type = protein
                        organism = synthetic construct
SEQUENCE: 9
TGAVTASNY                                                            9

SEQ ID NO: 10           moltype = AA   length = 6
FEATURE                 Location/Qualifiers
REGION                  1..6
                        note = Protein S antibody CDR-L1 sequence
source                  1..6
                        mol_type = protein
                        organism = synthetic construct
SEQUENCE: 10
QSVTSN                                                               6

SEQ ID NO: 11           moltype = AA   length = 11
FEATURE                 Location/Qualifiers
REGION                  1..11
                        note = Protein S antibody CDR-L1 sequence
source                  1..11
                        mol_type = protein
                        organism = synthetic construct
SEQUENCE: 11
QSLVHSDGNT Y                                                        11

SEQ ID NO: 12           moltype =    length =
SEQUENCE: 12
000

SEQ ID NO: 13           moltype =    length =
SEQUENCE: 13
000

SEQ ID NO: 14           moltype =    length =
SEQUENCE: 14
000

SEQ ID NO: 15           moltype =    length =
SEQUENCE: 15
000

SEQ ID NO: 16           moltype =    length =
SEQUENCE: 16
000

SEQ ID NO: 17           moltype =    length =
SEQUENCE: 17
000

SEQ ID NO: 18           moltype =    length =
SEQUENCE: 18
000

SEQ ID NO: 19           moltype =    length =
SEQUENCE: 19
000

SEQ ID NO: 20           moltype =    length =
SEQUENCE: 20
000
```

```
SEQ ID NO: 21           moltype = AA  length = 9
FEATURE                 Location/Qualifiers
REGION                  1..9
                        note = Protein S antibody CDR-L3 sequence
source                  1..9
                        mol_type = protein
                        organism = synthetic construct
SEQUENCE: 21
QAWDSNTVV                                                                       9

SEQ ID NO: 22           moltype = AA  length = 11
FEATURE                 Location/Qualifiers
REGION                  1..11
                        note = Protein S antibody CDR-L3 sequence
source                  1..11
                        mol_type = protein
                        organism = synthetic construct
SEQUENCE: 22
NSRDSSGNHV V                                                                   11

SEQ ID NO: 23           moltype = AA  length = 10
FEATURE                 Location/Qualifiers
REGION                  1..10
                        note = Protein S antibody CDR-L3 sequence
source                  1..10
                        mol_type = protein
                        organism = synthetic construct
SEQUENCE: 23
SSYTRSSTVV                                                                     10

SEQ ID NO: 24           moltype = AA  length = 9
FEATURE                 Location/Qualifiers
REGION                  1..9
                        note = Protein S antibody CDR-L3 sequence
source                  1..9
                        mol_type = protein
                        organism = synthetic construct
SEQUENCE: 24
QAWDSSTWV                                                                       9

SEQ ID NO: 25           moltype = AA  length = 9
FEATURE                 Location/Qualifiers
REGION                  1..9
                        note = Protein S antibody CDR-L3 sequence
source                  1..9
                        mol_type = protein
                        organism = synthetic construct
SEQUENCE: 25
QQRSNWPLT                                                                       9

SEQ ID NO: 26           moltype = AA  length = 9
FEATURE                 Location/Qualifiers
REGION                  1..9
                        note = Protein S antibody CDR-L3 sequence
source                  1..9
                        mol_type = protein
                        organism = synthetic construct
SEQUENCE: 26
QQYDNWPLT                                                                       9

SEQ ID NO: 27           moltype = AA  length = 8
FEATURE                 Location/Qualifiers
REGION                  1..8
                        note = Protein S antibody CDR-L3 sequence
source                  1..8
                        mol_type = protein
                        organism = synthetic construct
SEQUENCE: 27
MQALQTFT                                                                        8

SEQ ID NO: 28           moltype =   length =
SEQUENCE: 28
000

SEQ ID NO: 29           moltype =   length =
SEQUENCE: 29
000

SEQ ID NO: 30           moltype = AA  length = 9
```

```
FEATURE               Location/Qualifiers
REGION                1..9
                      note = Protein S antibody CDR-L3 sequence
source                1..9
                      mol_type = protein
                      organism = synthetic construct
SEQUENCE: 30
ALWYSDHFV                                                                    9

SEQ ID NO: 31         moltype = AA   length = 8
FEATURE               Location/Qualifiers
REGION                1..8
                      note = Protein S antibody CDR-L3 sequence
source                1..8
                      mol_type = protein
                      organism = synthetic construct
SEQUENCE: 31
QQYNNWPT                                                                     8

SEQ ID NO: 32         moltype = AA   length = 10
FEATURE               Location/Qualifiers
REGION                1..10
                      note = Protein S antibody CDR-L3 sequence
source                1..10
                      mol_type = protein
                      organism = synthetic construct
SEQUENCE: 32
MQATQFPHLT                                                                  10

SEQ ID NO: 33         moltype = AA   length = 10
FEATURE               Location/Qualifiers
REGION                1..10
                      note = Protein S antibody CDR-H1 sequence
source                1..10
                      mol_type = protein
                      organism = synthetic construct
SEQUENCE: 33
GGSISSSSYY                                                                  10

SEQ ID NO: 34         moltype = AA   length = 8
FEATURE               Location/Qualifiers
REGION                1..8
                      note = Protein S antibody CDR-H1 sequence
source                1..8
                      mol_type = protein
                      organism = synthetic construct
SEQUENCE: 34
GGTFSSYS                                                                     8

SEQ ID NO: 35         moltype = AA   length = 10
FEATURE               Location/Qualifiers
REGION                1..10
                      note = Protein S antibody CDR-H1 sequence
source                1..10
                      mol_type = protein
                      organism = synthetic construct
SEQUENCE: 35
GGSITSDGYH                                                                  10

SEQ ID NO: 36         moltype = AA   length = 8
FEATURE               Location/Qualifiers
REGION                1..8
                      note = Protein S antibody CDR-H1 sequence
source                1..8
                      mol_type = protein
                      organism = synthetic construct
SEQUENCE: 36
GFTFDDYA                                                                     8

SEQ ID NO: 37         moltype = AA   length = 8
FEATURE               Location/Qualifiers
REGION                1..8
                      note = Protein S antibody CDR-H1 sequence
source                1..8
                      mol_type = protein
                      organism = synthetic construct
SEQUENCE: 37
GFTFSTYG                                                                     8
```

-continued

```
SEQ ID NO: 38          moltype = AA  length = 9
FEATURE                Location/Qualifiers
REGION                 1..9
                       note = Protein S antibody CDR-H1 sequence
source                 1..9
                       mol_type = protein
                       organism = synthetic construct
SEQUENCE: 38
GYSISSGYY                                                              9

SEQ ID NO: 39          moltype = AA  length = 8
FEATURE                Location/Qualifiers
REGION                 1..8
                       note = Protein S antibody CDR-H1 sequence
source                 1..8
                       mol_type = protein
                       organism = synthetic construct
SEQUENCE: 39
GDTFSNHA                                                               8

SEQ ID NO: 40          moltype =     length =
SEQUENCE: 40
000

SEQ ID NO: 41          moltype =     length =
SEQUENCE: 41
000

SEQ ID NO: 42          moltype = AA  length = 8
FEATURE                Location/Qualifiers
REGION                 1..8
                       note = Protein S antibody CDR-H1 sequence
source                 1..8
                       mol_type = protein
                       organism = synthetic construct
SEQUENCE: 42
GHTFTGYY                                                               8

SEQ ID NO: 43          moltype = AA  length = 9
FEATURE                Location/Qualifiers
REGION                 1..9
                       note = Protein S antibody CDR-H1 sequence
source                 1..9
                       mol_type = protein
                       organism = synthetic construct
SEQUENCE: 43
GGSISSTNW                                                              9

SEQ ID NO: 44          moltype = AA  length = 8
FEATURE                Location/Qualifiers
REGION                 1..8
                       note = Protein S antibody CDR-H1 sequence
source                 1..8
                       mol_type = protein
                       organism = synthetic construct
SEQUENCE: 44
GGSISNYY                                                               8

SEQ ID NO: 45          moltype = AA  length = 7
FEATURE                Location/Qualifiers
REGION                 1..7
                       note = Protein S antibody CDR-H2 sequence
source                 1..7
                       mol_type = protein
                       organism = synthetic construct
SEQUENCE: 45
IYYSGNT                                                                7

SEQ ID NO: 46          moltype = AA  length = 8
FEATURE                Location/Qualifiers
REGION                 1..8
                       note = Protein S antibody CDR-H2 sequence
source                 1..8
                       mol_type = protein
                       organism = synthetic construct
SEQUENCE: 46
IIPIFGTT                                                               8

SEQ ID NO: 47          moltype = AA  length = 7
```

```
FEATURE                 Location/Qualifiers
REGION                  1..7
                        note = Protein S antibody CDR-H2 sequence
source                  1..7
                        mol_type = protein
                        organism = synthetic construct
SEQUENCE: 47
IYYTGNT                                                                          7

SEQ ID NO: 48           moltype = AA  length = 8
FEATURE                 Location/Qualifiers
REGION                  1..8
                        note = Protein S antibody CDR-H2 sequence
source                  1..8
                        mol_type = protein
                        organism = synthetic construct
SEQUENCE: 48
ITWNSGNI                                                                         8

SEQ ID NO: 49           moltype = AA  length = 8
FEATURE                 Location/Qualifiers
REGION                  1..8
                        note = Protein S antibody CDR-H2 sequence
source                  1..8
                        mol_type = protein
                        organism = synthetic construct
SEQUENCE: 49
IYYDGINK                                                                         8

SEQ ID NO: 50           moltype = AA  length = 7
FEATURE                 Location/Qualifiers
REGION                  1..7
                        note = Protein S antibody CDR-H2 sequence
source                  1..7
                        mol_type = protein
                        organism = synthetic construct
SEQUENCE: 50
IYYSGST                                                                          7

SEQ ID NO: 51           moltype = AA  length = 8
FEATURE                 Location/Qualifiers
REGION                  1..8
                        note = Protein S antibody CDR-H2 sequence
source                  1..8
                        mol_type = protein
                        organism = synthetic construct
SEQUENCE: 51
YIPIFGTT                                                                         8

SEQ ID NO: 52           moltype =     length =
SEQUENCE: 52
000

SEQ ID NO: 53           moltype =     length =
SEQUENCE: 53
000

SEQ ID NO: 54           moltype = AA  length = 8
FEATURE                 Location/Qualifiers
REGION                  1..8
                        note = Protein S antibody CDR-H2 sequence
source                  1..8
                        mol_type = protein
                        organism = synthetic construct
SEQUENCE: 54
INPNSGDT                                                                         8

SEQ ID NO: 55           moltype = AA  length = 7
FEATURE                 Location/Qualifiers
REGION                  1..7
                        note = Protein S antibody CDR-H2 sequence
source                  1..7
                        mol_type = protein
                        organism = synthetic construct
SEQUENCE: 55
IYQTGST                                                                          7

SEQ ID NO: 56           moltype = AA  length = 7
FEATURE                 Location/Qualifiers
```

```
REGION                   1..7
                         note = Protein S antibody CDR-H2 sequence
source                   1..7
                         mol_type = protein
                         organism = synthetic construct
SEQUENCE: 56
IYYIGIT                                                                   7

SEQ ID NO: 57            moltype = AA  length = 17
FEATURE                  Location/Qualifiers
REGION                   1..17
                         note = Protein S antibody CDR-H3 sequence
source                   1..17
                         mol_type = protein
                         organism = synthetic construct
SEQUENCE: 57
ARCSGYGYSS GRSYFDY                                                       17

SEQ ID NO: 58            moltype = AA  length = 11
FEATURE                  Location/Qualifiers
REGION                   1..11
                         note = Protein S antibody CDR-H3 sequence
source                   1..11
                         mol_type = protein
                         organism = synthetic construct
SEQUENCE: 58
EGGRVGADFD Y                                                             11

SEQ ID NO: 59            moltype = AA  length = 12
FEATURE                  Location/Qualifiers
REGION                   1..12
                         note = Protein S antibody CDR-H3 sequence
source                   1..12
                         mol_type = protein
                         organism = synthetic construct
SEQUENCE: 59
ARRLSTGPYF DY                                                            12

SEQ ID NO: 60            moltype = AA  length = 12
FEATURE                  Location/Qualifiers
REGION                   1..12
                         note = Protein S antibody CDR-H3 sequence
source                   1..12
                         mol_type = protein
                         organism = synthetic construct
SEQUENCE: 60
AKGRAVSDTF DI                                                            12

SEQ ID NO: 61            moltype = AA  length = 7
FEATURE                  Location/Qualifiers
REGION                   1..7
                         note = Protein S antibody CDR-H3 sequence
source                   1..7
                         mol_type = protein
                         organism = synthetic construct
SEQUENCE: 61
AESDLDY                                                                   7

SEQ ID NO: 62            moltype = AA  length = 18
FEATURE                  Location/Qualifiers
REGION                   1..18
                         note = Protein S antibody CDR-H3 sequence
source                   1..18
                         mol_type = protein
                         organism = synthetic construct
SEQUENCE: 62
ATTYSDIVTG YYNDAFDI                                                      18

SEQ ID NO: 63            moltype = AA  length = 20
FEATURE                  Location/Qualifiers
REGION                   1..20
                         note = Protein S antibody CDR-H3 sequence
source                   1..20
                         mol_type = protein
                         organism = synthetic construct
SEQUENCE: 63
ARGGLAGSHY KNYYYDGMDV                                                    20

SEQ ID NO: 64            moltype =    length =
```

```
SEQUENCE: 64
000

SEQ ID NO: 65             moltype =    length =
SEQUENCE: 65
000

SEQ ID NO: 66             moltype = AA   length = 14
FEATURE                   Location/Qualifiers
REGION                    1..14
                          note = Protein S antibody CDR-H3 sequence
source                    1..14
                          mol_type = protein
                          organism = synthetic construct
SEQUENCE: 66
ARDSQILWFG ELGY                                                          14

SEQ ID NO: 67             moltype = AA   length = 9
FEATURE                   Location/Qualifiers
REGION                    1..9
                          note = Protein S antibody CDR-H3 sequence
source                    1..9
                          mol_type = protein
                          organism = synthetic construct
SEQUENCE: 67
ARRFGELDY                                                                 9

SEQ ID NO: 68             moltype = AA   length = 11
FEATURE                   Location/Qualifiers
REGION                    1..11
                          note = Protein S antibody CDR-H3 sequence
source                    1..11
                          mol_type = protein
                          organism = synthetic construct
SEQUENCE: 68
AALSGDHAFD I                                                             11

SEQ ID NO: 69             moltype = AA   length = 106
FEATURE                   Location/Qualifiers
REGION                    1..106
                          note = Protein S monoclonal antibody variable light chain
                          sequence
source                    1..106
                          mol_type = protein
                          organism = synthetic construct
SEQUENCE: 69
SYELTQPPSV SVSPGQTASI TCSGDKLGDK YACWYQQKPG QSPVLVIYQD TKRPSGIPER         60
FSGSNSGNTA TLTISGTQAM DEADYYCQAW DSNTVVFGGG TKLTVL                       106

SEQ ID NO: 70             moltype = AA   length = 125
FEATURE                   Location/Qualifiers
REGION                    1..125
                          note = Protein S monoclonal antibody variable heavy chain
                          sequence
source                    1..125
                          mol_type = protein
                          organism = synthetic construct
SEQUENCE: 70
QLQLQESGPG LVKPSETLSL TCTVSGGSIS SSSYYWGWIR QPPGKGLEWI GNIYYSGNTY         60
YNPSLKSRVT ISVDTSKNQF SLKLSSMTAA DTAVYYCARC SGYGYSSGRS YFDYWGQETL        120
VTVSS                                                                   125

SEQ ID NO: 71             moltype = AA   length = 108
FEATURE                   Location/Qualifiers
REGION                    1..108
                          note = Protein S monoclonal antibody variable light chain
                          sequence
source                    1..108
                          mol_type = protein
                          organism = synthetic construct
SEQUENCE: 71
SSDLTQGPAV SVALGQTVRI TCQGDSLRNY YASWYQQKPG QAPVPVIYGK NDRPSGIPDR         60
FSGSISGNTA SLTITGAQAE DEAHYYCNSR DSSGNHVVFG GGTKLTVL                     108

SEQ ID NO: 72             moltype = AA   length = 118
FEATURE                   Location/Qualifiers
REGION                    1..118
                          note = Protein S monoclonal antibody variable heavy chain
                          sequence
```

```
source                  1..118
                        mol_type = protein
                        organism = synthetic construct
SEQUENCE: 72
QVQLVQSGAE VKKPGSSVKV SCKVSGGTFS SYSISWVRQA PGQGLEWMGG IIPIFGTTNY   60
AQKFQGRVTI TADESTSTAY MDLSSLKSED TAMYYCEGGR VGADFDYWGQ GTLVTVSS    118

SEQ ID NO: 73           moltype = AA  length = 110
FEATURE                 Location/Qualifiers
REGION                  1..110
                        note = Protein S monoclonal antibody variable light chain
                          sequence
source                  1..110
                        mol_type = protein
                        organism = synthetic construct
SEQUENCE: 73
QSALTQPASV SGSPGQSITI SCTGTSSDVG GYEFVSWYQH HPGKAPKLMI YDVSSRPSGV   60
SNRFSGSKSG NTASLTISGL QAEDEADYYC SSYTRSSTVV FGGGARLTVL            110

SEQ ID NO: 74           moltype = AA  length = 120
FEATURE                 Location/Qualifiers
REGION                  1..120
                        note = Protein S monoclonal antibody variable heavy chain
                          sequence
source                  1..120
                        mol_type = protein
                        organism = synthetic construct
SEQUENCE: 74
QVQLQESGPG LVKPSQTLSL TCTVSGGSIT SDGYHWSWIR QYPGKGLDWI GYIYYTGNTY   60
YNPSLKSRVT ISVGTSQNQF SLKLISVTAA DTAVYYCARR LSTGPYFDYW GQGTLVTVSS  120

SEQ ID NO: 75           moltype = AA  length = 106
FEATURE                 Location/Qualifiers
REGION                  1..106
                        note = Protein S monoclonal antibody variable light chain
                          sequence
source                  1..106
                        mol_type = protein
                        organism = synthetic construct
SEQUENCE: 75
SYELNQPPSV SVSPGQTASI TCSGDKLGDK YASWYQQKPG QSPVVAIYQN SKRPSGIPER   60
FSASNSGNTA TLTISGTQAL DEADYYCQAW DSSTWVFGGG TKLTVL                106

SEQ ID NO: 76           moltype = AA  length = 119
FEATURE                 Location/Qualifiers
REGION                  1..119
                        note = Protein S monoclonal antibody variable heavy chain
                          sequence
source                  1..119
                        mol_type = protein
                        organism = synthetic construct
SEQUENCE: 76
EVQLVESGGG LVQPGRSLRL SCAASGFTFD DYAMHWVRQA PGKGLEWVSG ITWNSGNIGY   60
ADSVKGRFTI SRDNAKNSLY LHMNSLRIED TAFYYCAKGR AVSDTFDIWG QGTMVTVSS   119

SEQ ID NO: 77           moltype = AA  length = 107
FEATURE                 Location/Qualifiers
REGION                  1..107
                        note = Protein S monoclonal antibody variable light chain
                          sequence
source                  1..107
                        mol_type = protein
                        organism = synthetic construct
SEQUENCE: 77
EIVLTQSPAT LSLSPGERAT LSCRASQSVS IYLAWYQQKP GQAPRLLIYD ASNRATGIPA   60
RFSGSGSGTD FTLTISSLEP EDFAVYYCQQ RSNWPLTFGP GTKVDIK               107

SEQ ID NO: 78           moltype = AA  length = 114
FEATURE                 Location/Qualifiers
REGION                  1..114
                        note = Protein S monoclonal antibody variable heavy chain
                          sequence
source                  1..114
                        mol_type = protein
                        organism = synthetic construct
SEQUENCE: 78
QVQLVESGGG VVQPGRSLRL SCAASGFTFS TYGFHWVRQP PGKGLEWVAV IYYDGINKYY   60
ADSVKGRFTI SRDNSKNTLF LQMNSLRAED TAVYYCAESD LDYWGQGTLV TVSS        114
```

```
SEQ ID NO: 79              moltype = AA  length = 107
FEATURE                    Location/Qualifiers
REGION                     1..107
                           note = Protein S monoclonal antibody variable light chain
                             sequence
source                     1..107
                           mol_type = protein
                           organism = synthetic construct
SEQUENCE: 79
EIVMTQSPAT LSVSPGERAT LSCRASQRIN SNLAWYQQKP GQAPRLLIYG ASTRATGIPA    60
RFSGSGSGTE FTLTISSLQS EDFAAYYCQQ YDNWPLTFGG GTKVEIK                 107

SEQ ID NO: 80              moltype = AA  length = 125
FEATURE                    Location/Qualifiers
REGION                     1..125
                           note = Protein S monoclonal antibody variable heavy chain
                             sequence
source                     1..125
                           mol_type = protein
                           organism = synthetic construct
SEQUENCE: 80
QVQLQESGPG LVKPSETLSL TCAVSGYSIS SGYYWGWIRQ PPGKGLDWIG SIYYSGSTYY    60
NPSLKSRVTI SVDTSKNQIS LKLSSVTAAD TAVYYCATTY SDIVTGYYND AFDIWGQGTM   120
VTVSS                                                              125

SEQ ID NO: 81              moltype = AA  length = 111
FEATURE                    Location/Qualifiers
REGION                     1..111
                           note = Protein S monoclonal antibody variable light chain
                             sequence
source                     1..111
                           mol_type = protein
                           organism = synthetic construct
SEQUENCE: 81
DIVMTQSPLS LPVTPGEPAS ISCRSSQSLL HSNGYNYLDW YLQKPGQSPQ LLIYLGSNRA    60
SGVPDRFSGS GSGTDFTLKI SRVEAEDVGV YYCMQALQTF TFGPGTKVDI K            111

SEQ ID NO: 82              moltype = AA  length = 127
FEATURE                    Location/Qualifiers
REGION                     1..127
                           note = Protein S monoclonal antibody variable heavy chain
                             sequence
source                     1..127
                           mol_type = protein
                           organism = synthetic construct
SEQUENCE: 82
QVQLVQSGAE VKKPGSSVKV SCKASGDTFS NHAINWVRQA PGQGLEWMGG YIPIFGTTNS    60
AQKFRGRVTI TADKSTNTAY MALSSLRSED TAVYYCARGG LAGSHYKNYY YDGMDVWGQG   120
TTVTVSS                                                            127

SEQ ID NO: 83              moltype =     length =
SEQUENCE: 83
000

SEQ ID NO: 84              moltype =     length =
SEQUENCE: 84
000

SEQ ID NO: 85              moltype =     length =
SEQUENCE: 85
000

SEQ ID NO: 86              moltype =     length =
SEQUENCE: 86
000

SEQ ID NO: 87              moltype = AA  length = 109
FEATURE                    Location/Qualifiers
REGION                     1..109
                           note = Protein S monoclonal antibody variable light chain
                             sequence
source                     1..109
                           mol_type = protein
                           organism = synthetic construct
SEQUENCE: 87
QAVVTQESAL TTSPGETVTL TCRSSTGAVT ASNYANWVQE KPDHLFTGLI GSTNNRAPGV    60
PARFSGSLIG DKAALTITGA QTEDEAIYFC ALWYSDHFVF GGGTKLTVL               109

SEQ ID NO: 88              moltype = AA  length = 121
```

```
FEATURE              Location/Qualifiers
REGION               1..121
                     note = Protein S monoclonal antibody variable heavy chain
                         sequence
source               1..121
                     mol_type = protein
                     organism = synthetic construct
SEQUENCE: 88
QVQLVQSGAE VKKPGASVKV SCKSSGHTFT GYYMHWVRQA PGQGLEWMGW INPNSGDTNY    60
AQKFQGRVTM TRDTSISTAY MEMSRLRSDD TAVYYCARDS QILWFGELGY WGQGTLVTVS   120
S                                                                  121

SEQ ID NO: 89        moltype = AA  length = 106
FEATURE              Location/Qualifiers
REGION               1..106
                     note = Protein S monoclonal antibody variable light chain
                         sequence
source               1..106
                     mol_type = protein
                     organism = synthetic construct
SEQUENCE: 89
EIVMTQSPAT LSVSPGERAT LSCRASQSVT SNLAWYQQKP GQAPRLLIYD ASTRATGIPA    60
RFSGSGSGTE FTLTISSLQS EDFAIYYCQQ YNNWPTFGQG TRLEIK                  106

SEQ ID NO: 90        moltype = AA  length = 116
FEATURE              Location/Qualifiers
REGION               1..116
                     note = Protein S monoclonal antibody variable heavy chain
                         sequence
source               1..116
                     mol_type = protein
                     organism = synthetic construct
SEQUENCE: 90
QVQLQESGPG LVKPSETLSL TCGVSGGSIS STNWWSWVRQ PPGKGLEWIG EIYQTGSTDY    60
DPSLKSRVTI SIDKSKNQFS LKLYSVTAAD TAVYYCARRF GELDYWGQGT LVTVSS       116

SEQ ID NO: 91        moltype = AA  length = 113
FEATURE              Location/Qualifiers
REGION               1..113
                     note = Protein S monoclonal antibody variable light chain
                         sequence
source               1..113
                     mol_type = protein
                     organism = synthetic construct
SEQUENCE: 91
DIVMTQTPLS SPVTLGQPAS ISCRSSQSLV HSDGNTYLSW LQQRPGQPPR LLIYKISNRF    60
SGVPDRFSGS GAGTDFTLKI SRVEAEDVGV YYCMQATQFP HLTFGGGTKV EIK          113

SEQ ID NO: 92        moltype = AA  length = 117
FEATURE              Location/Qualifiers
REGION               1..117
                     note = Protein S monoclonal antibody variable heavy chain
                         sequence
source               1..117
                     mol_type = protein
                     organism = synthetic construct
SEQUENCE: 92
QVQLQESGPG LVKPSETLSL TCTVSGGSIS NYYWNWIRQP PGKGLEWIGY IYYIGITDYN    60
PSLKSRVTIS VDTSKNQFSL KVTSVTAADT AVYYCAALSG DHAFDIWGQG TLVTVSS      117

SEQ ID NO: 93        moltype = DNA  length = 318
FEATURE              Location/Qualifiers
misc_feature         1..318
                     note = Protein S monoclonal antibody variable light chain
                         sequence
source               1..318
                     mol_type = other DNA
                     organism = synthetic construct
SEQUENCE: 93
tcctatgagc tgactcagcc accctcagtg tccgtgtccc caggacagac agccagcatc    60
acctgctctg gagataaatt gggggataaa tatgcttgct ggtatcagca gaagccaggc   120
cagtcccctg tactggtcat ctatcaagat actaagcggc cctcaggat ccctgagcga    180
ttctctggct ccaactctgg gaacacagcc actctgacca tcagcgggac ccaggctatg   240
gatgaggctg actattactg tcaggcgtgg gacagcaaca ctgtggtctt cggcggaggg   300
accaagctga ccgtccta                                                 318

SEQ ID NO: 94        moltype = DNA  length = 375
FEATURE              Location/Qualifiers
misc_feature         1..375
```

```
                                note = Protein S monoclonal antibody variable heavy chain
                                    sequence
source                          1..375
                                mol_type = other DNA
                                organism = synthetic construct
SEQUENCE: 94
cagctgcagc tgcaggagtc gggcccagga ctggtgaagc cttcggagac cctgtccctc   60
acctgcactg tctctggtgg ctccatcagc agtagtagtt actactgggg ctggatccgc  120
cagcccccgg ggaagggact ggagtggatt gggaatatct attatagtgg gaacacctac  180
tacaacccgt ccctcaagag tcgagtcacc atatccgtag acacgtccaa gaaccagttc  240
tccctgaagc tgagctctat gaccgccgca gacacggctg tgtattactg tgcgagatgt  300
agtggctacg ggtatagcag tggccggtcc tactttgact actggggcca ggaaaccctg  360
gtcaccgtct cctca                                                   375

SEQ ID NO: 95           moltype = DNA  length = 324
FEATURE                 Location/Qualifiers
misc_feature            1..324
                                note = Protein S monoclonal antibody variable light chain
                                    sequence
source                          1..324
                                mol_type = other DNA
                                organism = synthetic construct
SEQUENCE: 95
tcctctgacc tgactcaggg ccctgctgtg tctgtggccc tgggacagac agtcaggatc   60
acatgccaag agacagcct cagaaactat tatgcaagct ggtaccagca gaagccagga  120
caggcccctg tacctgtcat ctatggtaaa aacgaccggc cctcagggat cccagaccga  180
ttctctggct ccatctcagg aaacacagct tccttgacca tcactgggc tcaggcggaa  240
gatgaggctc actattactg taactcccgg gacagcagtg gtaaccatgt ggtattcggc  300
ggagggacca agctgaccgt cctg                                         324

SEQ ID NO: 96           moltype = DNA  length = 354
FEATURE                 Location/Qualifiers
misc_feature            1..354
                                note = Protein S monoclonal antibody variable heavy chain
                                    sequence
source                          1..354
                                mol_type = other DNA
                                organism = synthetic construct
SEQUENCE: 96
caggtgcagc tggtgcagtc tggggctgag gtgaagaagc ctgggtcctc ggtgaaggtc   60
tcctgcaagg tttctggagg caccttcagc agctattcta tcagctgggt gcgacaggcc  120
cctggacaag ggcttgagtg gatgggaggg atcatcccta tatttggtac aacaaactac  180
gcacagaagt tccagggcag agtcacgatc accgcggacg aatccacgag cacagccta  240
catggatctga gcagcctgaa atctgaggac acggccatgt attactgtga ggggggtaga  300
gtgggagcgg actttgacta ctgggggccag ggaaccctgg tcaccgtctc ctca       354

SEQ ID NO: 97           moltype = DNA  length = 330
FEATURE                 Location/Qualifiers
misc_feature            1..330
                                note = Protein S monoclonal antibody variable light chain
                                    sequence
source                          1..330
                                mol_type = other DNA
                                organism = synthetic construct
SEQUENCE: 97
cagtctgccc tgactcagcc tgcctccgtg tctgggtctc ctggacagtc gatcaccatc   60
tcctgcactg gaaccagcag tgacgttggt ggttatgaat ttgtctcctg gtaccaacat  120
cacccaggca aagcccccaa actcatgatt tatgatgtca gtagtcggcc ctcagggt   180
tctaatcgct tctctggctc caagtctggc aacacggcct ccctgaccat ctctgggctc  240
caggctgagg acgaggctga ttattactgc agctcatata cgcgcagcag cactgtggtg  300
ttcggcgcg gggccaggct gaccgtccta                                    330

SEQ ID NO: 98           moltype = DNA  length = 360
FEATURE                 Location/Qualifiers
misc_feature            1..360
                                note = Protein S monoclonal antibody variable heavy chain
                                    sequence
source                          1..360
                                mol_type = other DNA
                                organism = synthetic construct
SEQUENCE: 98
caggtgcagc tgcaggagtc gggcccagga ctggtgaagc cttcacagac cctgtccctc   60
acctgcactg tctctggtgg ctccatcacc agtgatggtt accactggag ctggatccgc  120
cagtacccag ggaagggcct ggactggatt ggatacatct attacactgg gaacacctac  180
tacaacccgt ccctcaagag tcgagtgacc atatcagtag gcacgtctca gaaccagttc  240
tccctgaagc tgatctctgt gactgccgcg gacacggccg tttattactg tgcgagaagg  300
ctgtcgactg ggcctacttt tgactactgg ggccagggaa ccctggtcac cgtctcctcc  360

SEQ ID NO: 99           moltype = DNA  length = 318
```

```
FEATURE              Location/Qualifiers
misc_feature         1..318
                     note = Protein S monoclonal antibody variable light chain
                        sequence
source               1..318
                     mol_type = other DNA
                     organism = synthetic construct
SEQUENCE: 99
tcctatgagc tgaatcagcc accctcagtg tccgtgtccc caggacagac agccagcatc    60
acctgctctg gagataaatt gggggataaa tatgcttcct ggtatcagca gaagccaggc   120
cagtcccctg tggtggccat ctatcaaaat agcaagcggc cctcaggat ccctgagcga   180
ttctctgcct ccaactctgg gaacacagcc actctgacca tcagcgggac ccaggctttg   240
gatgaggctg actattactg tcaggcgtgg gacagcagca cttgggtgtt cggcggaggg   300
accaagctga ccgtccta                                                 318

SEQ ID NO: 100       moltype = DNA   length = 357
FEATURE              Location/Qualifiers
misc_feature         1..357
                     note = Protein S monoclonal antibody variable heavy chain
                        sequence
source               1..357
                     mol_type = other DNA
                     organism = synthetic construct
SEQUENCE: 100
gaagtgcagc tggtggagtc tgggggaggc ttggtacagc ctggcaggtc cctgagactc    60
tcctgtgcag cctctggatt cacctttgat gattatgcca tgcactgggt ccggcaagct   120
ccagggaagg gcctgaatg gtctcaggt attacttgga atagtggtaa cataggctat   180
gcggactctg tgaagggccg attcaccatc tccagagaca cgccaagaa ctccctgtat   240
ctgcacatga acagtctgag aattgaggac acggccttct attactgtgc aaaaggccga   300
gcagtgtctg atacttttga tatctggggc caagggacaa tggtcaccgt ctcttca     357

SEQ ID NO: 101       moltype = DNA   length = 321
FEATURE              Location/Qualifiers
misc_feature         1..321
                     note = Protein S monoclonal antibody variable light chain
                        sequence
source               1..321
                     mol_type = other DNA
                     organism = synthetic construct
SEQUENCE: 101
gaaattgtgt tgacacagtc tccagccacc ctgtctttgt ctccagggga aagagccacc    60
ctctcctgca gggccagtca gagtgttagt atctacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcagcag cgtagcaact ggccctcac tttcggccct   300
gggaccaaag tggatatcaa a                                            321

SEQ ID NO: 102       moltype = DNA   length = 342
FEATURE              Location/Qualifiers
misc_feature         1..342
                     note = Protein S monoclonal antibody variable heavy chain
                        sequence
source               1..342
                     mol_type = other DNA
                     organism = synthetic construct
SEQUENCE: 102
caggtgcagt tggtggaatc tgggggaggc gtggtccagc ctggagggtc cctgagactc    60
tcctgtgcag cgtctggatt caccttcagt acctatggct tcactgggt ccgccagcct   120
ccaggcaagg gactggagtg ggtggcagtt atatattatg atggaattaa taaatattat   180
gcagactccg tgaagggccg attcaccatc tccagagaca attccaagaa cacgctgttt   240
cttcaaatga acagcctgag agccgaggac acggctgtgt attactgtgc ggagtccgac   300
ttggactact ggggccaggg aaccctggtc accgtctcct ca                      342

SEQ ID NO: 103       moltype = DNA   length = 321
FEATURE              Location/Qualifiers
misc_feature         1..321
                     note = Protein S monoclonal antibody variable light chain
                        sequence
source               1..321
                     mol_type = other DNA
                     organism = synthetic construct
SEQUENCE: 103
gaaatagtga tgacgcagtc tccagccacc ctgtctgtgt ctccagggga aagagccacc    60
ctctcctgca gggccagtca gagtattaac agcaacttag cctggtacca gcagaaacct   120
ggccaggctc ccaggctcct catctatggt gcatccacca gggccactgg tatcccgcc    180
aggttcagtg gcagtgggtc tgggacagag ttcactctca ccatcagcag cctgcagtct   240
gaagattttg cagcttatta ctgtcagcag tatgataact ggccgctcac tttcggcgga   300
gggaccaagg tggagatcaa a                                            321
```

```
SEQ ID NO: 104          moltype = DNA  length = 375
FEATURE                 Location/Qualifiers
misc_feature            1..375
                        note = Protein S monoclonal antibody variable heavy chain
                          sequence
source                  1..375
                        mol_type = other DNA
                        organism = synthetic construct
SEQUENCE: 104
caggtgcagc tgcaggagtc gggcccagga ctggtgaagc cttcggagac cctgtccctc   60
acctgcgctg tctctggtta ttccatcagc agtggttact actggggctg gatccggcag  120
cccccaggga aggggctgga ctggattggg agtatctatt atagtgggag tacctactac  180
aacccgtccc tcaagagtcg agtcaccata tcagttgaca cgtccaagaa ccagatctcc  240
ctgaagctga gctctgtgac cgccgcagac acggccgtgt attactgtgc gaccacgtat  300
tccgatattg tgactggtta ttataatgat gcttttgata tctgggccaa agggacaatg  360
gtcaccgtgt cttca                                                   375

SEQ ID NO: 105          moltype = DNA  length = 333
FEATURE                 Location/Qualifiers
misc_feature            1..333
                        note = Protein S monoclonal antibody variable light chain
                          sequence
source                  1..333
                        mol_type = other DNA
                        organism = synthetic construct
SEQUENCE: 105
gatattgtga tgactcagtc tccactctcc ctgcccgtca cccctggaga gccggcctcc   60
atctcctgca ggtctagtca gagcctcctg catagtaatg gatacaacta tttggattgg  120
tacctgcaga agccagggca gtctccacag ctcctgatct atttgggttc taatcgggcc  180
tccggggtcc ctgacaggtt cagtggcagt ggatcaggca cagattttac actgaaaatc  240
agcagagtgg aggctgagga tgttggggtt tattattgta tgcaagctct acaaactttc  300
actttcggcc ctgggaccaa agtggatatc aaa                               333

SEQ ID NO: 106          moltype = DNA  length = 381
FEATURE                 Location/Qualifiers
misc_feature            1..381
                        note = Protein S monoclonal antibody variable heavy chain
                          sequence
source                  1..381
                        mol_type = other DNA
                        organism = synthetic construct
SEQUENCE: 106
caggtgcagc tggtgcagtc tggggctgag gtgaagaagc ctgggtcctc ggtgaaggtc   60
tcctgtaagg cttctggaga cacctttcag aaccatgcta tcaactgggt gcgacaggcc  120
cctgacaaag gcttgagtg gatgggaggg tacatcccta tctttggtac aacaaactcc  180
gcacagaagt tccggggcag agtcacgatt accgcggaca atccacgaa cacagcctac  240
atggcgctga gcagcctgag atctgaggac acggccgttt attactgtgc gagagggggg  300
ctcgcgggga gtcattataa gaactactac tatgacggta tggacgtctg ggcccagggg  360
accacggtca ccgtctcctc a                                            381

SEQ ID NO: 107          moltype =     length =
SEQUENCE: 107
000

SEQ ID NO: 108          moltype =     length =
SEQUENCE: 108
000

SEQ ID NO: 109          moltype =     length =
SEQUENCE: 109
000

SEQ ID NO: 110          moltype =     length =
SEQUENCE: 110
000

SEQ ID NO: 111          moltype = DNA  length = 327
FEATURE                 Location/Qualifiers
misc_feature            1..327
                        note = Protein S monoclonal antibody variable light chain
                          sequence
source                  1..327
                        mol_type = other DNA
                        organism = synthetic construct
SEQUENCE: 111
caggctgttg tgactcagga atctgcactc accacatcac ctggtgaaac agtcacactc   60
acttgtcgct caagtactgg ggctgttaca gctagtaact atgccaactg ggtccaagaa  120
aaaccagatc atttgttcac tggtctaata ggtagtacca taaccgagc tccaggtgtt  180
cctgccagat tctcaggctc ctgattgga gacaaggctc cctcaccat cacagggca  240
```

```
cagactgagg atgaggcaat atatttctgt gctctatggt acagcgacca tttcgtgttc    300
ggtggaggaa ccaaactgac tgtccta                                        327

SEQ ID NO: 112           moltype = DNA   length = 363
FEATURE                  Location/Qualifiers
misc_feature             1..363
                         note = Protein S monoclonal antibody variable heavy chain
                             sequence
source                   1..363
                         mol_type = other DNA
                         organism = synthetic construct
SEQUENCE: 112
caggtgcaac tggtgcagtc tggggctgag gtgaagaagc ctggggcctc agtgaaggtc    60
tcctgcaagt cttctggcca caccttcacc ggctactata tgcactgggt gcgacaggcc    120
cctggacaaa ggcttgagtg gatgggatgg atcaaccctt acagtggtga cacaaaactac  180
gcacagaagt tcagggcag ggtcaccatg accagggaca cgtccatcag cacagcctac     240
atggagatga gcaggctgag atctgacgac acggccgtgt attactgtgc gagagactcc    300
caaatactat ggttcgggga gttaggctac tggggccagg gaaccctggt caccgtctcc    360
tcc                                                                  363

SEQ ID NO: 113           moltype = DNA   length = 318
FEATURE                  Location/Qualifiers
misc_feature             1..318
                         note = Protein S monoclonal antibody variable light chain
                             sequence
source                   1..318
                         mol_type = other DNA
                         organism = synthetic construct
SEQUENCE: 113
gaaatagtga tgacgcagtc tccagccacc ctgtctgtgt ctccagggga aagagccacc    60
ctctcctgca gggccagtca gagtgttacc agcaacttag cctggtacca gcagaaacct    120
ggccaggctc ccaggctcct catctatgat gcatccacca gggccactgg tatcccagcc    180
aggttcagtg gcagtgggtc tgggacagag ttcactctca ccatcagcag cctgcagtct    240
gaaagatttg caatttatta ctgtcagcag tataataact ggcccacctt cggccaaggg    300
acacgactgg agattaaa                                                  318

SEQ ID NO: 114           moltype = DNA   length = 348
FEATURE                  Location/Qualifiers
misc_feature             1..348
                         note = Protein S monoclonal antibody variable heavy chain
                             sequence
source                   1..348
                         mol_type = other DNA
                         organism = synthetic construct
SEQUENCE: 114
caggtgcagc tgcaggagtc gggcccagga ctggtgaagc cttcggagac cctgtccctc    60
acctgcactg tctctggtgg ctccatcagc agtactaact ggtggagttg ggtccgccag    120
cccccaggga aggggctgga gtggattggg gaaatctatc aaactgggag taccgactac    180
gacccgtccc tcaagagtcg agtcaccata tcaatagaca gtccaagaa ccagttctcc     240
ctgaagctga ctctgtgac cgccgcggac acggccgtgt attactgtgc gagaaggttc    300
ggggagttag actactgggg ccagggaacc ctggtcaccg tctcctca                 348

SEQ ID NO: 115           moltype = DNA   length = 339
FEATURE                  Location/Qualifiers
misc_feature             1..339
                         note = Protein S monoclonal antibody variable light chain
                             sequence
source                   1..339
                         mol_type = other DNA
                         organism = synthetic construct
SEQUENCE: 115
gatattgtga tgacccagac tccactctcc tcacctgtca cccttggaca gccggcctcc    60
atctcctgca ggtctagtca aagcctcgta cacagtgatg gaaacaccta cttgagttgg    120
cttcagcaga ggccaggcca gcctccaaga ctcctaattt ataagatttc taaccggttc    180
tctggggtcc cagacagatt cagtggcagt ggggcaggga cagatttcac actgaaaatc    240
agcagggtgg aagctgagga tgtcggggtt tattactgca tgcaagctac acaatttccc    300
catctcactt tcggcggagg gaccaaggtg gagatcaaa                           339

SEQ ID NO: 116           moltype = DNA   length = 351
FEATURE                  Location/Qualifiers
misc_feature             1..351
                         note = Protein S monoclonal antibody variable heavy chain
                             sequence
source                   1..351
                         mol_type = other DNA
                         organism = synthetic construct
SEQUENCE: 116
caggtgcagc tgcaggagtc gggcccagga ctggtgaagc cttcggagac cctgtccctc    60
acctgcactg tctctggtgg ctccatcagt aattactact ggaactggat ccggcagccc    120
```

```
ccagggaagg gactggagtg gattgggtat atctattaca ttgggatcac cgactacaac   180
ccctccctca agagtcgagt caccatatca gtagacacgt ccaagaacca gttctccctg   240
aaggtgacct ctgtgaccgc tgcggacacg gccgtgtatt actgtgcggc tctaagtggg   300
gatcatgctt ttgacatctg gggccaaggg acactggtca ccgtctcttc a           351

SEQ ID NO: 117          moltype = AA  length = 6
FEATURE                 Location/Qualifiers
REGION                  1..6
                        note = Protein S antibody CDR-L1 sequence
source                  1..6
                        mol_type = protein
                        organism = synthetic construct
SEQUENCE: 117
QGINNY                                                               6

SEQ ID NO: 118          moltype =    length =
SEQUENCE: 118
000

SEQ ID NO: 119          moltype = AA  length = 9
FEATURE                 Location/Qualifiers
REGION                  1..9
                        note = Protein S antibody CDR-L3 sequence
source                  1..9
                        mol_type = protein
                        organism = synthetic construct
SEQUENCE: 119
QQYNSYPRT                                                            9

SEQ ID NO: 120          moltype = AA  length = 10
FEATURE                 Location/Qualifiers
REGION                  1..10
                        note = Protein S antibody CDR-H1 sequence
source                  1..10
                        mol_type = protein
                        organism = synthetic construct
SEQUENCE: 120
GGSITNSNYY                                                          10

SEQ ID NO: 121          moltype = AA  length = 7
FEATURE                 Location/Qualifiers
REGION                  1..7
                        note = Protein S antibody CDR-H2 sequence
source                  1..7
                        mol_type = protein
                        organism = synthetic construct
SEQUENCE: 121
VYYSGTT                                                              7

SEQ ID NO: 122          moltype = AA  length = 14
FEATURE                 Location/Qualifiers
REGION                  1..14
                        note = Protein S antibody CDR-H3 sequence
source                  1..14
                        mol_type = protein
                        organism = synthetic construct
SEQUENCE: 122
VRESESYYYY GSDV                                                     14

SEQ ID NO: 123          moltype = AA  length = 9
FEATURE                 Location/Qualifiers
REGION                  1..9
                        note = Protein S antibody CDR-L3 sequence
source                  1..9
                        mol_type = protein
                        organism = synthetic construct
SEQUENCE: 123
QQYNSYPIT                                                            9

SEQ ID NO: 124          moltype = AA  length = 8
FEATURE                 Location/Qualifiers
REGION                  1..8
                        note = Protein S antibody CDR-H1 sequence
source                  1..8
                        mol_type = protein
                        organism = synthetic construct
SEQUENCE: 124
GFTFSSYN                                                             8
```

```
SEQ ID NO: 125         moltype = AA   length = 8
FEATURE                Location/Qualifiers
REGION                 1..8
                       note = Protein S antibody CDR-H2 sequence
source                 1..8
                       mol_type = protein
                       organism = synthetic construct
SEQUENCE: 125
ISSSSSYI                                                              8

SEQ ID NO: 126         moltype = AA   length = 14
FEATURE                Location/Qualifiers
REGION                 1..14
                       note = Protein S antibody CDR-H3 sequence
source                 1..14
                       mol_type = protein
                       organism = synthetic construct
SEQUENCE: 126
ARDEEWELLT GFDY                                                      14

SEQ ID NO: 127         moltype = AA   length = 6
FEATURE                Location/Qualifiers
REGION                 1..6
                       note = Protein S antibody CDR-L1 sequence
source                 1..6
                       mol_type = protein
                       organism = synthetic construct
SEQUENCE: 127
QSISTF                                                                6

SEQ ID NO: 128         moltype =    length =
SEQUENCE: 128
000

SEQ ID NO: 129         moltype = AA   length = 9
FEATURE                Location/Qualifiers
REGION                 1..9
                       note = Protein S antibody CDR-L3 sequence
source                 1..9
                       mol_type = protein
                       organism = synthetic construct
SEQUENCE: 129
QQSYSTPRT                                                             9

SEQ ID NO: 130         moltype = AA   length = 8
FEATURE                Location/Qualifiers
REGION                 1..8
                       note = Protein S antibody CDR-H1 sequence
source                 1..8
                       mol_type = protein
                       organism = synthetic construct
SEQUENCE: 130
GGSISGNY                                                              8

SEQ ID NO: 131         moltype = AA   length = 19
FEATURE                Location/Qualifiers
REGION                 1..19
                       note = Protein S antibody CDR-H3 sequence
source                 1..19
                       mol_type = protein
                       organism = synthetic construct
SEQUENCE: 131
ARDLDYFTWG AYSDWYFDL                                                 19

SEQ ID NO: 132         moltype =    length =
SEQUENCE: 132
000

SEQ ID NO: 133         moltype =    length =
SEQUENCE: 133
000

SEQ ID NO: 134         moltype =    length =
SEQUENCE: 134
000

SEQ ID NO: 135         moltype =    length =
SEQUENCE: 135
000
```

-continued

```
SEQ ID NO: 136          moltype = AA   length = 7
FEATURE                 Location/Qualifiers
REGION                  1..7
                        note = Protein S antibody CDR-L1 sequence
source                  1..7
                        mol_type = protein
                        organism = synthetic construct
SEQUENCE: 136
QSVGSSY                                                                   7

SEQ ID NO: 137          moltype = AA   length = 9
FEATURE                 Location/Qualifiers
REGION                  1..9
                        note = Protein S antibody CDR-L3 sequence
source                  1..9
                        mol_type = protein
                        organism = synthetic construct
SEQUENCE: 137
QQYGSSPYT                                                                 9

SEQ ID NO: 138          moltype = AA   length = 10
FEATURE                 Location/Qualifiers
REGION                  1..10
                        note = Protein S antibody CDR-H1 sequence
source                  1..10
                        mol_type = protein
                        organism = synthetic construct
SEQUENCE: 138
GDSVSNNNAA                                                               10

SEQ ID NO: 139          moltype = AA   length = 9
FEATURE                 Location/Qualifiers
REGION                  1..9
                        note = Protein S antibody CDR-H2 sequence
source                  1..9
                        mol_type = protein
                        organism = synthetic construct
SEQUENCE: 139
TYYRSKWYN                                                                 9

SEQ ID NO: 140          moltype = AA   length = 12
FEATURE                 Location/Qualifiers
REGION                  1..12
                        note = Protein S antibody CDR-H3 sequence
source                  1..12
                        mol_type = protein
                        organism = synthetic construct
SEQUENCE: 140
ARGSSWYRFF DY                                                            12

SEQ ID NO: 141          moltype = AA   length = 6
FEATURE                 Location/Qualifiers
REGION                  1..6
                        note = Protein S antibody CDR-L1 sequence
source                  1..6
                        mol_type = protein
                        organism = synthetic construct
SEQUENCE: 141
QNIHMW                                                                    6

SEQ ID NO: 142          moltype =      length =
SEQUENCE: 142
000

SEQ ID NO: 143          moltype = AA   length = 9
FEATURE                 Location/Qualifiers
REGION                  1..9
                        note = Protein S antibody CDR-L3 sequence
source                  1..9
                        mol_type = protein
                        organism = synthetic construct
SEQUENCE: 143
LQGQSYPFT                                                                 9

SEQ ID NO: 144          moltype = AA   length = 8
FEATURE                 Location/Qualifiers
REGION                  1..8
                        note = Protein S antibody CDR-H1 sequence
```

```
source                  1..8
                        mol_type = protein
                        organism = synthetic construct
SEQUENCE: 144
GYTFTNHW                                                                    8

SEQ ID NO: 145          moltype = AA  length = 8
FEATURE                 Location/Qualifiers
REGION                  1..8
                        note = Protein S antibody CDR-H2 sequence
source                  1..8
                        mol_type = protein
                        organism = synthetic construct
SEQUENCE: 145
IYPGGGYT                                                                    8

SEQ ID NO: 146          moltype = AA  length = 13
FEATURE                 Location/Qualifiers
REGION                  1..13
                        note = Protein S antibody CDR-H3 sequence
source                  1..13
                        mol_type = protein
                        organism = synthetic construct
SEQUENCE: 146
SRFGDQNWAW FAY                                                             13

SEQ ID NO: 147          moltype =     length =
SEQUENCE: 147
000

SEQ ID NO: 148          moltype = AA  length = 107
FEATURE                 Location/Qualifiers
REGION                  1..107
                        note = Protein S monoclonal antibody variable light chain
                          sequence
source                  1..107
                        mol_type = protein
                        organism = synthetic construct
SEQUENCE: 148
DIQMTQSPSS LSASVGDRVT ITCRASQGIN NYLAWFQQKP GKAPKSLIYA ASSLQSGVPS           60
KFSGSGSGTD FTLTISSLQP EDFATYYCQQ YNSYPRTFGQ GTKVEIK                        107

SEQ ID NO: 149          moltype = AA  length = 122
FEATURE                 Location/Qualifiers
REGION                  1..122
                        note = Protein S monoclonal antibody variable heavy chain
                          sequence
source                  1..122
                        mol_type = protein
                        organism = synthetic construct
SEQUENCE: 149
QLQLQESGPG LVKPSETLSL TCTVSGGSIT NSNYYWGWIR QPPGKGLEWI GSVYYSGTTY           60
YNPSLKSRVT ISVDPSKNQF SLKLSSVTAA DTAVYYCVRE SESYYYYGSD VWGQGTTVTV          120
SS                                                                        122

SEQ ID NO: 150          moltype = AA  length = 107
FEATURE                 Location/Qualifiers
REGION                  1..107
                        note = Protein S monoclonal antibody variable light chain
                          sequence
source                  1..107
                        mol_type = protein
                        organism = synthetic construct
SEQUENCE: 150
DIQMTQSPSS LSASVGDRVT ITCRASQGIN NYLAWFQQKP GKAPKSLIYA ASNLQSGVPL           60
KFSGSGSGTD FTLTISSLQP EDFATYYCQQ YNSYPITFGQ GTRLEIK                        107

SEQ ID NO: 151          moltype = AA  length = 121
FEATURE                 Location/Qualifiers
REGION                  1..121
                        note = Protein S monoclonal antibody variable heavy chain
                          sequence
source                  1..121
                        mol_type = protein
                        organism = synthetic construct
SEQUENCE: 151
EVQLVESGGG LVKPGGSLRL SCAASGFTFS SYNMNWVRQA PGRGLDWVSS ISSSSSYIYY           60
ADSVKGRFTI SRDNAKNSLY LQMNTLRAED TAVYYCARDE EWELLTGFDY WGQGTLVTVS          120
S                                                                         121
```

```
SEQ ID NO: 152          moltype = AA  length = 107
FEATURE                 Location/Qualifiers
REGION                  1..107
                        note = Protein S monoclonal antibody variable light chain
                          sequence
source                  1..107
                        mol_type = protein
                        organism = synthetic construct
SEQUENCE: 152
DIQMTQSPSS LSASVGDRVT ITCRASQSIS TFLNWYQQKP GKAPKLLIYA TSSLRSGVPS    60
RFSGSGSGTD FTLTISSLQP EDFAIYYCQQ SYSTPRTFGQ GTQVEIK                 107

SEQ ID NO: 153          moltype = AA  length = 125
FEATURE                 Location/Qualifiers
REGION                  1..125
                        note = Protein S monoclonal antibody variable heavy chain
                          sequence
source                  1..125
                        mol_type = protein
                        organism = synthetic construct
SEQUENCE: 153
QVQLQESGPG LVKPSETLSL TCTVSGGSIS GNYWSWIRQP PGKGLEWIGY IYYSGSTNYN    60
PSLKSRVTIS VDTSKNQFSL KLSSVTAADT AVYYCARDLD YFTWGAYSDW YFDLWGRGTL   120
VTVSS                                                               125

SEQ ID NO: 154          moltype =    length =
SEQUENCE: 154
000

SEQ ID NO: 155          moltype =    length =
SEQUENCE: 155
000

SEQ ID NO: 156          moltype = AA  length = 108
FEATURE                 Location/Qualifiers
REGION                  1..108
                        note = Protein S monoclonal antibody variable light chain
                          sequence
source                  1..108
                        mol_type = protein
                        organism = synthetic construct
SEQUENCE: 156
EIVLTQSPGT LSLSPGERAT LSCRASQSVG SSYLAWYQQK PGQAPRLLIS GASGRATGIP    60
DRFSGSGSGT DFTLTISRLE PEDFTVYYCQ QYGSSPYTFG QGTKLEIK                108

SEQ ID NO: 157          moltype = AA  length = 122
FEATURE                 Location/Qualifiers
REGION                  1..122
                        note = Protein S monoclonal antibody variable heavy chain
                          sequence
source                  1..122
                        mol_type = protein
                        organism = synthetic construct
SEQUENCE: 157
QVQLQQSGPG LVKPSQTLSL TCAISGDSVS NNNAAWNWIR QSPSRGLEWL GGTYYRSKWY    60
NDYAVSVKSR IIINPVTSKN QFSLQLNSVT PEDTAVYYCA RGSSWYRFFD YWGQGTLVTV   120
SS                                                                  122

SEQ ID NO: 158          moltype = AA  length = 107
FEATURE                 Location/Qualifiers
REGION                  1..107
                        note = Protein S monoclonal antibody variable light chain
                          sequence
source                  1..107
                        mol_type = protein
                        organism = synthetic construct
SEQUENCE: 158
DIQMNQSPSS LSASLGDTIT ITCRASQNIH MWLSWYQQKP GNIPKLLIFK TSNLHTGVPS    60
RFSGSGSGTD FTLTISSLQP EDIATYYCLQ GQSYPFTFGG GTKLEIK                 107

SEQ ID NO: 159          moltype = AA  length = 120
FEATURE                 Location/Qualifiers
REGION                  1..120
                        note = Protein S monoclonal antibody variable heavy chain
                          sequence
source                  1..120
                        mol_type = protein
                        organism = synthetic construct
```

```
SEQUENCE: 159
QVQLQQSGTE LVRPGTSVKM SCKAAGYTFT NHWIGWVKQR PGHGLEWIGD IYPGGGYTNY    60
NEKFKGKASL TADTSSTTAY MQLSSLTSED SAIYYCSRFG DQNWAWFAYW GQGTLVTVSA   120

SEQ ID NO: 160          moltype =    length =
SEQUENCE: 160
000

SEQ ID NO: 161          moltype =    length =
SEQUENCE: 161
000

SEQ ID NO: 162          moltype = DNA   length = 321
FEATURE                 Location/Qualifiers
misc_feature            1..321
                        note = Protein S monoclonal antibody variable light chain
                        sequence
source                  1..321
                        mol_type = other DNA
                        organism = synthetic construct
SEQUENCE: 162
gacatccaga tgacccagtc tccatcctca ctgtctgcat ctgtaggaga cagagtcacc    60
atcacttgtc gggcgagtca ggcattaac aattatttag cctggtttca gcagaaacca   120
gggaaagccc ctaagtccct gatctatgct gcatccagtt tgcaaagtgg ggtcccatca   180
aagttcagcg gcagtggatc tgggacagat ttcactctca ccatcagcag cctgcagcct   240
gaagattttg caacttatta ctgccaacag tataatagtt acccctcggac gttcggccaa   300
gggaccaagg tggaaatcaa a                                              321

SEQ ID NO: 163          moltype = DNA   length = 366
FEATURE                 Location/Qualifiers
misc_feature            1..366
                        note = Protein S monoclonal antibody variable heavy chain
                        sequence
source                  1..366
                        mol_type = other DNA
                        organism = synthetic construct
SEQUENCE: 163
cagctgcagc tgcaggagtc gggcccagga ctggtgaagc cttcggagac cctgtccctc    60
acctgcactg tctctggtgg ctccatcacc aatagtaatt actactgggg ctggatccgc   120
cagcccccag ggaagggact ggagtggatt gggagtgtct attatagtgg gaccacctac   180
tacaacccgt ccctcaagag tcgagtcacc atatccgtag acccgtccaa gaaccagttc   240
tccctgaagc tgagctctgt gaccgccgca gacacggctg tgtattactg tgcgagagag   300
agtgagagct actactacta cggttcggac gtctggggca agggaccac ggtcaccgtc   360
tcctca                                                                366

SEQ ID NO: 164          moltype = DNA   length = 321
FEATURE                 Location/Qualifiers
misc_feature            1..321
                        note = Protein S monoclonal antibody variable light chain
                        sequence
source                  1..321
                        mol_type = other DNA
                        organism = synthetic construct
SEQUENCE: 164
gacatccaga tgacccagtc tccatcctca ctgtctgcat ctgtaggaga cagagtcacc    60
atcacttgtc gggcgagtca ggcattaac aattatttag cctggtttca gcagaaacca   120
gggaaagccc ctaagtccct gatctatgct gcatccaatt tgcaaagtgg ggtcccatta   180
aagttcagcg gcagtggatc tgggacagat ttcactctca ccatcagcag cctgcagcct   240
gaagattttg caacttatta ctgccaacag tataatagtt acccgatcac cttcggccaa   300
gggacacgac tggagattaa a                                              321

SEQ ID NO: 165          moltype = DNA   length = 363
FEATURE                 Location/Qualifiers
misc_feature            1..363
                        note = Protein S monoclonal antibody variable heavy chain
                        sequence
source                  1..363
                        mol_type = other DNA
                        organism = synthetic construct
SEQUENCE: 165
gaggtgcagc tggttgagtc tgggggaggc ctggtcaagc ctggggggtc cctgagactc    60
tcctgtgcag cctctggatt caccttcagt agctataaca tgaactgggt ccgccaggct   120
ccagggaggg ggctggactg ggtctcatcc attagtagta gtagtagtta catatactac   180
gcagactcag tgaagggccg attcaccatc tccagagaca acgccaagaa ctcactgtat   240
ctgcaaatga ataccctgag agccgaggac acggctgttt attactgtgc gagagatgag   300
gagtgggagc tactgacggg cttttgactac tggggccagg gaaccctggt caccgtctcc   360
tca                                                                  363

SEQ ID NO: 166          moltype = DNA   length = 321
```

```
FEATURE              Location/Qualifiers
misc_feature         1..321
                     note = Protein S monoclonal antibody variable light chain
                         sequence
source               1..321
                     mol_type = other DNA
                     organism = synthetic construct
SEQUENCE: 166
gacatccaga tgacccagtc tccatcctcc ctgtctgcat ctgtaggaga cagagtcacc   60
atcacttgcc gggcaagtca gagcattagc acctttttaa attggtatca gcagaaacca  120
gggaaagccc ctaaactcct gatctatgct acatccagtt tgcgaagtgg ggtcccatca  180
aggttcagtg gcagtggatc tgggacagat ttcactctca ccatcagcag tctgcaacct  240
gaagattttg caatttatta ttgtcaacag agttacagta cccctcggac gttcggccaa  300
gggaccaagg tggaaatcaa a                                            321

SEQ ID NO: 167       moltype = DNA   length = 375
FEATURE              Location/Qualifiers
misc_feature         1..375
                     note = Protein S monoclonal antibody variable heavy chain
                         sequence
source               1..375
                     mol_type = other DNA
                     organism = synthetic construct
SEQUENCE: 167
caggtgcagc tgcaggagtc gggcccagga ctggtgaagc cttcggagac cctgtccctc   60
acctgcactg tctctggtgg ctccatcagt ggtaactact ggagctggat ccagcagccc  120
ccagggaagg gactggagtg gattgggtat atctattaca gtgggagcac caactacaat  180
ccctccctca agagtcgagt caccatatca gttgacacgt ccaagaacca gttctccctg  240
aagctgagct ctgtgaccgc tgcggatacg gccgtgtatt actgtgcgag agatcttgat  300
tactttactt gggggcttta ttctgactgg tacttcgatc tctggggccg tggcaccctg  360
gtcactgtct cctca                                                   375

SEQ ID NO: 168       moltype =   length =
SEQUENCE: 168
000

SEQ ID NO: 169       moltype =   length =
SEQUENCE: 169
000

SEQ ID NO: 170       moltype = DNA   length = 324
FEATURE              Location/Qualifiers
misc_feature         1..324
                     note = Protein S monoclonal antibody variable light chain
                         sequence
source               1..324
                     mol_type = other DNA
                     organism = synthetic construct
SEQUENCE: 170
gaaattgtgt tgacgcagtc tccaggcacc ctgtctttgt ctccagggga aagagccacc   60
ctctcctgca gggccagtca gagtgttggc agcagctact tagcctggta ccagcagaaa  120
cctggccagg ctcccaggct cctcatctct ggtgcatccg gcagggccac tggcatccca  180
gacaggttca gtggcagtgg gtctgggaca gacttcactc tcaccatcag cagactggag  240
cctgaagatt ttacagtgta ttactgtcag cagtatggta gctcaccgta cacttttggc  300
cagggggacca agctggagat caaa                                        324

SEQ ID NO: 171       moltype = DNA   length = 366
FEATURE              Location/Qualifiers
misc_feature         1..366
                     note = Protein S monoclonal antibody variable heavy chain
                         sequence
source               1..366
                     mol_type = other DNA
                     organism = synthetic construct
SEQUENCE: 171
caggtacagc tgcagcagtc aggtccagga ctggtgaagc cctcgcagac cctctcactc   60
acctgtgcca tctccgggga cagtgtctct aacaacaatg ctgcttggaa ctggatcagg  120
cagtcccat cgagaggcct tgagtggctg ggagggacat actacaggtc caagtggtat  180
aatgattatg cagtatctgt gaaaagtcga ataatcatca atccagtcac atccaagaac  240
cagttctccc tacagctgaa ctctgtgact cccgaggaca cggctgtgta ttactgtgca  300
agaggcagca gctggtacag gtttttttgac tactgggggcc agggaaccct ggtcaccgtc  360
tcctca                                                             366

SEQ ID NO: 172       moltype = DNA   length = 321
FEATURE              Location/Qualifiers
misc_feature         1..321
                     note = Protein S monoclonal antibody variable light chain
                         sequence
source               1..321
```

```
                            mol_type = other DNA
                            organism = synthetic construct
SEQUENCE: 172
gacatccaga tgaaccagtc tccatccagt ctgtctgcat ccctcggaga cacaattacc    60
atcacttgcc gtgccagtca gaacattcat atgtggttaa gctggtacca gcagaaacca   120
ggaaatattc ctaaactatt gatctttaag acttccaatt tgcacacagg cgtcccatca   180
aggtttagtg gcagtggatc tggaacagat ttcacattaa ccatcagcag tctgcagcct   240
gaagacattg ccacttacta ctgtctacag ggtcaaagtt atccgttcac gttcggaggg   300
gggaccaagc tggaaataaa g                                             321

SEQ ID NO: 173              moltype = DNA   length = 360
FEATURE                     Location/Qualifiers
misc_feature                1..360
                            note = Protein S monoclonal antibody variable heavy chain
                             sequence
source                      1..360
                            mol_type = other DNA
                            organism = synthetic construct
SEQUENCE: 173
caggtccagc tgcagcagtc tggaactgag ctggtaaggc ctgggacttc agtgaagatg    60
tcctgtaagg ctgctggata caccttcact aaccactgga taggttgggt aaagcagagg   120
cctggacatg gccttgagtg gattggagat atttacccta ggtggttta tactaactac   180
aatgagaagt tcaagggcaa ggcctcactg actgcagaca catcctccac cacagcctac   240
atgcagctca gcagcctgac atctgaggac tctgccatct attactgttc aagattcggg   300
gatcaaaact gggcctggtt tgcttactgg ggccaaggga ctctggtcac tgtctctgca   360

SEQ ID NO: 174              moltype = AA    length = 6
FEATURE                     Location/Qualifiers
REGION                      1..6
                            note = Hc-M1 VL CDR-1
source                      1..6
                            mol_type = protein
                            organism = synthetic construct
SEQUENCE: 174
QSISSY                                                                6

SEQ ID NO: 175              moltype =    length =
SEQUENCE: 175
000

SEQ ID NO: 176              moltype = AA    length = 8
FEATURE                     Location/Qualifiers
REGION                      1..8
                            note = Hc-M1 VL CDR-3
source                      1..8
                            mol_type = protein
                            organism = synthetic construct
SEQUENCE: 176
QQSYSSLT                                                              8

SEQ ID NO: 177              moltype = AA    length = 106
FEATURE                     Location/Qualifiers
REGION                      1..106
                            note = Hc-M1 VL V region
source                      1..106
                            mol_type = protein
                            organism = synthetic construct
SEQUENCE: 177
DIQMTQSPSS LSASVGDRVT ITCRASQSIS SYLNWYQQKP GKAPKLLIYA ASSLQSGVPS     60
RFSGSGSGTD FTLTISSLQP EDFATYYCQQ SYSSLTFGQG TRLEIK                   106

SEQ ID NO: 178              moltype = DNA   length = 318
FEATURE                     Location/Qualifiers
misc_feature                1..318
                            note = Hc-M1 VL
source                      1..318
                            mol_type = other DNA
                            organism = synthetic construct
SEQUENCE: 178
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacagtt ccctcacctt cggccaaggg   300
acacgactgg agattaaa                                                 318

SEQ ID NO: 179              moltype = AA    length = 8
FEATURE                     Location/Qualifiers
REGION                      1..8
```

```
                        note = Hc-M1 VH CDR-1
source                  1..8
                        mol_type = protein
                        organism = synthetic construct
SEQUENCE: 179
GISFSNAW                                                                    8

SEQ ID NO: 180          moltype = AA   length = 10
FEATURE                 Location/Qualifiers
REGION                  1..10
                        note = Hc-M1 VH CDR-2
source                  1..10
                        mol_type = protein
                        organism = synthetic construct
SEQUENCE: 180
IKANPDGGTT                                                                 10

SEQ ID NO: 181          moltype = AA   length = 15
FEATURE                 Location/Qualifiers
REGION                  1..15
                        note = Hc-M1 VH CDR-3
source                  1..15
                        mol_type = protein
                        organism = synthetic construct
SEQUENCE: 181
TTELDILLWF TSFDY                                                           15

SEQ ID NO: 182          moltype = AA   length = 124
FEATURE                 Location/Qualifiers
REGION                  1..124
                        note = Hc-M1 VH V region
source                  1..124
                        mol_type = protein
                        organism = synthetic construct
SEQUENCE: 182
EVQLVESGGG LVKPGGSLRL SCAASGISFS NAWMSWVRQA PGKGLEWVGR IKANPDGGTT           60
DYAAPVKGRF TISRDDSKNT LYLQMNSLKT EDTAVYYCTT ELDILLWFTS FDYWGQGTLV          120
TVSS                                                                      124

SEQ ID NO: 183          moltype = DNA   length = 372
FEATURE                 Location/Qualifiers
misc_feature            1..372
                        note = Hc-M1 VH
source                  1..372
                        mol_type = other DNA
                        organism = synthetic construct
SEQUENCE: 183
gaggtgcagc tggtggagtc tgggggaggc ttggtaaagc ctggggggtc ccttagactc           60
tcctgtgcag cctctggaat cagtttcagt aacgcctgga tgagctgggt ccgccaggct         120
ccagggaagg ggctggaatg ggttggccgt attaaagcca atcctgatgg tgggacaaca         180
gactacgctg cacccgtgaa aggcagattc accatctcaa gagatgattc aaaaaacacg         240
ctatatctgc aaatgaacag cctgaaaacc gaggacacag ccgtgtatta ctgtaccaca         300
gagttggaca tttttactat ggttcacctc tttgactact ggggccaggg aaccctggtc         360
accgtctcct ca                                                             372

SEQ ID NO: 184          moltype = AA   length = 6
FEATURE                 Location/Qualifiers
REGION                  1..6
                        note = Od-M4 VL CDR-1
source                  1..6
                        mol_type = protein
                        organism = synthetic construct
SEQUENCE: 184
NIGGKS                                                                      6

SEQ ID NO: 185          moltype =    length =
SEQUENCE: 185
000

SEQ ID NO: 186          moltype = AA   length = 11
FEATURE                 Location/Qualifiers
REGION                  1..11
                        note = Od-M4 VL CDR-3
source                  1..11
                        mol_type = protein
                        organism = synthetic construct
SEQUENCE: 186
QVWEITSDHP A                                                               11
```

| SEQ ID NO: 187 | moltype = AA   length = 108 |
| --- | --- |
| FEATURE | Location/Qualifiers |
| REGION | 1..108 |
| | note = Od-M4 VL V region |
| source | 1..108 |
| | mol_type = protein |
| | organism = synthetic construct |

SEQUENCE: 187
```
SYVLTQPPSV SVAPGQTARI TCGGDNIGGK SVHWYQQKPG QAPVMVVYDD SDRPSGIPER    60
FAGSNSGNTA TLAISRVEAG DEADYYCQVW EITSDHPAFG GGTRLTVL               108
```

| SEQ ID NO: 188 | moltype = DNA   length = 324 |
| --- | --- |
| FEATURE | Location/Qualifiers |
| misc_feature | 1..324 |
| | note = Od-M4 VL |
| source | 1..324 |
| | mol_type = other DNA |
| | organism = synthetic construct |

SEQUENCE: 188
```
tcctatgtgc tgactcagcc accctcggtg tcagtggccc caggacagac ggccaggatt    60
acctgtgggg gagacaacat tggaggtaaa agtgtgcact ggtaccagca gaagccaggc   120
caggcccctg tgatggtcgt ctatgatgat agcgaccggc cctcagggat ccctgagcga   180
ttcgctggct ccaattctgg gaacacggcc accctggcca tcagcagggt cgaagccggg   240
gatgaggccg actattactg tcaggtgtgg gagataacta gtgatcatcc ggcattcggc   300
ggagggacca ggctgaccgt ccta                                          324
```

| SEQ ID NO: 189 | moltype = AA   length = 8 |
| --- | --- |
| FEATURE | Location/Qualifiers |
| REGION | 1..8 |
| | note = Od-M4 VH CDR-1 |
| source | 1..8 |
| | mol_type = protein |
| | organism = synthetic construct |

SEQUENCE: 189
```
GFTFSSYS                                                              8
```

| SEQ ID NO: 190 | moltype = AA   length = 8 |
| --- | --- |
| FEATURE | Location/Qualifiers |
| REGION | 1..8 |
| | note = Od-M4 VH CDR-2 |
| source | 1..8 |
| | mol_type = protein |
| | organism = synthetic construct |

SEQUENCE: 190
```
ISSSTRTI                                                              8
```

| SEQ ID NO: 191 | moltype = AA   length = 9 |
| --- | --- |
| FEATURE | Location/Qualifiers |
| REGION | 1..9 |
| | note = Od-M4 VH CDR-3 |
| source | 1..9 |
| | mol_type = protein |
| | organism = synthetic construct |

SEQUENCE: 191
```
ARERSAFDY                                                             9
```

| SEQ ID NO: 192 | moltype = AA   length = 116 |
| --- | --- |
| FEATURE | Location/Qualifiers |
| REGION | 1..116 |
| | note = Od-M4 VH V region |
| source | 1..116 |
| | mol_type = protein |
| | organism = synthetic construct |

SEQUENCE: 192
```
EVQLVESGGG LVQPGGSLRL SCAASGFTFS SYSMNWVRQA PGKGLEWVAY ISSSTRTIFY    60
ADSVKGRFTI SRDNAKNSLY LQMNSLRDED TAFYYCARER SAFDYWGQGT LVTVSS       116
```

| SEQ ID NO: 193 | moltype = DNA   length = 348 |
| --- | --- |
| FEATURE | Location/Qualifiers |
| misc_feature | 1..348 |
| | note = Od-M4 VH |
| source | 1..348 |
| | mol_type = other DNA |
| | organism = synthetic construct |

SEQUENCE: 193
```
gaggtgcagc tggtggagtc tgggggaggc ttggtacagc ctgggggtc cctgagactc      60
tcctgtgcag cctctggatt caccttcagt agctatagca tgaactgggt ccgccaggct   120
ccagggaagg ggctggagtg ggttgcatac attagtagta gtactcgtac atattctac    180
gcagactctg tgaagggccg attcaccatc tccagagaca tgccaagaa ctcactgtat   240
```

```
ctgcaaatga acagcctgag agacgaggac acggctttt attattgtgc gagagaacgt   300
tcggccttg actactgggg ccagggaacc ctggtcaccg tctcctca                348
```

```
SEQ ID NO: 194          moltype = AA  length = 6
FEATURE                 Location/Qualifiers
REGION                  1..6
                        note = Od-M7 VL CDR-1
source                  1..6
                        mol_type = protein
                        organism = synthetic construct
SEQUENCE: 194
KLGDKY                                                              6

SEQ ID NO: 195          moltype =    length =
SEQUENCE: 195
000

SEQ ID NO: 196          moltype = AA  length = 9
FEATURE                 Location/Qualifiers
REGION                  1..9
                        note = Od-M7 VL CDR-3
source                  1..9
                        mol_type = protein
                        organism = synthetic construct
SEQUENCE: 196
QAWDSSTVG                                                           9

SEQ ID NO: 197          moltype = AA  length = 106
FEATURE                 Location/Qualifiers
REGION                  1..106
                        note = Od-M7 VL V region
source                  1..106
                        mol_type = protein
                        organism = synthetic construct
SEQUENCE: 197
SYELTQPPSV SVSPGQTASI TCSGDKLGDK YVFWYQQKPG QSPVLVIYQD SKRPSGIPER   60
FSGSNSGNTA TLTISGTQTM DEADYYCQAW DSSTVGFGGG TKLAVL                  106

SEQ ID NO: 198          moltype = DNA  length = 318
FEATURE                 Location/Qualifiers
misc_feature            1..318
                        note = Od-M7 VL
source                  1..318
                        mol_type = other DNA
                        organism = synthetic construct
SEQUENCE: 198
tcctatgagc tgactcagcc accctcagtg tccgtgtccc caggacagac agccagcatc   60
acctgctctg gagataaatt gggggataaa tatgtttct ggtatcagca agaagccaggc   120
cagtcccctg tgttggtcat ctatcaagat agcaagcggc cctcagggat ccctgagcga   180
ttctctggct ccaactctgg gaacacagcc actctgacca tcagcgggac ccagactatg   240
gatgaggctg actattactg tcaggcgtgg gacagcagca ctgtgggatt cggcggaggg   300
accaagctgg ccgtcctg                                                 318

SEQ ID NO: 199          moltype = AA  length = 8
FEATURE                 Location/Qualifiers
REGION                  1..8
                        note = Od-M7 VH CDR-1
source                  1..8
                        mol_type = protein
                        organism = synthetic construct
SEQUENCE: 199
GYTFTNYY                                                            8

SEQ ID NO: 200          moltype = AA  length = 8
FEATURE                 Location/Qualifiers
REGION                  1..8
                        note = Od-M7 VH CDR-2
source                  1..8
                        mol_type = protein
                        organism = synthetic construct
SEQUENCE: 200
ITPSGGTT                                                            8

SEQ ID NO: 201          moltype = AA  length = 15
FEATURE                 Location/Qualifiers
REGION                  1..15
                        note = Od-M7 VH CDR-3
source                  1..15
                        mol_type = protein
```

```
                    organism = synthetic construct
SEQUENCE: 201
ARAGVQLDRR GWFDP                                                      15

SEQ ID NO: 202          moltype = AA  length = 122
FEATURE                 Location/Qualifiers
REGION                  1..122
                        note = Od-M7 VH V region
source                  1..122
                        mol_type = protein
                        organism = synthetic construct
SEQUENCE: 202
QVQLVQSGSE VKKPGASVKV SCKASGYTFT NYYIHWVRQA PGQGLEWMGI ITPSGGTTSY      60
AQKFQGRVTM TRDTSTNTVY MGLSSLRSED TAMYYCARAG VQLDRRGWFD PWGQGTLVTV     120
SS                                                                   122

SEQ ID NO: 203          moltype = DNA  length = 366
FEATURE                 Location/Qualifiers
misc_feature            1..366
                        note = Od-M7 VH
source                  1..366
                        mol_type = other DNA
                        organism = synthetic construct
SEQUENCE: 203
caggtgcagc tggtgcagtc tgggtctgag gtgaagaagc tggggcctc agtgaaggtt       60
tcctgcaagg catctggata cacccttcacc aactactata cacactgggt gcggcaggcc   120
cctggacaag gcttgagtg atgggaata atcaccccta gtggtggtac cacaagctac      180
gcacagaagt tccagggcag agtcactatg accaggaca cgtccacgaa cacagtctac     240
atggggctga gcagcctgag atctgaggac acggccatgt attactgtgc gagagccggg   300
gtacaactgg atcgacgagg gtggttcgac ccctggggcc agggaaccct ggtcaccgtc    360
tcctca                                                               366

SEQ ID NO: 204          moltype = AA  length = 6
FEATURE                 Location/Qualifiers
REGION                  1..6
                        note = Od-M67 VL CDR-1
source                  1..6
                        mol_type = protein
                        organism = synthetic construct
SEQUENCE: 204
KLGDKY                                                                 6

SEQ ID NO: 205          moltype =   length =
SEQUENCE: 205
000

SEQ ID NO: 206          moltype = AA  length = 9
FEATURE                 Location/Qualifiers
REGION                  1..9
                        note = Od-M67 VL CDR-3
source                  1..9
                        mol_type = protein
                        organism = synthetic construct
SEQUENCE: 206
QAWDSSTAV                                                              9

SEQ ID NO: 207          moltype = AA  length = 106
FEATURE                 Location/Qualifiers
REGION                  1..106
                        note = Od-M67 VL V region
source                  1..106
                        mol_type = protein
                        organism = synthetic construct
SEQUENCE: 207
SYELTQPPSV SVSPGQTASI TCSGDKLGDK YAFWYQQKPG QSPVLVIYQD NKRPSGIPER      60
FSGSNSGNTA TLTISGTQAV DEADYYCQAW DSSTAVFGGG TKLTVL                   106

SEQ ID NO: 208          moltype = DNA  length = 318
FEATURE                 Location/Qualifiers
misc_feature            1..318
                        note = Od-M67 VL
source                  1..318
                        mol_type = other DNA
                        organism = synthetic construct
SEQUENCE: 208
tcctatgagc tgactcagcc acccctcagtg tccgtgtccc cgggacagac agccagcatc    60
acctgctctg gagataaatt ggggataaa tatgctttct ggtatcagca gaagccaggc    120
cagtcccctg tgctggtcat ctatcaagat aacaagcggc cctcagggat ccctgagcga   180
ttctctggct ccaactctgg gaacacagcc actctaacca tcagcgggac ccaggctgtg   240
```

```
gatgaggctg actattactg tcaggcgtgg gacagcagca ctgcggtatt cggcggaggg    300
accaagctga ccgtccta                                                  318
```

| SEQ ID NO: 209 | moltype = AA  length = 8 |
|---|---|
| FEATURE | Location/Qualifiers |
| REGION | 1..8 |
|  | note = Od-M67 VH CDR-1 |
| source | 1..8 |
|  | mol_type = protein |
|  | organism = synthetic construct |

SEQUENCE: 209
GYTFTSYY                                                              8

| SEQ ID NO: 210 | moltype = AA  length = 8 |
|---|---|
| FEATURE | Location/Qualifiers |
| REGION | 1..8 |
|  | note = Od-M67 VH CDR-2 |
| source | 1..8 |
|  | mol_type = protein |
|  | organism = synthetic construct |

SEQUENCE: 210
TSPSGRST                                                              8

| SEQ ID NO: 211 | moltype = AA  length = 17 |
|---|---|
| FEATURE | Location/Qualifiers |
| REGION | 1..17 |
|  | note = Od-M67 VH CDR-3 |
| source | 1..17 |
|  | mol_type = protein |
|  | organism = synthetic construct |

SEQUENCE: 211
ARGGVTIHLE RRGYFDY                                                   17

| SEQ ID NO: 212 | moltype = AA  length = 124 |
|---|---|
| FEATURE | Location/Qualifiers |
| REGION | 1..124 |
|  | note = Od-M67 VH V region |
| source | 1..124 |
|  | mol_type = protein |
|  | organism = synthetic construct |

SEQUENCE: 212
QVQLVQSGAE VKKPGASVKV SCKASGYTFT SYYIHWVRQA PGQGLEWMGV TSPSGRSTSF    60
AQKFQGRVTM TRDTSTSAVY MDLDSLRSED TAVYYCARGG VTIHLERRGY FDYWGQGTLV    120
IVSS                                                                 124

| SEQ ID NO: 213 | moltype = DNA  length = 372 |
|---|---|
| FEATURE | Location/Qualifiers |
| misc_feature | 1..372 |
|  | note = Od-M67 VH |
| source | 1..372 |
|  | mol_type = other DNA |
|  | organism = synthetic construct |

SEQUENCE: 213
```
caggtgcagc tggtgcagtc tgggcctgag gtgaagaagc ctggggcctc agtgaaggtt    60
tcctgcaagg catctggata caccttcacc agctactata cacactgggt acgacaggcc   120
cctggacaag gcttgagtg gatgggagta accagcccta gtggtcgtag cacaagcttc    180
gcacagaagt tccagggcag agtcaccatg accaggaca cgtccacgag cgcagtctat    240
atggacctgg acagcctgag atctgaggac acggccgtgt attactgtgc gagaggggga    300
gtgacgatac acctggaacg acggggctac tttgactact ggggccaggg aaccctggtc    360
attgtctcct ca                                                        372
```

| SEQ ID NO: 214 | moltype = AA  length = 107 |
|---|---|
| FEATURE | Location/Qualifiers |
| REGION | 1..107 |
|  | note = Kappa light chain |
| source | 1..107 |
|  | mol_type = protein |
|  | organism = synthetic construct |

SEQUENCE: 214
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                 107

| SEQ ID NO: 215 | moltype = AA  length = 106 |
|---|---|
| FEATURE | Location/Qualifiers |
| REGION | 1..106 |
|  | note = Lambda light chain |
| source | 1..106 |
|  | mol_type = protein |
|  | organism = synthetic construct |

```
SEQUENCE: 215
GQPKAAPSVT LFPPSSEELQ ANKATLVCLI SDFYPGAVTV AWKADSSPVK AGVETTTPSK   60
QSNNKYAASS YLSLTPEQWK SHRSYSCQVT HEGSTVEKTV APTECS                106

SEQ ID NO: 216          moltype = AA  length = 676
FEATURE                 Location/Qualifiers
source                  1..676
                        mol_type = protein
                        organism = Homo sapiens
SEQUENCE: 216
MRVLGGRCGA LLACLLLVLP VSEANFLSKQ QASQVLVRKR RANSLLEETK QGNLERECIE   60
ELCNKEEARE VFENDPETDY FYPKYLVCLR SFQTGLFTAA RQSTNAYPDL RSCVNAIPDQ  120
CSPLPCNEDG YMSCKDGKAS FTCTCKPGWQ GEKCEFDINE CKDPSNINGG CSQICDNTPG  180
SYHCSCKNGF VMLSNKKDCK DVDECSLKPS ICGTAVCKNI PGDFECECPE GYRYNLKSKS  240
CEDIDECSEN MCAQLCVNYP GGYTCYCDGK KGFKLAQDQK SCEVVSVCLP LNLDTKYELL  300
YLAEQFAGVV LYLKFRLPEI SRFSAEFDFR TYDSEGVILY AESIDHSAWL LIALRGGKIE  360
VQLKNEHTSK ITTGGDVINN GLWNMVSVEE LEHSISIKIA KEAVMDINKP GPLFKPENGL  420
LETKVYFAGF PRKVESELIK PINPRLDGCI RSWNLMKQGA SGIKEIIQEK QNKHCLVTVE  480
KGSYYPGSGI AQFHIDYNNV SSAEGWHVNV TLNIRPSTGT GVMLALVSGN NTVPFAVSLV  540
DSTSEKSQDI LLSVENTVIY RIQALSLCSD QQSHLEFRVN RNNLELSTPL KIETISHEDL  600
QRQLAVLDKA MKAKVATYLG GLPDVPFSAT PVNAFYNGCM EVNINGVQLD LDEAISKHND  660
IRAHSCPSVW KKTKNS                                                 676

SEQ ID NO: 217          moltype = AA  length = 330
FEATURE                 Location/Qualifiers
source                  1..330
                        mol_type = protein
                        organism = Homo sapiens
SEQUENCE: 217
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 218          moltype = AA  length = 327
FEATURE                 Location/Qualifiers
source                  1..327
                        mol_type = protein
                        organism = Homo sapiens
SEQUENCE: 218
ASTKGPSVFP LAPCSRSTSE STAALGCLVK DYFPEPVTVS WNSGALTSGV HTFPAVLQSS   60
GLYSLSSVVT VPSSSLGTKT YTCNVDHKPS NTKVDKRVES KYGPPCPSCP APEFLGGPSV  120
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSLGK                                     327
```